(12) United States Patent
Lippard et al.

(10) Patent No.: US 8,709,743 B2
(45) Date of Patent: Apr. 29, 2014

(54) INHIBITORS OF BACTERIAL NITRIC OXIDE SYNTHASE, AND RELATED SCREENING METHODS

(75) Inventors: Stephen J. Lippard, Cambridge, MA (US); Lindsey E. McQuade, Union City, CA (US); Evgeny A. Nudler, New York, NY (US)

(73) Assignee: Massachusetts Institute of Technology, Cambridge, MA (US)

( * ) Notice: Subject to any disclaimer, the term of this patent is extended or adjusted under 35 U.S.C. 154(b) by 521 days.

(21) Appl. No.: 12/808,889

(22) PCT Filed: Dec. 17, 2008

(86) PCT No.: PCT/US2008/087137
§ 371 (c)(1),
(2), (4) Date: Apr. 21, 2011

(87) PCT Pub. No.: WO2009/079549
PCT Pub. Date: Jun. 25, 2009

(65) Prior Publication Data
US 2011/0201042 A1    Aug. 18, 2011

Related U.S. Application Data

(60) Provisional application No. 61/091,059, filed on Aug. 22, 2008, provisional application No. 61/014,165, filed on Dec. 17, 2007.

(51) Int. Cl.
*C12Q 1/02* (2006.01)
(52) U.S. Cl.
USPC ............. 435/29; 435/252.1; 549/388; 546/79
(58) Field of Classification Search
USPC ..................... 435/29, 252.1; 549/388; 546/79
See application file for complete search history.

(56) References Cited

U.S. PATENT DOCUMENTS

| 5,759,835 A | 6/1998 | Rosazza et al. |
| 2002/0197653 A1 | 12/2002 | Shair et al. |

FOREIGN PATENT DOCUMENTS

WO   WO 2007149105 A2 * 12/2007

OTHER PUBLICATIONS

Nolan et al. J. Am. Chem. Soc. (2005) 127(48): 16812-16823.*
Kato et al. Microbiol. Immunol. (2001) 45(1): 69-78.*
Hildebrand, S. A., "Fluorescence-Based Detection Methodologies for Nitric Oxide Using Transition Metal Scaffolds", Dissertation, Massachusetts Institute of Technology, 2004.
Johnson, E. G. et al., "Plant-Pathogenic *Streptomyces* Species Produce Nitric Oxide Synthase-Derived Nitric Oxide in Response to Host Signals", *Chemistry & Biology*, 15:43-50 (Elsevier Ltd., Jan. 2008).
Lim, M. H. et al., "Direct Nitric Oxide Detection in Aqueous Solution by Copper(II) Fluorescein Complexes", *J. Am. Chem. Soc.*, 128:14364-14373 (American Chemical Society, USA, 2006).
Lim, M. H. et al., "Metal-Based Turn-On Fluorescent Probes for Sensing Nitric Oxide", *Acc. Chem. Res.*, 40:41-51 (American Chemical Society, USA, 2007).
Lim, M. H. et al., "Visualization of nitric oxide in living cells by a copper-based fluorescent probe", *Nature Chemical Biology*, 2(7):375-380 (Nature Publishing Group, 2006).
International Search Report from PCT/US2008/087137 dated Aug. 26, 2009.
Written Opinion of the International Searching Authority from PCT/US2008/087137 dated Aug. 26, 2009.

* cited by examiner

*Primary Examiner* — Susan Hanley
(74) *Attorney, Agent, or Firm* — Alan W. Steele; Foley Hoag LLP

(57) ABSTRACT

The invention relates in part to compounds that act as highly nitric oxide (NO)-specific turn-on fluorescent probes. The present invention also relates to the use of these fluorescein-based sensors to screen selectively for inhibitors of bacterial nitric oxide synthase (bNOS). Compounds of the present invention readily detect nitric oxide produced in vivo. Therefore they can be used in an assay that measures NO production by bNOS. Using a sensor of the invention one can screen libraries of small molecules for inhibitors of bNOS.

24 Claims, 12 Drawing Sheets

|          | + excess NO (g) | Time ($F_{max}$, min) |
|----------|-----------------|------------------------|
| Cu(FL₁)  | 2.5-fold        | 60                     |
| Cu(FL₂)  | 8.3-fold        | 70                     |
| Cu(FL₃)  | 3.4-fold        | 15                     |
| Cu(FL₄)  | 31-fold         | 20                     |
| Cu(FL₅)  | 16-fold         | 5                      |

INHIBITORS OF BACTERIAL NITRIC OXIDE SYNTHASE, AND RELATED SCREENING METHODS

RELATED APPLICATIONS

This application is the U.S. National Stage of International Patent Application No. PCT/US2008/087137, filed Dec. 17, 2008, which claims the benefit of priority to U.S. Provisional Patent Application Ser. No. 61/014,165, filed Dec. 17, 2007; and U.S. Provisional Patent Application Ser. No. 61/091,059, filed Aug. 22, 2008.

GOVERNMENT SUPPORT

This invention was made with government support under Grant No. 1DP1OD000799 awarded by the National Institutes of Health; and Grant No. CHE0611944 awarded by the National Science Foundation. The government has certain rights in the invention.

BACKGROUND

Fluorescent Sensors

Fluorescence technology has revolutionized cell biology and many areas of biochemistry. In certain instances, fluorescent molecules may be used to trace molecular and physiological events in living cells. Certain sensitive and quantitative fluorescence detection devices have made fluorescence measurements an ideal readout for in vitro biochemical assays. In addition, some fluorescence measurement systems may be useful for determining the presence of analytes in environmental samples. Finally, because fluorescence detection systems are often responsive, sensitive and reliable, fluorescence measurements are often critical for many high-throughput screening applications.

The feasibility of using fluorescence technology for a particular application is often limited by the availability of an appropriate fluorescent sensor. There are a number of features that are desirable in fluorescent sensors, some of which may or may not be present in any particular sensor. First, fluorescent sensors should produce a perceptible change in fluorescence upon binding a desired analyte. Second, fluorescent sensors should selectively bind a particular analyte. Third, to allow concentration changes to be monitored, fluorescent sensors should have a $K_d$ near the median concentration of the species under investigation. Fourth, fluorescent sensors, especially when used intracellularly, should produce a signal with a high brightness, the product of the quantum yield and extinction coefficient. Fifth, the wavelengths of both the light used to excite the fluorescent molecule (excitation wavelengths) and of the emitted light (emission wavelengths) are often important. If possible, for intracellular use, a fluorescent sensor should have excitation wavelengths exceeding 340 nm to permit use with glass microscope objectives and prevent UV-induced cell damage, and have emission wavelengths approaching 500 nm to avoid autofluorescence from native substances in the cell and allow use with typical fluorescence microscopy optical filter sets. Excitation and emission at even longer wavelengths, approaching the near-IR, are also of value. Sixth, ideal sensors should allow for passive and irreversible loading into cells. Finally, ideal sensors should be water soluble and non-toxic, and they should exhibit increased fluorescence with increasing levels of analyte.

Nitric Oxide in Biological Systems

Since the discovery in the 1980s that nitric oxide (NO) is the endothelium-derived relaxing factor (EDRF), postulated biological roles for NO have continued to proliferate. For example, in addition to cardiovascular signaling, NO also seems to function as a neurotransmitter that may be important in memory and as a weapon to fight infection when released by immune system macrophages. Uncovering these roles and deciphering their implications is complicated by the array of reactions that this gaseous molecule undergoes. In a biological environment, NO can react with a range of targets, including dioxygen, oxygen radicals, thiols, amines and transition metal ions. Some of the products formed, such as $ONOO^-$, $NO_2$ and $NO^+$, are pathophysiological agents, whereas others, such as S-nitrosothiols, may in fact themselves be NO-transfer agents. Transition metal centers, especially iron in oxyhemoglobin, can rapidly scavenge free NO, thereby altering the amount available for signaling purposes.

The concentration-dependent lifetime of NO as well as its ability to diffuse freely through cellular membranes further complicate the delineation of these various processes. With a lifetime of up to 10 min under some conditions and a diffusion range of 100-200 μm, the biological action of NO can be distant from its point of origin. A diffusional spread of 200 μm corresponds to a volume containing approximately 2 million synapses.

A variety of analytical methods are available to monitor aspects of NO in biology, each having certain limitations. The Griess assay, for instance, is useful for estimating total NO production, but it is not very sensitive, cannot give real-time information and only measures the stable oxidation product, nitrite. Although more sensitive and selective for NO, the chemiluminescent gas phase reaction of NO with ozone requires purging aqueous samples with an inert gas to strip NO into an analyzer; therefore, it, too, is incapable of monitoring intracellular NO. Electrochemical sensing using microsensors provides in situ real-time detection of NO; the only spatial information obtained, however, is directly at the electrode tip and is therefore influenced by the placement of the probe.

Fluorescent NO sensors include DAF (diaminofluorescein) and DAN (2,3-diaminonaphthalene), the aromatic vicinal diamines of which react with nitrosating agents ($NO^+$ or $NO_2$) to afford fluorescent triazole compounds. DAF compounds can report intracellular NO, but their sensing ability relies on NO autoxidation products and not direct detection. A rhodamine-type fluorescent NO indicator similarly senses autoxidation products.

Fluorescent nitric oxide cheletropic traps (FNOCTs) are fluorescent versions of molecules that have been used as EPR spin probes and do react directly with NO. The initially formed nitroxide radical species formed are not fluorescent, however. Addition of a common biological reductant, such as ascorbic acid, is required to reduce the nitroxide and display increased fluorescence intensity.

In addition, fluorescein-based sensors, and methods of making and using the same were recently disclosed in Lippard et al., U.S. patent application Ser. No. 11/498,280, filed Aug. 1, 2006; the contents of which are hereby incorporated by reference in their entirety.

SUMMARY

In one aspect, the present invention is directed to the use of fluorescein-based sensors to screen selectively for inhibitors of bacterial nitric oxide synthase (bNOS).

*B. anthracis*, or anthrax, is an acute, life-threatening infectious agent because it is highly resistant to the immune response of the host. Inhalation anthrax is especially dangerous due to its ease of spread and need for effective treatment immediately after exposure to ensure survival. Dalldorf, F. G.; Kaufmann, A. F.; Brachman, P. S., Woolsorters' disease. An experimental model. Arch. Pathol. 1971, 92, 41 8-426. Deliberate distribution of anthrax is a potential mode of bioterrorism, as exemplified by the incident in 2001 where anthrax spores were sent through the U.S. Postal Service as a white powder. Interestingly, it is herein disclosed that *B. anthracis* bacteria produce nitric oxide when they are taken up by macrophages, and use this NO to protect themselves against the host immune response, which produces large amounts of reactive oxygen species (ROS) like hydrogen peroxide ($H_2O_2$) to kill bacterial invaders. Bacteria pretreated with NO have increased viability, and their DNA is not damaged upon exposure to hydrogen peroxide. Bacteria lacking bNOS do not produce NO, as confirmed by a lack of fluorescence when incubated with NO-specific CuFL. These knock-out cells have limited virulence in mice, due to the lack of cytoprotection by nitric oxide. The results just discussed led to the hypothesis disclosed herein that bNOS could be used as a biological target for treating anthrax infection, because small molecules that selectively inhibit the bacterial enzyme over the eukaryotic enzyme would act as effective drugs. Moreover, other bNOS containing pathogenic bacteria may also be inhibited in this way, if NO proves to be a general virulence factor. For example, *Staphylococcus aureus*, which is responsible for many staph infections including pneumonia, endocarditis, toxic shock syndrome, and forms of meningitis, might be inhibited. Therefore, herein it is herein proposed that the inhibition of bacterial NOS may be used as a method for treating bacterial infections.

Figure 1:
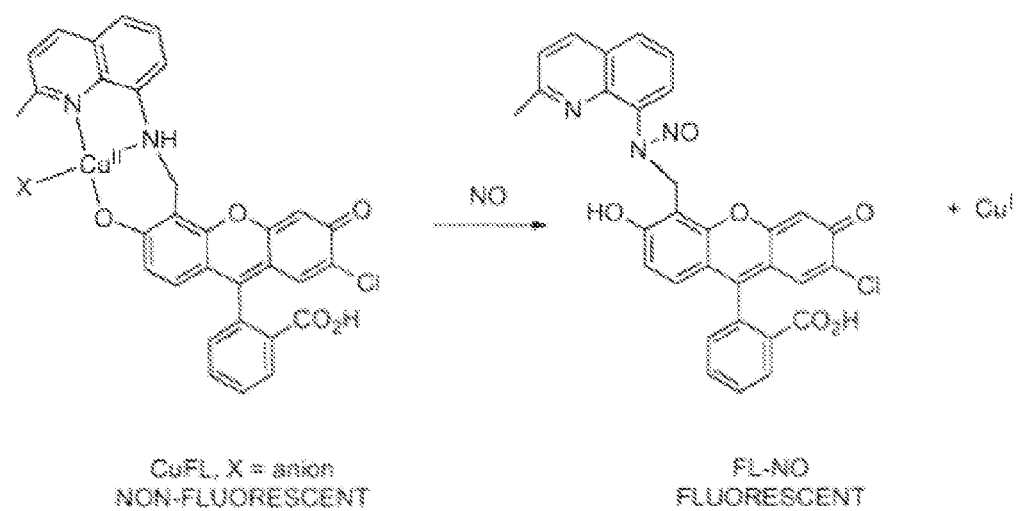
FIG. 1 depicts the structure of CuFL and an exemplary NO detection scheme.
Figure 2:
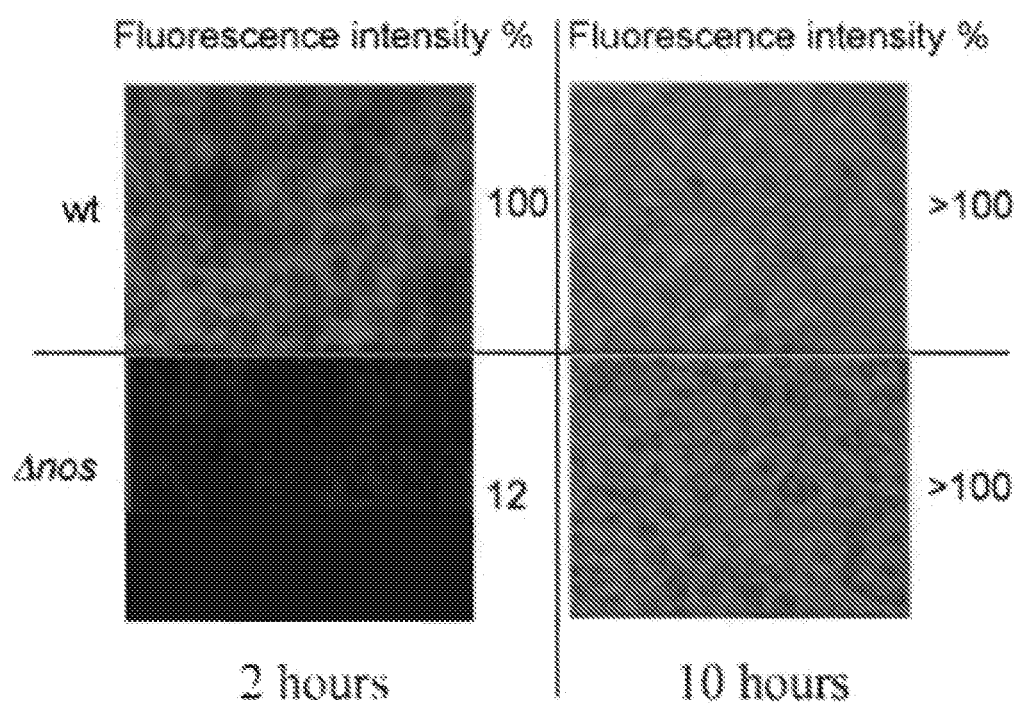
FIG. 2 depicts visualization of fluorescence enhancement by CuFL. Wild-type (wt) bacteria with bNOS produce NO within 2 h (first row), whereas a bNOS deficient strain (Δnos) shows fluorescent enhancement only from macrophage-induced NO production (about 8-12 h, second row).

Another aspect of the invention relates to screening methods for the determination of small-molecule bNOS inhibitors. Because turn-on fluorescent sensors such as CuFL readily detect nitric oxide produced in vivo they can be used in an assay that measures NO production from bNOS. With such a sensor one can readily screen large (about 300,000) libraries of small molecules for potential inhibitors of bNOS. By monitoring the fluorescence of a sample of *B. anthracis*, incubated with both an NO-sensitive probe (such as CuFL) and a small molecule from the library, one can determine which compounds have the ability to inhibit bNOS by the lack fluorescence. The best inhibitors can then be selected and incubated them together with an NO-sensitive probe in *B. anthracis* that have been taken up by macrophages. In this manner, the selectivity of a molecule for bNOS (from *B. anthracis*) over iNOS (from macrophages) can be investigated, because bNOS produces NO very rapidly (in about 1 to 2 hours or earlier), whereas iNOS takes about 8 to 12 h (FIG. 2). Any small molecule capable of inhibiting bNOS but not iNOS can be investigated as a potential lead for developing a therapeutic agent against anthrax and other pathogenic infections.

Therefore, as described above, one aspect of the present invention is directed to the use of fluorescein-based sensors to screen for inhibitors of bacterial nitric oxide synthase (bNOS) in a direct, immediate and selective fashion. In certain embodiments, there is a positive change in fluorescence upon exposure of NO to a subject composition. Without limiting the invention to a particular mechanism of action or otherwise circumscribing the scope of the teachings herein, it is believed that the sensors detect NO via the redox chemistry of their transition metal components with NO. For example, in certain embodiments, the initial fluorescence of the sensor may be quenched in the presence of a paramagnetic copper (II) complex. Upon addition of NO, the copper (II) center is reduced to the diamagnetic copper(I) with closed d-shells, resulting in an increase in fluorescence.

Exemplary Advantages Over Existing Methods of No Detection

Before the advent of direct, NO-specific fluorescent probes, the absence or presence of nitric oxide was typically determined by indirect means, for example by monitoring the formation of its oxidation products. Green, L. C.; Wagner, D. A.; Glogowski, J.; Skiper, P. L.; Wishnok, J. S.; Tannenbaum, S. R., Analysis of nitrate, nitrites and [$^{15}$N] nitrate in biological samples. Anal. Biochem. 1982, 126, 131-138. Although this method is still viable and falls within the scope of this invention, it is valuable to have a direct sensor of NO for rapid detection of the molecule. Fluorescent sensors such as CuFL respond rapidly to increased concentrations of NO, have low cytotoxicity, are bright and cell membrane permeable, making them excellent tools for in vivo visualization. There is no requirement for complicated instrumentation to use these sensors in cells, just simple incubation in growth media and the ability to detect fluorescence. The proposed screening method offers many benefits. First, detection by fluorescence microscopy is easy to implement, as most screening facilities already have the required set-up. Second, the signal is easy to observe and quantify, because the sensor becomes quite bright relative to the "off" state (see FIG. 2). Third, it can be adapted to a wide range of fluorescent sensors, including improved versions of CuFL and other indirect fluorescent sensors that monitor oxidation products of NO or other reactive oxygen and nitrogen species (RONS). Finally, and importantly, because the timing of NO production differs greatly between bacteria (about 1-2 h or earlier) and macrophages (about 8-12 h), the assays described herein provide a means to detect inhibition of both enzymes. Although a double screen takes longer to perform, it provides valuable information about selectivity of potential therapeutic agents, allowing one to pick target molecules with reduced toxic side effects to the patient. This strategy may expedite the drug development process of potential targets.

Figure 3:
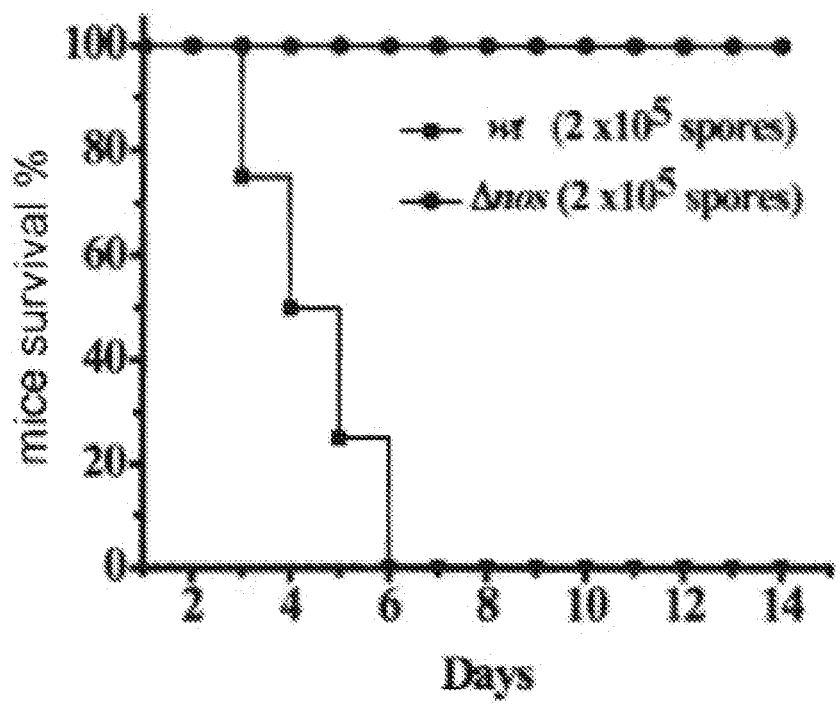
FIG. 3 depicts survival of A/J susceptible mice inoculated with either wild type Sterne or bNOS deficient anthrax spores. Top panel represents the LD100. Bottom panel represents the LD50, and is adjusted for the reduced virulence of the Δnos bacteria.
Figure 3:
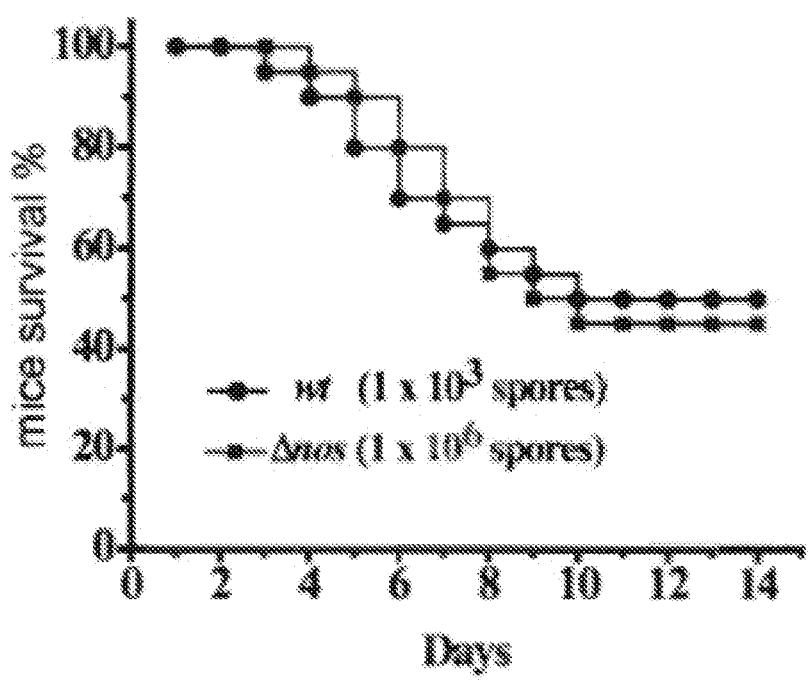

In addition, since most pharmaceutical companies already use some type of chemical screening methodology in their regular drug development process, the unique approach to chemical screening described herein should be easy to incorporate into pre-existing platforms, making it highly suitable for industrialization. In addition, any potential inhibitors that emerge from this screen are candidates for drug development, because effective treatment of anthrax infection requires a good, efficient antibacterial, and it has already demonstrated the drastically reduced virulence of bNOS deficient *B. anthracis* in mice (see FIG. 3). Six- to seven-week-old mice were infected with either wild type or bNOS deficient anthrax spores and inoculated with either wild type Sterne or bNOS deficient anthrax spores. The top panel represents the $LD_{100}$. The bottom panel represents the $LD_{50}$, and it adjusted for the reduced virulence of the Δnos bacteria monitored. The Δnos bacteria were three orders of magnitude less virulent than the wild type, implicating bNOS as an important virulence factor in an infected mammalian model.

DEFINITIONS

For convenience, before further description of the present invention, certain terms employed in the specification, examples and appended claims are collected here. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used herein to mean "including but not limited to". "Including" and "including but not limited to" are used interchangeably.

The term "fluorophore" is art-recognized and refers to a molecule or moiety, generally a polyaromatic hydrocarbon or heterocycle, that has the ability to fluoresce. The ability to fluoresce, or "fluorescence", of a fluorophore is generally understood to result from a three-stage process: (i) excitation, in which a photon is absorbed by the fluorophore, creating an excited electronic state in which the fluorophore has greater energy relative to the normal electronic state of the fluorophore; (ii) excited state lifetime, during which the fluorophore remains in the excited electronic state but also during which the energy of the state is partially dissipated; and (iii) emission, in which a photon of lower energy is emitted. Thus, a fluorophore absorbs a different wavelength of light (the "excitation wavelength") than it emits (the "emission wavelength"). Examples of fluorophores are described in more detail below. The terms "excitation wavelength" and "emission wavelength" are well-known in the art. The term "quantum yield" is art-recognized and refers to the efficiency of photon emission by the fluorophore and is described in more detail below.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below.

The term "ligand" is art-recognized and refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes known to those of skill in the art, which include, for example, terminal (i.e., bound to a single metal ion) and bridging (i.e., one atom of the Lewis base bound to more than one metal ion).

The terms "Lewis acid" and "Lewis acidic" are art-recognized and refer to chemical moieties which can accept a pair of electrons from a Lewis base as defined above.

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The terms "coordinate bond" or "coordination bond" are art-recognized and refer to an interaction between an electron pair donor and a coordination site on a metal ion leading to an attractive force between the electron pair donor and the metal ion. The use of these terms is not intended to be limiting, in so much as certain coordinate bonds may also be classified as having more or less covalent character (if not entirely covalent character) depending on the nature of the metal ion and the electron pair donor.

The term "coordination site" is art-recognized and refers to a point on a metal ion that can accept an electron pair donated, for example, by a ligand or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and means a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A metal ion complex is a coordination complex in which the metal ion is a metal ion. In general, the terms "compound," "composition," "agent" and the like discussed herein include complexes, coordination complexes and metal ion complexes. As a general matter, the teachings of *Advanced Inorganic Chemistry* by Cotton and Wilkinson are referenced as supplementing the definitions herein in regard to coordination complexes and related matters. In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands. If a coordination complex is charged, in that the metal ion and any Lewis bases in the aggregate are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetraflurorborate, hexafluorophosphate, and monocarboxylates, and dianions such as sulfate. In some cases, coordination complexes themselves may serve as counterions to another coordination complex. The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors including theoretical considerations such as kinetic versus thermodynamic effects, as well as the actual synthetic procedures utilized to make the coordination complex, such as the extent of reaction, acidity, concentration of chloride. These considerations are applicable to other counterions as well. Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "synthetic" is art-recognized and refers to production by in vitro chemical or enzymatic synthesis.

The term "meso compound" is art-recognized and means a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular Formula but differ in the connectivity of the atoms. Accordingly, a "regioselective process" is one which favors the production of a particular regioisomer over others, e.g., the reaction produces a statistically significant excess of a certain regioisomer. The term "epimers" is art-recognized and refers to molecules with identical chemical constitution and containing more than one stereocenter, but which differ in configuration at only one of these stereocenters.

"Small molecule" is an art-recognized term. In certain embodiments, this term refers to a molecule which has a molecular weight of less than about 2000 amu, or less than about 1000 amu, and even less than about 500 amu.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like.

The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

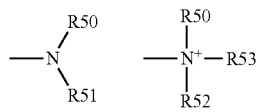

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

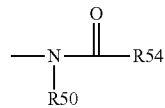

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

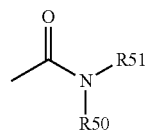

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art-recognized and includes such moieties as may be represented by the general formulas:

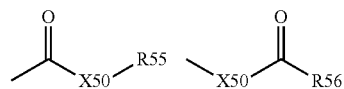

wherein X50 is a bond or represents an oxygen or a sulfur, and R55 represents a hydrogen, an alkyl, an alkenyl, —(CH$_2$)$_m$—R61, or a pharmaceutically acceptable salt. R56 represents a hydrogen, an alkyl, an alkenyl or —(CH$_2$)$_m$—R61, where m and R61 are defined above. Where X50 is an oxygen and R55 or R56 is not hydrogen, the Formula represents an "ester". Where X50 is an oxygen, and R55 is as defined above, the moiety is referred to herein as a carboxyl group, and particularly when R55 is a hydrogen, the Formula represents a "carboxylic acid". Where X50 is an oxygen, and R56 is hydrogen, the Formula represents a "formate". In general, where the oxygen atom of the above Formula is replaced by sulfur, the Formula represents a "thiocarbonyl" group. Where X50 is a sulfur and R55 or R56 is not hydrogen, the Formula represents a "thioester." Where X50 is a sulfur and R55 is hydrogen, the Formula represents a "thiocarboxylic acid." Where X50 is a sulfur and R56 is hydrogen, the Formula represents a "thioformate." On the other hand, where X50 is a bond, and R55 is not hydrogen, the above Formula represents a "ketone"

group. Where X50 is a bond, and R55 is hydrogen, the above Formula represents an "aldehyde" group.

The term "carboxyl" is art recognized and includes such moieties as may be represented by the general formulas:

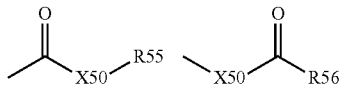

wherein X50 represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where R55 is not hydrogen, the above formula represents a "ketone" group. Where R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

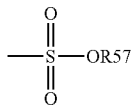

in which R57 is an electron pair, hydrogen, alkyl, cycloalkyl, or aryl.

The term "sulfate" is art recognized and includes a moiety that may be represented by the general formula:

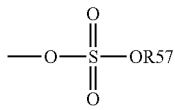

in which R57 is as defined above.

The term "sulfonamido" is art recognized and includes a moiety that may be represented by the general formula:

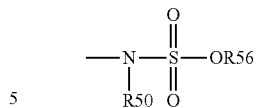

in which R50 and R56 are as defined above.

The term "sulfamoyl" is art-recognized and refers to a moiety that may be represented by the general formula:

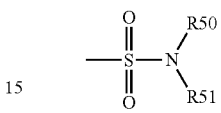

in which R50 and R51 are as defined above.

The term "sulfonyl" is art-recognized and refers to a moiety that may be represented by the general formula:

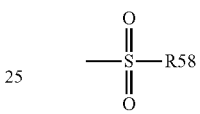

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

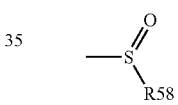

in which R58 is defined above.

The term "phosphoryl" is art-recognized and may in general be represented by the formula:

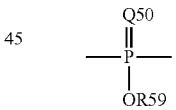

wherein Q50 represents S or O, and R59 represents hydrogen, a lower alkyl or an aryl. When used to substitute, e.g., an alkyl, the phosphoryl group of the phosphorylalkyl may be represented by the general formulas:

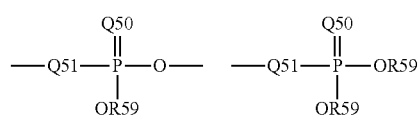

wherein Q50 and R59, each independently, are defined above, and Q51 represents O, S or N. When Q50 is S, the phosphoryl moiety is a "phosphorothioate".

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: N.Y., 1991). Protected forms of the inventive compounds are included within the scope of this invention.

The phrase "hydroxyl-protecting group" is art-recognized and includes those groups intended to protect a hydroxyl group against undesirable reactions during synthetic procedures and includes, for example, benzyl or other suitable esters or ethers groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "Gram-positive bacteria" is an art recognized term for bacteria characterized by having as part of their cell wall structure peptidoglycan as well as polysaccharides and/or teichoic acids and are characterized by their blue-violet color reaction in the Gram-staining procedure.

The term "Gram-negative bacteria" is an art recognized term for bacteria characterized by the presence of a double membrane surrounding each bacterial cell.

General Description of Fluorescein-Based Ligands

A variety of fluorescein-based ligands are contemplated for use in certain aspects of the present invention. In certain embodiments, the subject ligands form coordination complexes with a variety of metal ions, in particular copper (II), with a concomitant change in the fluorescent properties of the resulting metal complex as compared to the uncomplexed ligand. A variety of methods of preparing such ligands and the coordination complexes, of assaying for the binding activity of such ligands, and of using such compositions are taught in Lippard et al., U.S. patent application Ser. No. 11/498,280, filed Aug. 1, 2006; the contents of which are hereby incorporated by reference in their entirety. A number of different ligands and metal ions are contemplated for the subject coordination complexes, as set out in more detail below.

The carbon positions at which substitutions are able to be made on a fluorescein molecule are numbered according to the system shown in the figure below. This system is known to those of skill in the art, and will be used to refer to various atoms of the fluorescein molecules in the description, exemplification, and claims below.

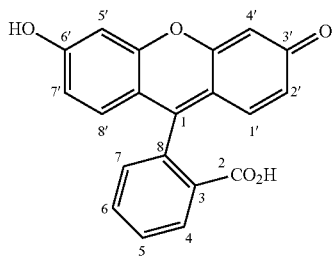

By way of a general, non-limiting description, fluorescein exists in three isomeric forms that are favored under different conditions shown below. The free acid is favorable under aqueous conditions and in polar solvents, the lactone is present in non-polar media, and the zwitterion is an isolable intermediate. Addition of acetate, benzoate or silyl protecting groups to the phenols imposes the lactone isomer. In a stable lactone form, fluoresceins may be purified by standard experimental techniques and identified by NMR and IR spectroscopy. In general, it is the deprotonated free acid form of fluorescein which is responsible for the observed strong fluorescence.

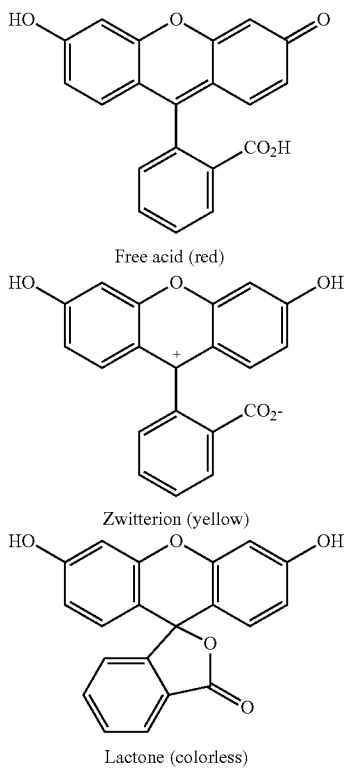

Fluorescence Assays

Fluorescence of a sensor provided by the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon, Molecular Dynamics or Zeiss. In certain embodiments, the device is coupled to a signal amplifier and a computer for data processing.

In general, assays using sensors provided by the present invention involve contacting a sample with such a sensor and measuring fluorescence. The presence of a ligand that interacts with the sensor may alter fluorescence of the sensor in many different ways. Essentially any change in fluorescence caused by the ligand may be used to determine the presence of the ligand and, optionally, the concentration of the ligand in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the sensor to fluoresce. To determine the excitation spectrum for a sensor in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by ligand in a sample may be used as the basis for determining the presence, and optionally, the concentration of metal in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a ligand in a sample may be used to determine the presence or concentration of the ligand in the sample. Changes in excitation or emission spectra may be measured as ratios of two wavelengths. A range of changes are possible, from about a few nms to 5, 10, 15, 25, 50, 75, 100 or more nms.

Quantum yield may be obtained by comparison of the integrated area of the corrected emission spectrum of the sample with that of a reference solution. A preferred reference solution is a solution of fluorescein in 0.1 N NaOH, quantum efficiency 0.95. The concentration of the reference is adjusted to match the absorbance of the test sample. The quantum yields may be calculated using the following equation.

$$\Phi_{sample} = \Phi_{standard} \times \frac{\int emission_{sample}}{\int emission_{standard}} \times \frac{Abs_{standard}}{Abs_{sample}}$$

A change in quantum yield caused by a ligand may be used as the basis for detecting the presence of the ligand in a sample and may optionally be used to determine the concentration of the ligand. A range of changes are possible in the subject invention. For example, the difference in the quantum yield for a subject sensor in the presence of a ligand may be about 10%, 25%, 50%, 75% the quantum yield, or it may be 2, 3, 5, 10, 100, 200, 1000, 10000 times greater or more. The same values may be used to describe changes observed in intensity in such the subject assays.

It is expected that some samples will contain compounds that compete with the sensor for the ligand. In such cases, the fluorescence measurement will reflect this competition. In one variation, the fluorescence may be used to determine the presence or concentration of one or more such ligand-competing compounds in a sample.

IN VITRO ASSAYS. In one variation, the presence of NO in a sample is detected by contacting the sample with a sensor that is sensitive to the presence of NO. The fluorescence of the solution is then determined using one of the above-described devices, preferably a spectrofluorimeter. Optionally, the fluorescence of the solution may be compared against a set of standard solutions containing known quantities of the NO. Comparison to standards may be used to calculate the concentration of NO. The concentration of NO may change over time and the fluorescent signal of the sensor may serve to monitor those changes.

IN VIVO ASSAYS. In another variation, the presence of NO in a biological sample may be determined using a fluorescence microscope and the subject sensors. The biological sample is contacted with the sensor and fluorescence is visualized using appropriate magnification, excitation wavelengths and emission wavelengths.

Biological samples may include bacterial or eukaryotic cells, tissue samples, lysates, or fluids from a living organism. In certain embodiments, the biological sample is a bacterial cell. In certain embodiments, the bacterial cell is *E. coli*. In certain embodiments, the eukaryotic cells are cells of the immune system. In certain embodiments, the eukaryotic cells are macrophages. In certain embodiments, the eukaryotic cells are nerve cells, particularly glutamate neurons. In other embodiments, the eukaryotic cells are neurons with mossy fiber terminals isolated from the hippocampus. Tissue samples are preferably sections of the peripheral or central nervous systems, and in particular, sections of the hippocampus containing mossy fiber terminals. It is also anticipated that the detection of NO in a cell may include detection of NO in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices.

In certain embodiments of the above assays, the sensor is an NO sensor and the ligand is NO. The solution or biological sample is contacted with an NO sensor, and fluorescence of the sensor is excited by light with an appropriate wavelength for the fluorophore of the sensor as known to one of skill in the art. Light emitted by the sensor is detected by detecting light of the expected emission wavelength of the fluorophore of the sensor as known to one of skill in the art.

Methods of Using Fluorescein-Based Ligands

In general, the subject invention is directed to a method of detecting and quantifying the concentration of NO in a sample, comprising: measuring the fluorescence of a fluorescein-based sensor in a sample; and comparing the measured fluorescence to the fluorescence of the fluorescein-based sensor in the absence of NO; thereby detecting and quantifying the amount of NO present in said sample.

One aspect of the invention relates to a method of determining if a small molecule is a bNOS inhibitor, comprising the steps of:

a) preparing a first solution comprising a bacterium that expresses a gene for a non-native bNOS contained in a plasmid, and a small molecule;

b) adding to the first solution a transition metal-containing fluorescein-based sensor, thereby forming a first mixture;

c) incubating the first mixture for a first period of time, thereby forming a first sample;

d) measuring the fluorescence of the first sample;

e) preparing a second solution comprising a bacterium that contains an empty plasmid, and a small molecule;

f) adding to the second solution the transition metal-containing fluorescein-based sensor, thereby forming a second mixture;

g) incubating the second mixture for a second period of time, thereby forming a second sample;

h) measuring the fluorescence of the second sample; and i) comparing the fluorescence of the first sample with the fluorescence of the second sample.

In certain embodiments, the present invention relates to the aforementioned method, wherein the bacterium is *E. coli*.

In certain embodiments, the present invention relates to the aforementioned method, wherein the bacterium is *E. coli*; and the gene for a non-native bNOS is from *Bacillus anthracis*.

In certain embodiments, the present invention relates to the aforementioned method, wherein the bacterium is *E. coli*; and the gene for a non-native bNOS is from *Bacillus anthracis* Sterne.

Another aspect of the invention relates to a method of determining if a small molecule is a bNOS inhibitor, comprising the steps of:

a) preparing a first solution comprising bacteria taken up by macrophages, wherein said bacteria expresses bNOS;

b) adding to the first solution a transition metal-containing fluorescein-based sensor, thereby forming a first mixture;

c) incubating the first mixture for a first period of time, thereby forming a first sample;

d) measuring the fluorescence of the first sample;

e) preparing a second solution comprising the first solution and a small molecule;

f) adding to the second solution the transition metal-containing fluorescein-based sensor, thereby forming a second mixture;

g) incubating the second mixture for a second period of time, thereby forming a second sample;

h) measuring the fluorescence of the second sample; and i) comparing the fluorescence of the first sample with the fluorescence of the second sample.

Another aspect of the invention relates to a method of determining if a small molecule is a selective bNOS inhibitor, comprising the steps of:

a) preparing a first solution comprising bacteria taken up by macrophages, wherein said bacteria expresses bNOS;

b) adding to the first solution a transition metal-containing fluorescein-based sensor, thereby forming a first mixture;

c) incubating the first mixture for a first period of time, thereby forming a first sample;

d) measuring the fluorescence of the first sample;

e) incubating the first sample for a second time, thereby forming a second sample;

f) measuring the fluorescence of the second sample;

g) preparing a second solution comprising the first solution and a small molecule;

h) adding to the second solution the transition metal-containing fluorescein-based sensor, thereby forming a second mixture;

i) incubating the second mixture for a third time, thereby forming a third sample;

j) measuring the fluorescence of the third sample;

k) incubating the third sample for a fourth time, thereby forming a fourth sample;

l) measuring the fluorescence of the fourth sample;

m) comparing the fluorescence of the first sample with the fluorescence of the third sample, and comparing the fluorescence of the second sample with the fluorescence of the fourth sample.

In certain embodiments, the present invention relates to any one of the aforementioned methods, wherein the bacteria is selected from the group consisting of Gram-positive bacteria that express native bNOS.

In certain embodiments, the present invention relates to any one of the aforementioned methods, wherein the bacteria is selected from the group consisting of Gram-positive bacteria that express non-native bNOS.

In certain embodiments, the present invention relates to any one of the aforementioned methods, wherein the bacteria is selected from the group consisting of Gram-negative bacteria that express native bNOS.

In certain embodiments, the present invention relates to any one of the aforementioned methods, wherein the bacteria is selected from the group consisting of Gram-negative bacteria that express non-native bNOS.

In certain embodiments, the present invention relates to any one of the aforementioned methods, wherein the bacteria is *Bacillus* spp.

In certain embodiments, the present invention relates to any one of the aforementioned methods, wherein the bacteria is *Bacillus subtilis*.

In certain embodiments, the present invention relates to any one of the aforementioned methods, wherein the bacteria is *Bacillus anthracis*.

In certain embodiments, the present invention relates to any one of the aforementioned methods, wherein the bacteria is *Bacillus anthracis* Sterne.

In certain embodiments, the present invention relates to any one of the aforementioned methods, wherein the bacteria is *Staphylococcus* spp.

In certain embodiments, the present invention relates to any one of the aforementioned methods, wherein the bacteria is *Staphylococcus aureus*.

In certain embodiments, the present invention relates to any one of the aforementioned methods, wherein the bacteria is methicillin-resistant *Staphylococcus aureus*.

In certain embodiments, the present invention relates to any one of the aforementioned methods, wherein the bacteria is *Norcardia* spp.

In certain embodiments, the present invention relates to any one of the aforementioned methods, wherein the fluorescein-based sensor is represented by formula I:

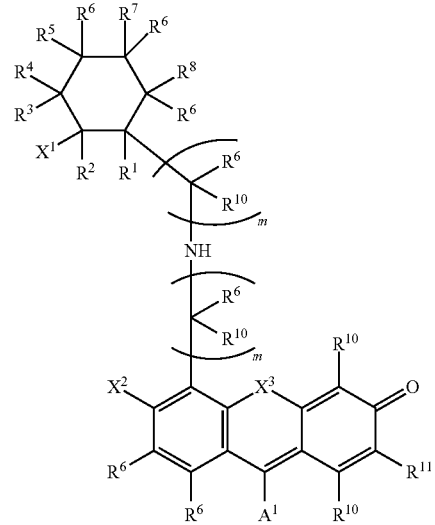

wherein, independently for each occurrence, $A^1$ is aryl or heteroaryl, both of which are optionally substituted with one or more of halogen, alkoxyl, —OH, —N($R^{12}$)$_2$, —COR$^{12}$, —CO$_2$R$^{12}$, —N($R^{12}$)C(O)R$^{12}$, or —C(O)N($R^{12}$)$_2$;

$X^1$ is —OR$^9$, —SR$^9$, —N=R$^9$, or —N($R^{13}$)R$^9$;

$X^2$ is —OR$^{13}$, —SR$^{13}$, or —N($R^{13}$)$_2$;

$X^3$ is —O—, —S—, or —N($R^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N($R^9$)$_2$, —COR$^9$, —CO$_2$R$^9$, —N($R^9$)C(O)R$^9$, or —C(O)N($R^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or ($C_1$-$C_6$)alkyl;

m represents independently for each occurrence 0, 1, 2, 3, or 4; and the stereochemical configuration at any stereocenter of the fluorescein-based sensor represented by I is R, S, or a mixture of these configurations.

In certain embodiments, the present invention relates to any one of the aforementioned methods, wherein $A^1$ is aryl optionally substituted with —CO$_2$R$^{12}$.

In certain embodiments, the present invention relates to any one of the aforementioned methods, wherein $X^1$ is —N=R$^9$.

In certain embodiments, the present invention relates to any one of the aforementioned methods, wherein $X^2$ is —OR$^{13}$.

In certain embodiments, the present invention relates to any one of the aforementioned methods, wherein $X^3$ is —O—.

In certain embodiments, the present invention relates to any one of the aforementioned methods, wherein $R^1$ and $R^8$ taken together form a bond.

In certain embodiments, the present invention relates to any one of the aforementioned methods, wherein $R^5$ and $R^7$ taken together form a bond.

In certain embodiments, the present invention relates to any one of the aforementioned methods, wherein $R^{10}$ is H or alkyl.

In certain embodiments, the present invention relates to any one of the aforementioned methods, wherein $R^2$ and $R^3$ taken together form a bond.

In certain embodiments, the present invention relates to any one of the aforementioned methods, wherein $R^4$ and $R^9$ taken together form a 5-6 member ring optionally substituted with one or more of alkyl, aryl, aralkyl, or halogen.

In certain embodiments, the present invention relates to any one of the aforementioned methods, wherein $R^6$ is H or alkyl.

In certain embodiments, the present invention relates to any one of the aforementioned methods, wherein $R^{11}$ is halogen.

In certain embodiments, the present invention relates to any one of the aforementioned methods, wherein $R^{12}$ is H.

In certain embodiments, the present invention relates to any one of the aforementioned methods, wherein $R^{13}$ is H.

In certain embodiments, the present invention relates to any one of the aforementioned methods, wherein m is 0 or 1.

In certain embodiments, the present invention relates to any one of the aforementioned methods, wherein $A^1$ is aryl optionally substituted with $-CO_2R^{12}$, $X^1$ is $-N=R^9$, $X^2$ is $-OR^{13}$, $X^3$ is $-O-$, and $R^4$ and $R^9$ taken together form a 5-6 memeber ring optionally substituted with one or more of alkyl, aryl, aralkyl, or halogen.

In certain embodiments, the present invention relates to any one of the aforementioned methods, wherein $A^1$ is aryl optionally substituted with $-CO_2R^{12}$; $X^1$ is $-N=R^9$, $X^2$ is $-OR^{13}$; $X^3$ is $-O-$; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H.

In certain embodiments, the present invention relates to any one of the aforementioned methods, wherein the fluorescein-based sensor is represented by formula Ia:

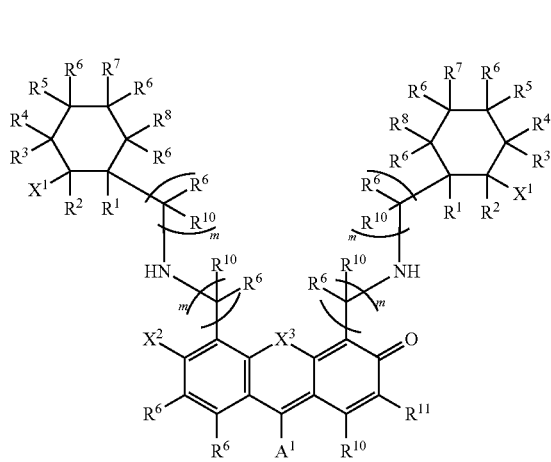

Ia wherein, independently for each occurrence, $A^1$ is aryl or heteroaryl, both of which are optionally substituted with one or more of halogen, alkoxyl, $-OH$, $-N(R^{12})_2$, $-COR^{12}$, $-CO_2R^{12}$, $-N(R^{12})C(O)R^{12}$, or $-C(O)N(R^{12})_2$;

$X^1$ is $-OR^9$, $-SR^9$, $-N=R^9$, or $-N(R^{13})R^9$;

$X^2$ is $-OR^{13}$, $-SR^{13}$, or $-N(R^{13})_2$;

$X^3$ is $-O-$, $-S-$, or $-N(R^{13})-$;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, $-COR^{12}$, or $-CO_2R^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, $-N(R^9)_2$, $-COR^9$, $-CO_2R^9$, $-N(R^9)C(O)R^9$, or $-C(O)N(R^9)_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or $(C_1-C_6)$alkyl;

m represents independently for each occurrence 0, 1, 2, 3, or 4; and the stereochemical configuration at any stereocenter of the fluorescein-based sensor represented by Ia is R, S, or a mixture of these configurations.

In certain embodiments, the present invention relates to any one of the aforementioned methods, wherein $A^1$ is aryl optionally substituted with $-CO_2R^{12}$.

In certain embodiments, the present invention relates to any one of the aforementioned methods, wherein $X^1$ is $-N=R^9$.

In certain embodiments, the present invention relates to any one of the aforementioned methods, wherein $X^2$ is $-OR^{13}$.

In certain embodiments, the present invention relates to any one of the aforementioned methods, wherein $X^3$ is $-O-$.

In certain embodiments, the present invention relates to any one of the aforementioned methods, wherein $R^1$ and $R^8$ taken together form a bond.

In certain embodiments, the present invention relates to any one of the aforementioned methods, wherein $R^5$ and $R^7$ taken together form a bond.

In certain embodiments, the present invention relates to any one of the aforementioned methods, wherein $R^{10}$ is H or alkyl.

In certain embodiments, the present invention relates to any one of the aforementioned methods, wherein $R^2$ and $R^3$ taken together form a bond.

In certain embodiments, the present invention relates to any one of the aforementioned methods, wherein $R^4$ and $R^9$ taken together form a 5-6 member ring optionally substituted with one or more of alkyl, aryl, aralkyl, or halogen.

In certain embodiments, the present invention relates to any one of the aforementioned methods, wherein $R^6$ is H or alkyl.

In certain embodiments, the present invention relates to any one of the aforementioned methods, wherein $R^{11}$ is halogen.

In certain embodiments, the present invention relates to any one of the aforementioned methods, wherein $R^{11}$ is H.

In certain embodiments, the present invention relates to any one of the aforementioned methods, wherein $R^{12}$ is H.

In certain embodiments, the present invention relates to any one of the aforementioned methods, wherein $R^{13}$ is H.

In certain embodiments, the present invention relates to any one of the aforementioned methods, wherein m is 0 or 1.

In certain embodiments, the present invention relates to any one of the aforementioned methods, wherein $A^1$ is aryl optionally substituted with $-CO_2R^{12}$, $X^1$ is $-N=R^9$, $X^2$ is $-OR^{13}$, $X^3$ is $-O-$, and $R^4$ and $R^9$ taken together form a 5-6 member ring optionally substituted with one or more of alkyl, aryl, aralkyl, or halogen.

In certain embodiments, the present invention relates to any one of the aforementioned methods, wherein $A^1$ is aryl optionally substituted with $-CO_2R^{12}$; $X^1$ is $-N=R^9$, $X^2$ is $-OR^{13}$; $X^3$ is $-O-$; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H.

In certain embodiments, the present invention relates to any one of the aforementioned methods, wherein $A^1$ is aryl optionally substituted with $-CO_2R^{12}$; $X^1$ is $-N=R^9$, $X^2$ is $-OR^{13}$; $X^3$ is $-O-$; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^H$ is H; and $R^{10}$ and $R^{12}$ are H.

In certain embodiments, the present invention relates to any one of the aforementioned methods, wherein the fluorescein-based sensor is represented by formula II:

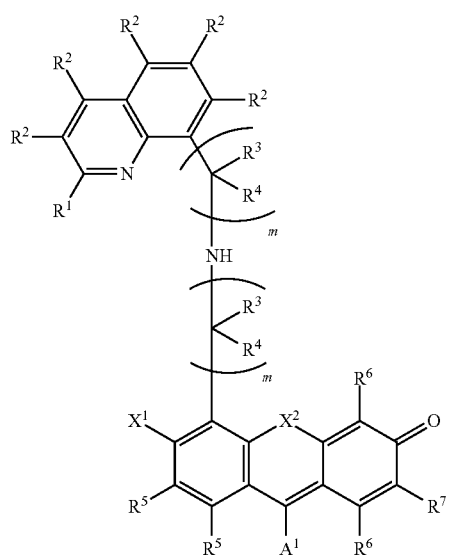

II wherein, independently for each occurrence, $A^1$ is aryl or heteroaryl, both of which are optionally substituted with one or more of halogen, alkoxyl, $-OH$, $-N(R^8)_2$, $-COR^8$, or $-CO_2R^8$;

$X^1$ is $-OR^6$, $-SR^6$, or $-N(R^6)_2$;

$X^2$ is $-O-$, $-S-$, or $-N(R^6)-$;

$R^1$ represents independently for each occurrence H, alkyl, hydroxyalkyl, aryl, aralkyl, halogen, alkoxyl, $-N(R^8)_2$, $-COR^8$, $-CO_2R^8$, $-N(R^8)C(O)R^8$, or $-C(O)N(R^8)_2$;

$R^2$, $R^3$, and $R^5$ each represent independently for each occurrence H, alkyl, halogen, alkoxyl, $-COR^8$, or $-CO_2R^8$;

$R^4$ and $R^6$ each represent independently for each occurrence H or alkyl;

$R^7$ is halogen;

$R^8$ represents independently for each occurrence H, alkyl, aryl, heteroaryl, or aralkyl;

m represents independently for each occurrence 0, 1, or 2; and the stereochemical configuration at any stereocenter of the fluorescein-based sensor represented by II is R, S, or a mixture of these configurations.

In certain embodiments, the present invention relates to any one of the aforementioned methods, wherein $A^1$ is aryl optionally substituted with one or more of $-CO_2R^8$.

In certain embodiments, the present invention relates to any one of the aforementioned methods, wherein $X^1$ is $-OR^6$.

In certain embodiments, the present invention relates to any one of the aforementioned methods, wherein $X^2$ is $-O-$.

In certain embodiments, the present invention relates to any one of the aforementioned methods, wherein $R^1$, $R^2$, $R^3$, and $R^5$ each represent independently for each occurrence H or alkyl.

In certain embodiments, the present invention relates to any one of the aforementioned methods, wherein $R^4$ and $R^6$ are H.

In certain embodiments, the present invention relates to any one of the aforementioned methods, wherein $R^7$ is chloride.

In certain embodiments, the present invention relates to any one of the aforementioned methods, wherein $R^8$ represents independently for each occurrence H or alkyl.

In certain embodiments, the present invention relates to any one of the aforementioned methods, wherein $A^1$ is aryl optionally substituted with $-CO_2R^8$, $X^1$ is $-OR^6$, and $X^2$ is $-O-$.

In certain embodiments, the present invention relates to any one of the aforementioned methods, wherein $A^1$ is aryl optionally substituted with $-CO_2R^8$; $X^1$ is $-OR^6$; $X^2$ is $-O-$; $R^1$, $R^2$, $R^3$, and $R^5$ each represent independently for each occurrence H or alkyl; $R^4$ and $R^6$ are H; and $R^7$ is chloride.

In certain embodiments, the present invention relates to any one of the aforementioned methods, wherein $A^1$ is aryl optionally substituted with $-CO_2R^8$; $X^1$ is $-OR^6$; $X^2$ is $-O-$; $R^1$, $R^2$, $R^3$, and $R^5$ each represent independently for each occurrence H or alkyl; $R^4$ and $R^6$ are H; $R^7$ is chloride; $R^8$ is H; and m represents independently for each occurrence 0 or 1.

In certain embodiments, the present invention relates to any one of the aforementioned methods, wherein the fluorescein-based sensor is represented by formula IIa:

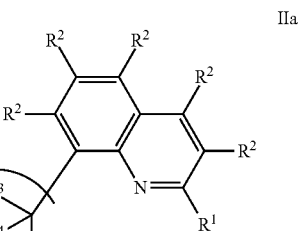
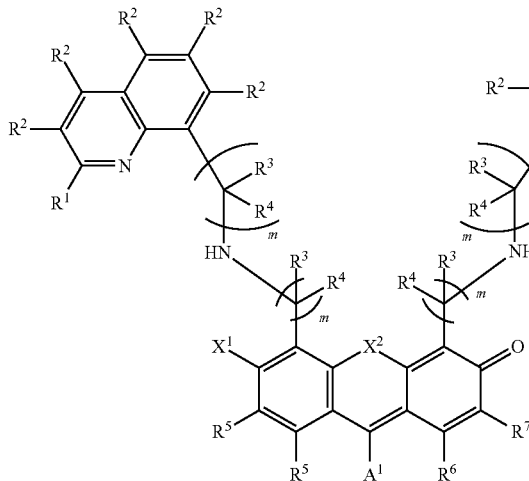

wherein, independently for each occurrence, $A^1$ is aryl or heteroaryl, both of which are optionally substituted with one or more of halogen, alkoxyl, —OH, —N(R$^8$)$_2$, —COR$^8$, or —CO$_2$R$^8$;

$X^1$ is —OR$^6$, —SR$^6$, or —N(R$^6$)$_2$;

$X^2$ is —O—, —S—, or —N(R$^6$)—;

$R^1$ represents independently for each occurrence H, alkyl, hydroxyalkyl, aryl, aralkyl, halogen, alkoxyl, —N(R$^8$)$_2$, —COR$^8$, —CO$_2$R$^8$, —N(R$^8$)C(O)R$^8$, or —C(O)N(R$^8$)$_2$;

$R^2$, $R^3$, and $R^5$ each represent independently for each occurrence H, alkyl, halogen, alkoxyl, —COR$^8$, or —CO$_2$R$^8$;

$R^4$ and $R^6$ each represent independently for each occurrence H or alkyl;

$R^7$ is H or halogen;

$R^8$ represents independently for each occurrence H, alkyl, aryl, heteroaryl, or aralkyl;

m represents independently for each occurrence 0, 1, or 2; and the stereochemical configuration at any stereocenter of the fluorescein-based sensor represented by IIa is R, S, or a mixture of these configurations.

In certain embodiments, the present invention relates to any one of the aforementioned methods, wherein $A^1$ is aryl optionally substituted with one or more of —CO$_2$R$^8$.

In certain embodiments, the present invention relates to any one of the aforementioned methods, wherein $X^1$ is —OR$^6$.

In certain embodiments, the present invention relates to any one of the aforementioned methods, wherein $X^2$ is —O—.

In certain embodiments, the present invention relates to any one of the aforementioned methods, wherein $R^1$, $R^2$, $R^3$, and $R^5$ each represent independently for each occurrence H or alkyl.

In certain embodiments, the present invention relates to any one of the aforementioned methods, wherein $R^4$ and $R^6$ are H.

In certain embodiments, the present invention relates to any one of the aforementioned methods, wherein $R^7$ is chloride.

In certain embodiments, the present invention relates to any one of the aforementioned methods, wherein $R^7$ is H.

In certain embodiments, the present invention relates to any one of the aforementioned methods, wherein $R^8$ represents independently for each occurrence H or alkyl.

In certain embodiments, the present invention relates to any one of the aforementioned methods, wherein $A^1$ is aryl optionally substituted with —CO$_2$R$^8$, $X^1$ is —OR$^6$, and $X^2$ is —O—.

In certain embodiments, the present invention relates to any one of the aforementioned methods, wherein $A^1$ is aryl optionally substituted with —CO$_2$R$^8$; $X^1$ is —OR$^6$; $X^2$ is —O—; $R^1$, $R^2$, $R^3$, and $R^5$ each represent independently for each occurrence H or alkyl; $R^4$ and $R^6$ are H; and $R^7$ is chloride.

In certain embodiments, the present invention relates to any one of the aforementioned methods, wherein $A^1$ is aryl optionally substituted with —CO$_2$R$^8$; $X^1$ is —OR$^6$; $X^2$ is —O—; $R^1$, $R^2$, $R^3$, and $R^5$ each represent independently for each occurrence H or alkyl; $R^4$ and $R^6$ are H; and $R^7$ is H.

In certain embodiments, the present invention relates to any one of the aforementioned methods, wherein $A^1$ is aryl optionally substituted with —CO$_2$R$^8$; $X^1$ is —OR$^6$; $X^2$ is —O—; $R^1$, $R^2$, $R^3$, and $R^5$ each represent independently for each occurrence H or alkyl; $R^4$ and $R^6$ are H; $R^7$ is chloride; $R^8$ is H; and m represents independently for each occurrence 0 or 1.

In certain embodiments, the present invention relates to any one of the aforementioned methods, wherein $A^1$ is aryl optionally substituted with —CO$_2$R$^8$; $X^1$ is —OR$^6$; $X^2$ is —O—; $R^1$, $R^2$, $R^3$, and $R^5$ each represent independently for each occurrence H or alkyl; $R^4$ and $R^6$ are H; $R^7$ is H; $R^8$ is H; and m represents independently for each occurrence 0 or 1.

In certain embodiments, the present invention relates to any one of the aforementioned methods, wherein the fluorescein-based sensor is selected from the group consisting of

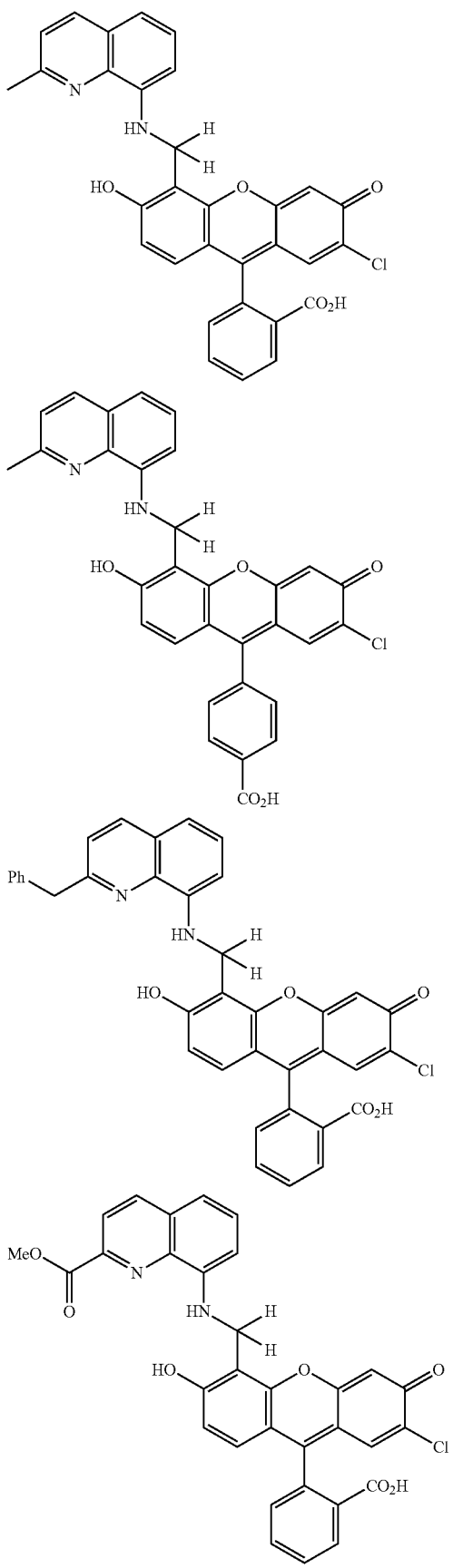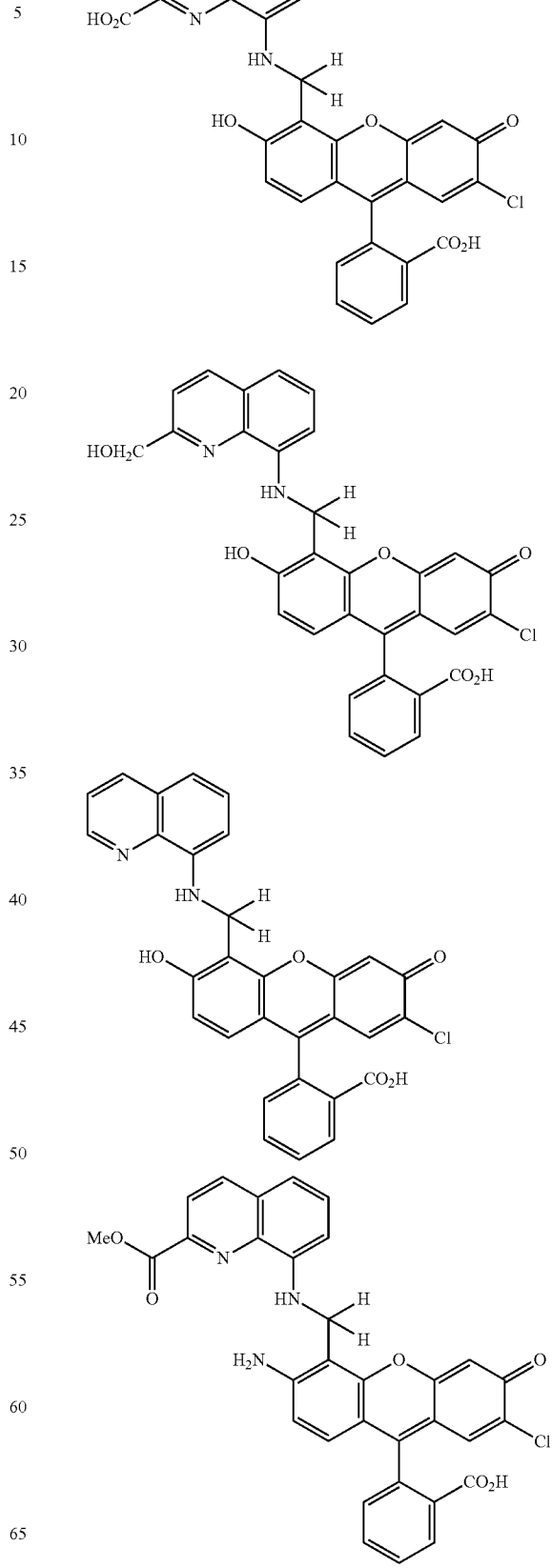

31
-continued
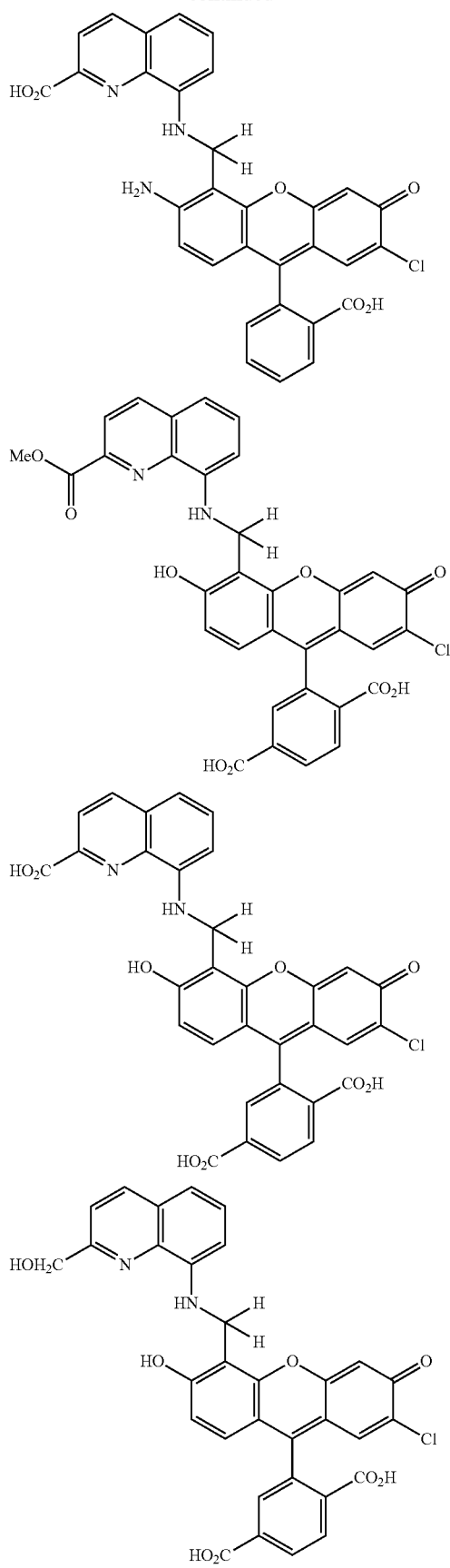
32
-continued
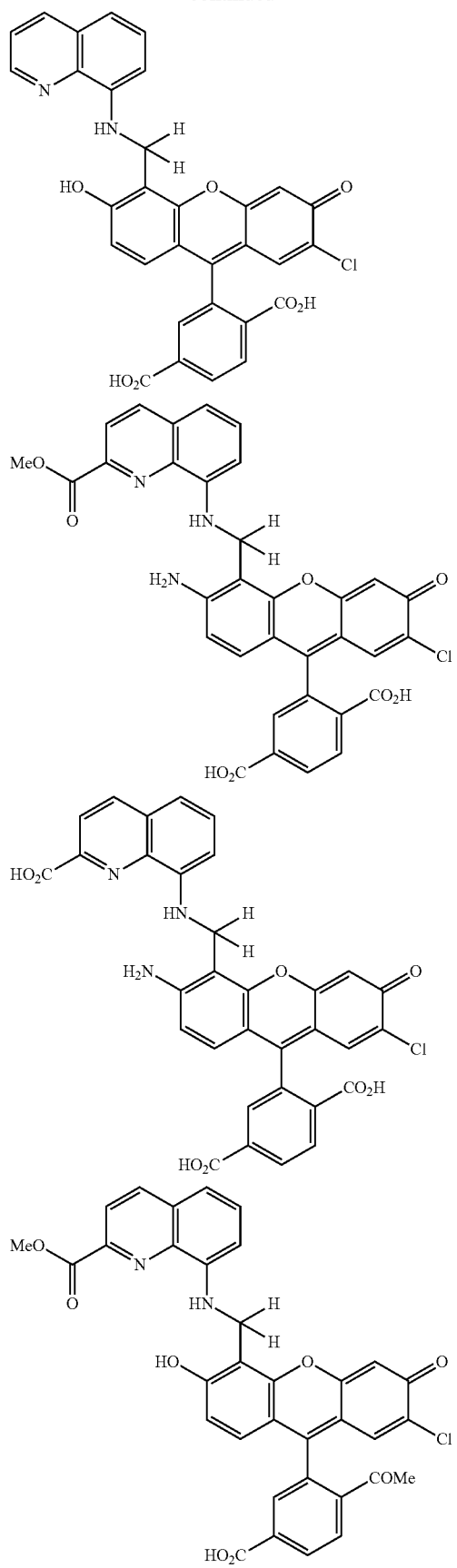

33
-continued
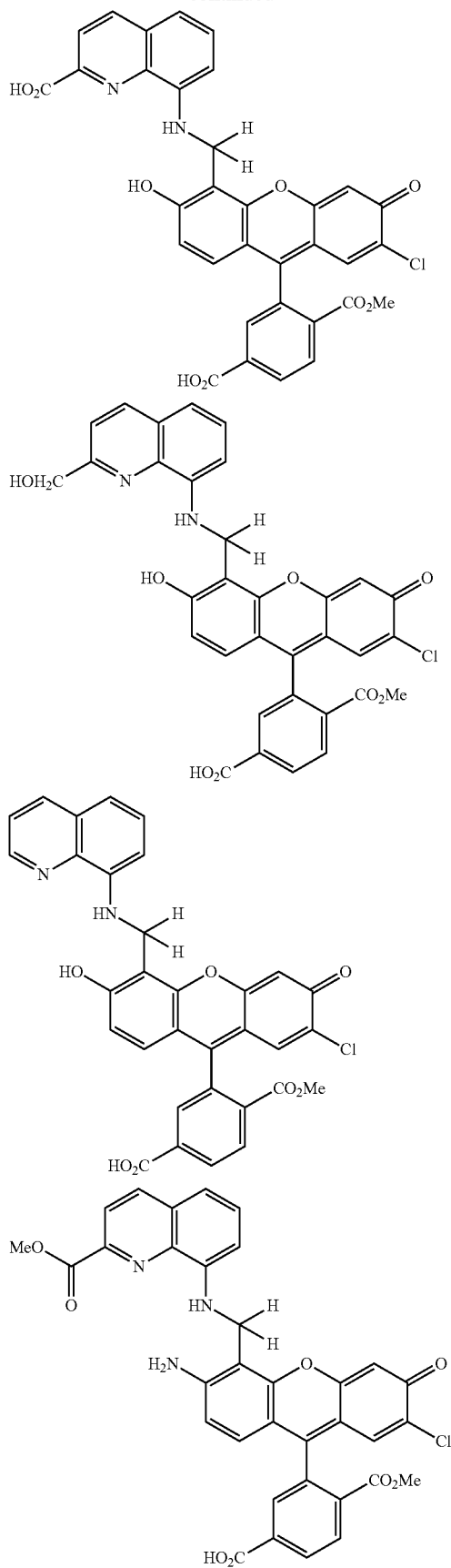
34
-continued
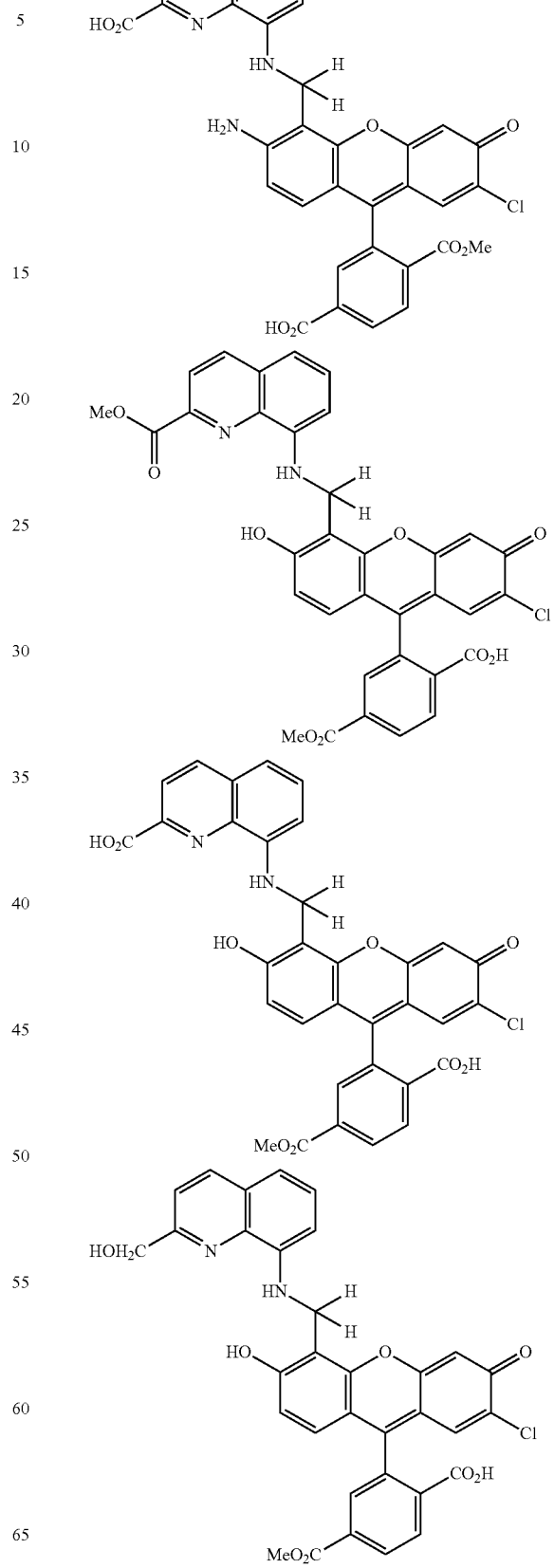

-continued
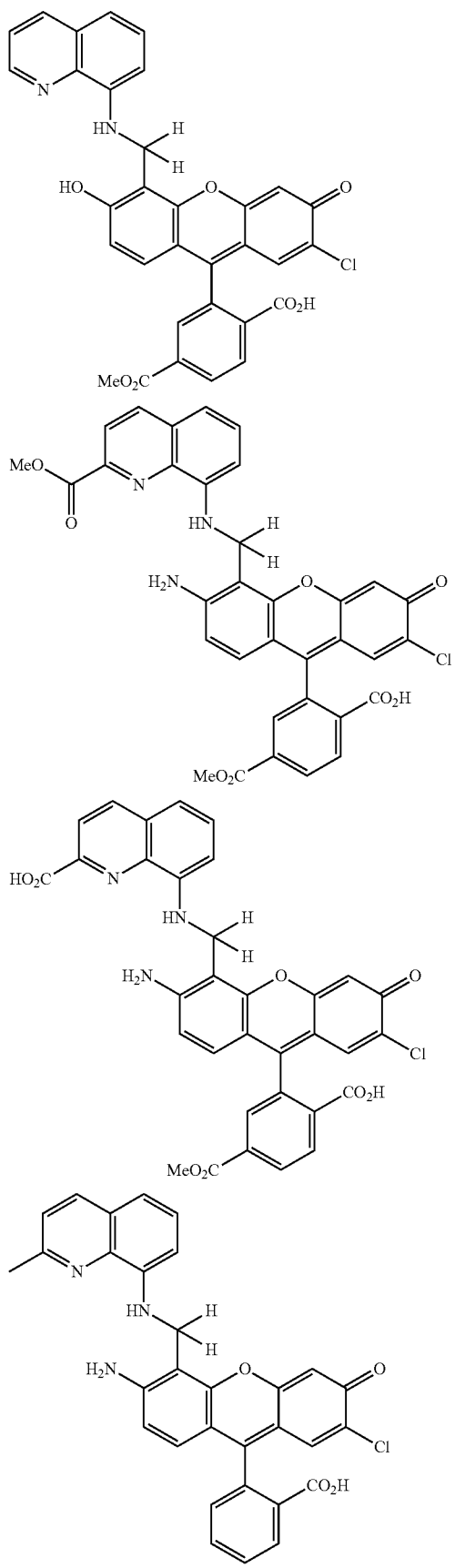
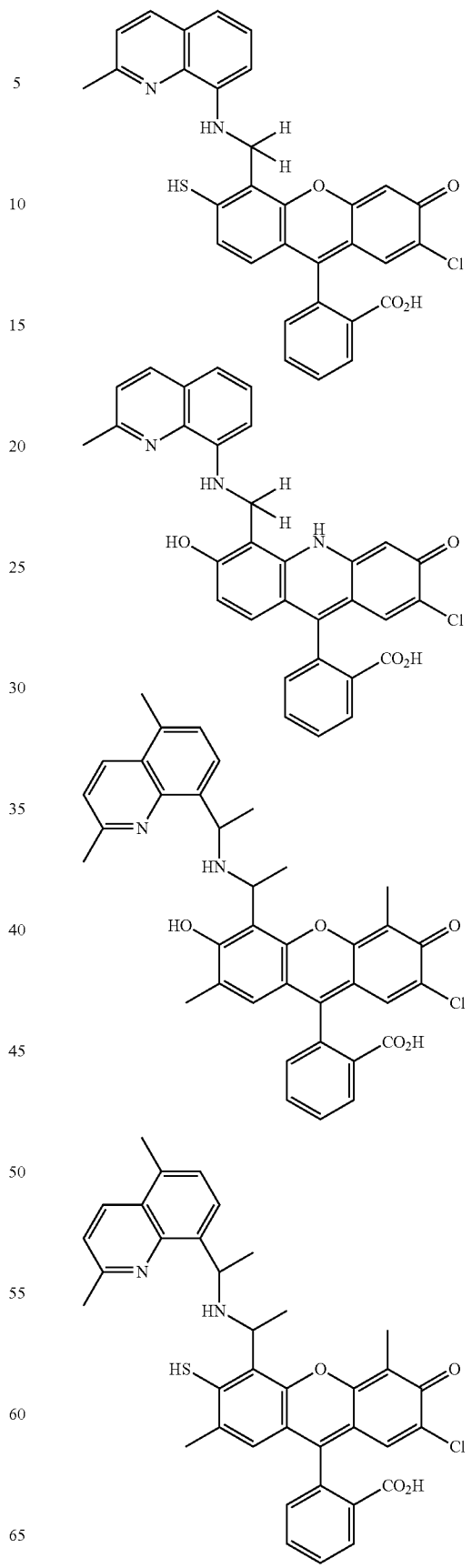

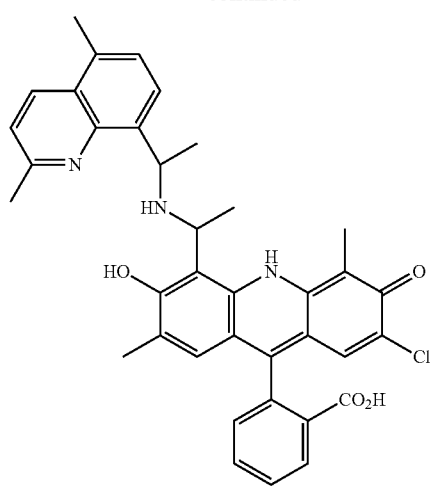
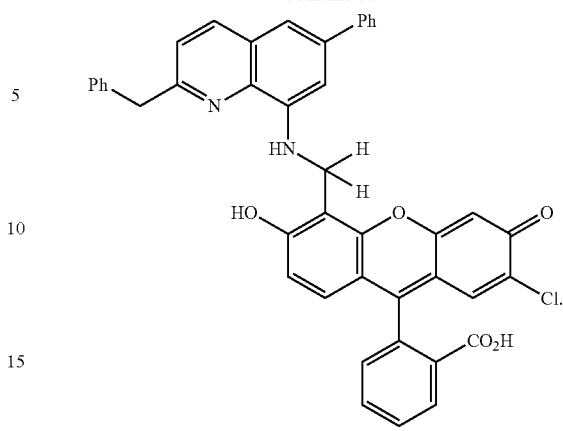
In certain embodiments, the present invention relates to any one of the aforementioned methods, wherein the fluorescein-based sensor is selected from the group consisting of
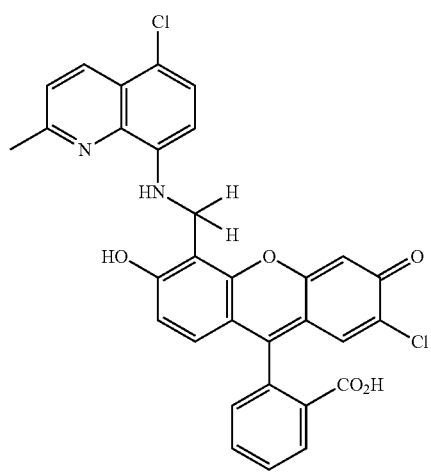
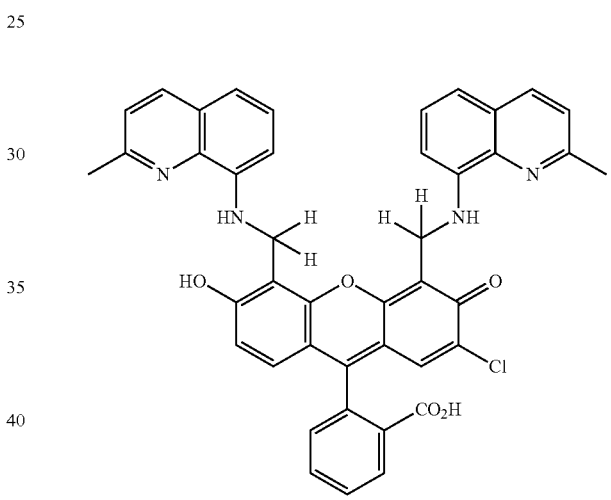
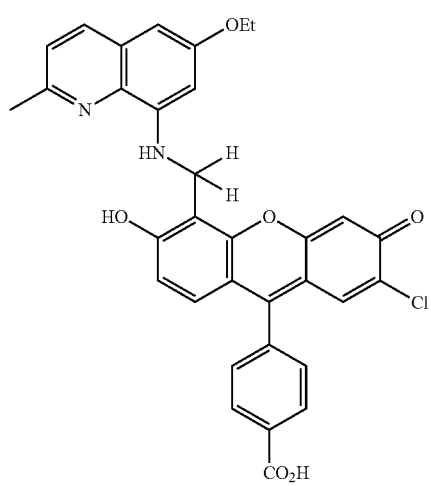
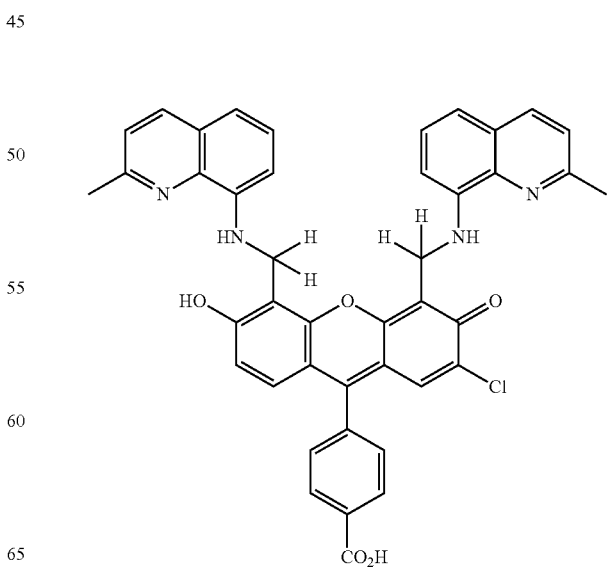

| 39 -continued | 40 -continued |
|---|---|
| 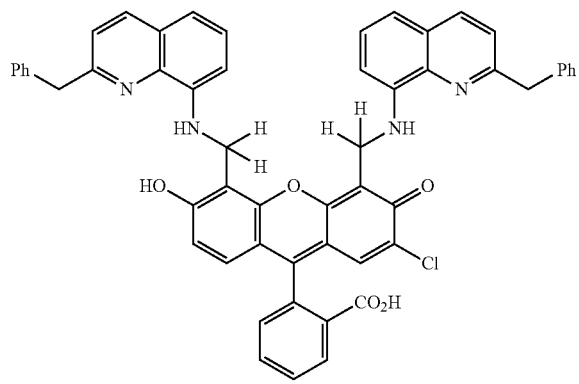 | 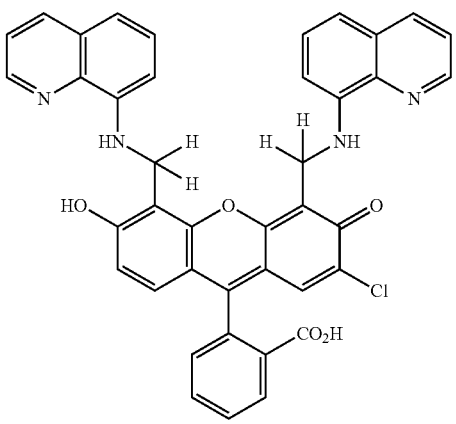 |
| 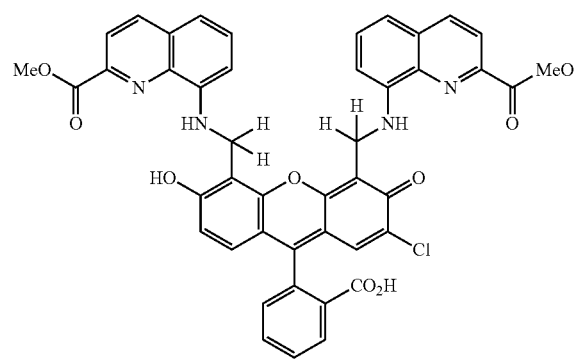 | 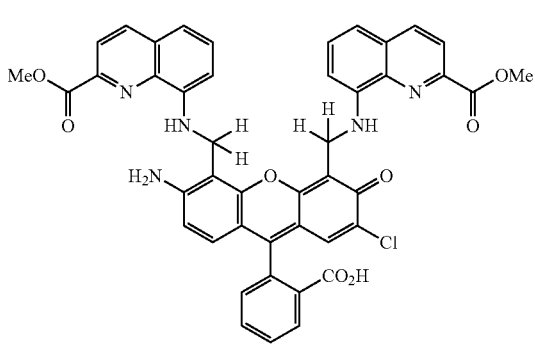 |
| 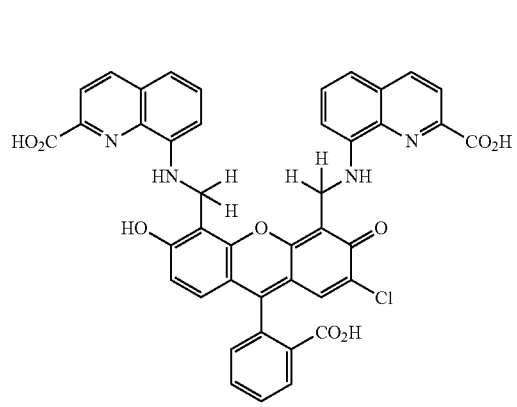 | 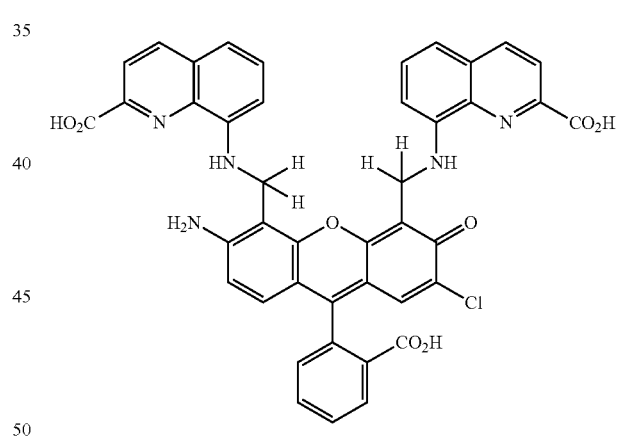 |
| 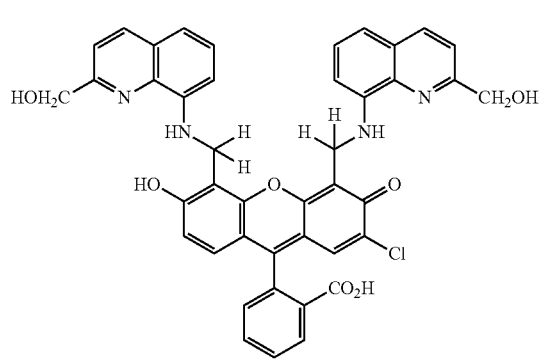 | 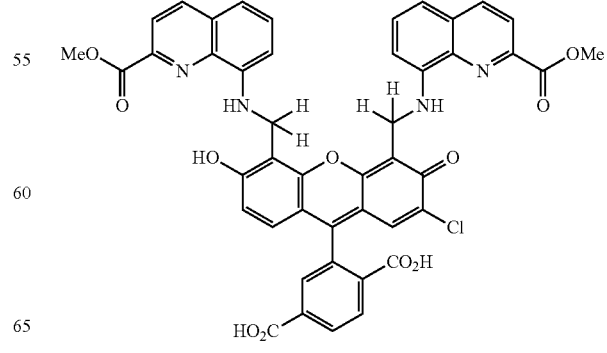 |

41
-continued
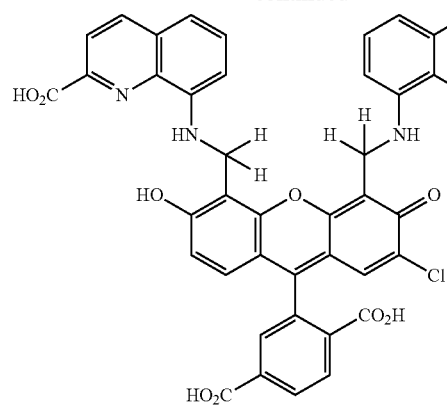
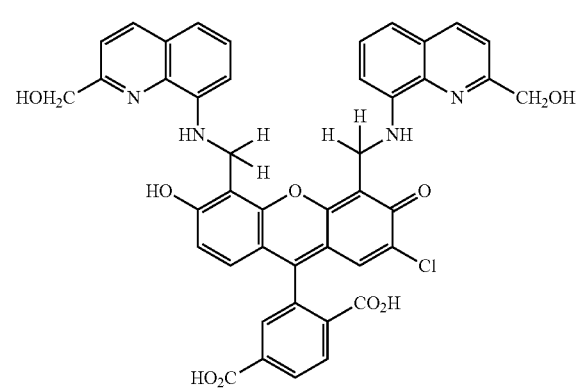
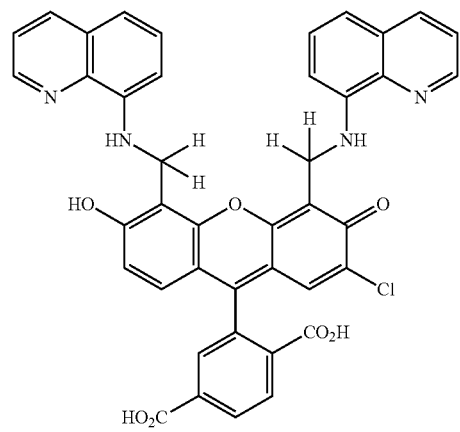
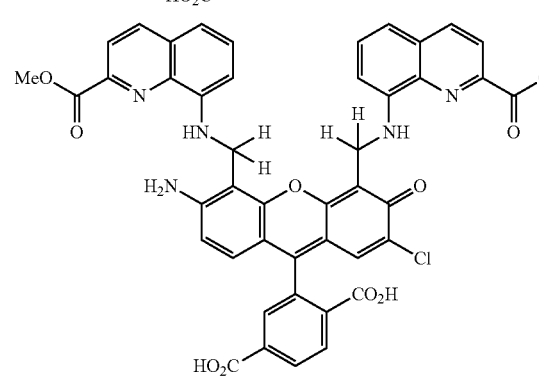
42
-continued
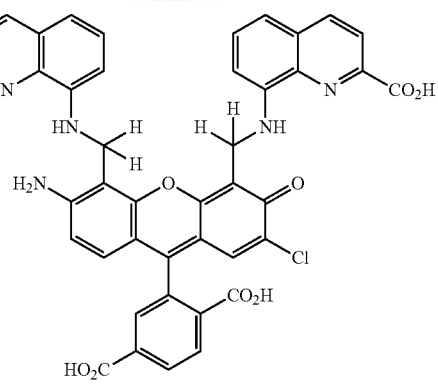
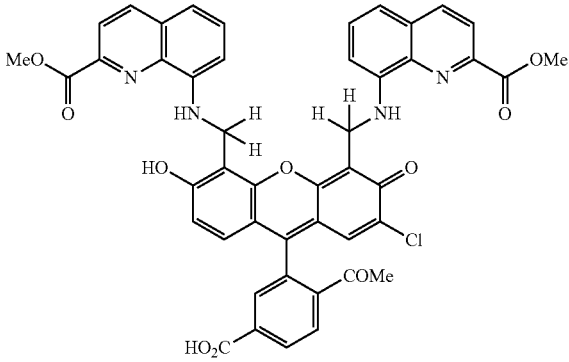
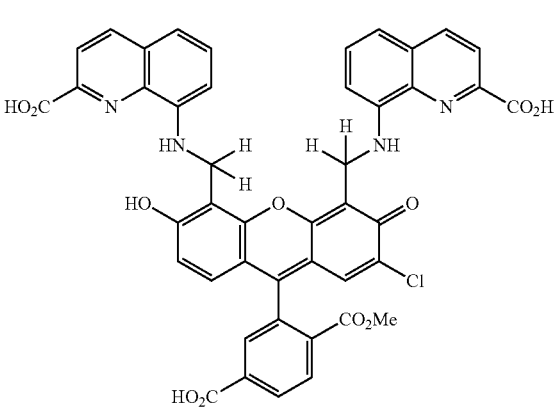
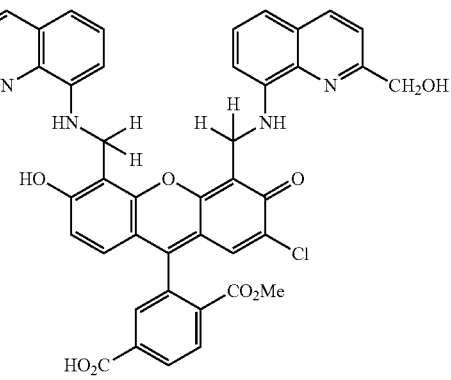

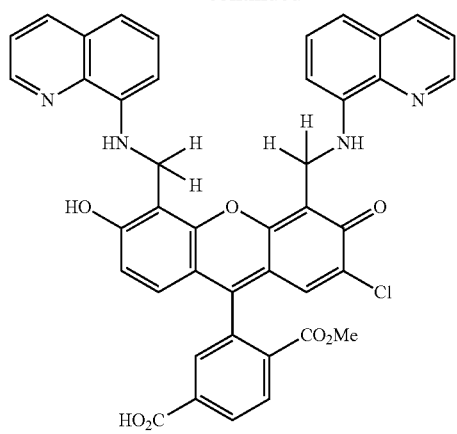
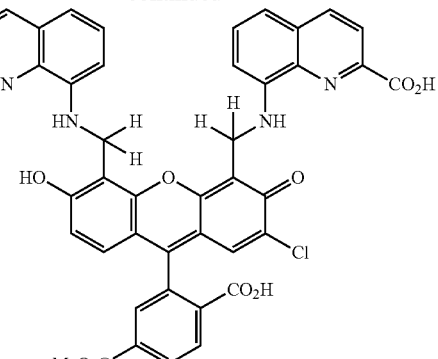
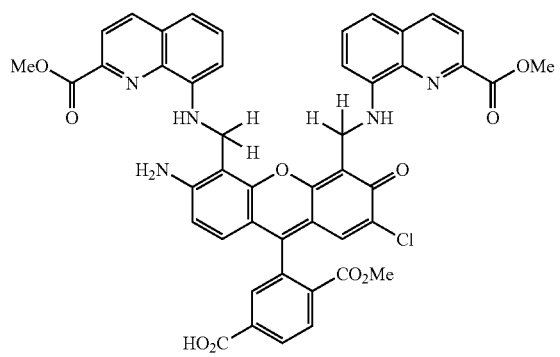
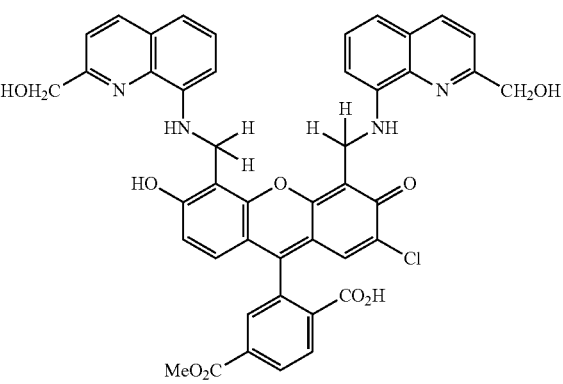
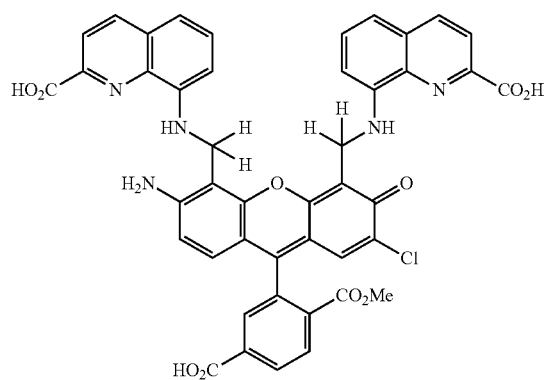
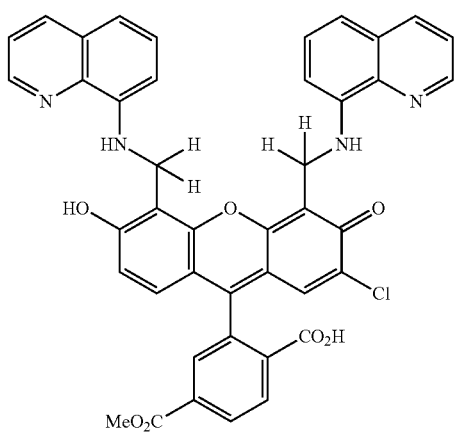
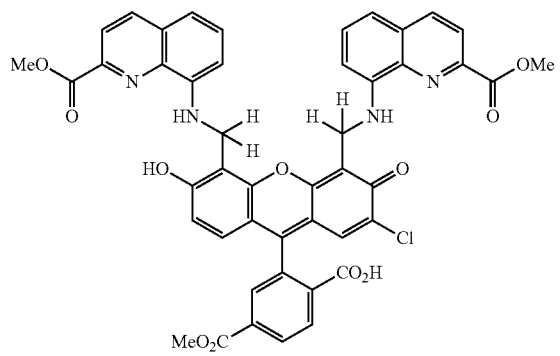
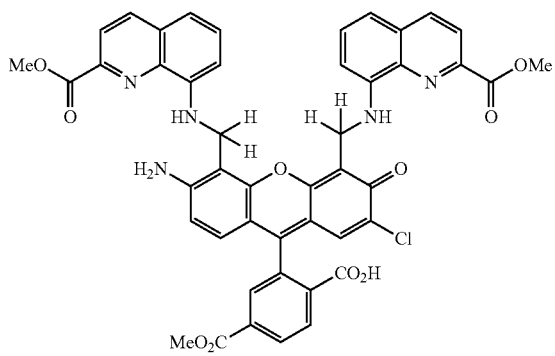

45
-continued
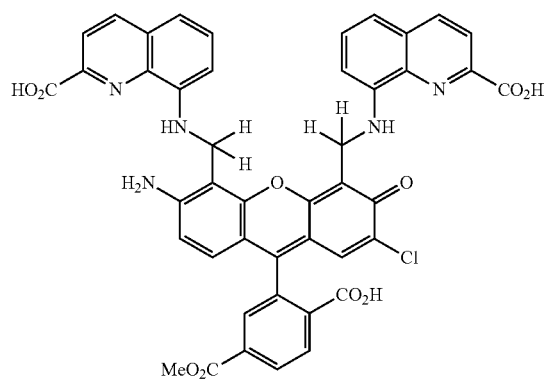
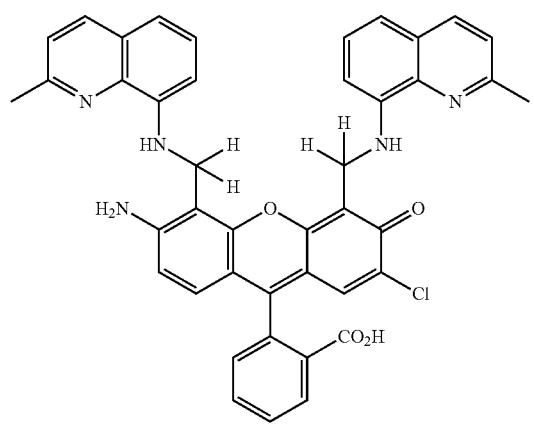
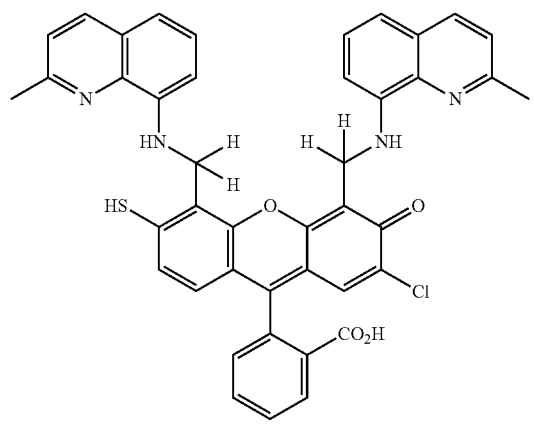
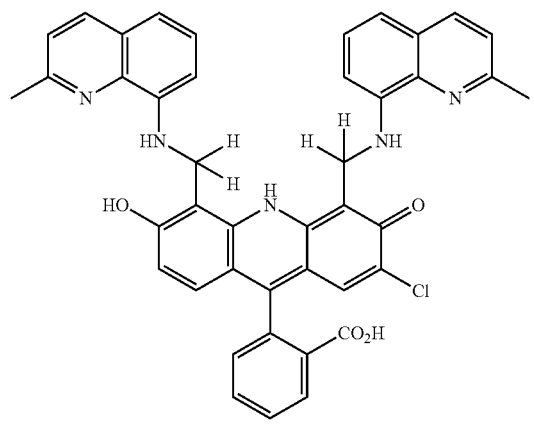
46
-continued
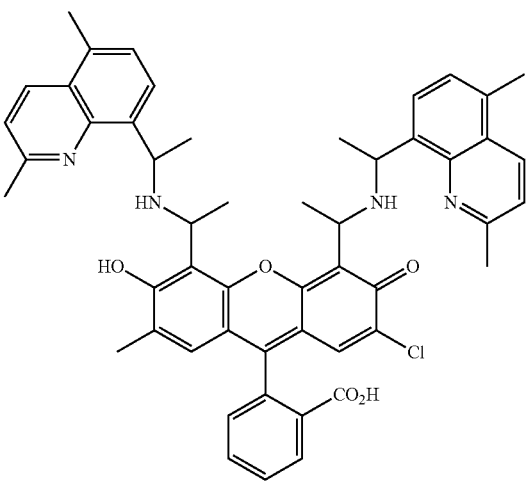
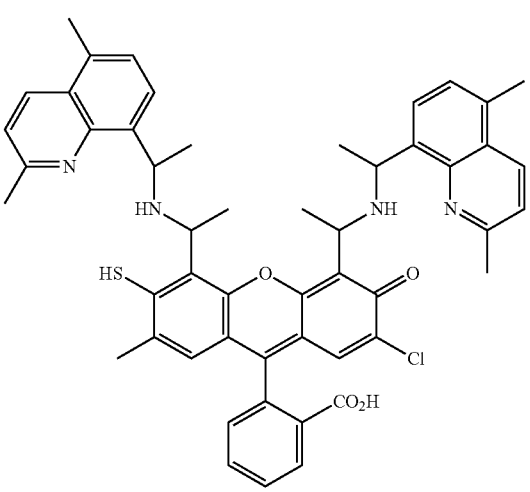
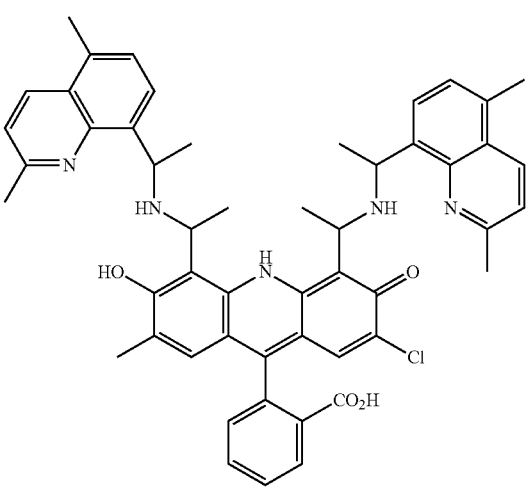

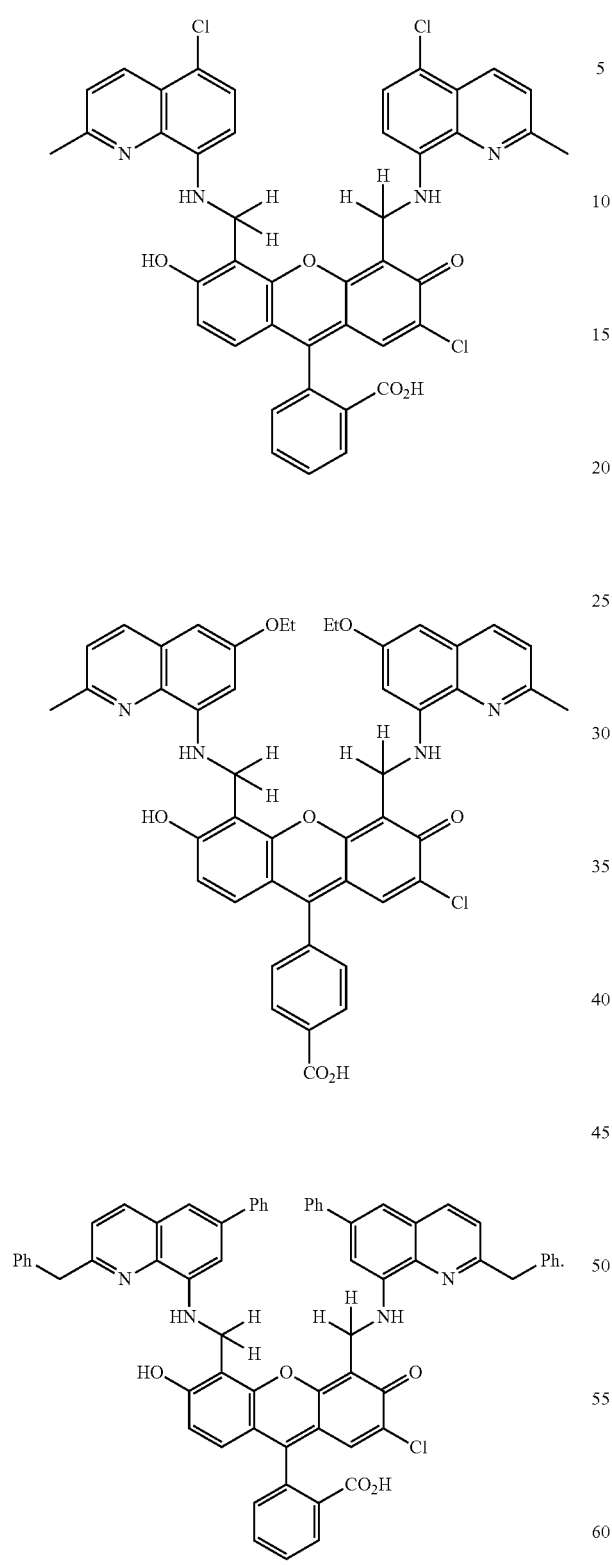
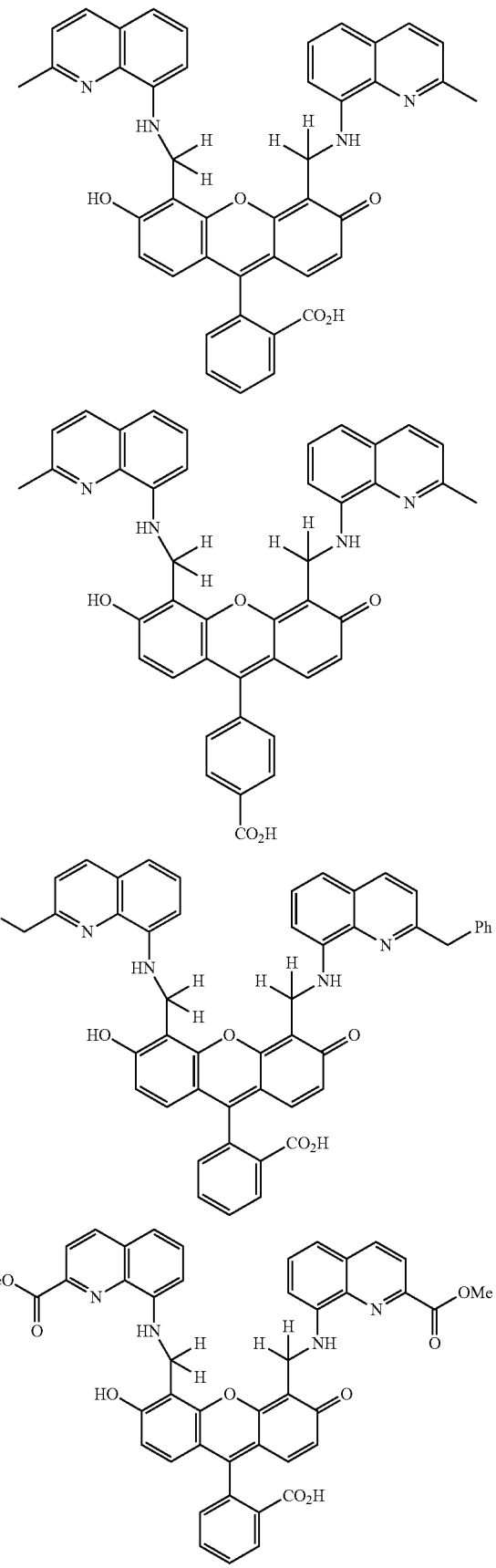
In certain embodiments, the present invention relates to any one of the aforementioned methods, wherein the fluorescein-based sensor is selected from the group consisting of 49
-continued
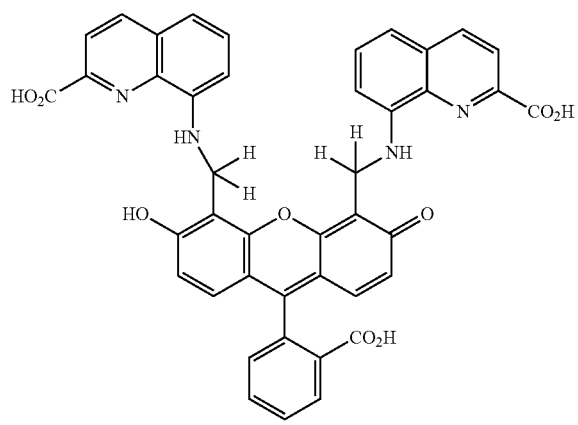
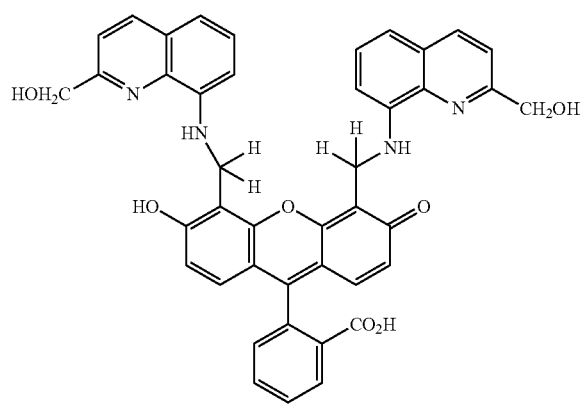
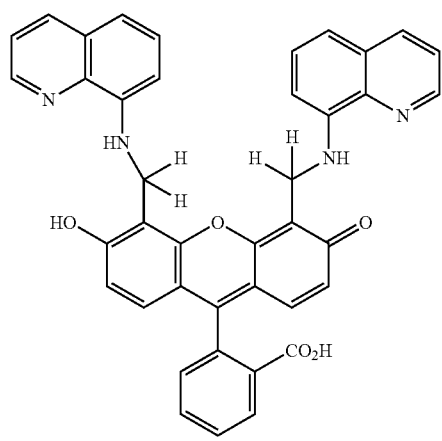
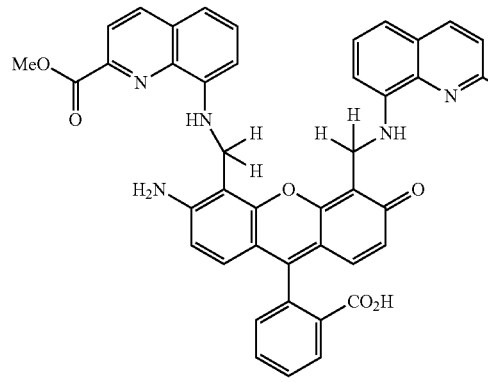
50
-continued
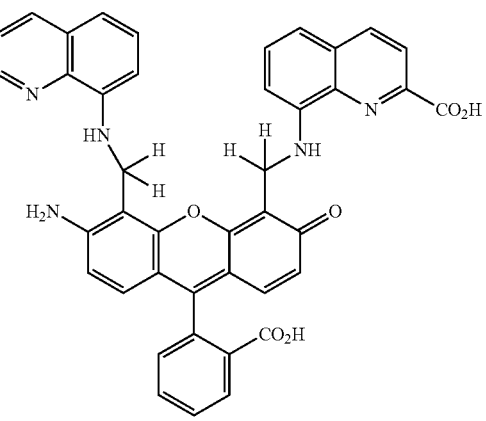
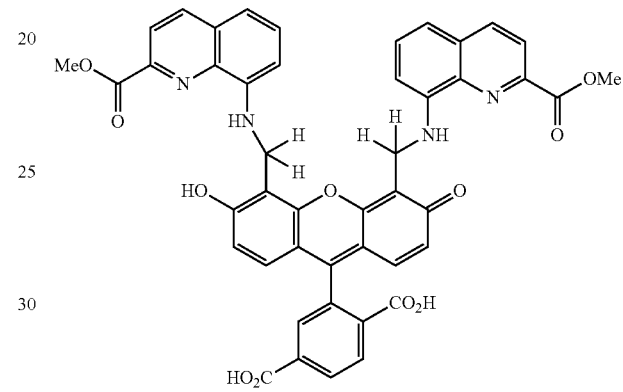
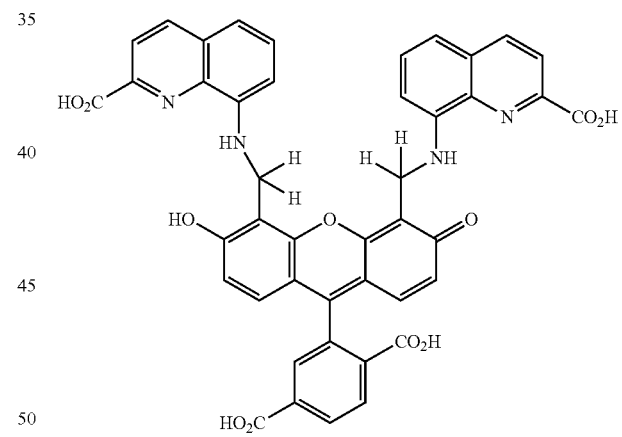
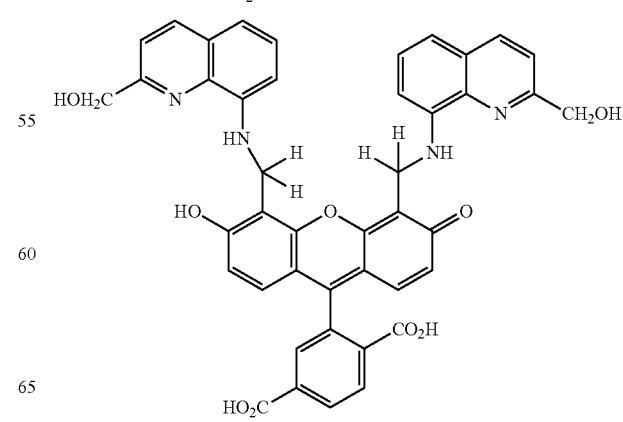

51
-continued
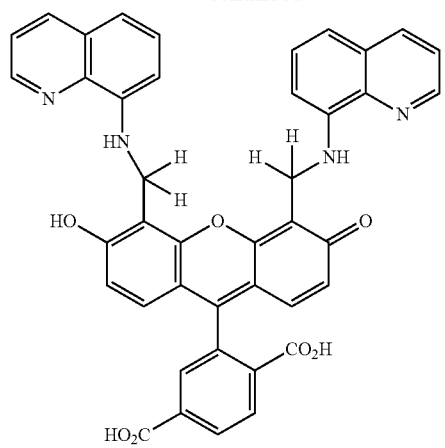
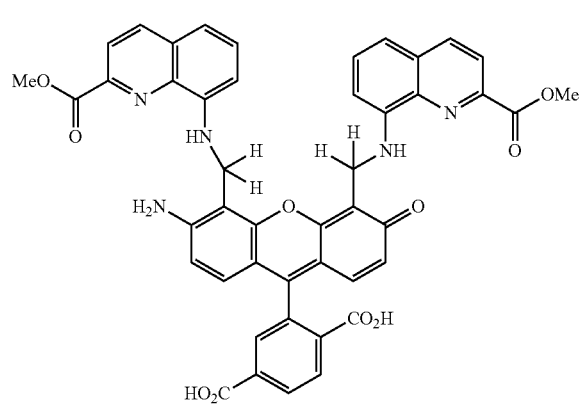
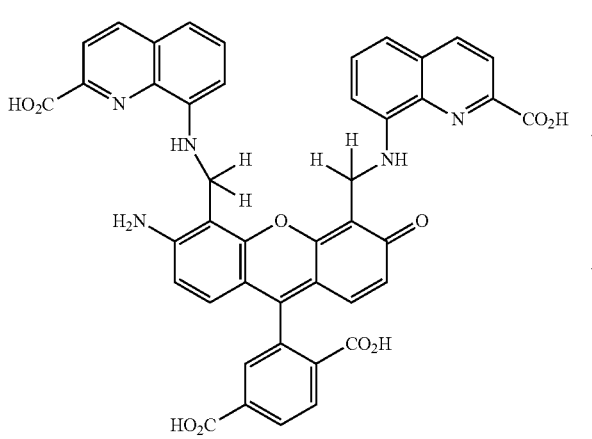
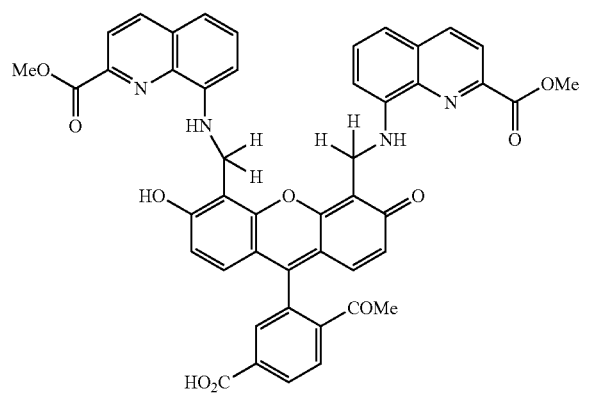
52
-continued
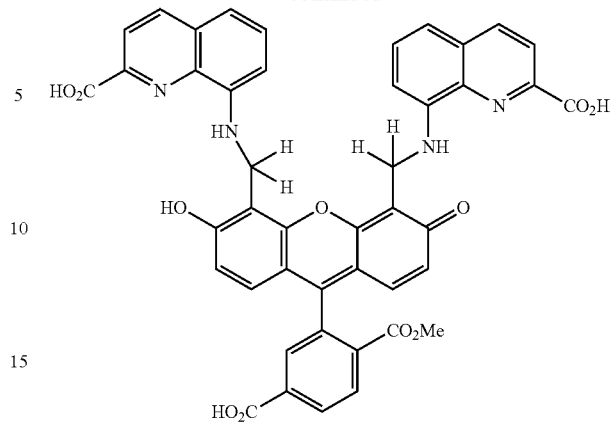
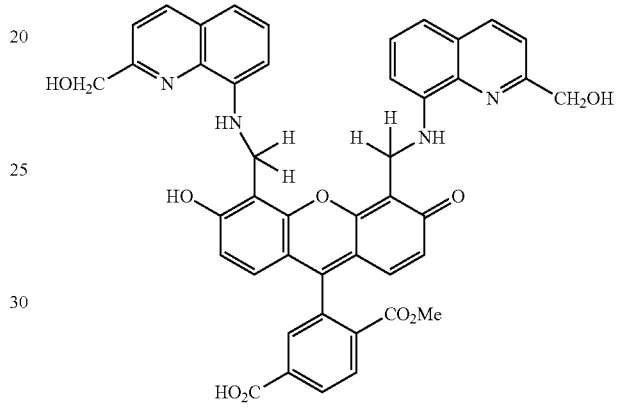
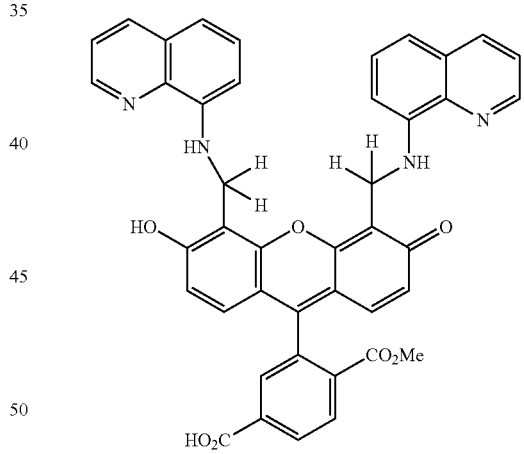
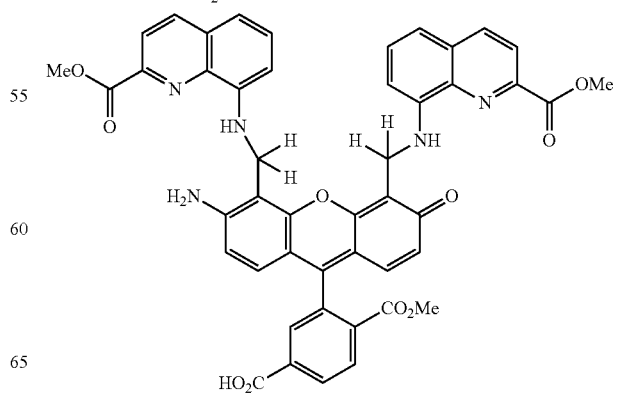

53
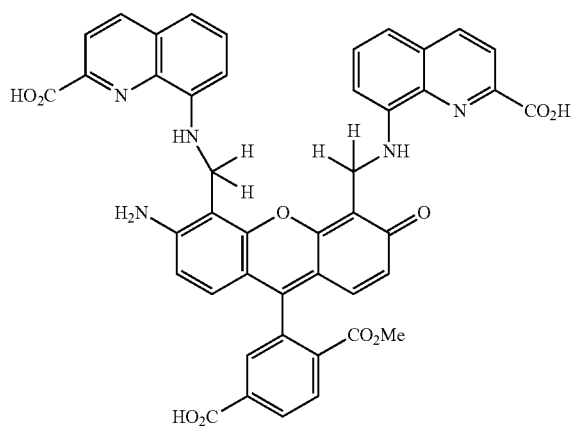
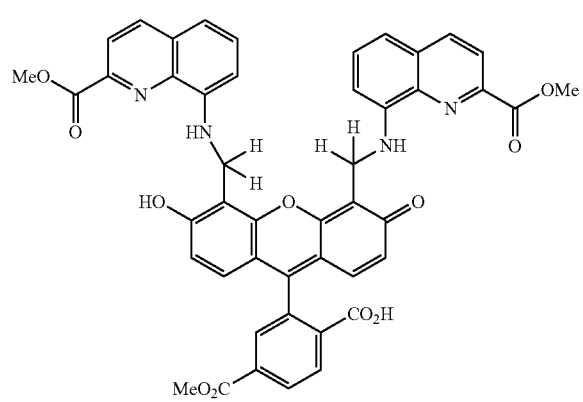
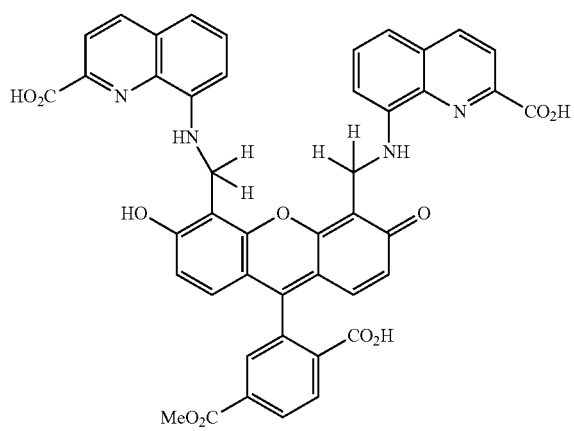
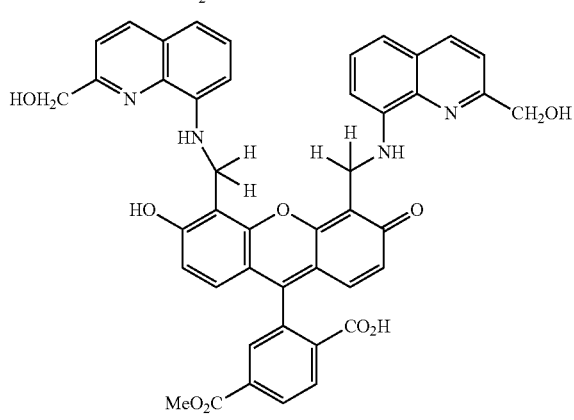
54
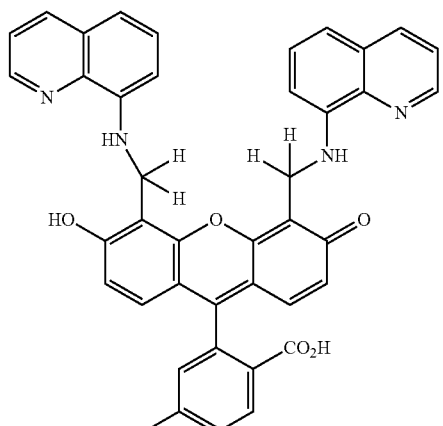
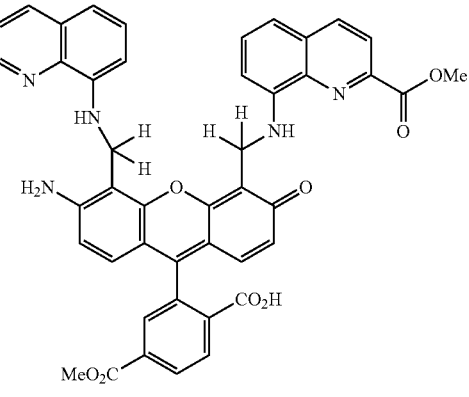
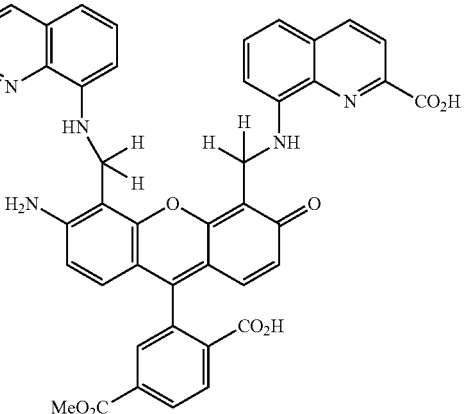
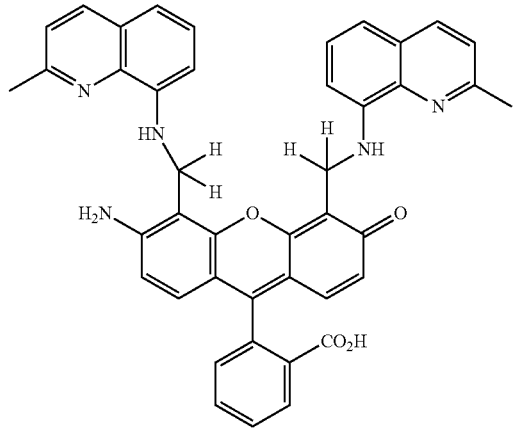

55
-continued
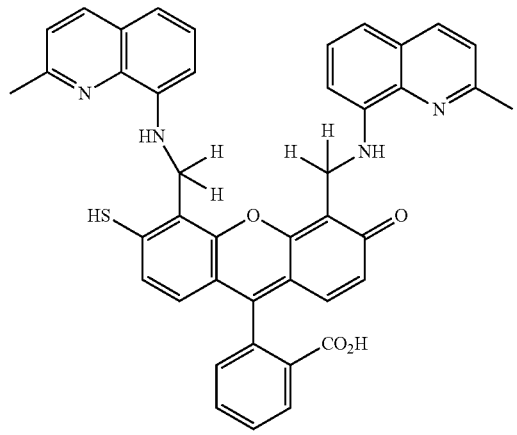
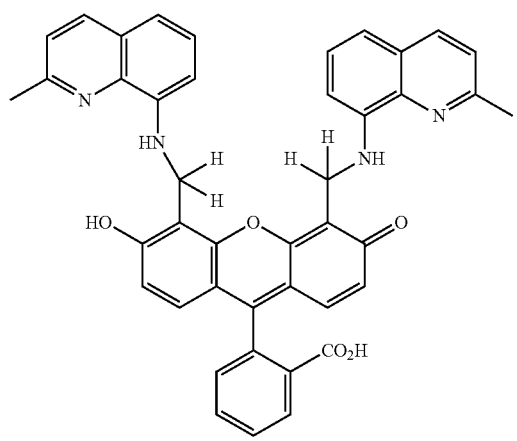
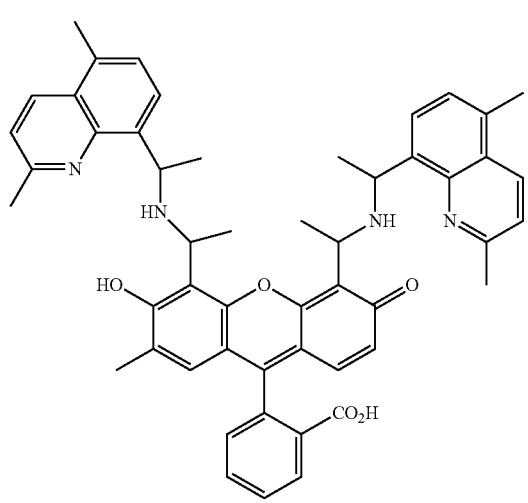
56
-continued
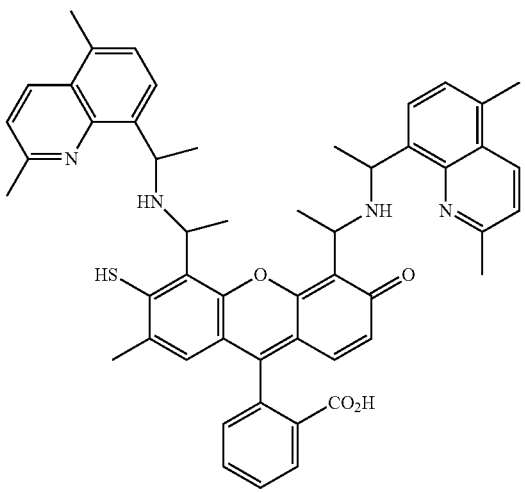
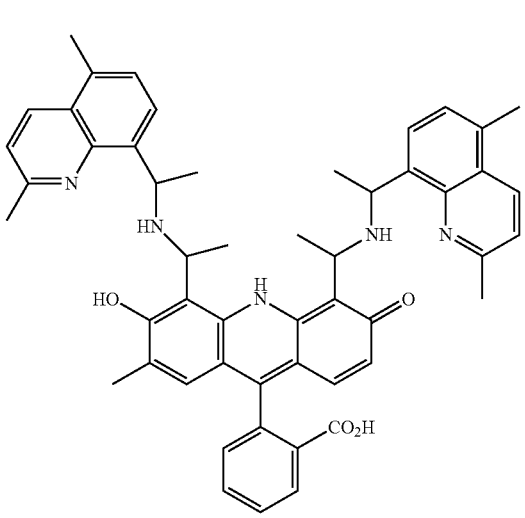
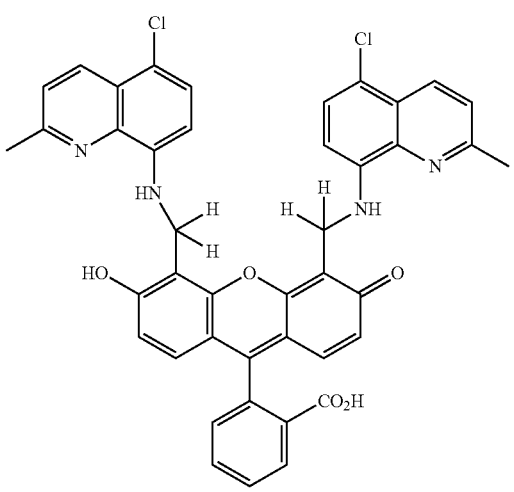

57
-continued
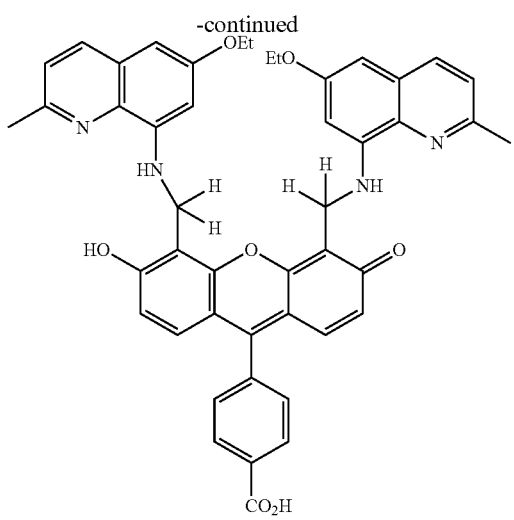
In certain embodiments, the present invention relates to any one of the aforementioned methods, wherein the fluorescein-based sensor is selected from the group consisting of:
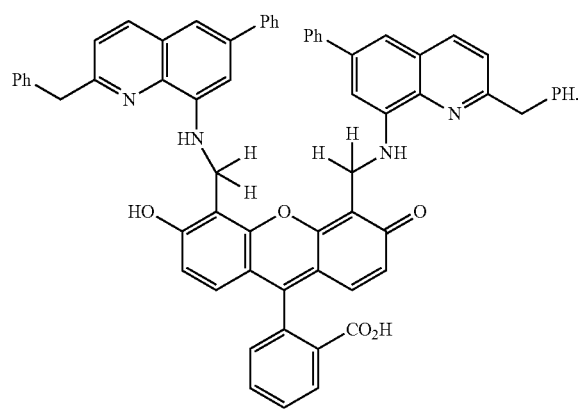
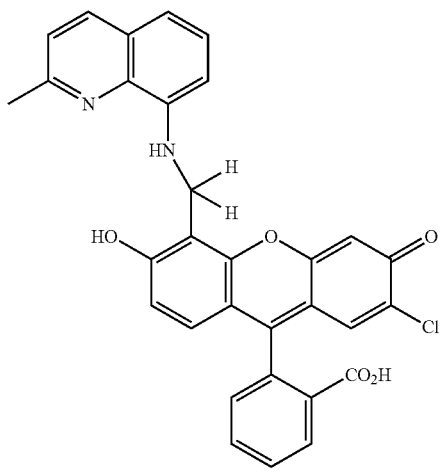
58
-continued
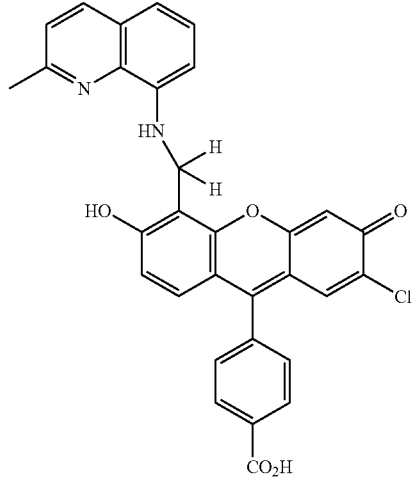
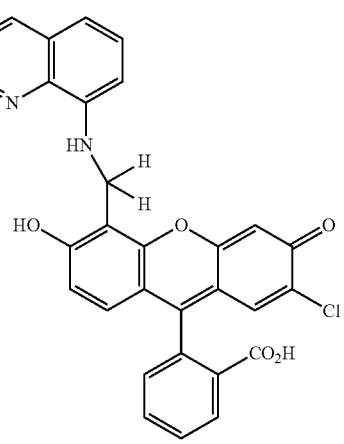
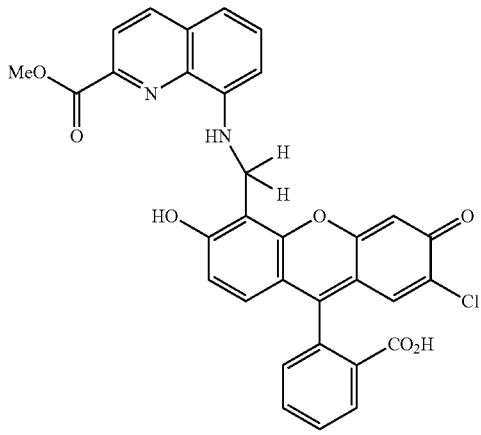

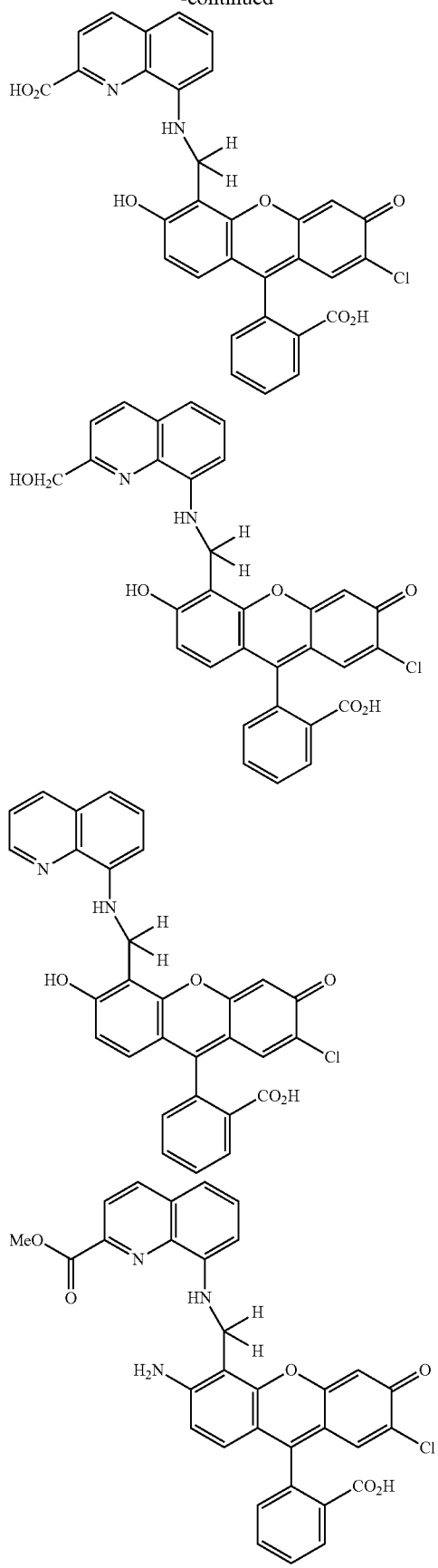

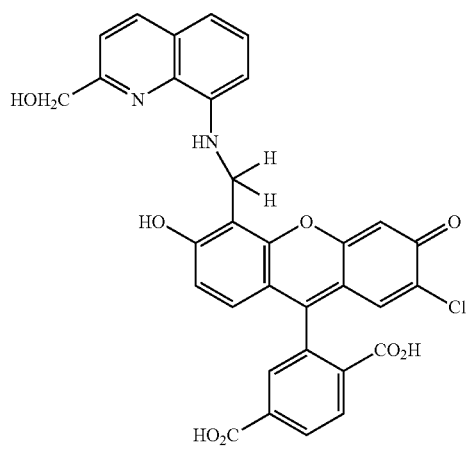
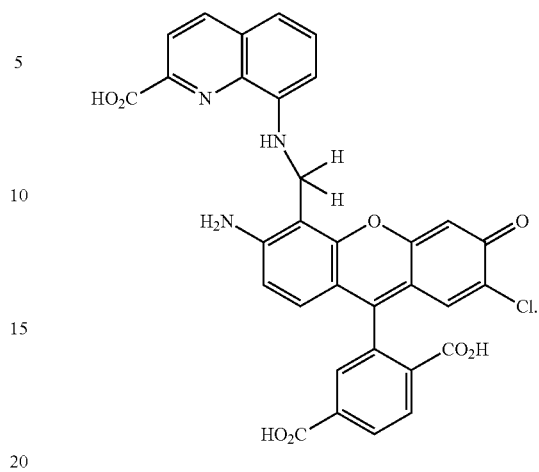
In certain embodiments, the present invention relates to any one of the aforementioned methods, wherein the fluorescein-based sensor is selected from the group consisting of:
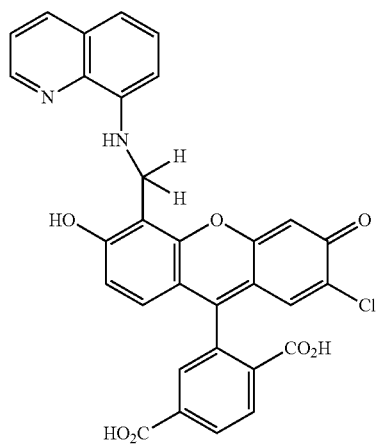
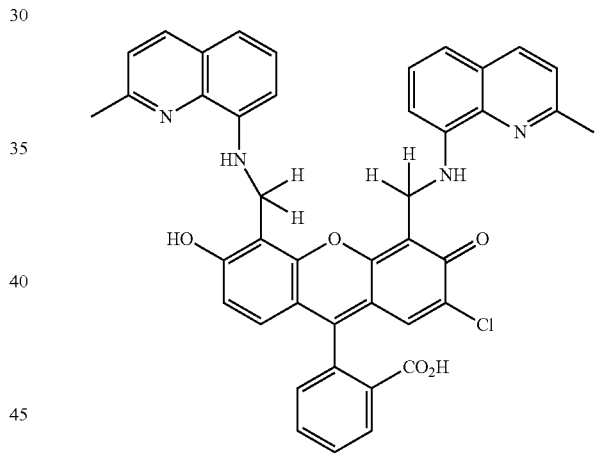
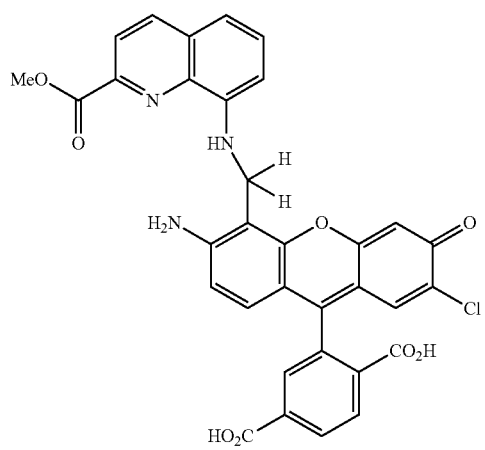
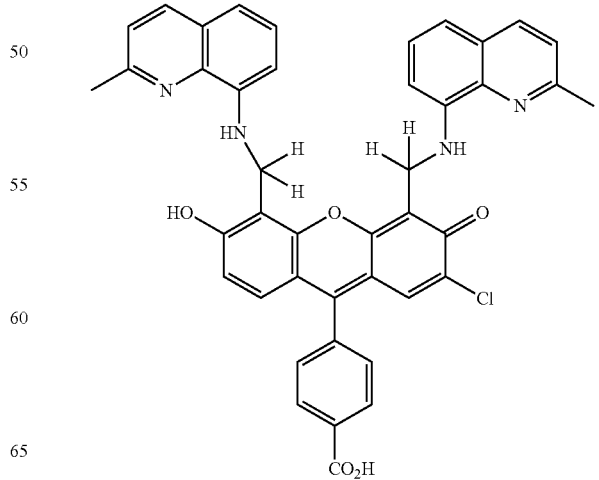

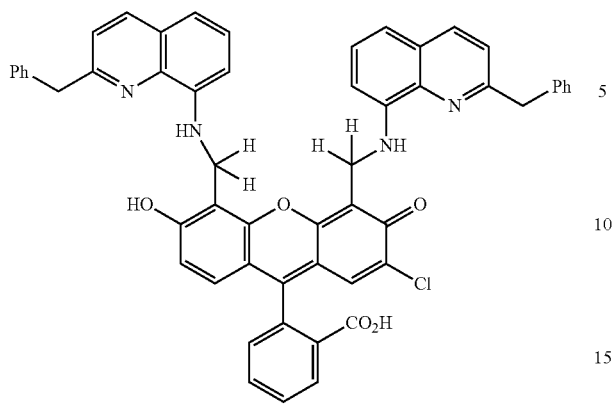
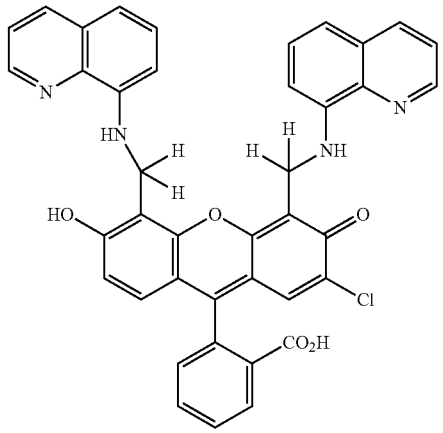
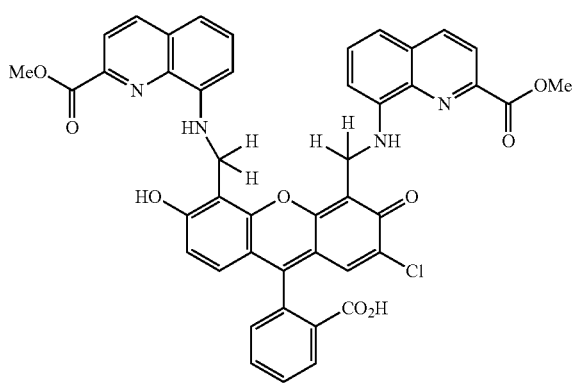
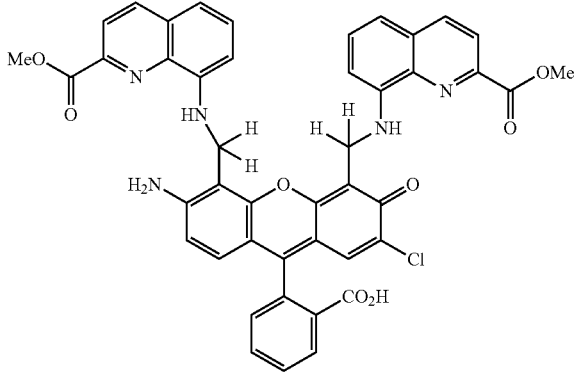
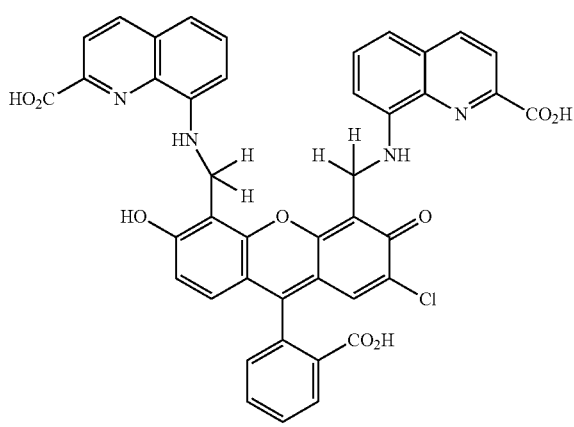
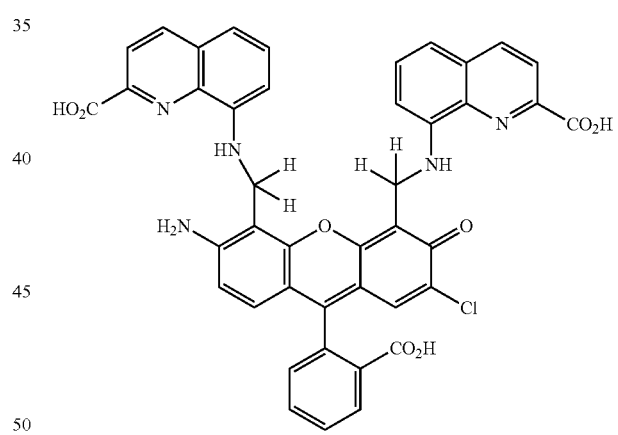
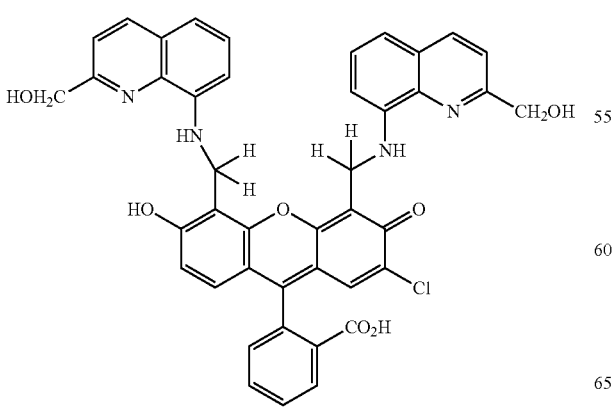
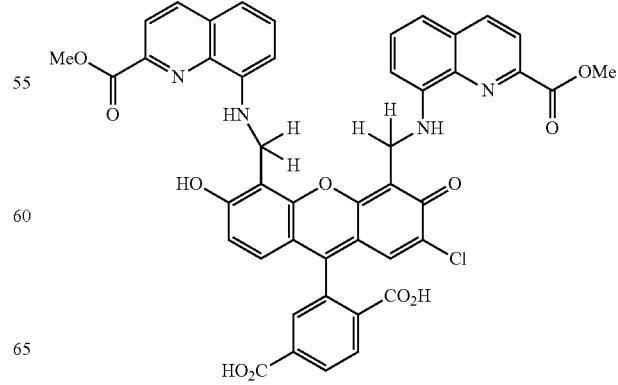

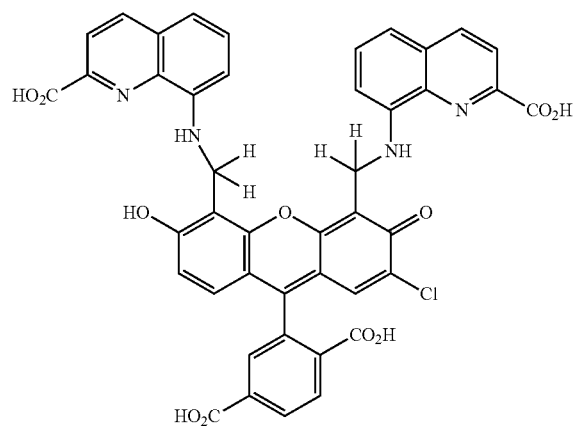
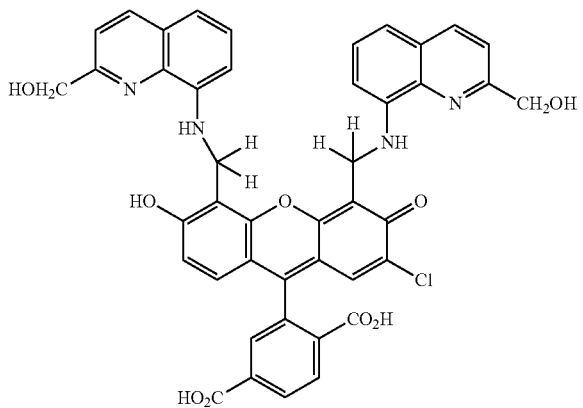
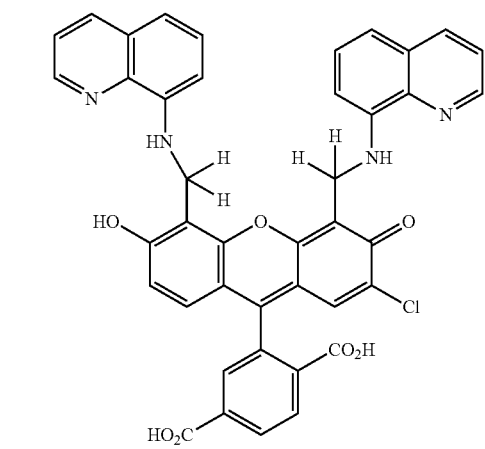
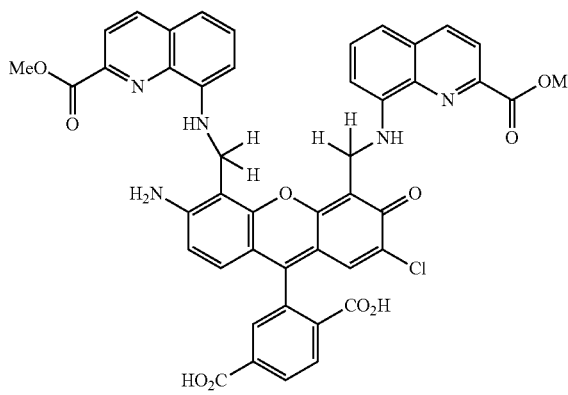
In certain embodiments, the present invention relates to any one of the aforementioned methods, wherein the fluorescein-based sensor is selected from the group consisting of:
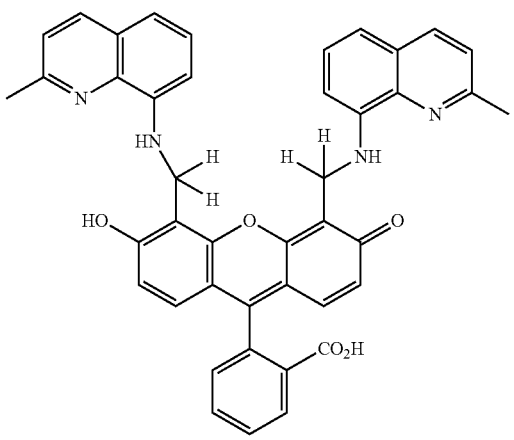
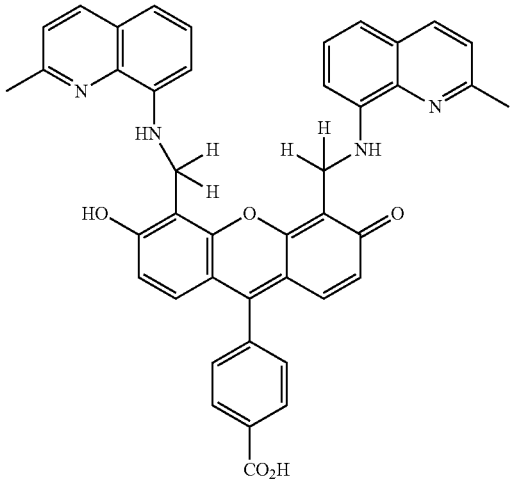

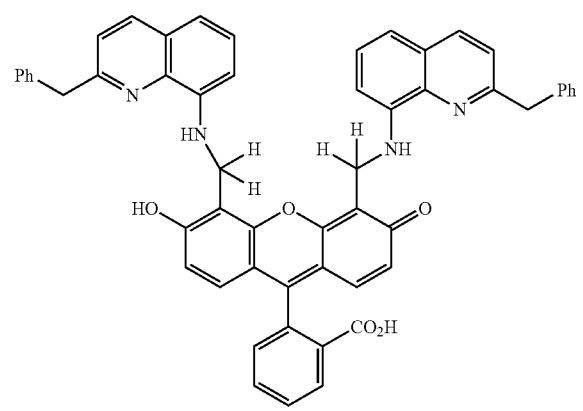
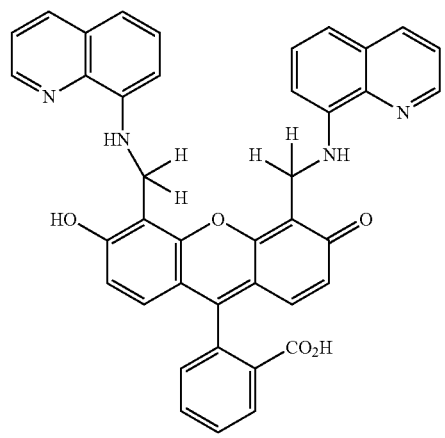
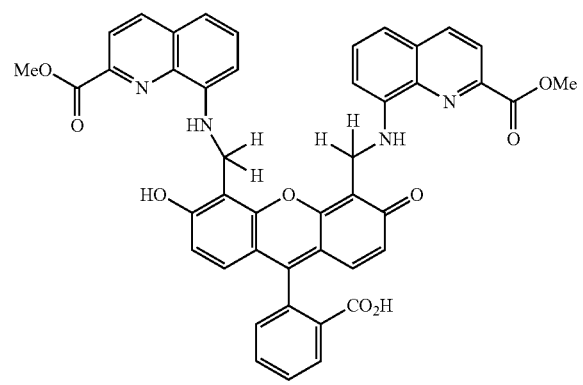
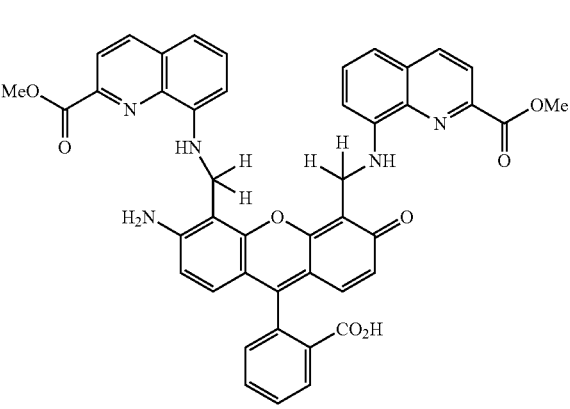
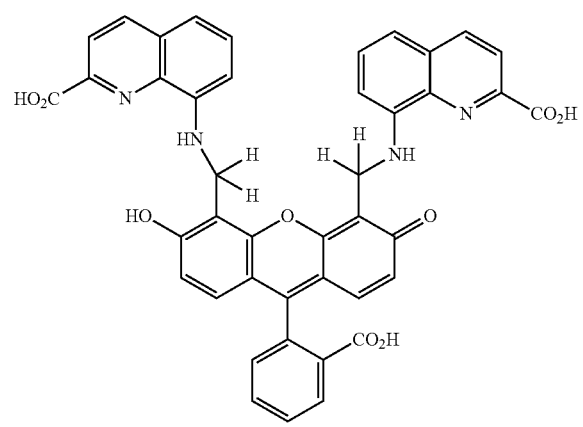
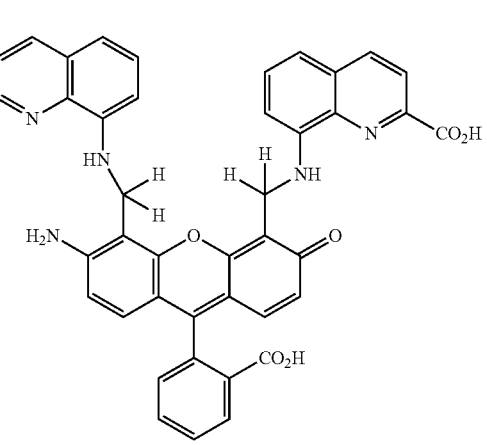
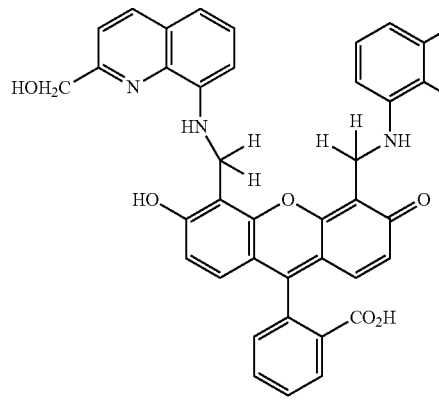
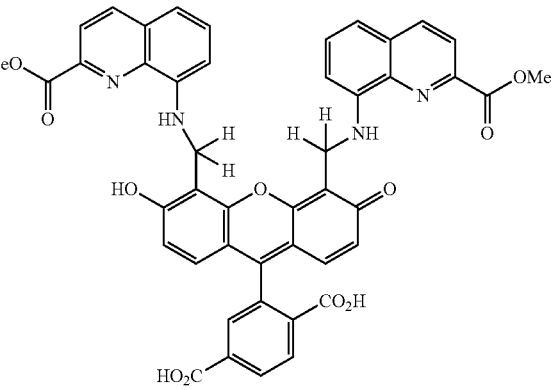

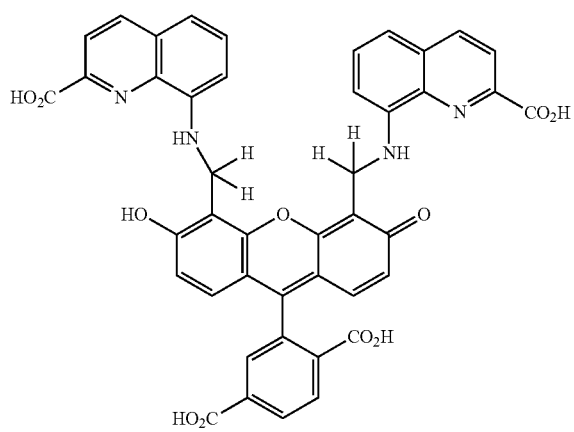

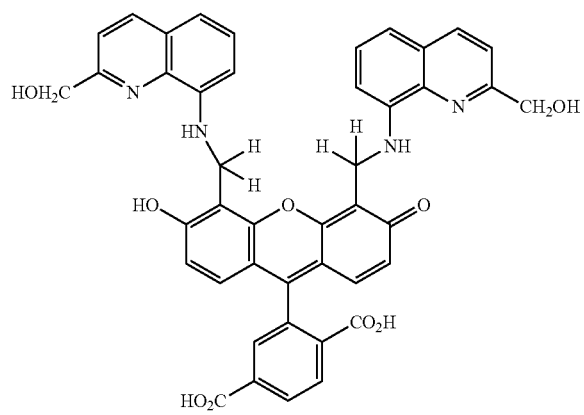

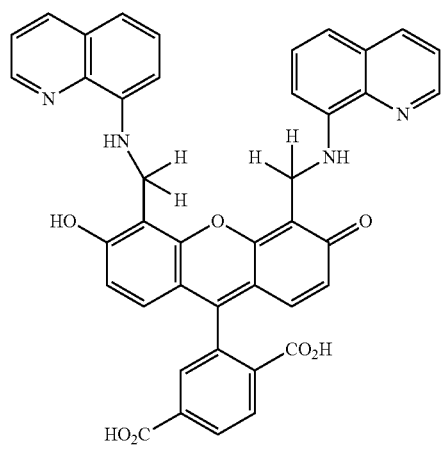

In certain embodiments, the present invention relates to any one of the aforementioned methods, wherein the fluorescein-based sensor is In certain embodiments, the present invention relates to any one of the aforementioned methods, wherein the fluorescein-based sensor is

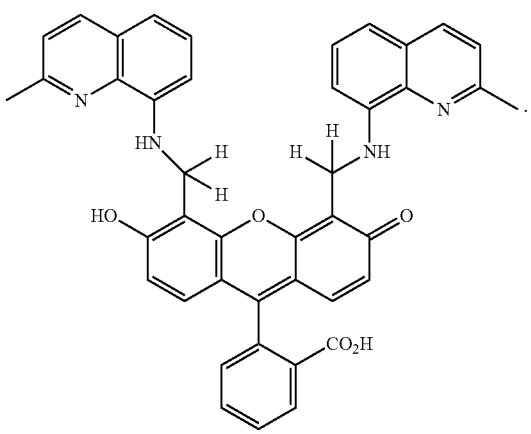

In certain embodiments, the present invention relates to any one of the aforementioned methods, wherein the transition metal is Mn, Cu, Co, Fe, Ni, Zn, Ru, or Rh.

In certain embodiments, the present invention relates to any one of the aforementioned methods, wherein the transition metal is Cu, Co, Ru, or Rh.

In certain embodiments, the present invention relates to any one of the aforementioned methods, wherein the transition metal is Cu. In certain embodiments, the present invention relates to any one of the aforementioned methods, wherein the transition-metal containing fluorescein-based sensor is represented by formula III:

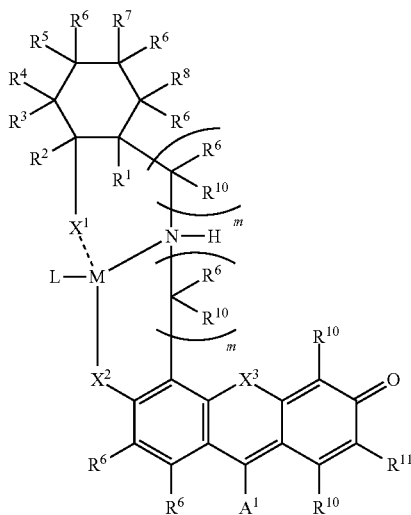

wherein, independently for each occurrence, $A^1$ is aryl or heteroaryl, both of which are optionally substituted with one or more of halogen, alkoxyl, —OH, —N(R$^{12}$)$_2$, —COR$^{12}$, —CO$_2$R$^{12}$, —N(R$^{12}$)C(O)R$^{12}$, or —C(O)N(R$^{12}$)$_2$;

L is a ligand;

M is a transition metal;

$X^1$ is —OR$^9$, —SR$^9$, —N=R$^9$, or —N(R$^{13}$)R$^9$;

$X^2$ is —O—, —S—, or —N(R$^{13}$)—;

$X^3$ is —O—, —S—, or —N(R$^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N(R$^9$)$_2$, —COR$^9$, —CO$_2$R$^9$, —N(R$^9$)C(O)R$^9$, or —C(O)N(R$^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or (C$_1$-C$_6$)alkyl;

m represents independently for each occurrence 0, 1, 2, 3, or 4; and the stereochemical configuration at any stereocenter of the transition-metal containing fluorescein-based sensor represented by III is R, S, or a mixture of these configurations.

In certain embodiments, the present invention relates to any one of the aforementioned methods, wherein $A^1$ is aryl optionally substituted with —CO$_2$R$^{12}$.

In certain embodiments, the present invention relates to any one of the aforementioned methods, wherein $X^1$ is —N=R$^9$.

In certain embodiments, the present invention relates to any one of the aforementioned methods, wherein $X^2$ is —O—.

In certain embodiments, the present invention relates to any one of the aforementioned methods, wherein $X^3$ is —O—.

In certain embodiments, the present invention relates to any one of the aforementioned methods, wherein $R^1$ and $R^8$ taken together form a bond.

In certain embodiments, the present invention relates to any one of the aforementioned methods, wherein $R^5$ and $R^7$ taken together form a bond.

In certain embodiments, the present invention relates to any one of the aforementioned methods, wherein $R^{10}$ is H or alkyl.

In certain embodiments, the present invention relates to any one of the aforementioned methods, wherein $R^2$ and $R^3$ taken together form a bond.

In certain embodiments, the present invention relates to any one of the aforementioned methods, wherein $R^4$ and $R^9$ taken together form a 5-6 member ring optionally substituted with one or more of alkyl, aryl, aralkyl, or halogen.

In certain embodiments, the present invention relates to any one of the aforementioned methods, wherein $R^6$ is H or alkyl.

In certain embodiments, the present invention relates to any one of the aforementioned methods, wherein $R^{11}$ is halogen.

In certain embodiments, the present invention relates to any one of the aforementioned methods, wherein $R^{12}$ is H.

In certain embodiments, the present invention relates to any one of the aforementioned methods, wherein $R^{13}$ is H.

In certain embodiments, the present invention relates to any one of the aforementioned methods, wherein m is 0 or 1.

In certain embodiments, the present invention relates to any one of the aforementioned methods, wherein $A^1$ is aryl optionally substituted with —CO$_2$R$^{12}$, $X^1$ is —N=R$^9$, $X^2$ is —OR$^{13}$, $X^3$ is —O—, and $R^4$ and $R^9$ taken together form a 5-6 member ring optionally substituted with one or more of alkyl, aryl, aralkyl, or halogen.

In certain embodiments, the present invention relates to any one of the aforementioned methods, wherein $A^1$ is aryl optionally substituted with —CO$_2$R$^{12}$; $X^1$ is —N=R$^9$, $X^2$ is —OR$^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H.

In certain embodiments, the present invention relates to any one of the aforementioned methods, wherein M is Mn, Cu, Co, Fe, Ni, Zn, Ru, or Rh.

In certain embodiments, the present invention relates to any one of the aforementioned methods, wherein M is Cu, Co, Ru, or Rh.

In certain embodiments, the present invention relates to any one of the aforementioned methods, wherein M is Cu.

In certain embodiments, the present invention relates to any one of the aforementioned methods, wherein L is halogen, alkoxy, —OC(O)alkyl, —OC(O)aryl, or —OC(O)aralkyl.

In certain embodiments, the present invention relates to any one of the aforementioned methods, wherein L is halogen.

In certain embodiments, the present invention relates to any one of the aforementioned methods, wherein the transition-metal containing fluorescein-based sensor is represented by formula IIIa:

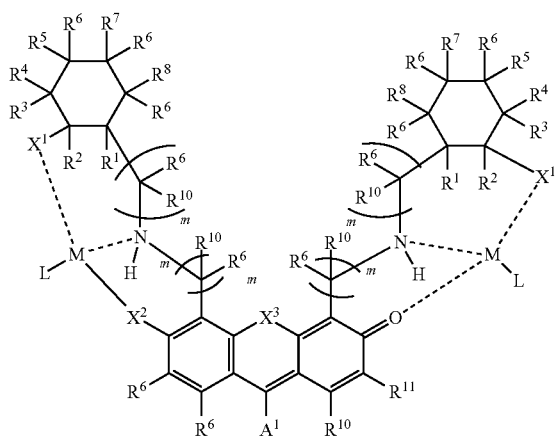

IIIa wherein, independently for each occurrence, $A^1$ is aryl or heteroaryl, both of which are optionally substituted with one or more of halogen, alkoxyl, —OH, —N(R$^{12}$)$_2$, —COR$^{12}$, —CO$_2$R$^{12}$, —N(R$^{12}$)C(O)R$^{12}$, or —C(O)N(R$^{12}$)$_2$;

L is a ligand;

M is a transition metal;

$X^1$ is —OR$^9$, —SR$^9$, —N=R$^9$, or —N(R$^{13}$)R$^9$;

$X^2$ is —O—, —S—, or —N(R$^{13}$)—;

$X^3$ is —O—, —S—, or —N(R$^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N(R$^9$)$_2$, —COR$^9$, —CO$_2$R$^9$, —N(R$^9$)C(O)R$^9$, or —C(O)N(R$^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or (C$_1$-C$_6$)alkyl;

m represents independently for each occurrence 0, 1, 2, 3, or 4; and the stereochemical configuration at any stereocenter of the transition-metal containing fluorescein-based sensor represented by IIIa is R, S, or a mixture of these configurations.

In certain embodiments, the present invention relates to any one of the aforementioned methods, wherein $A^1$ is aryl optionally substituted with —CO$_2$R$^{12}$.

In certain embodiments, the present invention relates to any one of the aforementioned methods, wherein $X^1$ is —N=R$^9$.

In certain embodiments, the present invention relates to any one of the aforementioned methods, wherein $X^2$ is —O—.

In certain embodiments, the present invention relates to any one of the aforementioned methods, wherein $X^3$ is —O—.

In certain embodiments, the present invention relates to any one of the aforementioned methods, wherein $R^1$ and $R^8$ taken together form a bond.

In certain embodiments, the present invention relates to any one of the aforementioned methods, wherein $R^5$ and $R^7$ taken together form a bond.

In certain embodiments, the present invention relates to any one of the aforementioned methods, wherein $R^{10}$ is H or alkyl.

In certain embodiments, the present invention relates to any one of the aforementioned methods, wherein $R^2$ and $R^3$ taken together form a bond.

In certain embodiments, the present invention relates to any one of the aforementioned methods, wherein $R^4$ and $R^9$ taken together form a 5-6 member ring optionally substituted with one or more of alkyl, aryl, aralkyl, or halogen.

In certain embodiments, the present invention relates to any one of the aforementioned methods, wherein $R^6$ is H or alkyl.

In certain embodiments, the present invention relates to any one of the aforementioned methods, wherein $R^H$ is halogen.

In certain embodiments, the present invention relates to any one of the aforementioned methods, wherein $R^{11}$ is H.

In certain embodiments, the present invention relates to any one of the aforementioned methods, wherein $R^{12}$ is H.

In certain embodiments, the present invention relates to any one of the aforementioned methods, wherein $R^{13}$ is H.

In certain embodiments, the present invention relates to any one of the aforementioned methods, wherein m is 0 or 1.

In certain embodiments, the present invention relates to any one of the aforementioned methods, wherein $A^1$ is aryl optionally substituted with —CO$_2$R$^{12}$, $X^1$ is —N=R$^9$, $X^2$ is —OR$^{13}$, $X^3$ is —O—, and $R^4$ and $R^9$ taken together form a 5-6 member ring optionally substituted with one or more of alkyl, aryl, aralkyl, or halogen.

In certain embodiments, the present invention relates to any one of the aforementioned methods, wherein $A^1$ is aryl optionally substituted with —CO$_2$R$^{12}$; $X^1$ is —N=R$^9$, $X^2$ is —OR$^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H.

In certain embodiments, the present invention relates to any one of the aforementioned methods, wherein $A^1$ is aryl optionally substituted with —CO$_2$R$^{12}$; $X^1$ is —N=R$^9$, $X^2$ is —OR$^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is H; and $R^{10}$ and $R^{12}$ are H.

In certain embodiments, the present invention relates to any one of the aforementioned methods, wherein M is Mn, Cu, Co, Fe, Ni, Zn, Ru, or Rh.

In certain embodiments, the present invention relates to any one of the aforementioned methods, wherein M is Cu, Co, Ru, or Rh.

In certain embodiments, the present invention relates to any one of the aforementioned methods, wherein M is Cu.

In certain embodiments, the present invention relates to any one of the aforementioned methods, wherein L is halogen, alkoxy, —OC(O)alkyl, —OC(O)aryl, or —OC(O)aralkyl.

In certain embodiments, the present invention relates to any one of the aforementioned methods, wherein L is halogen.

In certain embodiments, the present invention relates to any one of the aforementioned methods, wherein the transition-metal containing fluorescein-based sensor is represented by formula IV:

IV wherein, independently for each occurrence, $A^1$ is aryl or heteroaryl, both of which are optionally substituted with one or more of halogen, alkoxyl, —OH, —N(R$^8$)$_2$, —COR$^8$, or —CO$_2$R$^8$;

L is a ligand;

M is a transition metal;

$X^1$ is —O—, —S—, or —N(R$^6$)—;

$X^2$ is —O—, —S—, or —N(R$^6$)—;

$R^1$ represents independently for each occurrence H, alkyl, hydroxyalkyl, aryl, aralkyl, halogen, alkoxyl, —N(R$^8$)$_2$, —COR$^8$, —CO$_2$R$^8$, —N(R$^8$)C(O)R$^8$, or —C(O)N(R$^8$)$_2$;

$R^2$, $R^3$, and $R^5$ each represent independently for each occurrence H, alkyl, halogen, alkoxyl, —COR$^8$, or —CO$_2$R$^8$;

$R^4$ and $R^6$ each represent independently for each occurrence H or alkyl;

$R^7$ is halogen;

$R^8$ represents independently for each occurrence H, alkyl, aryl, heteroaryl, or aralkyl;

m represents independently for each occurrence 0, 1, or 2;

the stereochemical configuration at any stereocenter of the transition-metal containing fluorescein-based sensor represented by IV is R, S, or a mixture of these configurations; and $R^1$ is optionally coordinated to M.

In certain embodiments, the present invention relates to any one of the aforementioned methods, wherein $A^1$ is aryl optionally substituted with one or more of —CO$_2$R$^8$.

In certain embodiments, the present invention relates to any one of the aforementioned methods, wherein $X^1$ is —O—.

In certain embodiments, the present invention relates to any one of the aforementioned methods, wherein $X^2$ is —O—.

In certain embodiments, the present invention relates to any one of the aforementioned methods, wherein $R^1$, $R^2$, $R^3$, and $R^5$ each represent independently for each occurrence H or alkyl.

In certain embodiments, the present invention relates to any one of the aforementioned methods, wherein $R^4$ and $R^6$ are H.

In certain embodiments, the present invention relates to any one of the aforementioned methods, wherein $R^7$ is chloride.

In certain embodiments, the present invention relates to any one of the aforementioned methods, wherein $R^8$ represents independently for each occurrence H or alkyl.

In certain embodiments, the present invention relates to any one of the aforementioned methods, wherein $A^1$ is aryl optionally substituted with —CO$_2$R$^8$, $X^1$ is —OR$^6$, and $X^2$ is —O—.

In certain embodiments, the present invention relates to any one of the aforementioned methods, wherein $A^1$ is aryl optionally substituted with —CO$_2$R$^8$; $X^1$ is —O—; $X^2$ is —O—; $R^1$, $R^2$, $R^3$, and $R^5$ each represent independently for each occurrence H or alkyl; $R^4$ and $R^6$ are H; and $R^7$ is chloride.

In certain embodiments, the present invention relates to any one of the aforementioned methods, wherein $A^1$ is aryl optionally substituted with —CO$_2$R$^8$; $X^1$ is —O—; $X^2$ is —O—; $R^1$, $R^2$, $R^3$, and $R^5$ each represent independently for each occurrence H or alkyl; $R^4$ and $R^6$ are H; $R^7$ is chloride; $R^8$ is H; m represents independently for each occurrence 0 or 1.

In certain embodiments, the present invention relates to any one of the aforementioned methods, wherein M is Mn, Cu, Co, Fe, Ni, Zn, Ru, or Rh.

In certain embodiments, the present invention relates to any one of the aforementioned methods, wherein M is Cu, Co, Ru, or Rh.

In certain embodiments, the present invention relates to any one of the aforementioned methods, wherein M is Cu.

In certain embodiments, the present invention relates to any one of the aforementioned methods, wherein L is halogen, alkoxy, —OC(O)alkyl, —OC(O)aryl, or —OC(O)aralkyl.

In certain embodiments, the present invention relates to any one of the aforementioned methods, wherein L is halogen.

In certain embodiments, the present invention relates to any one of the aforementioned methods, wherein the transition-metal containing fluorescein-based sensor is represented by formula IVa:

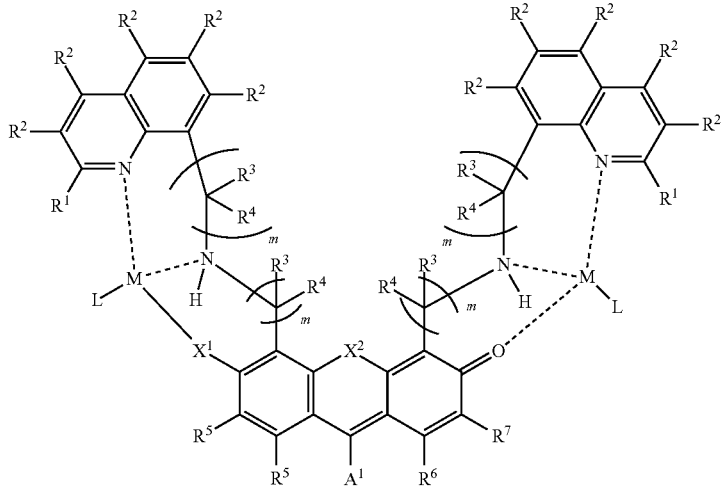

IVa wherein, independently for each occurrence,

A$^1$ is aryl or heteroaryl, both of which are optionally substituted with one or more of halogen, alkoxyl, —OH, —N(R$^8$)$_2$, —COR$^8$, or —CO$_2$R$^8$;

L is a ligand;

M is a transition metal;

X$^1$ is —O—, —S—, or —N(R$^6$)—;

X$^2$ is —O—, —S—, or —N(R$^6$)—;

R$^1$ represents independently for each occurrence H, alkyl, hydroxyalkyl, aryl, aralkyl, halogen, alkoxyl, —N(R$^8$)$_2$, —COR$^8$, —CO$_2$R$^8$, —N(R$^8$)C(O)R$^8$, or —C(O)N(R$^8$)$_2$;

R$^2$, R$^3$, and R$^5$ each represent independently for each occurrence H, alkyl, halogen, alkoxyl, —COR$^8$, or —CO$_2$R$^8$;

R$^4$ and R$^6$ each represent independently for each occurrence H or alkyl;

R$^7$ is H or halogen;

R$^8$ represents independently for each occurrence H, alkyl, aryl, heteroaryl, or aralkyl;

m represents independently for each occurrence 0, 1, or 2;

the stereochemical configuration at any stereocenter of the transition-metal containing fluorescein-based sensor represented by IVa is R, S, or a mixture of these configurations; and R$^1$ is optionally coordinated to M.

In certain embodiments, the present invention relates to any one of the aforementioned methods, wherein A$^1$ is aryl optionally substituted with one or more of —CO$_2$R$^8$.

In certain embodiments, the present invention relates to any one of the aforementioned methods, wherein X$^1$ is —O—.

In certain embodiments, the present invention relates to any one of the aforementioned methods, wherein X$^2$ is —O—.

In certain embodiments, the present invention relates to any one of the aforementioned methods, wherein R$^1$, R$^2$, R$^3$, and R$^5$ each represent independently for each occurrence H or alkyl.

In certain embodiments, the present invention relates to any one of the aforementioned methods, wherein R$^4$ and R$^6$ are H.

In certain embodiments, the present invention relates to any one of the aforementioned methods, wherein R$^7$ is chloride.

In certain embodiments, the present invention relates to any one of the aforementioned methods, wherein R$^7$ is H.

In certain embodiments, the present invention relates to any one of the aforementioned methods, wherein R$^8$ represents independently for each occurrence H or alkyl.

In certain embodiments, the present invention relates to any one of the aforementioned methods, wherein A$^1$ is aryl optionally substituted with —CO$_2$R$^8$, X$^1$ is —OR$^6$, and X$^2$ is —O—.

In certain embodiments, the present invention relates to any one of the aforementioned methods, wherein A$^1$ is aryl optionally substituted with —CO$_2$R$^8$; X$^1$ is —O—; X$^2$ is —O—; R$^1$, R$^2$, R$^3$, and R$^5$ each represent independently for each occurrence H or alkyl; R$^4$ and R$^6$ are H; and R$^7$ is chloride.

In certain embodiments, the present invention relates to any one of the aforementioned methods, wherein A$^1$ is aryl optionally substituted with —CO$_2$R$^8$; X$^1$ is —O—; X$^2$ is —O—; R$^1$, R$^2$, R$^3$, and R$^5$ each represent independently for each occurrence H or alkyl; R$^4$ and R$^6$ are H; and R$^7$ is H.

In certain embodiments, the present invention relates to any one of the aforementioned methods, wherein A$^1$ is aryl optionally substituted with —CO$_2$R$^8$; X$^1$ is —O—; X$^2$ is —O—; R$^1$, R$^2$, R$^3$, and R$^5$ each represent independently for each occurrence H or alkyl; R$^4$ and R$^6$ are H; R$^7$ is chloride; R$^8$ is H; m represents independently for each occurrence 0 or 1.

In certain embodiments, the present invention relates to any one of the aforementioned methods, wherein A$^1$ is aryl optionally substituted with —CO$_2$R$^8$; X$^1$ is —O—; X$^2$ is —O—; R$^1$, R$^2$, R$^3$, and R$^5$ each represent independently for each occurrence H or alkyl; R$^4$ and R$^6$ are H; R$^7$ is H; R$^8$ is H; m represents independently for each occurrence 0 or 1.

In certain embodiments, the present invention relates to any one of the aforementioned methods, wherein M is Mn, Cu, Co, Fe, Ni, Zn, Ru, or Rh. In certain embodiments, the present invention relates to any one of the aforementioned methods, wherein M is Cu, Co, Ru, or Rh.

In certain embodiments, the present invention relates to any one of the aforementioned methods, wherein M is Cu.

In certain embodiments, the present invention relates to any one of the aforementioned methods, wherein L is halogen, alkoxy, —OC(O)alkyl, —OC(O)aryl, or —OC(O)aralkyl.

In certain embodiments, the present invention relates to any one of the aforementioned methods, wherein L is halogen.

Exemplary Compounds of the Invention

One aspect of the invention relates to a compound of formula Ia:

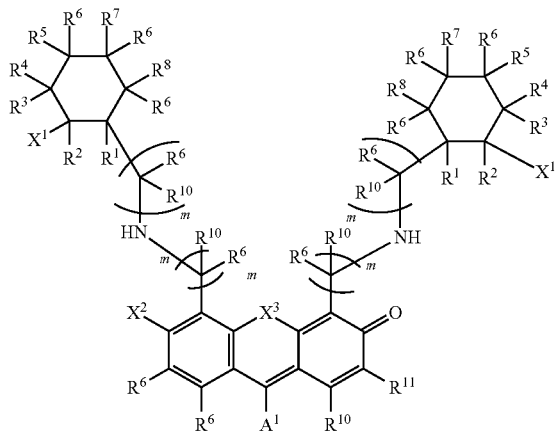

wherein, independently for each occurrence, $A^1$ is aryl or heteroaryl, both of which are optionally substituted with one or more of halogen, alkoxyl, —OH, —N(R$^{12}$)$_2$, —COR$^{12}$, —CO$_2$R$^{12}$, —N(R$^{12}$)C(O)R$^{12}$, or —C(O)N(R$^{12}$)$_2$;

$X^1$ is —OR$^9$, —SR$^9$, —N=R$^9$, or —N(R$^{13}$)R$^9$;

$X^2$ is —OR$^{13}$, —SR$^{13}$, or —N(R$^{13}$)$_2$;

$X^3$ is —O—, —S—, or —N(R$^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N(R$^9$)$_2$, —COR$^9$, —CO$_2$R$^9$, —N(R$^9$)C(O)R$^9$, or —C(O)N(R$^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or (C$_1$-C$_6$)alkyl;

m represents independently for each occurrence 0, 1, 2, 3, or 4; and the stereochemical configuration at any stereocenter of the compound represented by Ia is R, S, or a mixture of these configurations.

In certain embodiments, the present invention relates to any one of the aforementioned compounds, wherein $A^1$ is aryl optionally substituted with —CO$_2$R$^{12}$.

In certain embodiments, the present invention relates to any one of the aforementioned compounds, wherein $X^1$ is —N=R$^9$.

In certain embodiments, the present invention relates to any one of the aforementioned compounds, wherein $X^2$ is —OR$^{13}$.

In certain embodiments, the present invention relates to any one of the aforementioned compounds, wherein $X^3$ is —O—.

In certain embodiments, the present invention relates to any one of the aforementioned compounds, wherein $R^1$ and $R^8$ taken together form a bond.

In certain embodiments, the present invention relates to any one of the aforementioned compounds, wherein $R^5$ and $R^7$ taken together form a bond.

In certain embodiments, the present invention relates to any one of the aforementioned compounds, wherein $R^{10}$ is H or alkyl.

In certain embodiments, the present invention relates to any one of the aforementioned compounds, wherein $R^2$ and $R^3$ taken together form a bond.

In certain embodiments, the present invention relates to any one of the aforementioned compounds, wherein $R^4$ and $R^9$ taken together form a 5-6 member ring optionally substituted with one or more of alkyl, aryl, aralkyl, or halogen.

In certain embodiments, the present invention relates to any one of the aforementioned compounds, wherein $R^6$ is H or alkyl.

In certain embodiments, the present invention relates to any one of the aforementioned compounds, wherein $R^{11}$ is halogen. In certain embodiments, the present invention relates to any one of the aforementioned compounds, wherein $R^{11}$ is H.

In certain embodiments, the present invention relates to any one of the aforementioned compounds, wherein $R^{12}$ is H.

In certain embodiments, the present invention relates to any one of the aforementioned compounds, wherein $R^{13}$ is H.

In certain embodiments, the present invention relates to any one of the aforementioned compounds, wherein m is 0 or 1.

In certain embodiments, the present invention relates to any one of the aforementioned compounds, wherein $A^1$ is aryl optionally substituted with —CO$_2$R$^{12}$, $X^1$ is —N=R$^9$, $X^2$ is —OR$^{13}$, $X^3$ is —O—, and $R^4$ and $R^9$ taken together form a 5-6 member ring optionally substituted with one or more of alkyl, aryl, aralkyl, or halogen.

In certain embodiments, the present invention relates to any one of the aforementioned compounds, wherein $A^1$ is aryl optionally substituted with —CO$_2$R$^{12}$; $X^1$ is —N=R$^9$, $X^2$ is —OR$^{13}$; $X^3$ is —O—; $R^4$ and $R^9$ taken together form a 5-6 member substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H. In certain embodiments, the present invention relates to any one of the aforementioned compounds, wherein $A^1$ is aryl optionally substituted with —CO$_2$R$^{12}$; $X^1$ is —N=R$^9$, $X^2$ is —OR$^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is H; and $R^{10}$ and $R^{12}$ are H.

One aspect of the invention relates to a compound of formula IIa:

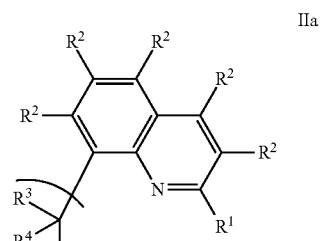
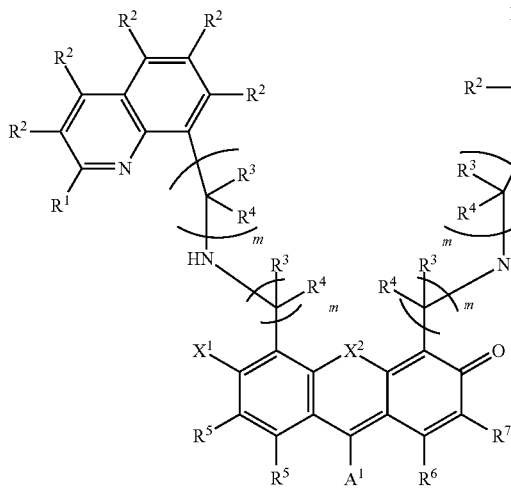

wherein, independently for each occurrence,

A$^1$ is aryl or heteroaryl, both of which are optionally substituted with one or more of halogen, alkoxyl, —OH, —N(R$^8$)$_2$, —COR$^8$, or —CO$_2$R$^8$;

X$^1$ is —OR$^6$, —SR$^6$, or —N(R$^6$)$_2$;

X$^2$ is —O—, —S—, or —N(R$^6$)—;

R$^1$ represents independently for each occurrence H, alkyl, hydroxyalkyl, aryl, aralkyl, halogen, alkoxyl, —N(R$^8$)$_2$, —COR$^8$, —CO$_2$R$^8$, —N(R$^8$)C(O)R$^8$, or —C(O)N(R$^8$)$_2$;

R$^2$, R$^3$, and R$^5$ each represent independently for each occurrence H, alkyl, halogen, alkoxyl, —COR$^8$, or —CO$_2$R$^8$;

R$^4$ and R$^6$ each represent independently for each occurrence H or alkyl;

R$^7$ is H or halogen;

R$^8$ represents independently for each occurrence H, alkyl, aryl, heteroaryl, or aralkyl;

m represents independently for each occurrence 0, 1, or 2; and the stereochemical configuration at any stereocenter of the compound represented by IIa is R, S, or a mixture of these configurations.

In certain embodiments, the present invention relates to any one of the aforementioned compounds, wherein A$^1$ is aryl optionally substituted with one or more of —CO$_2$R$^8$.

In certain embodiments, the present invention relates to any one of the aforementioned compounds, wherein X$^1$ is —OR$^6$.

In certain embodiments, the present invention relates to any one of the aforementioned compounds, wherein X$^2$ is —O—.

In certain embodiments, the present invention relates to any one of the aforementioned compounds, wherein R$^1$, R$^2$, R$^3$, and R$^5$ each represent independently for each occurrence H or alkyl.

In certain embodiments, the present invention relates to any one of the aforementioned compounds, wherein R$^4$ and R$^6$ are H.

In certain embodiments, the present invention relates to any one of the aforementioned compounds, wherein R$^7$ is chloride. In certain embodiments, the present invention relates to any one of the aforementioned compounds, wherein R$^7$ is H.

In certain embodiments, the present invention relates to any one of the aforementioned compounds, wherein R$^8$ represents independently for each occurrence H or alkyl.

In certain embodiments, the present invention relates to any one of the aforementioned compounds, wherein A$^1$ is aryl optionally substituted with —CO$_2$R$^8$, X$^1$ is —OR$^6$, and X$^2$ is —O—.

In certain embodiments, the present invention relates to any one of the aforementioned compounds, wherein A$^1$ is aryl optionally substituted with —CO$_2$R$^8$; X$^1$ is —OR$^6$; X$^2$ is —O—; R$^1$, R$^2$, R$^3$, and R$^5$ each represent independently for each occurrence H or alkyl; R$^4$ and R$^6$ are H; and R$^7$ is chloride. In certain embodiments, the present invention relates to any one of the aforementioned compounds, wherein A$^1$ is aryl optionally substituted with —CO$_2$R$^8$; X$^1$ is —OR$^6$; X$^2$ is —O—; R$^1$, R$^2$, R$^3$, and R$^5$ each represent independently for each occurrence H or alkyl; R$^4$ and R$^6$ are H; and R$^7$ is H.

In certain embodiments, the present invention relates to any one of the aforementioned compounds, wherein A$^1$ is aryl optionally substituted with —CO$_2$R$^8$; X$^1$ is —OR$^6$; X$^2$ is —O—; R$^1$, R$^2$, R$^3$, and R$^5$ each represent independently for each occurrence H or alkyl; R$^4$ and R$^6$ are H; R$^7$ is chloride; R$^8$ is H; and m represents independently for each occurrence 0 or 1. In certain embodiments, the present invention relates to any one of the aforementioned compounds, wherein A$^1$ is aryl optionally substituted with —CO$_2$R$^8$; X$^1$ is —OR$^6$; X$^2$ is —O—; R$^1$, R$^2$, R$^3$, and R$^5$ each represent independently for each occurrence H or alkyl; R$^4$ and R$^6$ are H; R$^7$ is H; R$^8$ is H; and m represents independently for each occurrence 0 or 1.

One aspect of the invention relates to a compound selected from the group consisting of:

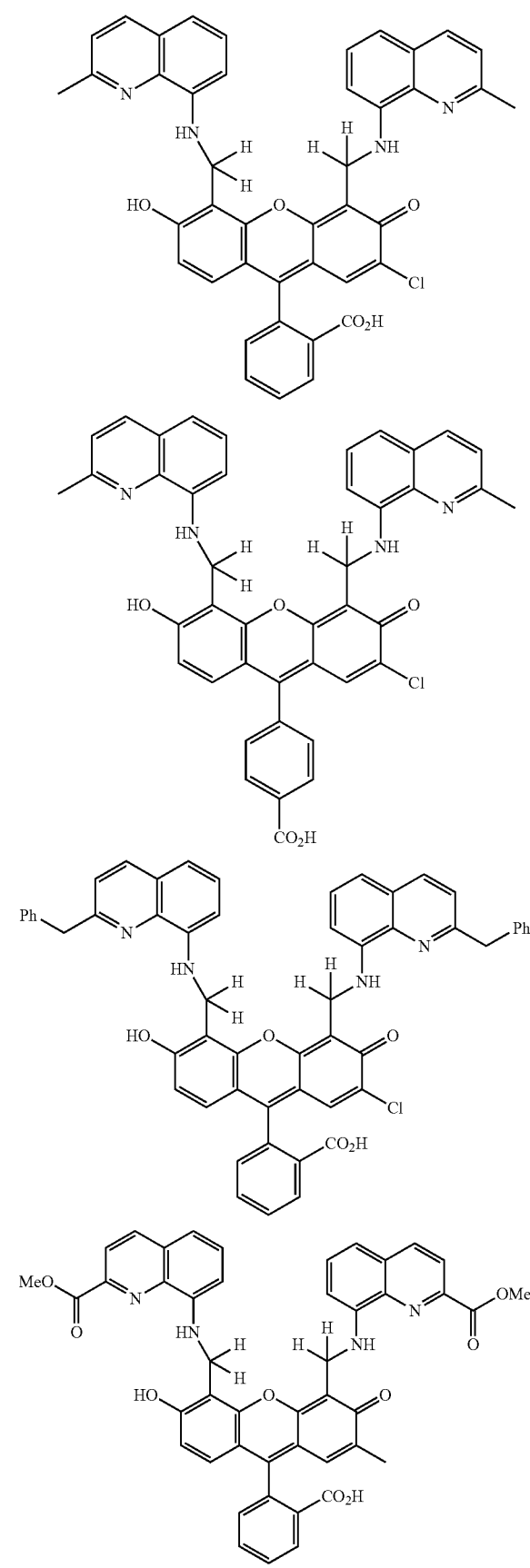
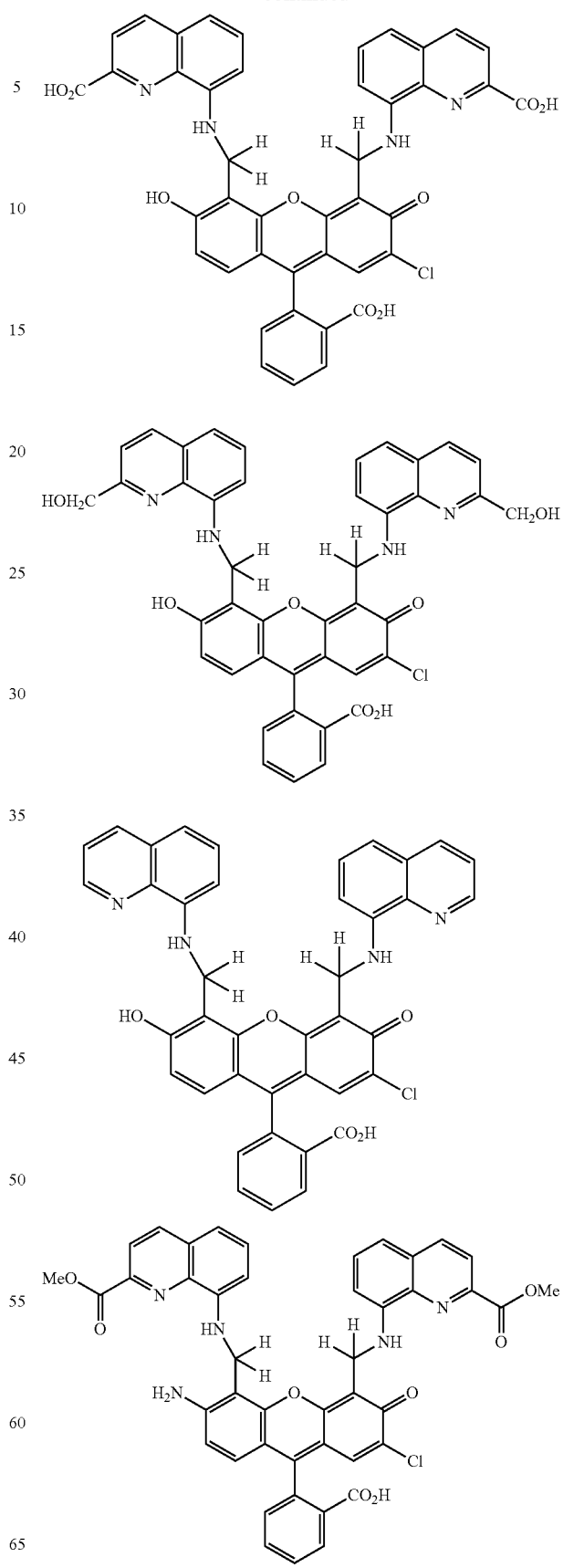

85
-continued
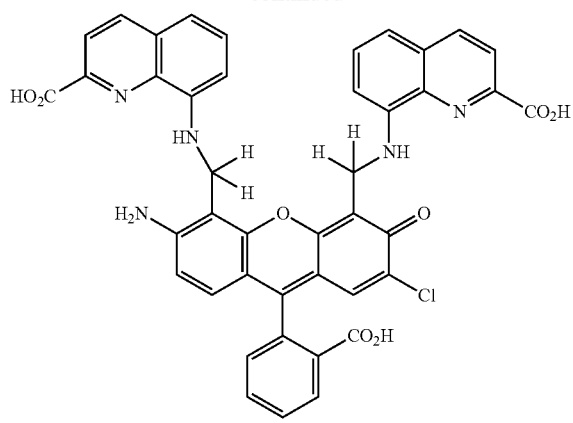
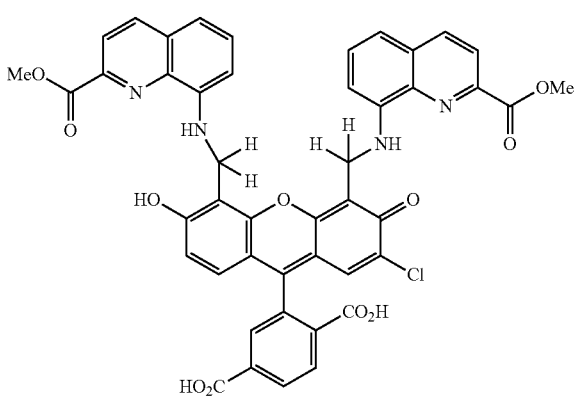
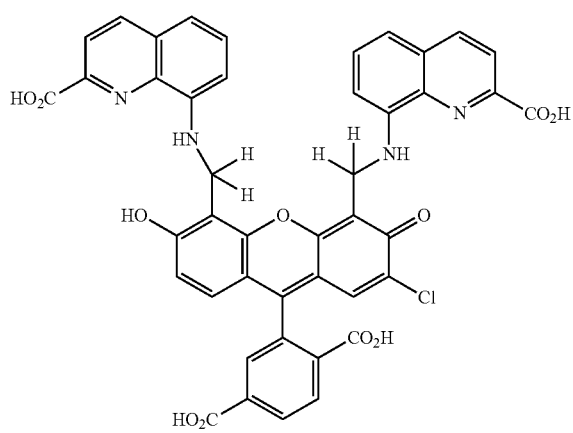
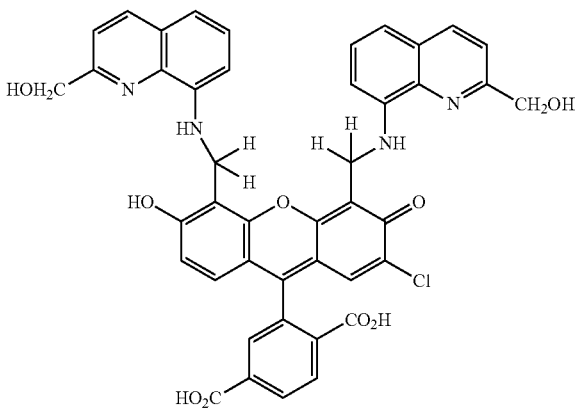
86
-continued
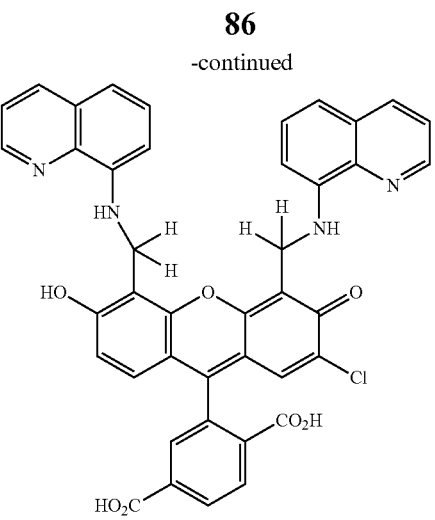
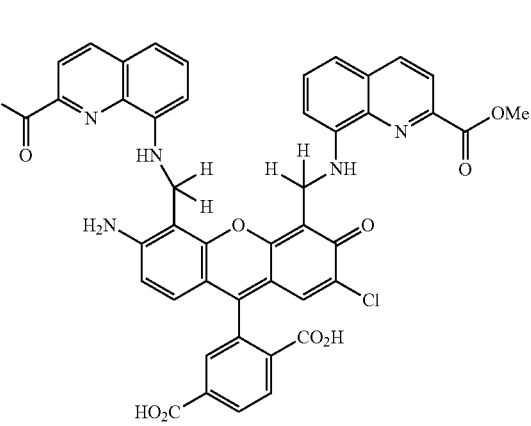
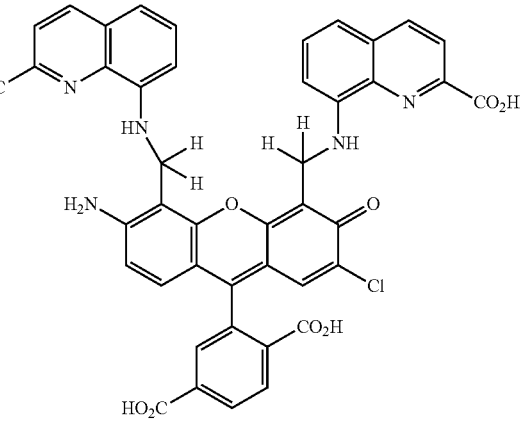
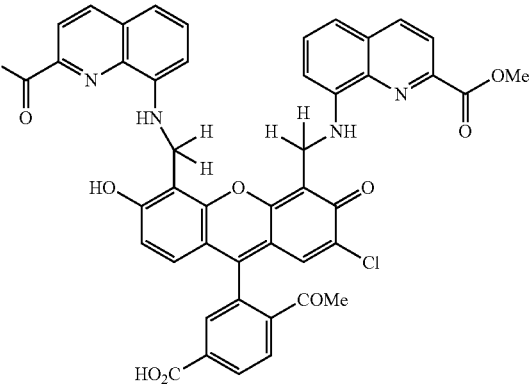

87
-continued
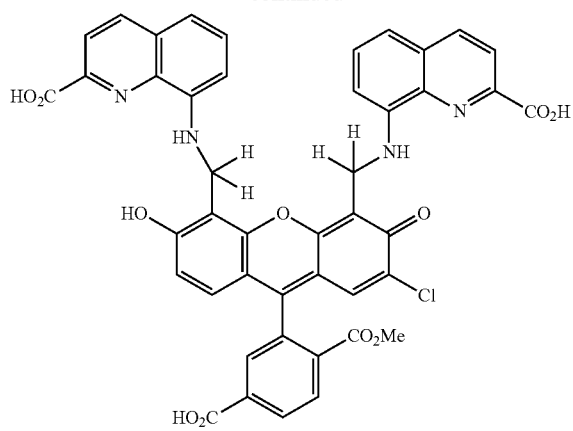
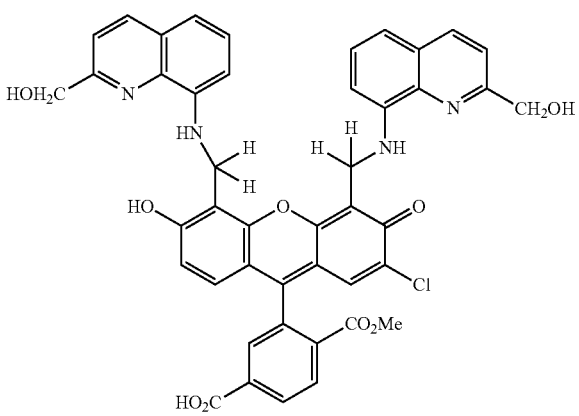
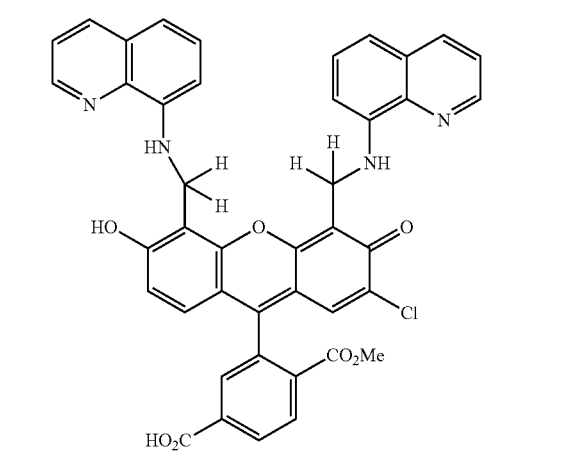
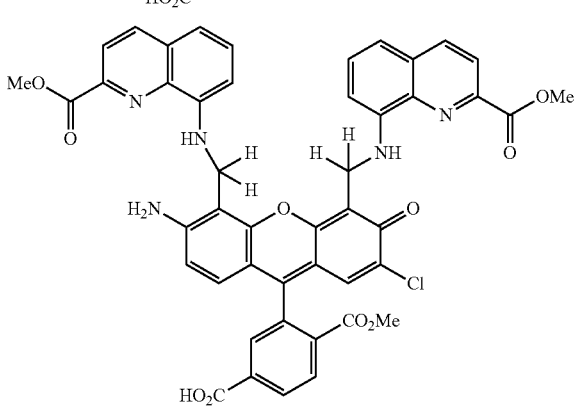
88
-continued
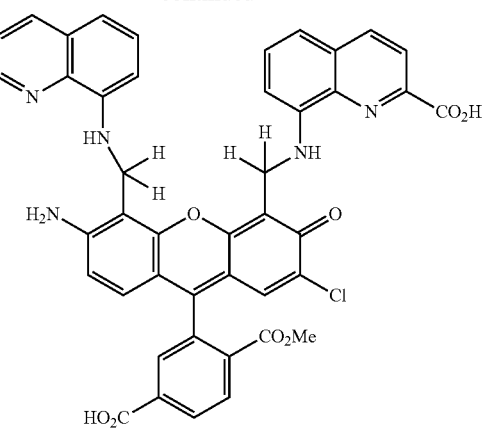
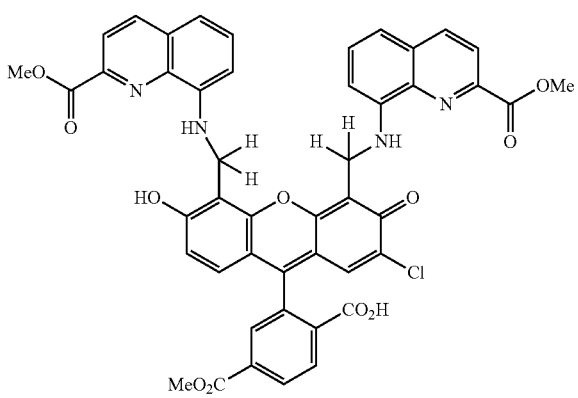
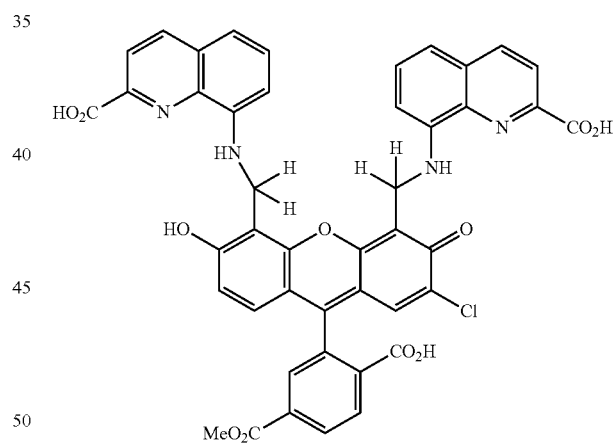
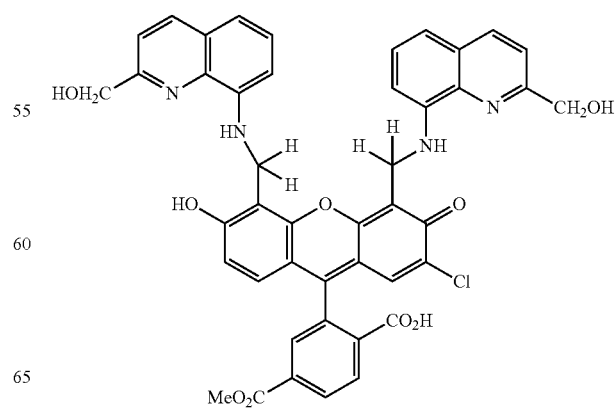

89
-continued
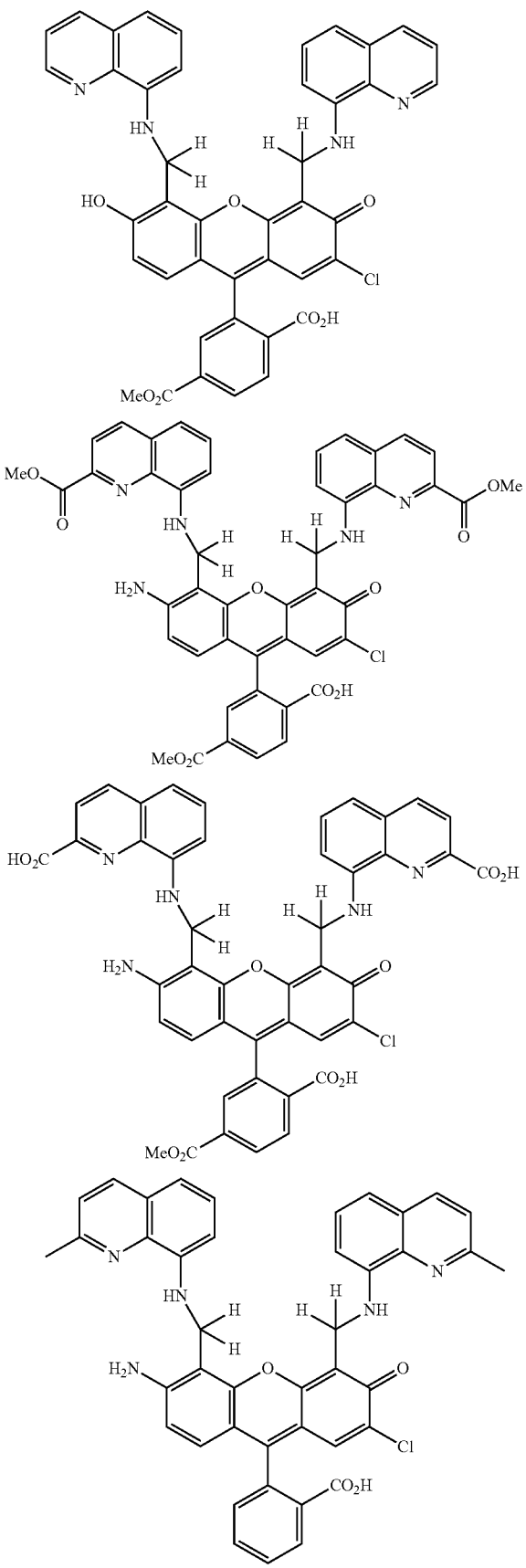
90
-continued
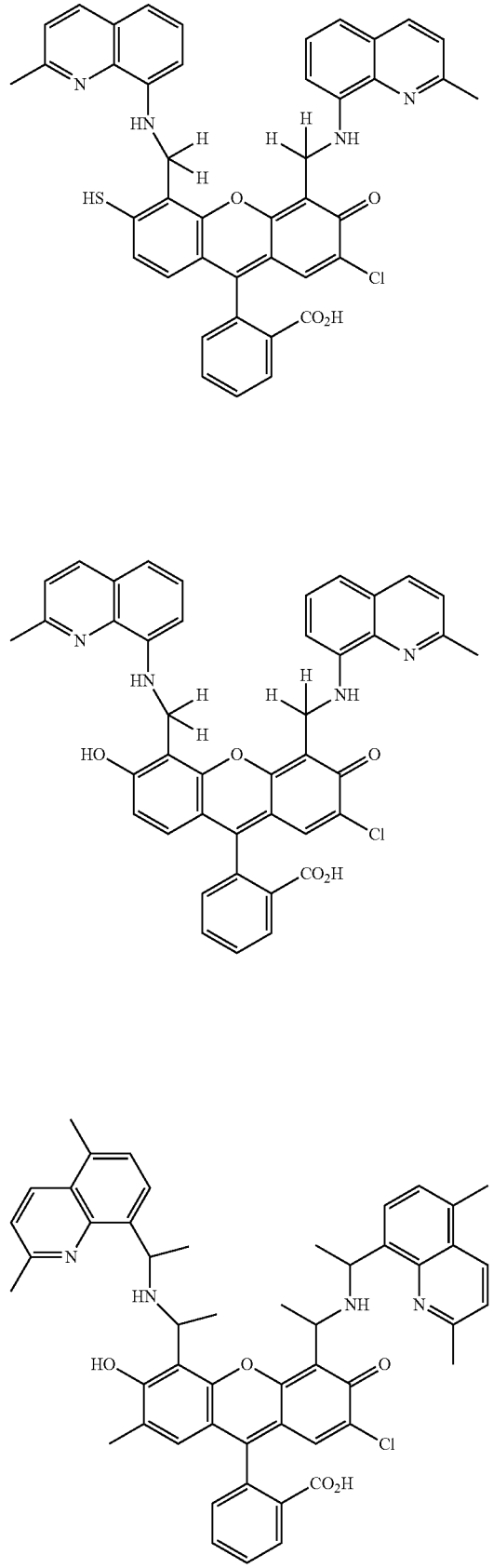

91
-continued
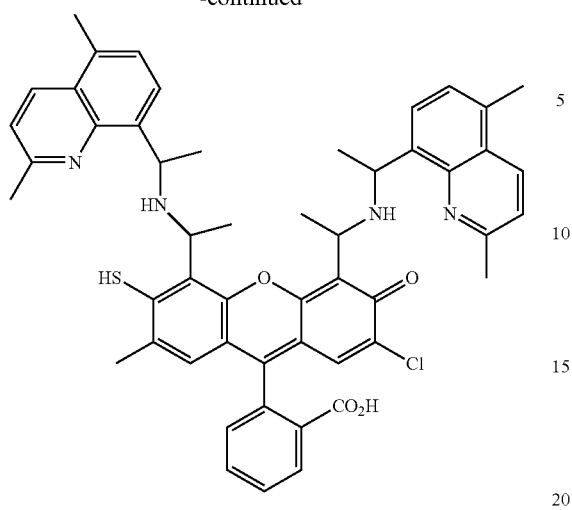
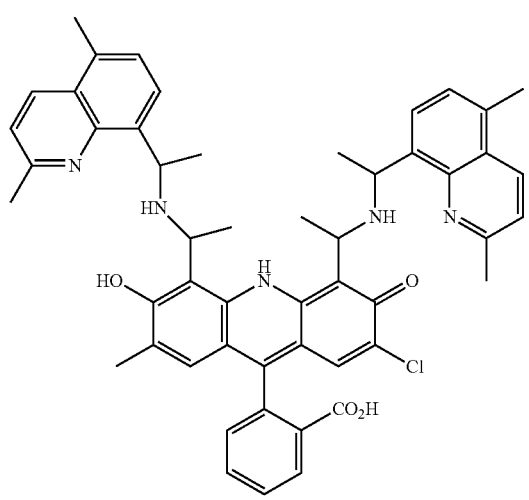
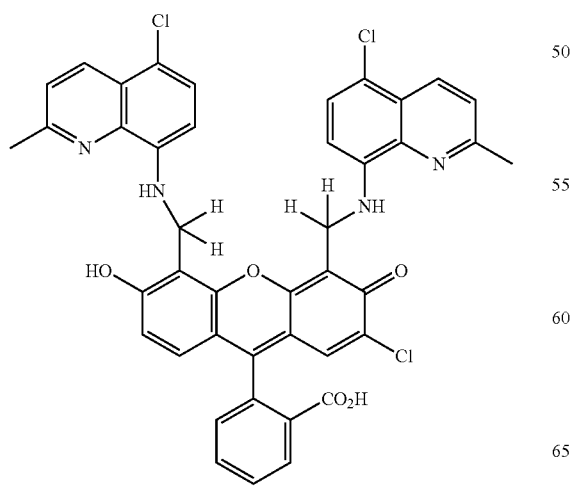
92
-continued
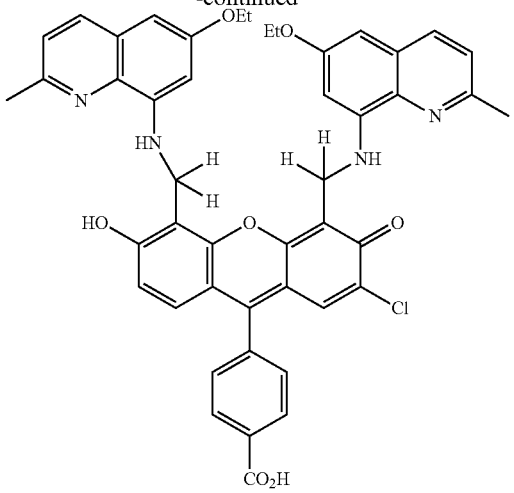
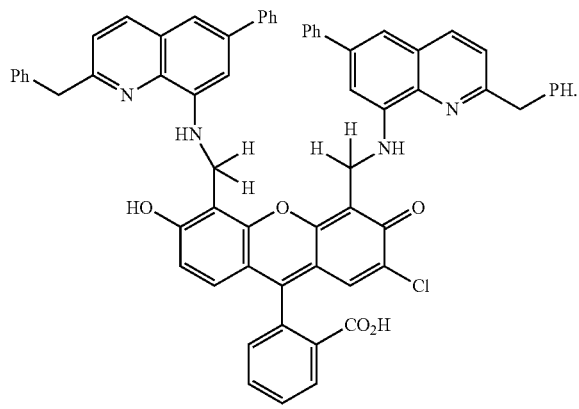
One aspect of the invention relates to a compound selected from the group consisting of:
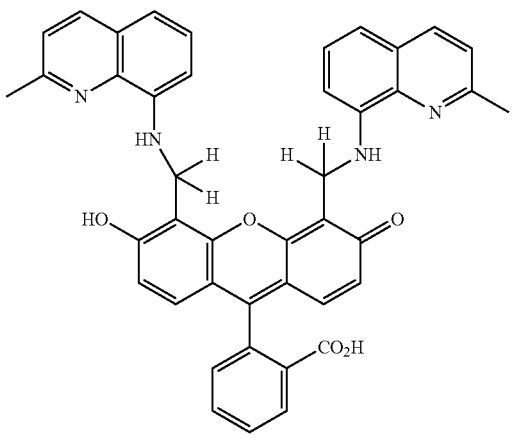

-continued
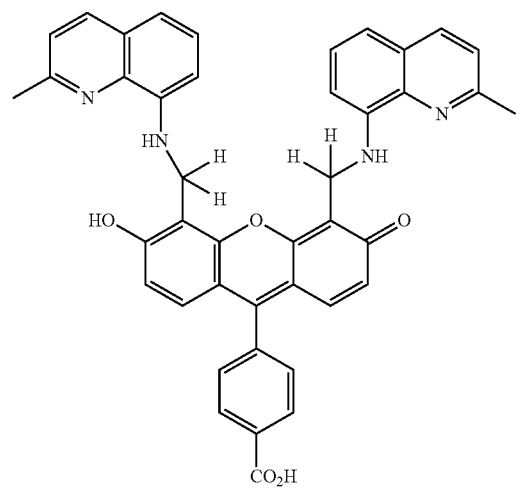
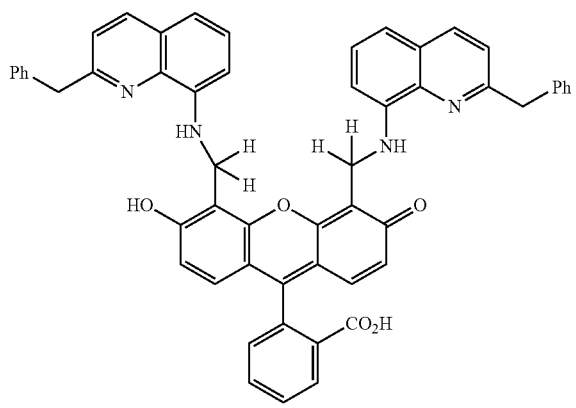
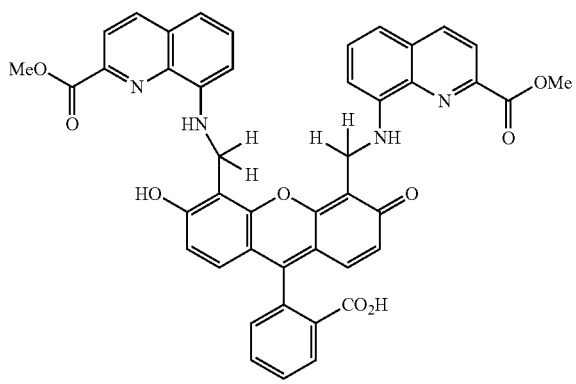
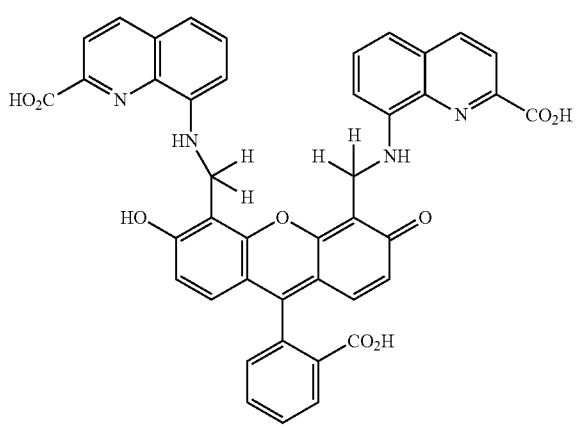
-continued
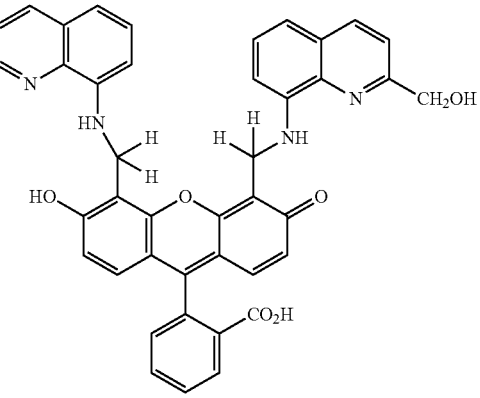
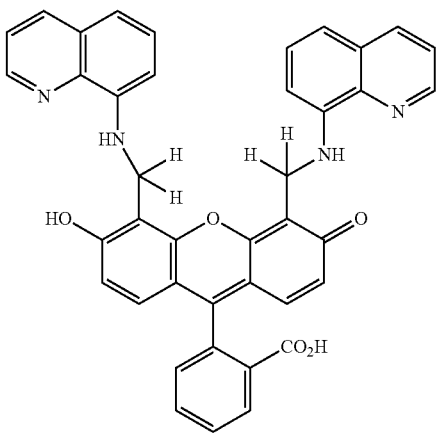
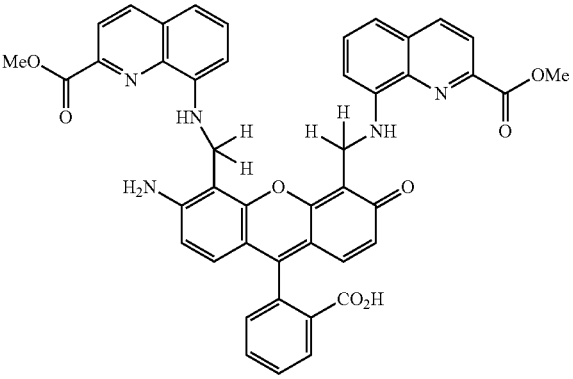
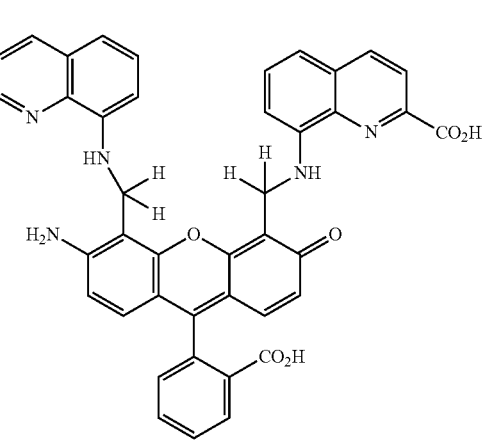

95
-continued

96
-continued

97
-continued
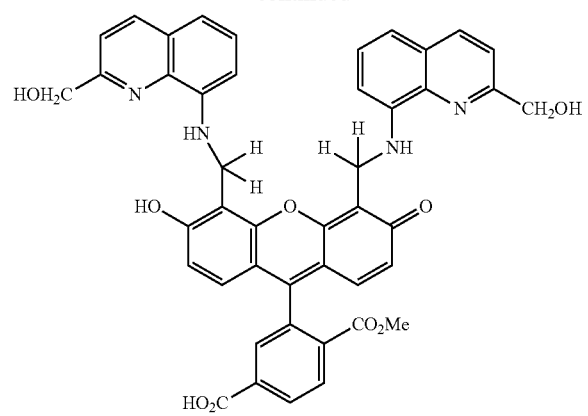
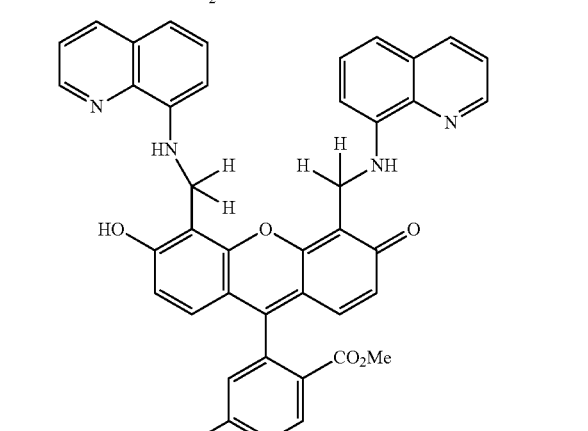
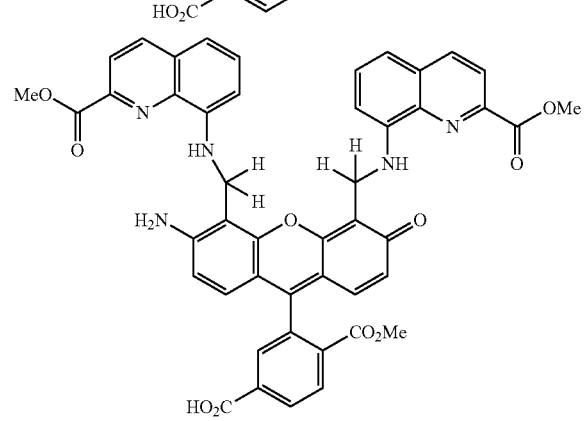
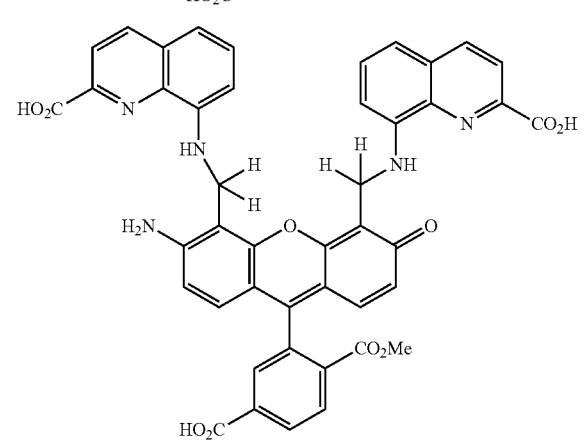
98
-continued
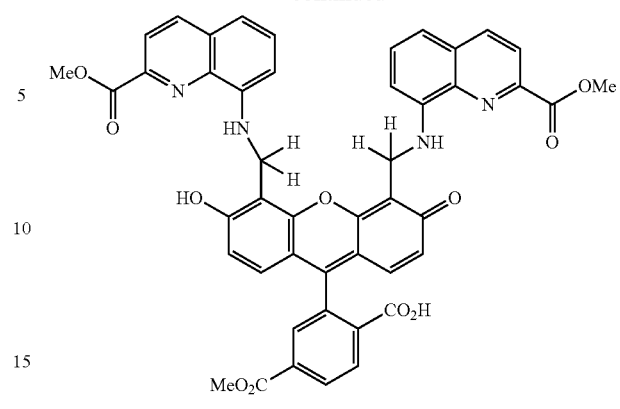
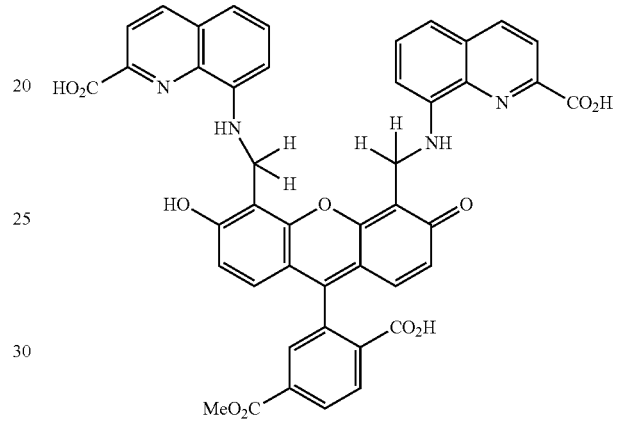
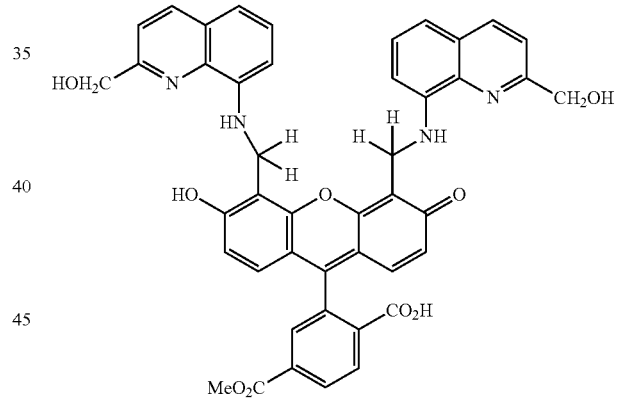
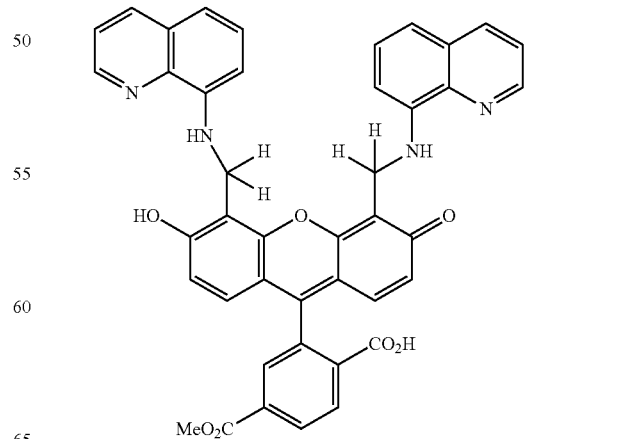

99
-continued
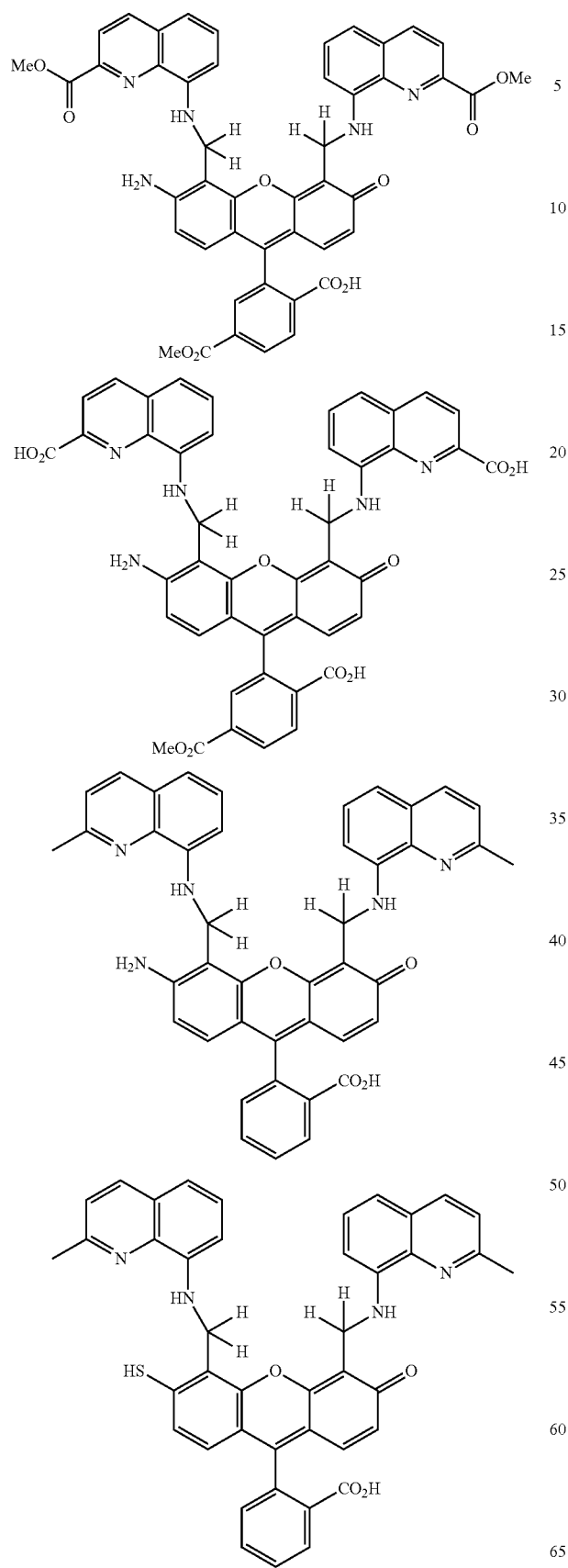
100
-continued
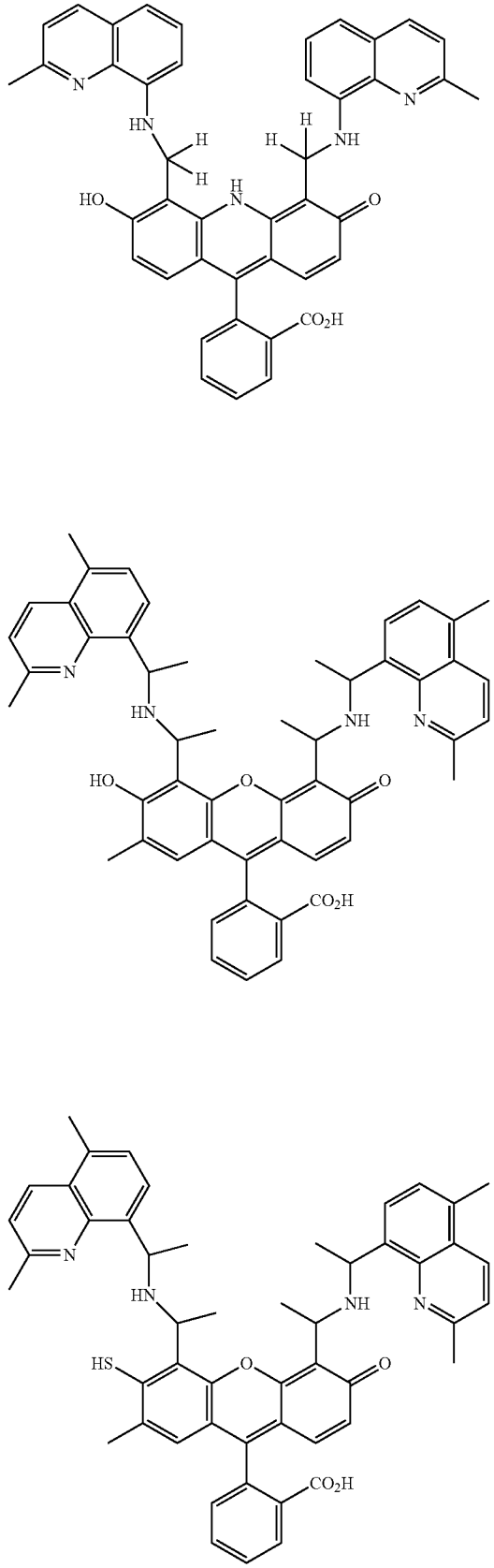

101
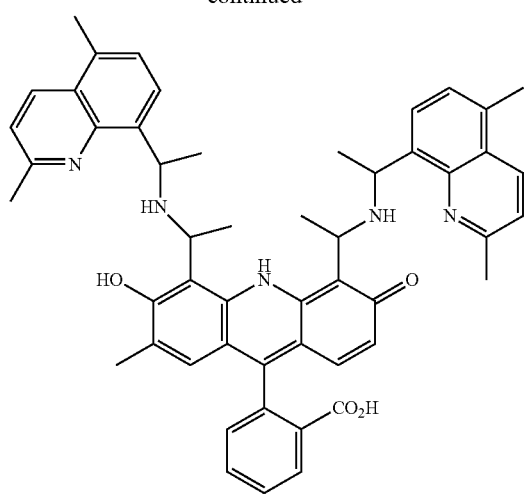
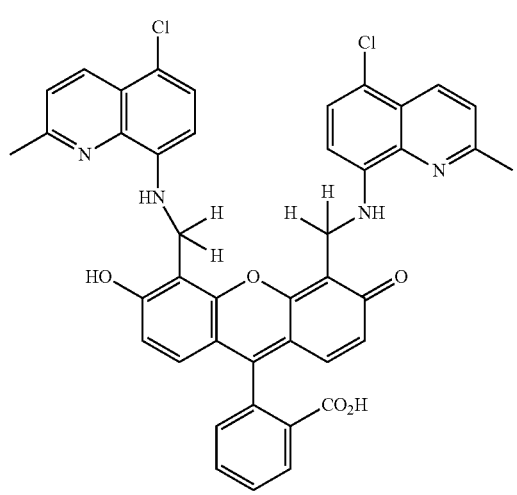
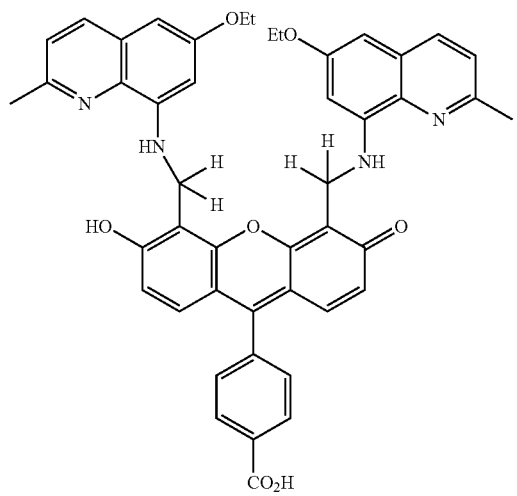
102
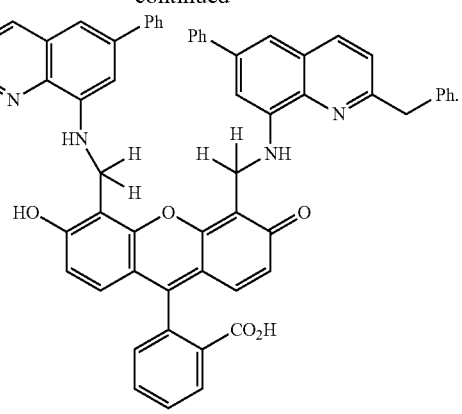
In certain embodiments, the present invention relates to any one of the aforementioned compounds, wherein the compound is selected from the group consisting of:
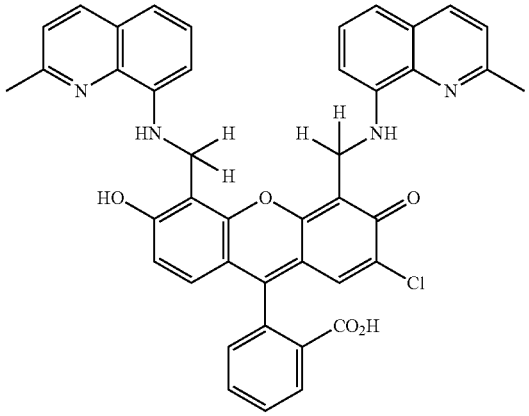
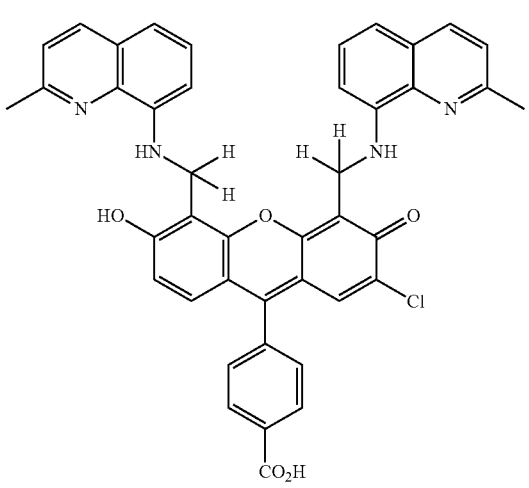

103
-continued
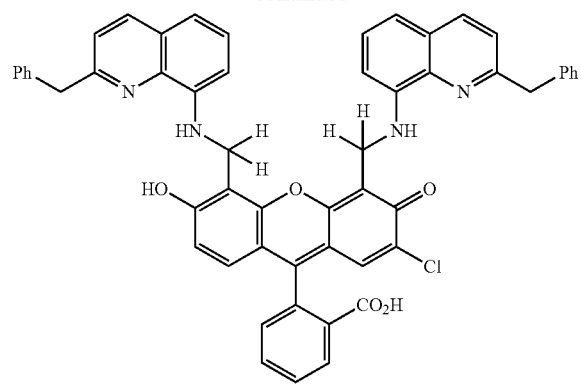
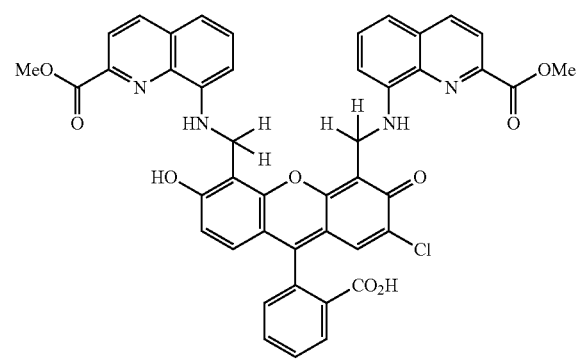
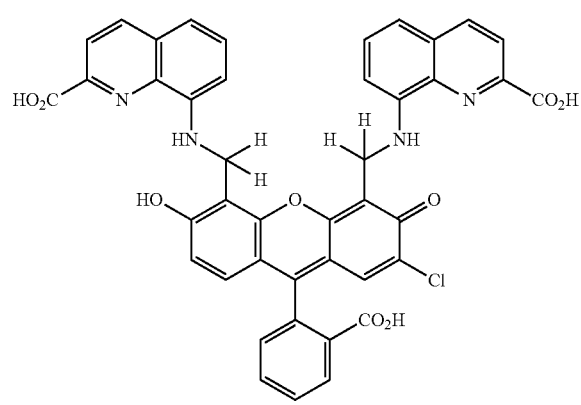
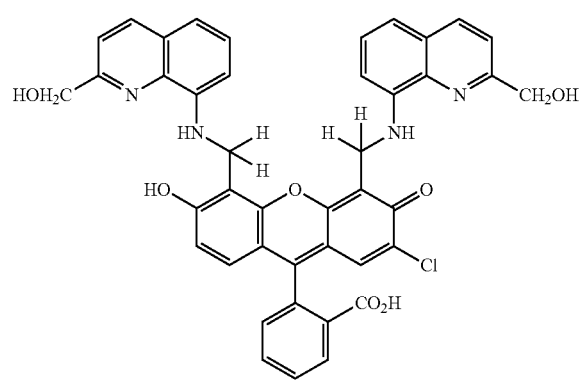
104
-continued
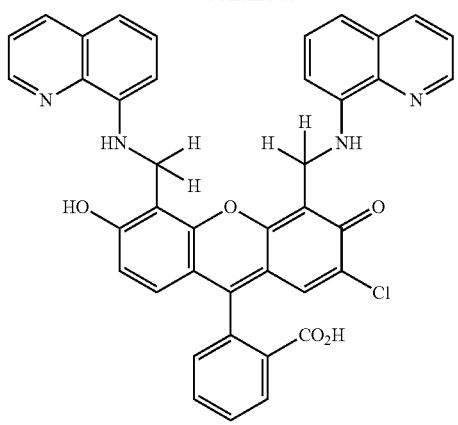
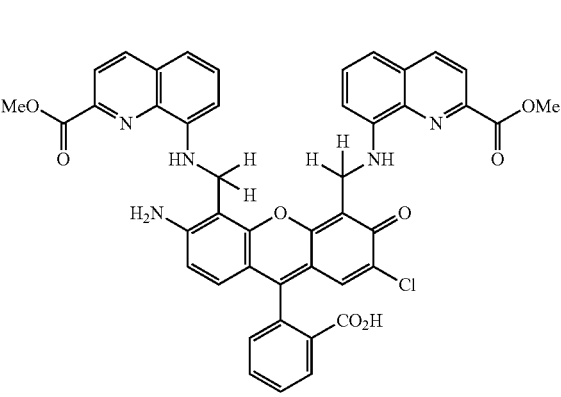
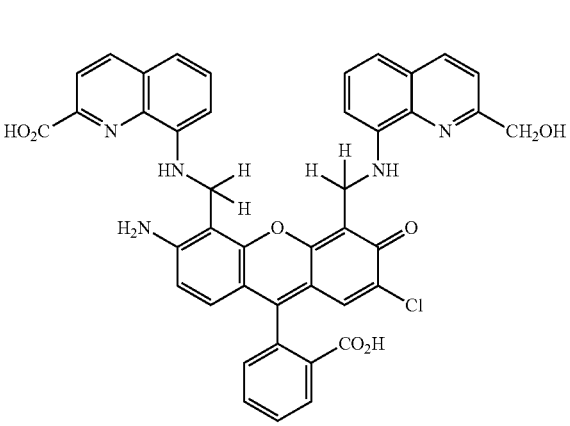
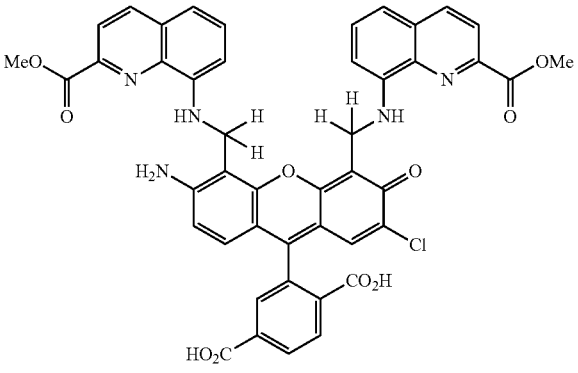

105
-continued
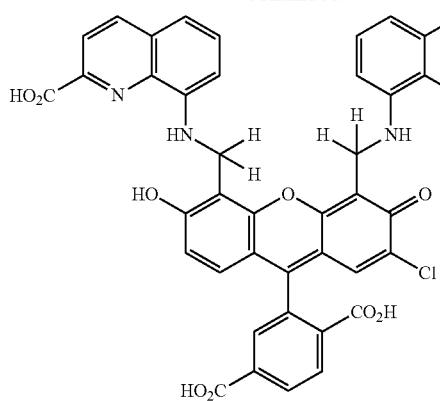
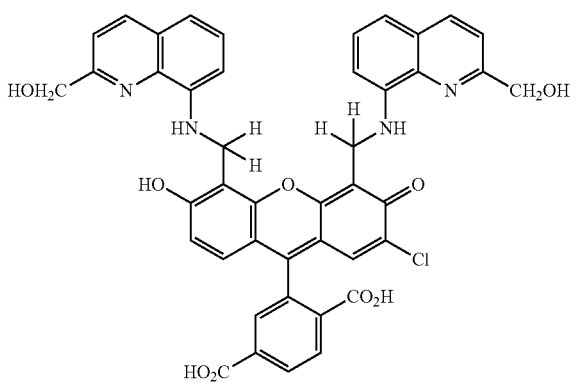
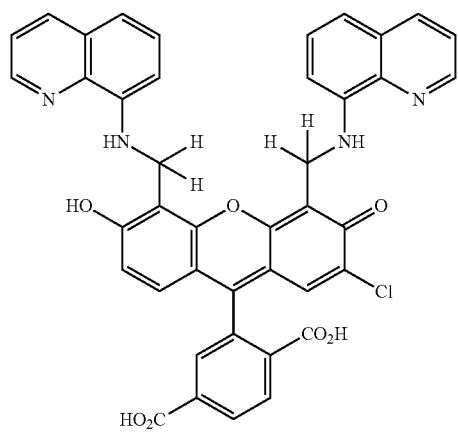
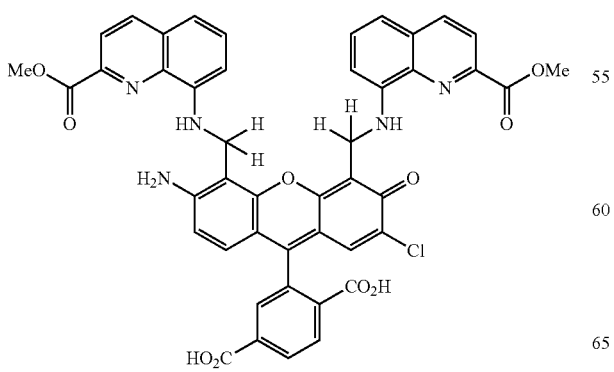
106
-continued
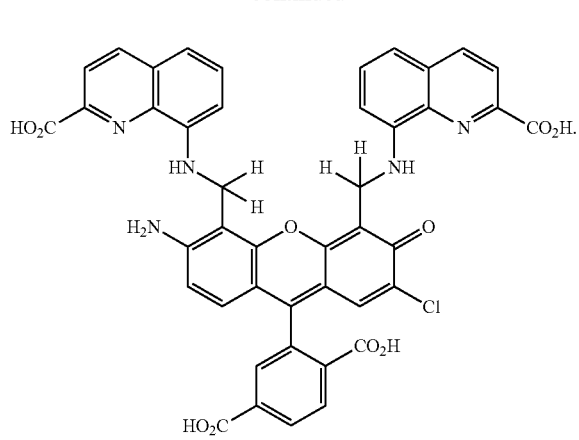
In certain embodiments, the present invention relates to any one of the aforementioned compounds, wherein the compound is selected from the group consisting of:
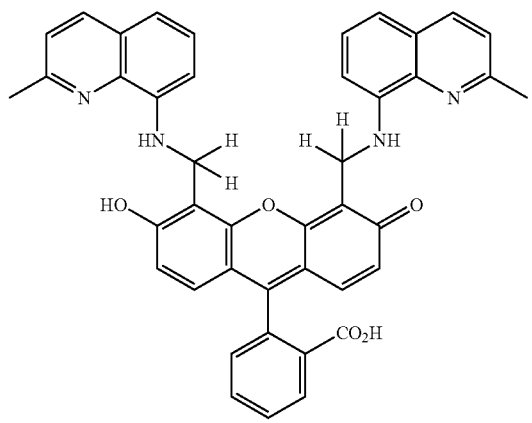
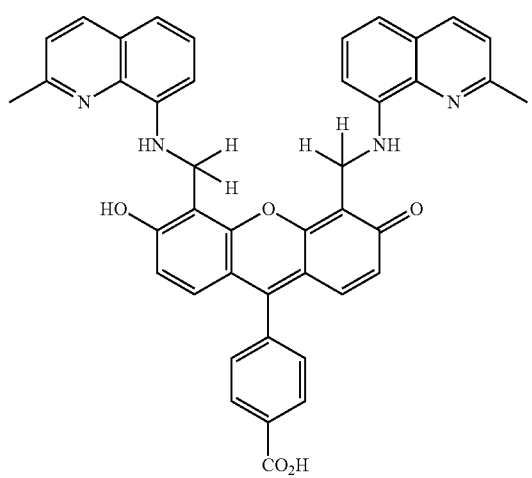

| 107 -continued | 108 -continued |
|---|---|
| 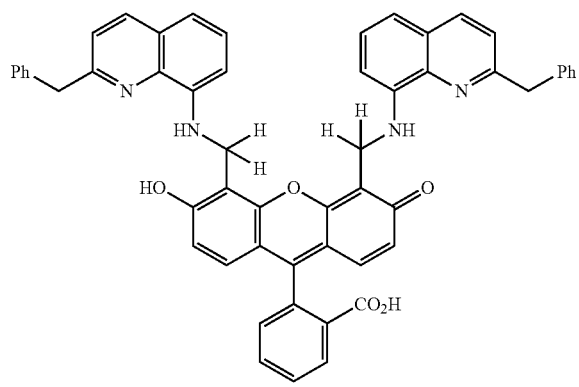 | 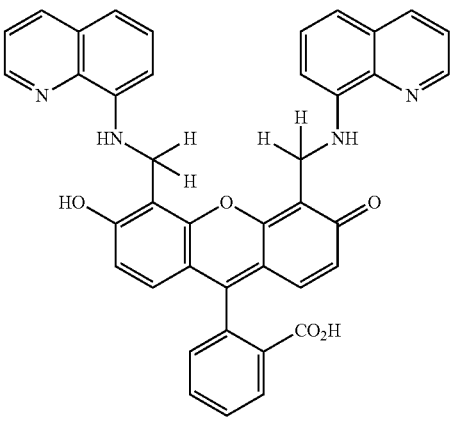 |
| 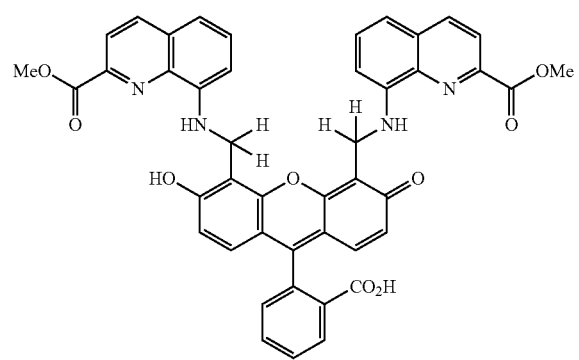 | 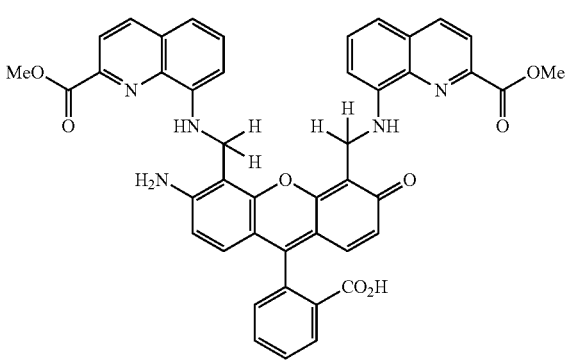 |
| 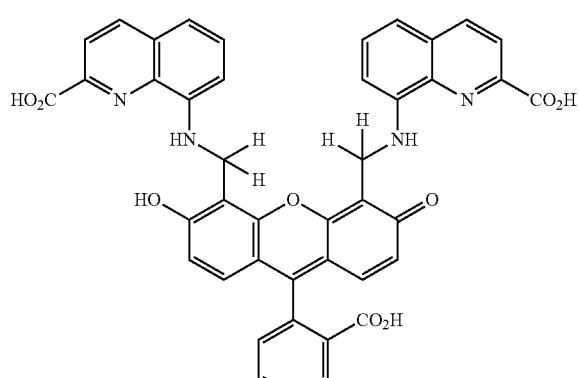 | 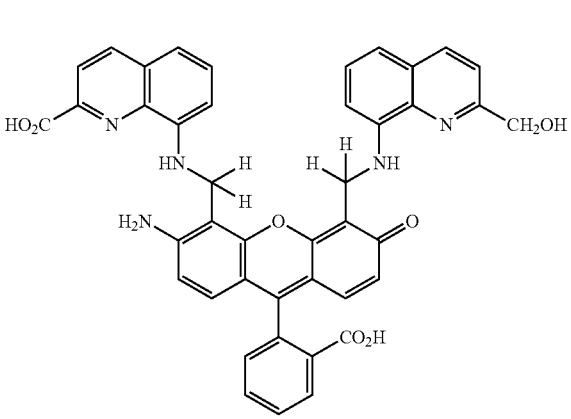 |
| 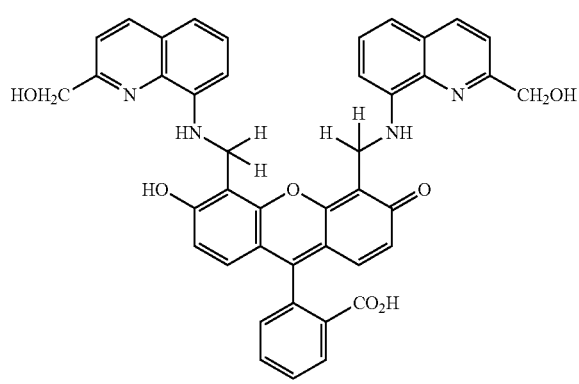 | 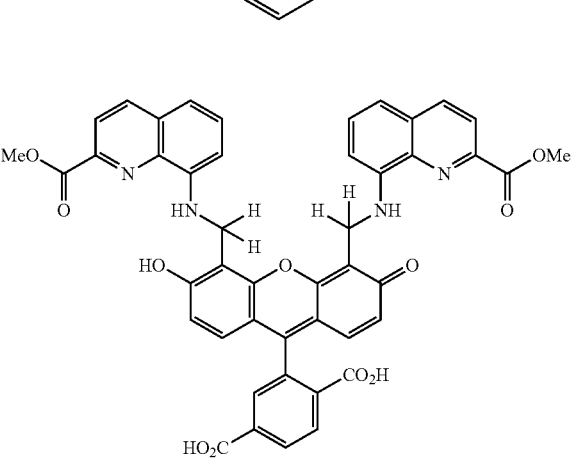 |

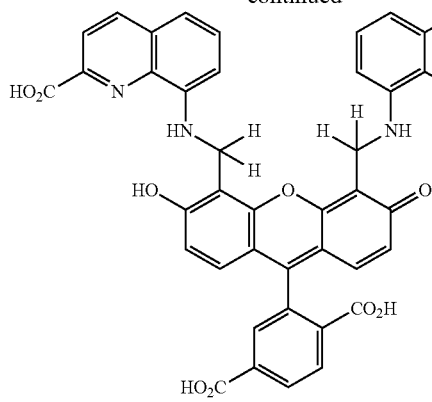
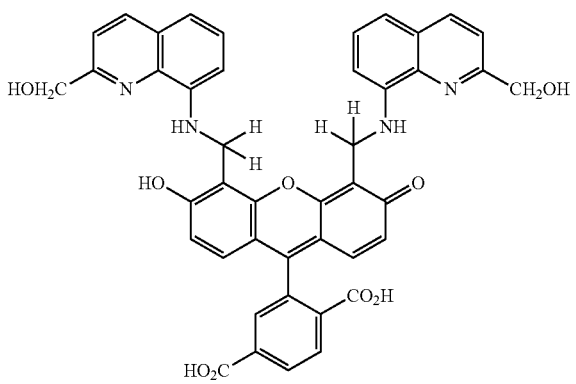
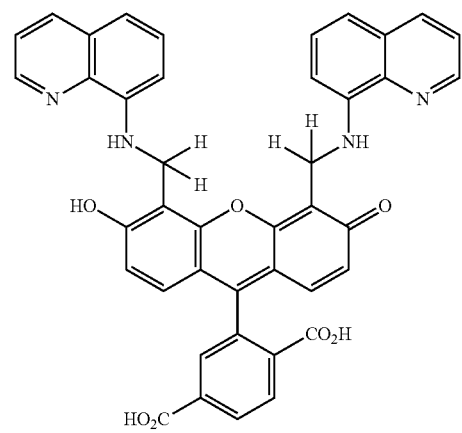
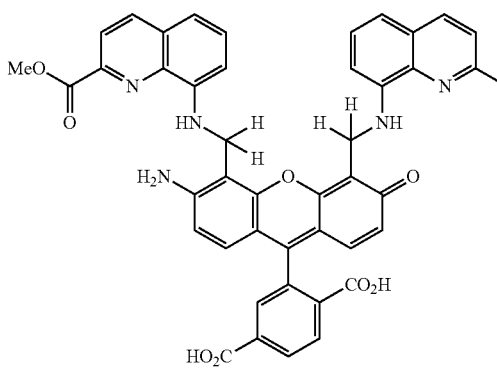
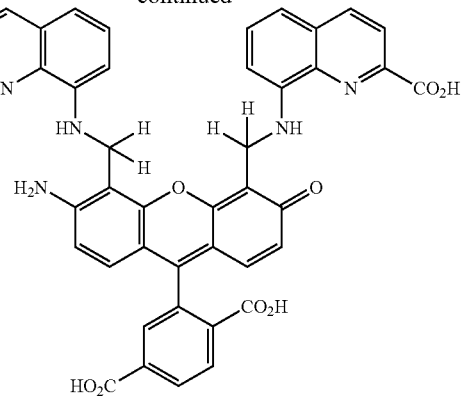
One aspect of the invention relates to a compound of formula A:
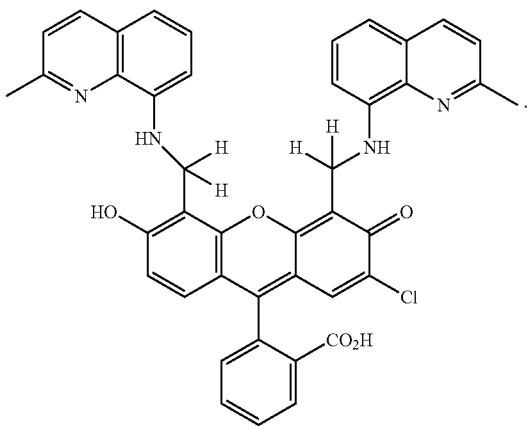
A
One aspect of the invention relates to a compound of formula B:
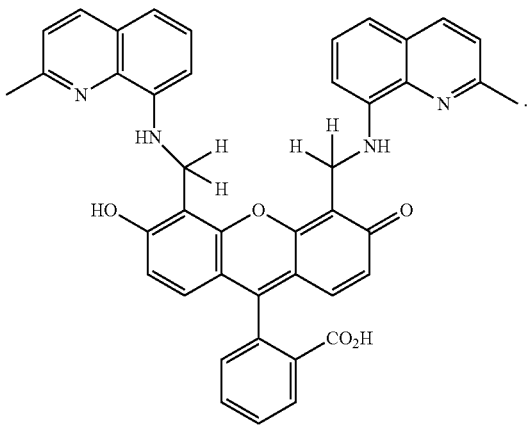
B
One aspect of the invention relates to a compound of any one of claims 106-142, further comprising a transition metal, wherein the transition metal is Mn, Cu, Co, Fe, Ni, Zn, Ru, or Rh. In certain embodiments, the present invention relates to any one of the aforementioned compounds, wherein the transition metal is Cu, Co, Ru, or Rh. In certain embodiments, the present invention relates to any one of the aforementioned compounds, wherein the transition metal is Cu.

One aspect of the invention relates to a compound of formula IIIa:

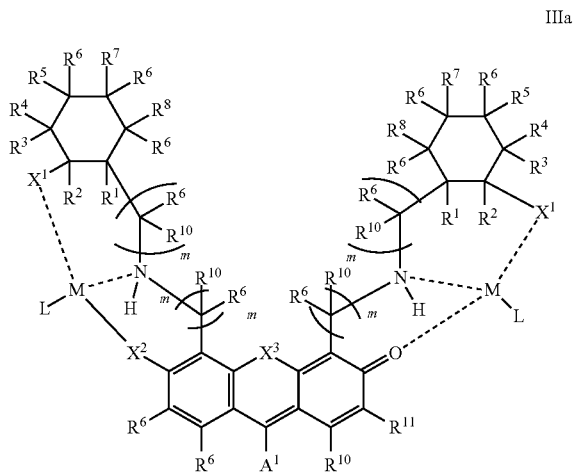

IIIa wherein, independently for each occurrence, $A^1$ is aryl or heteroaryl, both of which are optionally substituted with one or more of halogen, alkoxyl, —OH, —N($R^{12}$)$_2$, —COR$^{12}$, —CO$_2$R$^{12}$, —N(R$^{12}$)C(O)R$^{12}$, or —C(O)N(R$^{12}$)$_2$;

L is a ligand;

M is a transition metal;

$X^1$ is —OR$^9$, —SR$^9$, —N=R$^9$, or —N(R$^{13}$)R$^9$;

$X^2$ is —O—, —S—, or —N(R$^{13}$)—;

$X^3$ is —O—, —S—, or —N(R$^{13}$)—;

$R^1$, $R^3$, $R^5$, $R^7$, $R^8$ and $R^{10}$ each represent independently for each occurrence H, alkyl, aryl or heteroaryl; or $R^1$ and $R^8$ taken together form a bond; or $R^5$ and $R^7$ taken together form a bond;

$R^2$, $R^4$, and $R^6$ each represent independently for each occurrence H, alkyl, aryl, heteroaryl, aralkyl, halogen, alkoxyl, —COR$^{12}$, or —CO$_2$R$^{12}$; or $R^2$ and $R^3$ taken together form a bond; or $R^4$ and $R^9$ taken together form a 5-6 member ring optionally substituted with one or more of alkyl, hydroxyalkyl, aryl, aralkyl, halogen, alkoxyl, —N(R$^9$)$_2$, —COR$^9$, —CO$_2$R$^9$, —N(R$^9$)C(O)R$^9$, or —C(O)N(R$^9$)$_2$;

$R^9$ is H, alkyl, aryl, heteroaryl, or aralkyl;

$R^{11}$ is H, alkyl, aryl, heteroaryl, aralkyl, or halogen;

$R^{12}$ represents independently for each occurrence H, alkyl, aryl, heteroaryl, or aralkyl;

$R^{13}$ represents independently for each occurrence H or ($C_1$-$C_6$)alkyl;

m represents independently for each occurrence 0, 1, 2, 3, or 4; and the stereochemical configuration at any stereocenter of the transition-metal containing compound represented by IIIa is R, S, or a mixture of these configurations.

In certain embodiments, the present invention relates to any one of the aforementioned compounds, wherein $A^1$ is aryl optionally substituted with —CO$_2$R$^{12}$.

In certain embodiments, the present invention relates to any one of the aforementioned compounds, wherein $X^1$ is —N=R$^9$.

In certain embodiments, the present invention relates to any one of the aforementioned compounds, wherein $X^2$ is —O—.

In certain embodiments, the present invention relates to any one of the aforementioned compounds, wherein $X^3$ is —O—.

In certain embodiments, the present invention relates to any one of the aforementioned compounds, wherein $R^1$ and $R^8$ taken together form a bond.

In certain embodiments, the present invention relates to any one of the aforementioned compounds, wherein $R^5$ and $R^7$ taken together form a bond.

In certain embodiments, the present invention relates to any one of the aforementioned compounds, wherein $R^{10}$ is H or alkyl.

In certain embodiments, the present invention relates to any one of the aforementioned compounds, wherein $R^2$ and $R^3$ taken together form a bond.

In certain embodiments, the present invention relates to any one of the aforementioned compounds, wherein $R^4$ and $R^9$ taken together form a 5-6 member ring optionally substituted with one or more of alkyl, aryl, aralkyl, or halogen.

In certain embodiments, the present invention relates to any one of the aforementioned compounds, wherein $R^6$ is H or alkyl.

In certain embodiments, the present invention relates to any one of the aforementioned compounds, wherein $R^{11}$ is halogen. In certain embodiments, the present invention relates to any one of the aforementioned compounds, wherein $R^{11}$ is H.

In certain embodiments, the present invention relates to any one of the aforementioned compounds, wherein $R^{12}$ is H.

In certain embodiments, the present invention relates to any one of the aforementioned compounds, wherein $R^{13}$ is H.

In certain embodiments, the present invention relates to any one of the aforementioned compounds, wherein m is 0 or 1.

In certain embodiments, the present invention relates to any one of the aforementioned compounds 6, wherein $A^1$ is aryl optionally substituted with —CO$_2$R$^{12}$, $X^1$ is —N=R$^9$, $X^2$ is —OR$^{13}$, $X^3$ is —O—, and $R^4$ and $R^9$ taken together form a 5-6 member ring optionally substituted with one or more of alkyl, aryl, aralkyl, or halogen.

In certain embodiments, the present invention relates to any one of the aforementioned compounds, wherein $A^1$ is aryl optionally substituted with —CO$_2$R$^{12}$; $X^1$ is —N=R$^9$, $X^2$ is —OR$^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is halogen; and $R^{10}$ and $R^{12}$ are H. In certain embodiments, the present invention relates to any one of the aforementioned compounds, wherein $A^1$ is aryl optionally substituted with —CO$_2$R$^{12}$; $X^1$ is —N=R$^9$, $X^2$ is —OR$^{13}$; $X^3$ is —O—; $R^4$ and $R^9$ taken together form a 5-6 member ring optionally substituted with one or more of alkyl, aryl, aralkyl, or halogen; $R^6$ and $R^{10}$ each represent independently for each occurrence H or alkyl; $R^{11}$ is H; and $R^{10}$ and $R^{12}$ are H.

In certain embodiments, the present invention relates to any one of the aforementioned compounds, wherein M is Mn, Cu, Co, Fe, Ni, Zn, Ru, or Rh. In certain embodiments, the present invention relates to any one of the aforementioned compounds, wherein M is Cu, Co, Ru, or Rh. In certain embodiments, the present invention relates to any one of the aforementioned compounds, wherein M is Cu.

In certain embodiments, the present invention relates to any one of the aforementioned compounds, wherein L is halogen, alkoxy, —OC(O)alkyl, —OC(O)aryl, or —OC(O)aralkyl. In certain embodiments, the present invention relates to any one of the aforementioned compounds, wherein L is halogen.

One aspect of the invention relates to a compound of formula IVa:

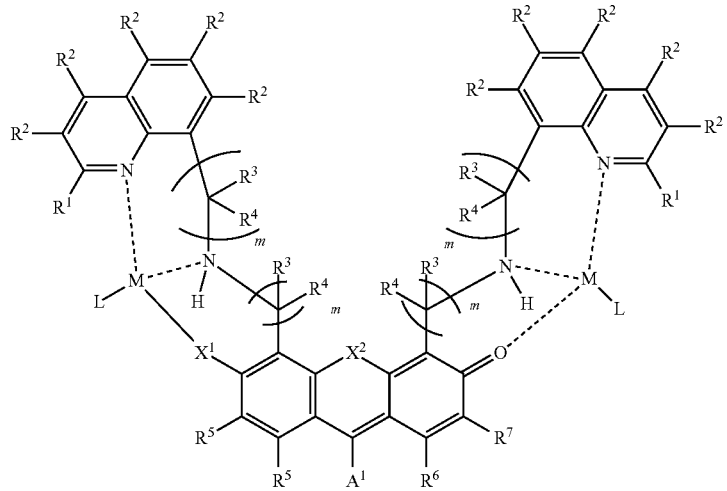

IVa wherein, independently for each occurrence, $A^1$ is aryl or heteroaryl, both of which are optionally substituted with one or more of halogen, alkoxyl, —OH, —N($R^8$)$_2$, —CO$R^8$, or —CO$_2R^8$;

L is a ligand;

M is a transition metal;

$X^1$ is —O—, —S—, or —N($R^6$)—;

$X^2$ is —O—, —S—, or —N($R^6$)—;

$R^1$ represents independently for each occurrence H, alkyl, hydroxyalkyl, aryl, aralkyl, halogen, alkoxyl, —N($R^8$)$_2$, —CO$R^8$, —CO$_2R^8$, —N($R^8$)C(O)$R^8$, or —C(O)N($R^8$)$_2$;

$R^2$, $R^3$, and $R^5$ each represent independently for each occurrence H, alkyl, halogen, alkoxyl, —CO$R^8$, or —CO$_2R^8$;

$R^4$ and $R^6$ each represent independently for each occurrence H or alkyl;

$R^7$ is H or halogen;

$R^8$ represents independently for each occurrence H, alkyl, aryl, heteroaryl, or aralkyl;

m represents independently for each occurrence 0, 1, or 2;

the stereochemical configuration at any stereocenter of the transition-metal containing compound represented by IVa is R, S, or a mixture of these configurations; and $R^1$ is optionally coordinated to M.

In certain embodiments, the present invention relates to any one of the aforementioned compounds, wherein $A^1$ is aryl optionally substituted with one or more of —CO$_2R^8$.

In certain embodiments, the present invention relates to any one of the aforementioned compounds, wherein $X^1$ is —O—.

In certain embodiments, the present invention relates to any one of the aforementioned compounds, wherein $X^2$ is —O—.

In certain embodiments, the present invention relates to any one of the aforementioned compounds, wherein $R^1$, $R^2$, $R^3$, and $R^5$ each represent independently for each occurrence H or alkyl.

In certain embodiments, the present invention relates to any one of the aforementioned compounds, wherein $R^4$ and $R^6$ are H.

In certain embodiments, the present invention relates to any one of the aforementioned compounds, wherein $R^7$ is chloride. In certain embodiments, the present invention relates to any one of the aforementioned compounds, wherein $R^7$ is H.

In certain embodiments, the present invention relates to any one of the aforementioned compounds, wherein $R^8$ represents independently for each occurrence H or alkyl.

In certain embodiments, the present invention relates to any one of the aforementioned compounds, wherein $A^1$ is aryl optionally substituted with —CO$_2R^8$, $X^1$ is —O$R^6$, and $X^2$ is —O—.

In certain embodiments, the present invention relates to any one of the aforementioned compounds, wherein $A^1$ is aryl optionally substituted with —CO$_2R^8$; $X^1$ is —O—; $X^2$ is —O—; $R^1$, $R^2$, $R^3$, and $R^5$ each represent independently for each occurrence H or alkyl; $R^4$ and $R^6$ are H; and $R^7$ is chloride. In certain embodiments, the present invention relates to any one of the aforementioned compounds, wherein $A^1$ is aryl optionally substituted with —CO$_2R^8$; $X^1$ is —O—; $X^2$ is —O—; $R^1$, $R^2$, $R^3$, and $R^5$ each represent independently for each occurrence H or alkyl; $R^4$ and $R^6$ are H; and $R^7$ is H.

In certain embodiments, the present invention relates to any one of the aforementioned compounds, wherein $A^1$ is aryl optionally substituted with —CO$_2R^8$; $X^1$ is —O—; $X^2$ is —O—; $R^1$, $R^2$, $R^3$, and $R^5$ each represent independently for each occurrence H or alkyl; $R^4$ and $R^6$ are H; $R^7$ is chloride; $R^8$ is H; m represents independently for each occurrence 0 or 1. In certain embodiments, the present invention relates to any one of the aforementioned compounds, wherein $A^1$ is aryl optionally substituted with —CO$_2R^8$; $X^1$ is —O—; $X^2$ is —O—; $R^1$, $R^2$, $R^3$, and $R^5$ each represent independently for each occurrence H or alkyl; $R^4$ and $R^6$ are H; $R^7$ is H; $R^8$ is H; m represents independently for each occurrence 0 or 1.

In certain embodiments, the present invention relates to any one of the aforementioned compounds 3, wherein M is Mn, Cu, Co, Fe, Ni, Zn, Ru, or Rh. In certain embodiments, the present invention relates to any one of the aforementioned compounds, wherein M is Cu, Co, Ru, or Rh. In certain embodiments, the present invention relates to any one of the aforementioned compounds, wherein M is Cu.

In certain embodiments, the present invention relates to any one of the aforementioned compounds, wherein L is halogen, alkoxy, —OC(O)alkyl, —OC(O)aryl, or —OC(O) aralkyl. In certain embodiments, the present invention relates to any one of the aforementioned compounds, wherein L is halogen.

Methods of Treatment

Another aspect of the present invention relates to a method of treating a bacterial infection in a mammal, comprising the step of administering to a mammal in need thereof a therapeutically effective amount of an inhibitor of a bacterial nitric oxide synthase. In certain embodiments, the present invention relates to the aforementioned method, wherein said mammal is a human.

In certain embodiments, the present invention relates to either of the aforementioned methods, wherein said bacteria is *Bacillus* spp., *Staphylococcus* spp. or *Norcardia* spp. In certain embodiments, the present invention relates to either of the aforementioned methods, wherein said bacteria is *Bacillus subtilis*, *Bacillus anthracis*, *Bacillus anthracis* Sterne, *Staphylococcus aureus*, or methicillin-resistant *Staphylococcus aureus*.

In certain embodiments, the present invention relates to any one of the aforementioned methods, wherein said inhibitor has an $IC_{50}$ against said bacterial nitric oxide synthase of less than or equal to 1 micromolar. In certain embodiments, the present invention relates to any one of the aforementioned methods, wherein said inhibitor has an $IC_{50}$ against said bacterial nitric oxide synthase of less than or equal to 100 nanomolar. In certain embodiments, the present invention relates to any one of the aforementioned methods, wherein said inhibitor has an $IC_{50}$ against said bacterial nitric oxide synthase of less than or equal to 10 nanomolar.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

In part, the subject invention is directed to a diagnostic kit for nitric oxide, comprising: a) a fluorescein-based ligand of the subject invention; and b) instructions for using said ligand to detect nitric oxide in a sample.

EXEMPLIFICATION

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified.

Example One

Synthesis of Copper-Fluorescein Sensors

Figure 4:
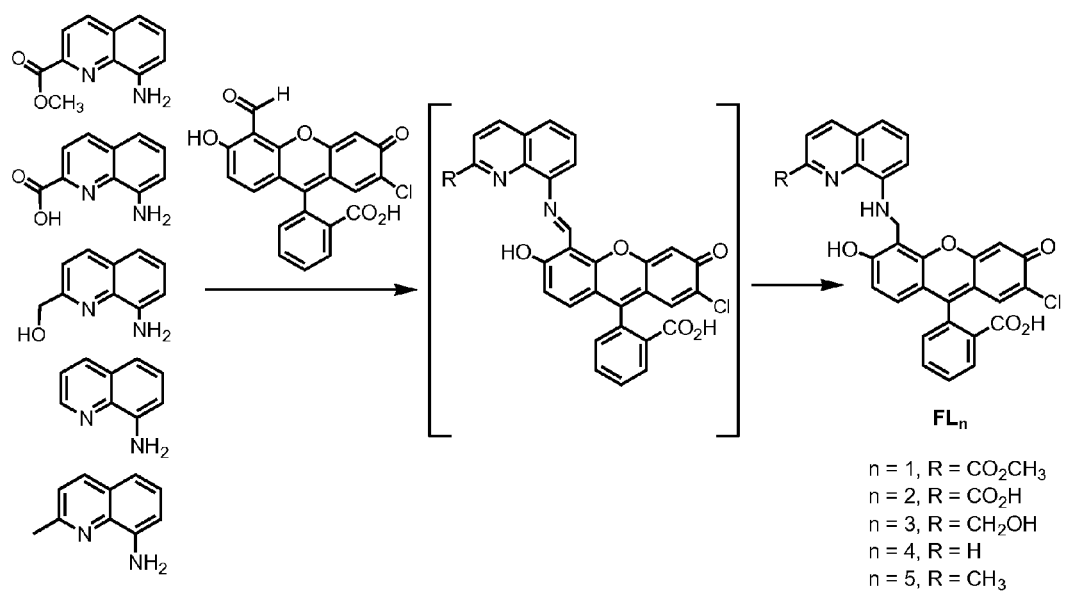
FIG. 4 depicts synthetic strategies for five fluorescein ligands $FL_n$ (n=1-5).
Figure 5:
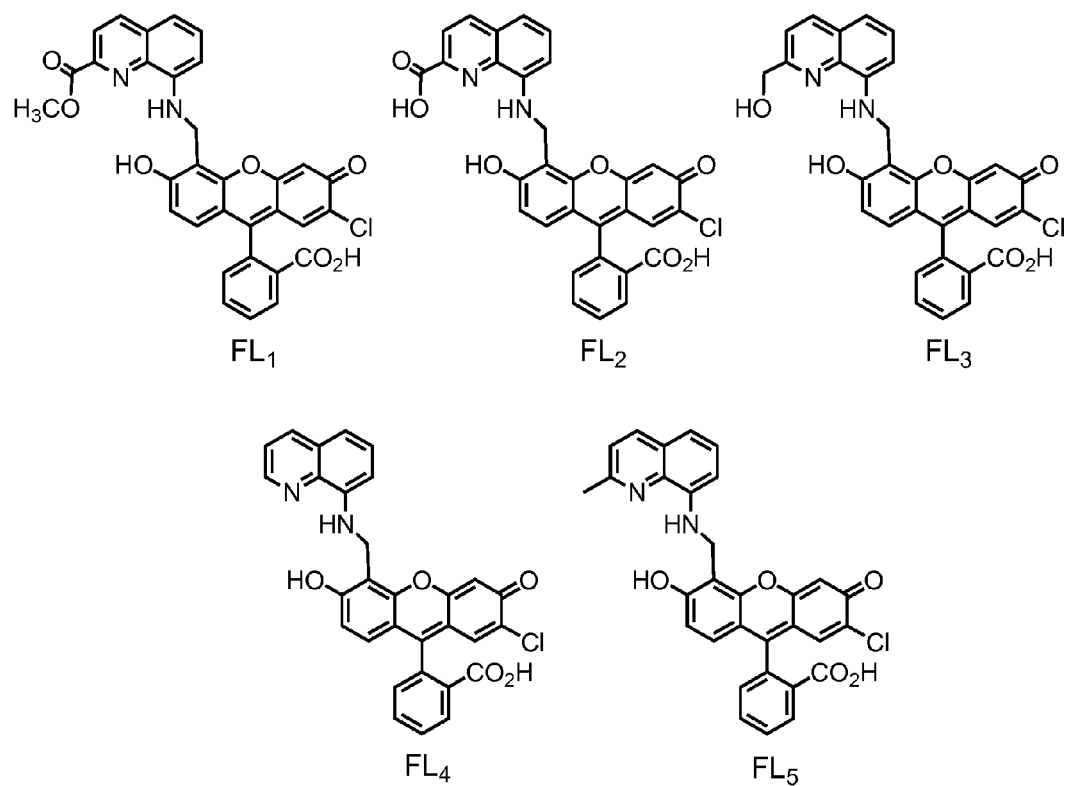
FIG. 5 depicts the structures of the five fluorescein ligands produced according to the syn two Gram-positive bacteria THAT express bNOS, *Bacillus subtilis* and *Bacillus anthracis*, are capable of producing NO in vivo by hijacking a non-committed cellular reductase to provide electrons for substrate oxidation (see FIG. 2). This conclusion was confirmed by use of a highly NO-specific turn-on fluorescent probe (CuFL). Lim, M. H.; Wong, B. A.; Pitcock, J., William, H.; Mokshagundam, D.; Bai, M.-H.; Lippard, S. J., Direct Nitric Oxide Detection in Aqueous Solution by Copper(11) Fluorescein Complexes. J. Am. Chem. Soc. 2006, 128, 14364-14373; Lim, M. H.; Xu, D.; Lippard, S. J., Visualization of Nitric Oxide in Living Cells by Fluorescence Detection. Nat. Chem. Biol. 2006, 2, 375-380.
Figure 6:
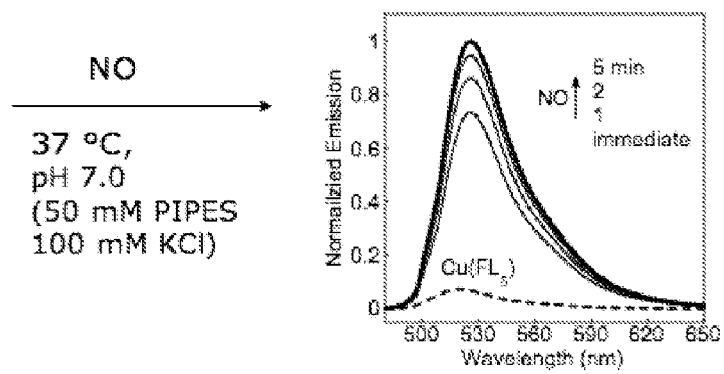

FIG. 4 depicts the synthetic strategies for the five fluorescein ligands $FL_n$ (n=1-5). FIG. 5 depicts the structures of the five fluorescein ligands. Fluorescence studies of the five sensors are depicted in FIG. 6.

Example Two

Detailed Synthetic Method For Copper-Fluorescein Sensor $Cu(FL_5)$

Derivatized fluorescein molecules are excellent biosensors because they excite and emit in a region of the visible spectrum that is relatively free of interference. We prepared the fluorescein-based ligand $FL_5$ (FIG. 7) by reacting 7'-chloro-4'-fluorescein-carboxaldehyde with 8-aminoquinaldine. We generated the Cu(II) fluorescein-based NO probe $Cu(FL_5)$ (FIG. 4) in situ reacting $FL_5$ (prepared as described below) with $CuCl_2$ in a 1:1 ratio in buffered aqueous solution (50 mM PIPES, pH 7.0, 100 mM KCl). The Cu(II) species exhibited a blue-shifted $\lambda_{max}$ at 499 nm ($\epsilon$=4.0×10$^4$ M$^{-1}$cm$^{-1}$), compared to that of $FL_5$ (504 nm, $\epsilon$=4.2×10$^4$ M$^{-1}$cm$^{-1}$). A Job's plot was constructed to evaluate the nature of the $FL_5$:Cu(II) complex by following the UV-vis absorption spectral change at 512 nm in pH 7.0 buffered solution. A break at 0.5 indicated the formation of a 1:1 complex. The negative ion electrospray mass spectrum of this species displays a peak with m/z of 632.0 corresponding to [Cu(FL$_5$)Cl—H]$^-$ (calcd. m/z 632.0). When $FL_5$ was titrated with $CuCl_2$ at 25° C., the absorption changes could be fit to a one-step binding equation with an apparent dissociation constant ($K_d$) of 1.5±0.3 µM for Cu(II) ion.

A. Synthesis of 2-{2-chloro-6-hydroxy-5-[(2-methyl-quinolin-8-ylamino)-methyl]-3-oxo-3H-xanthen-9-yl}-benzoic acid (FL$_5$). To 2 mL of EtOAc were added 7'-chloro-4'-fluorescein-carboxalde (30 mg, 0.076 mmol) and 8-aminoquinaldine (12 mg, 0.076 mmol). After the reaction was stirred overnight at room temperature, the solvent was removed under reduced pressure. The residue was dissolved in 2 mL of MeOH and the reaction solution was cooled to 0° C. A portion of NaBH$_4$ (14 mg, 0.38 mmol) was added and the reaction solution was stirred at 0° C. for 1 h before being allowed to come slowly to room temperature with stirring overnight. The solvent was removed under reduced pressure and the crude material was purified by preparative TLC on silica gel (CH$_2$Cl$_2$:MeOH, 20:1 v/v): R$_f$=0.34, affording the FL product as a magenta solid (9 mg, 0.017 mmol, 22%).

B. Alternative synthesis of 2-{2-chloro-6-hydroxy-5-[(2-methyl-quinolin-8-ylamino)-methyl]-3-oxo-3H-xanthen-9-yl}-benzoic acid (FL$_5$). 7'-chloro-4'-fluorescein-carboxaldehyde (75.4 mg, 0.191 mmol) and 8-aminoquinaldine (46.6 mg, 0.295 mmol) were combined in 10 mL of methanol and stirred at room temperature for 1 h. The resulting dark red suspension was cooled to 0° C. and sodium borohydride (22.9 mg, 0.605 mmol) was added, causing the suspension to clarify into a bright red solution. The reaction was stirred while warming to room temperature for 1 h, and then quenched with 10 mL of water. The solvents were removed under reduced pressure and the crude material was purified by column chromatography on silica gel (CH$_2$Cl$_2$:CH$_3$OH, 49:1 v/v) to afford FL$_5$ as a red solid (30.8 mg, 0.057 mmol, 30%). This alternative synthesis produced higher yields of FL$_5$.

Additionally, the product was purified by column chromatography rather than preparative TLC, as outlined in procedure "A" above.

C. Synthesis of 2-{2-chloro-6-hydroxy-5-[((2-methylquinolin-8-yl)(nitroso)amino)-methyl]-3-oxo-3H-xanthen-9-yl}-benzoic acid, $FL_5$-NO. Sodium nitrite ($Na^{14}NO_2$ or $Na^{15}NO_2$, 5 mg, 72 μmol, in 100 μL dd $H_2O$) was added to a mixture of $FL_5$ (1.5 mg, 2.8 μmol, in 200 μL $CH_3OH$) and 0.3 M NaOH (aq, 100 μL) on ice. Hydrochloric acid (100 μL, 6 M aq) was slowly introduced to the reaction solution on ice, affording a reddish precipitate. After the solution was centrifuged, LC-MS analyses of both the supernatant and the precipitate, redissolved in $MeOH/H_2O$, were performed. The latter revealed a mixture of $FL_5$-NO and $FL_5$ (data not shown). The supernatant mostly contained the expected product $FL_5$-NO. Excess sodium nitrite was removed from the supernatant by dialysis using a Spectra/Pro® CE (Spectrum®) membrane (MW cutoff 500). An orange solid sample (0.6 mg, 1.1 μmol, 39%) of $FL_5$-NO was obtained by lyophilization and characterized without further purification. TLC (silica, 1:9 $CH_3OH:CH_2Cl_2$) showed only one component with $R_f$=0.6.

Example Three

Fluorescence and Mechanistic Studies of $Cu(FL_5)$ with NO

Figure 8:
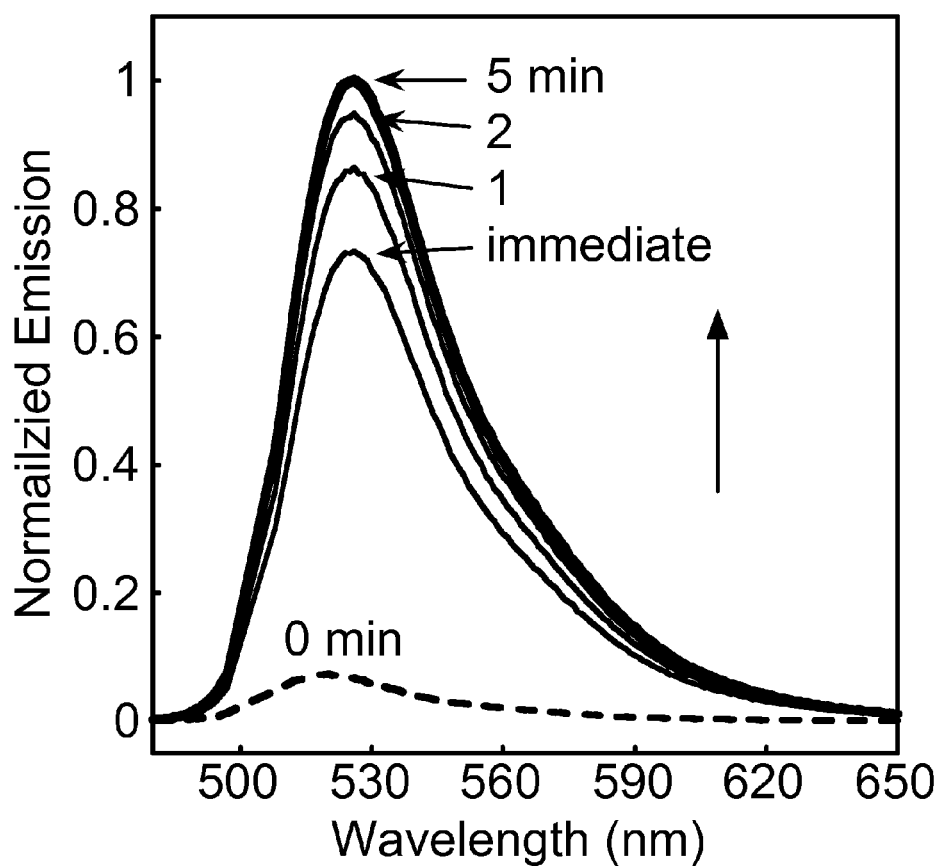
Figure 9:
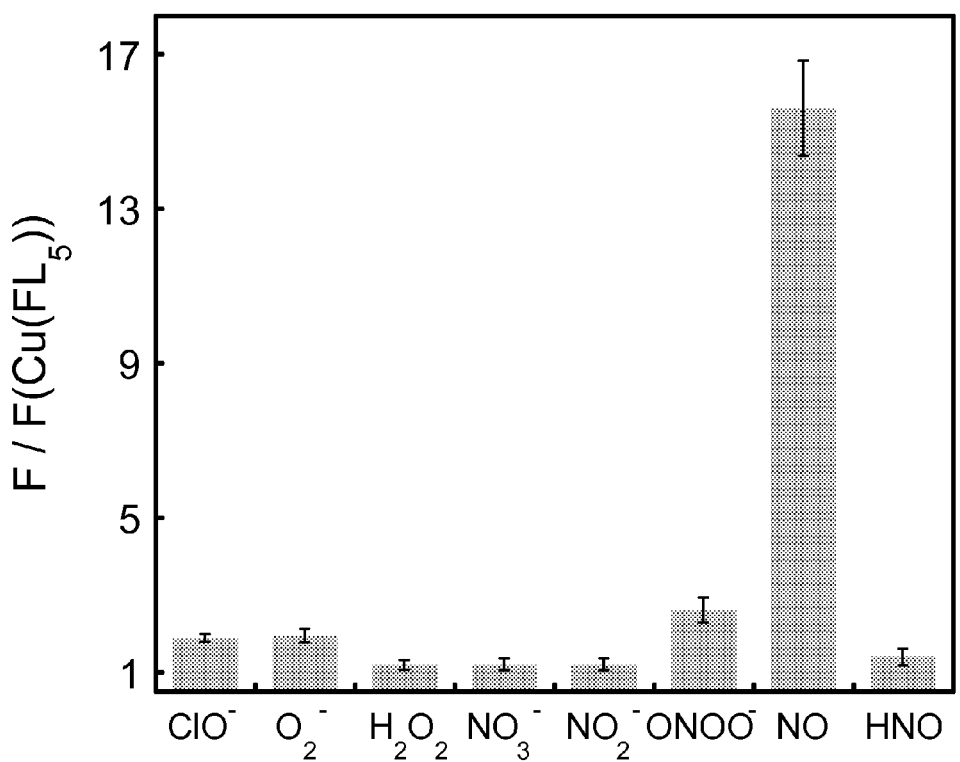

The fluorescence of a 1 μM $FL_5$ solution was diminished by 18±3% upon introduction of an equimolar quantity of $CuCl_2$ at 37° C. Addition of excess NO to a buffered aqueous $Cu(FL_5)$ solution led to an immediate 11.2±1.5-fold increase in fluorescence (FIG. 8). Fluorescence was also enhanced when $Cu(FL_5)$ was allowed to react with the NO-releasing chemical agent S-nitroso-N-acetyl-D,L-penicillamine (SNAP) at pH 7.0 (50 mM PIPES, 100 mM KCl) over a 30 min time interval. This result demonstrates rapid NO detection with significant turn-on emission at a physiologically relevant pH. The lower detection limit for NO is 5 nM. The fluorescence response of the $Cu(FL_5)$ probe detects NO specifically over other reactive species present in biological systems, including $O_2^-$, $ClO^-$, $H_2O_2$, HNO, $NO_2^-$, $NO_3^-$, and $ONOO^-$ (FIG. 9).

A commercially available NO probe, DAF-2 (o-diaminofluorescein), was used for comparison with $Cu(FL_5)$. The fluorescence of DAF-2 is unchanged in the presence of NO and the absence of $O_2$ over a period of 1 h. It only displays turn-on fluorescence when $O_2$ is present, indicating that DAF-2 is incapable of direct NO detection. $Cu(FL_5)$, however, shows an immediate fluorescence response under both anaerobic and aerobic conditions.

In a control experiment, a copper-free $FL_5$ solution treated with excess NO displayed only a small, 1.5±0.2-fold increase in fluorescence over 30 min. In addition, the fluorescence was only marginally increased (1.3±0.2-fold) upon addition of NO to the $Cu(FL_5)$ solution in the presence of excess N,N'-1,2-ethanediylbis-(N-(carboxymethyl)glycine) (EDTA), which chelates Cu(II) ion. Both results indicate that the binding of $FL_5$ to Cu(II) is indispensable for fluorescence enhancement by NO.

Figure 7:
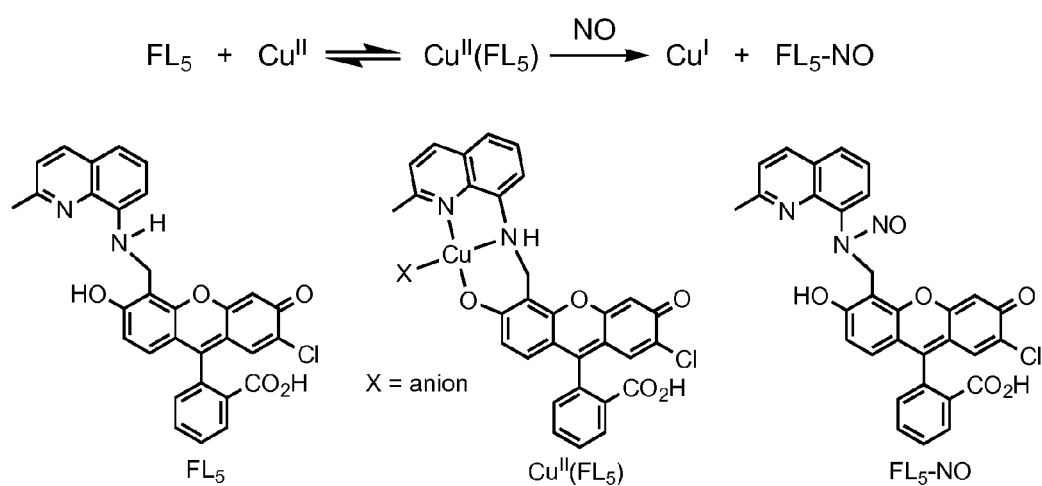

As depicted in FIG. 7, NO detection by $Cu(FL_5)$ occurs, formally, by nitric oxide-induced reduction of Cu(II) to Cu(I), forming $NO^+$, which nitrosates the ligand with concomitant dissociation from copper and fluorescence turn-on. The mechanism of turn-on emission of $Cu(FL_5)$ by NO was investigated by EPR, UV-vis, NMR and fluorescence spectroscopy and by liquid chromatography-mass spectrometry (LC-MS, low resolution MS). The EPR experiment revealed a 2.9-fold decrease of the axial Cu(II) signal upon $Cu(FL_5)$ reaction with 5 equivalents of NO in DMF, confirming the formation of a Cu(I) species. A mixture of $FL_5$ and $[Cu(CH_3CN)_4](BF_4)$ shows the same fluorescence intensity as that of $FL_5$ and exhibited only a 1.3±0.1-fold increase in fluorescence over 30 min when treated with excess NO. This result indicates that $Cu(I)(FL_5)$ is not the species responsible for the fluorescence increase in the NO reaction of $Cu(FL_5)$.

LC-MS analyses of the NO reaction product with $Cu(FL_5)$ (pH 7.0 buffered aqueous solution) revealed a major peak (93±3%) in the chromatogram with m/z=564.7, 600.5, and 1128.9, masses corresponding to those of $[FL_5+NO-2H]^-$ (calcd. m/z 564.1), $[FL_5+NO—H+Cl]^-$ (calcd. m/z 600.0), and $[2(FL_5+NO)-3H]^-$ (calcd. m/z 1129.2), respectively. This species, which results from nitrosation of the $FL_5$ ligand ($FL_5$-NO, FIG. 7), is stable for several days at pH 7.0, indicating the irreversibility of the NO reaction with $Cu(FL_5)$. $FL_5$-NO was independently prepared by the reaction of $FL_5$ with $HNO_2$ and was analyzed by LC-MS, revealing only one LC peak with m/z=564.6, 600.1, and 1129.2 and appearing at the same retention time as that of the reaction product of $Cu(FL_5)$ with NO. The electrospray mass spectrum of $FL_5$-$^{15}NO$ obtained from a reaction of $FL_5$ with $H^{15}NO_2$ exhibited the shifts in m/z (565.8, 601.3, and 1131.2) expected for the Δm/z values of $^{14}NO$ vs $^{15}NO$. ESI-MS/MS analysis of the major peaks with m/z=564.6 or 565.8 indicated that a NO functionality is embedded in the final NO reaction product. High resolution MS of $FL_5$-$^{14}NO$ and $FL$-$^{15}NO$ were also obtained, showing m/z=600.0729 for $FL_5$-$^{14}NO$ and 601.0736 for $FL_5$-$^{15}NO$, corresponding to $[FL_5+NO—H+Cl]^-$ (calcd. m/z 600.0729 and 601.0700).

Upon addition of excess NO, a 499 nm peak in the UV-vis spectrum of $Cu(FL_5)$ in pH 7.0 buffered solution red-shifted back to the $\lambda_{max}$ characteristic of $FL_5$ or the synthetic $FL_5$-NO compound (504 nm), which differs from the band formed in the reaction of $FL_5$ with 1 equivalent of Cu(I) added as $[Cu(CH_3CN)_4](BF_4)$ (506 nm). This result indicates that the nitrosation reaction may occur at the metal binding site, which has one oxygen and two nitrogen donor atoms, releasing the nitrosated ligand from the copper center. The optical spectrum of the reaction of a pH 7.0 solution of $Cu(FL_5)$ with NO exhibited the same features as that of the dianionic form of $FL_5$ at pH 7.0. In addition, the spectrum of the NO reaction solution closely resembled that of the monoanionic fluorescein formed by lowering the pH from 7.0 to 5.0. These spectroscopic observations are consistent with those of fluorescein, the properties of which vary with pH, and strongly imply that $FL_5$ nitrosation does not occur at a hydroxyl group on the xanthene ring. To pinpoint the position of $FL_5$ nitrosation, an $^{15}N$ NMR spectrum of $FL_5$-$^{15}NO$ was recorded, revealing $^{15}N$ chemical shifts at 167.33 and 169.61 ppm vs $CH_3NO_2$ in a relative ratio of 7:3. These values are in the range previously reported for N-nitrosamines. The presence of two separate chemical shifts might arise from different isomers in solution, the Δδ of 2.29 being similar to that of previously reported of N-nitrosamines. A $^1H$ NMR spectrum of the isolated $FL_5$-NO molecule also revealed the presence of a 7:3 isomeric mixture. Both the $^{15}N$ chemical shift values and the existence of isomers in the $^{15}N$ NMR spectrum of $FL_5$-NO clearly demonstrate that $FL_5$ is N-nitrosated at the secondary amine functionality, as illustrated in FIG. 4. Lastly, $FL_5$-NO is brighter than $FL_5$ or $Cu(FL_5)$, the respective quantum yields being $\Phi_{FL-NO}=0.58\pm0.02$ and $\Phi_{FL}=0.077\pm0.002$.

Taken together, these results demonstrate that $Cu(FL_5)$ is capable of fluorescent NO detection via NO-induced metal reduction followed by the release of the nitrosated ligand from copper with concomitant fluorescence enhancement (FIG. 7). Formation of an N-nitrosamine was previously observed in the reaction of NO with a Cu(II) complex containing two anthracene groups as light-emitting units in aqueous methanol solution with fluorescence turn-on over 46 min. Other copper fluorophore complexes have been reported as fluorescent NO indicators and similarly operate via reduction of Cu(II) to Cu(I) by NO.

Example Four

Cu(FL$_5$) Detection of NO Produced by cNOS

We investigated the ability of Cu(FL$_5$) to detect NO produced in SK—N—SH human neuroblastoma cells under physiological conditions, since constitutive NO synthase ("cNOS") in this cell line can be activated by estrogen to produce NO. Estrogen administration leads to an increase in the cytosolic Ca(II) concentration that alters the structure of calmodulin, which in turn activates cNOS. The NO-dependent fluorescence response, monitored after simultaneous administration of 17β-estradiol (100 nM) and Cu(FL$_5$) (1 µM) to the cells, was complete within 5 min with a 4.0±0.6-fold increase in fluorescence (FIGS. 10a and b). We also demonstrated an increase in cytosolic Ca(II) levels following addition of 17β-estradiol to SK—N—SH cells using the calcium dye fluo-4 AM, which is consistent with estrogen induction of Ca(II)-dependent NO production. A notably weaker fluorescence response was observed in the presence of the cNOS inhibitor N$^G$-nitro-L-arginine (L-NNA), pinpointing nitric oxide to be responsible for the fluorescence change (FIG. 10c). In a control experiment, stimulated SK—N—SH cells incubated with FL$_5$ in the absence of Cu(II) ion exhibited no fluorescence increase over a period of 25 min. This result demonstrates that Cu(FL$_5$), but not FL$_5$, is responsible for the fluorescence change. As another control, HeLa cells were co-treated with 17β-estradiol (100 nM) and Cu(FL$_5$) (1 µM). The absence of turn-on emission in these cells indicates that the fluorescence response of Cu(FL$_5$) is not a consequence of its interaction with 17β-estradiol.

The value of Cu(FL$_5$) as a probe for NO-related research has been further demonstrated by comparing its ability to image NO in cells with that of a commercially available sensor DAF-2 DA (o-diaminofluorescein diacetate). Firstly, Cu(FL$_5$) visualizes NO in the estradiol-stimulated neuroblastoma cells with brighter fluorescence than DAF-2 DA (o-diaminofluorescein diacetate). In addition, there was only a slight fluorescence increase of DAF-2 DA-treated cells 30 min after activation of cNOS, whereas Cu(FL$_5$) provided complete fluorescence enhancement within 5 min. These results reveal that Cu(FL$_5$) allows fast and direct visualization of NO in live cells.

Example Five

Cu(FL$_5$) Detection of NO Produced by iNOS

In macrophages, nitric oxide is produced by inducible NO synthases ("iNOS"). Time-dependent NO production by Raw 264.7 cells pretreated with bacterial lipopolysaccharide (LPS) and interferon-γ (IFN-γ) has been previously demonstrated by using the Griess assay. This method colorimetrically determines the concentration of NO$_2^-$ resulting from NO oxidation in the extracellular space. Fluorescence detection of NO production by stimulated macrophage cells was also achieved by incubation of the extracellular fluid with DAN and DAFs. These dyes improved the sensitivity of Griess assay, but were unable to reveal NO production inside cells with spatial and temporal fidelity. The present Cu(FL$_5$) construct, however, readily detects NO produced in activated Raw 264.7 cells by fluorescence turn-on. Macrophage cells were incubated with LPS (500 ng/mL) and IFN-γ (250 U/mL) for 4 h, after which 1 µM Cu(FL$_5$) was applied. The fluorescence response was monitored at 2 h intervals by microscopy (FIG. 11a). The average fluorescence slowly increased over 12 h in almost every region of the treated cells.

The production of nitric oxide in LPS- and IFN-γ treated macrophages was independently confirmed by the Griess assay, which revealed identical kinetics of NO formation inside and outside the cells over the 12 h period of the experiment. To investigate further the origin of fluorescence detected by Cu(FL$_5$), iNOS was silenced in Raw 264.7 cells by short hairpin RNA (shRNA)-induced RNA interference (RNAi) (FIG. 11b). Upon stimulation by LPS and IFN-γ, the cells with iNOS attenuated displayed a much weaker fluorescence response than those harboring only the plasmid vector (FIG. 11c), clearly demonstrating that the fluorescence enhancement is caused by nitric oxide production in Raw 264.7 cells. In addition, a notably weaker fluorescence response was observed for stimulated Raw 264.7 cells in the presence of N$^G$-methyl-L-arginine (L-NMA), a known inhibitor of iNOS that attenuates NO production, than in its absence. As a control experiment, turn-on fluorescence emission was not observed after FL$_5$ treatment without Cu(II) ion for Raw 264.7 cells stimulated by LPS and IFN-γ over the 12 h incubation period and for HeLa cells treated with LPS and IFN-γ prior to Cu(FL$_5$) incubation.

Example Six

NO Imaging in a Raw 264.7 and SK—N—SH Co-Culture

Figure 12:
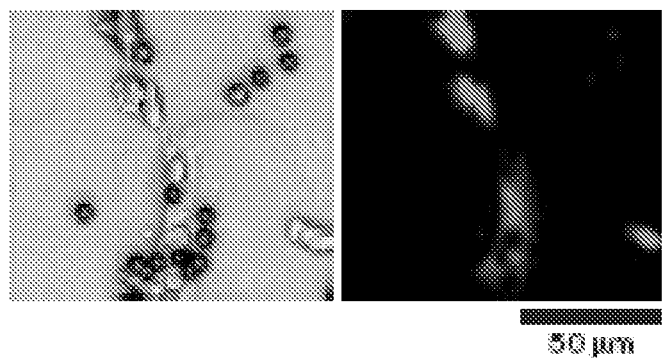

The fluorescence response was also monitored in a mixture of Raw 264.7 and SK—N—SH cells grown on the same plate and co-treated with 17β-estradiol (100 nM) and Cu(FL$_5$) (1 µM) for 10 min. As shown in FIG. 12, a fluorescence increase was observed exclusively in the SK—N—SH cells following cNOS activation by 17β-estradiol-triggered Ca(II) release into cytosol. This result demonstrates that Cu(FL$_5$) might be used to provide information about which types of cells are producing NO in a heterogeneous tissue, and possibly be useful for identifying the time and location of intercellular signaling events.

Example Seven

Cytotoxicity of Cu(FL$_5$) and FL$_5$-NO

To test the toxicity of Cu(FL$_5$), a MTT [3-(4,5-dimethylthiazol-2-yl)-2,5-diphenyltetrazolium bromide] assay was performed on SK—N—SH cells after 5 days of incubation with Cu(FL$_5$) (1 µM). The result [80±9% survival of cells] indicates that the Cu(II)-containing probe is not toxic to SK—N—SH cells under the conditions of NO imaging employed herein.

The MTT assay also indicated 90±3% survival of Raw 264.7 cells after incubation with Cu(FL$_5$) (1 µM) for 5 days, indicating that Cu(FL$_5$) is not toxic to this cell line. Furthermore, Cu(FL$_5$) does not affect the expression of iNOS in Raw 264.7 cells upon introduction of LPS and IFN-γ, which suggests that the concentration of Cu(FL$_5$) used for imaging does not interrupt the biological pathways required for NO production via gene expression.

Lastly, the toxicity of $FL_5$-NO, the product of the reaction of $Cu(FL_5)$ with NO, was examined in SK—N—SH cells by the MTT assay, which revealed 97±2% cell survival after 5 days. Thus, both $Cu(FL_5)$ and $FL_5$-NO are not toxic under the conditions used here for bioimaging of NO.

Example Eight

Cell Cultures and Assays

Raw 264.7, SK—N—SH, and HeLa cells were purchased from the American Type Culture Collection (ATCC). All three cell lines were maintained in Dulbecco's modified Eagles' media (DMEM) (GibcoBRL) containing 10% (v/v) heat-inactivated fetal bovine serum (FBS) (HyClone), 1 mM sodium pyruvate (Sigma), 100 units/mL penicillin, 100 µg/mL streptomycin (Invitrogen), and 0.1 mM nonessential amino acid solution for minimal essential medium (Sigma). All cells were grown at 37° C. in a humidified atmosphere of 10% $CO_2$. A nitrite assay was performed with Griess reagents (Promega) on Raw 264.7 cells grown in DMEM free of phenol red. Calcium sensor fluo-4 AM was purchased from Invitrogen. The expression of iNOS in Raw 264.7 cells was analyzed by Western blot on the extracts of cells stimulated by LPS and INF-γ. The protein was silenced by short hairpin RNA-induced RNAi and the resulting cell lines were used in fluorescence imaging by $Cu(FL_5)$.

Example Nine

Discussion of Examples 2-8

An imaging agent to detect NO directly in vitro at neutral pH as well as in live cells has been devised. The probe is a Cu(II) complex $Cu(FL_5)$ (FIG. 7) containing a fluorescein-based ligand that provides suitable excitation and emission wavelengths as well as brightness for NO bioimaging. This Cu(II)-based compound directly captures NO in a reaction that generates Cu(I) and NO. The latter reacts irreversibly with the fluorescein-based ligand $FL_5$, which is nitrosated and released from copper with significant turn-on fluorescence (FIG. 7, FIG. 8). This mechanism was proved by detailed spectroscopic, magnetic, and mass spectrometric measurements. A comparison of $Cu(FL_5)$ with DAF-2 clearly reveals that only $Cu(FL_5)$ can directly detect NO with fluorescence turn-on in the absence of oxygen. The ability of $Cu(FL_5)$ to image NO specifically over other reactive nitrogen or oxygen species in living organisms (FIG. 9), such as $O_2^-$, $ClO^-$, HNO, $NO_2^-$, $NO_3^-$, $ONOO^-$, and $H_2O_2$, increases its value for a wide range of biological studies.

Figure 10:
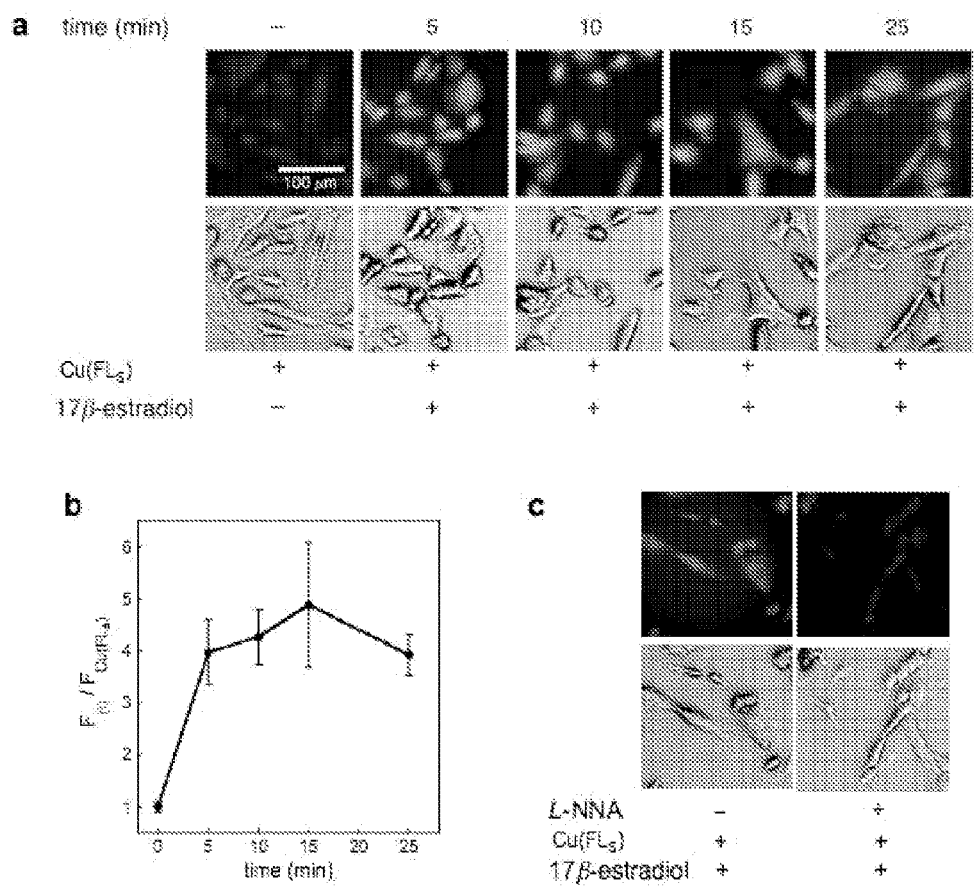
Figure 11:
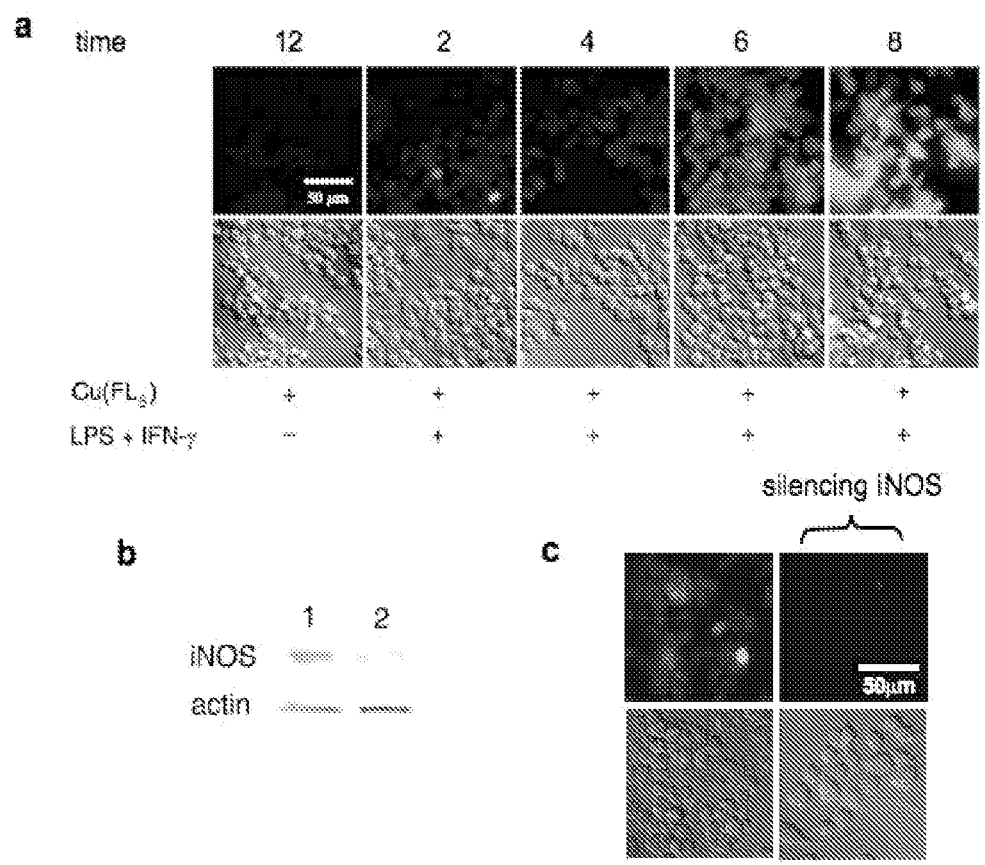

In mammalian cells, nitric oxide is produced by three isoforms of NO synthase (NOS): neuronal NOS (nNOS), endothelial NOS (eNOS) and inducible NOS (iNOS), the catalytic activities of which are well-studied. Functionally, NOS can be categorized as cNOS or iNOS. cNOS, including nNOS and eNOS, is regulated by the cytosolic calcium concentration and produces physiological quantities of NO. The Ca(II)-independent iNOS that provides the pathophysiological concentrations of NO is controlled by gene transcription. We applied $Cu(FL_5)$ to image NO production in Raw 264.7 murine macrophage and SK—N—SH human neuroblastoma cells (FIGS. 10 and 11). Our studies in both cell lines demonstrate that $Cu(FL_5)$ affords direct visual detection of NO production in a time- and concentration-dependent manner from both cNOS and iNOS in living cells with greater than about 4-fold fluorescence enhancement and spatial resolution at a cellular level. Cell-type specific fluorescent NO imaging in a co-culture of the two cell lines reveals that $Cu(FL_5)$ is capable of detecting a source of nitric oxide production in a complex and heterogeneous biological system (FIG. 12).

Solution and live cell studies (FIGS. 8, 10, and 11) clearly demonstrate that $Cu(FL_5)$ is the species responsible for NO detection with fluorescence turn-on. Since the $K_d$ of $Cu(FL_5)$ is 1.5 µM in 50 mM PIPES, pH 7.0, 100 mM KCl, however, the intensity of the observed signal might reflect both the degree of $Cu(FL_5)$ integrity and the amount of NO produced in the cells. Since the concentrations of $FL_5$, Cu(II), and $Cu(FL_5)$ inside cells have yet to be quantified, one cannot presently delineate how these two variables affect the intracellular fluorescence signal. A comparison of NO sensing by $Cu(FL_5)$ vs the commonly used DAF-2 DA reagent, however, reveals that $Cu(FL_5)$ provides rapid NO production with bright fluorescence signals in live cells, which is a significant improvement over this and other organic molecule-based NO probes.

Since the N-nitrosamine $FL_5$-NO generated by the chemistry of $Cu(FL_5)$ in nitric oxide detection is a member of a class of reactive molecules, potential cytotoxicity was investigated. An MTT assay indicates that it is not toxic at the concentration required for NO imaging in the present studies, since 97±2% of SK—N—SH cells treated with $FL_5$-NO for 5 days survived. Another potential problem is that the copper ion in this $Cu(FL_5)$ might damage cells before or following its reaction with NO. In order to address this possibility, an MTT cytotoxicity assay on cells treated with 1 µM $Cu(FL_5)$ was performed, which indicated them to be largely viable (>80%) after 5 days. Thus, under the conditions used for the present NO bioimaging experiments, the toxicity of $Cu(FL_5)$ is negligible.

The cytosol contains thiols that bind Cu(II) and possibly convert it to Cu(I), a species that might itself react with oxidized NO products such as $NO^1$ or $N_2O_3$. Since $NO^1$ is rapidly hydrolyzed to $NO_2^-$ in water, it will not interfere with NO imaging by $Cu(FL_5)$. S-nitrosothiols, formed by reactions of thiols with NO in the presence of $O_2$, react with both $Cu(II)(FL_5)$ and $Cu(I)(FL_5)$ to display turn-on fluorescence as demonstrated in experiments with SNAP. At present one cannot completely rule out the possibility that the fluorescence increase results from reaction of $Cu(FL_5)$ with S-nitrosothiols produced by NO in the stimulated cells. Finally, reduction of Cu(II) by thiols may not alter the integrity or otherwise disrupt the NO-imaging ability of $Cu(FL_5)$ in cells. Cu(II) binding to $FL_5$ is necessary for fluorescence turn-on by NO. Moreover, a mixture of $FL_5$ and Cu(I) does not lead to a fluorescence increase either in the presence or absence of NO, compared to $FL_5$ alone. These experiments strongly support the conclusion that the turn-on fluorescence in the stimulated cells results from the direct reaction of $Cu(FL_5)$ with NO and that intracellular thiols do not interfere with this chemistry.

In summary, Cu(II)-based fluorescein compound $Cu(FL_5)$ for imaging NO based on redox chemistry was synthesized. Reduction of $Cu(FL_5)$ by NO to Cu(I) with nitrosation of the $FL_5$ ligand is accompanied by bright visible light emission. The probe readily passes through cell membranes and can detect NO under physiological conditions. Studies of $Cu(FL_5)$ in pH 7.0 aqueous buffered solutions indicate that the NO response is direct, rapid, and specific. Application of $Cu(FL_5)$ to cultures of macrophage and neuroblastoma cells reveals the time-dependent production of NO measurable by fluorescence enhancement, demonstrating the ability of the reagent to image NO over a wide range of concentrations. The power of $Cu(FL_5)$ is also manifested in its ability to select out cells that emit NO in a background of those that do not with spatiotemporal resolution at a cellular level.

These results will encourage the use of Cu(FL$_5$) as a direct nitric oxide probe for investigating NO biology in a variety of contexts.

Example Ten

Exemplary Approach to a bNOS Inhibitor Screen

The four bacterial strains used in the screen will be *Bacillus anthracis* Sterne (wt), *Bacillus anthracis* Δnos (bNOS deficient anthrax, as a negative control), *Escherichia coli* MG1655 [pBNOSB su(l/V)] and *Escherichia coli* MG1655 (wt, as a negative control). Bacteria cells will be grown in about 1 mL Luria-Bertani (LB) media at 37 C in 5 mL plastic tubes in a shaker to $OD_{600}$ of about 0.3. In some experiments, even though this step is not required, cells will be precipitated in a low-speed centrifuge, then the LB media will be discarded and the cells resuspended in about 0.5 mL M9 minimal media with 0.1% glucose and incubated for about another 30 min. Cell culture aliquots will be transferred to 96- or 384-well plates and preincubated with small molecule compounds for, in some cases, about 1 to 2 h. The CuFL will be added (CuFL is generated by mixing the ligand FL and $CuCl_2$ in a 1:1 ratio, see above) to 20 μM. One hour later, fluorescence will be measured and compared with the negative control.

Example Eleven bNOS Inhibitor Screening

Using *E. coli* Top 10 pIG cells (where pIG cells are *E. coli* with a plasmid containing the bNOS gene from *B. anthracis* Sterne) the conditions of the screen were optimized using the following protocol:

Step 1: Incubated cells overnight in a shaker in Luria-Bertini (LB) medium supplemented with 100 μg/mL ampicillin at 37° C.

Step 2: In the morning, diluted cells 1:100 in LB and re-incubated until the $OD_{600}$ is 0.3-0.4 (approximately 2 h)

Step 3: Induced expression of the bNOS gene by adding arabinose (aqueous) and re-incubated for an induction time (note: the control cells were diluted with the equivalent volume of water)

Step 4: Introduced cells into 384-well plates and added sensor (CuFL, pre-generated by mixing $CuCl_2$ and FL in a 1:1 ratio) and re-incubated Step 5: Measured fluorescence of cells +/− arabinose induction and compared the ratio of $F_+/F_-$ Many aspects of the initial screen were optimized. The best results were obtained when single colonies were grown overnight. The optimal concentration of arabinose with which to induce expression of the bNOS gene was 0.5% (w/v), and the optimal induction time (time in step 3 to leave the cells incubating before the sensor was added) was overnight (22 h) in a shaker. The results did not change significantly when different concentrations of the sensor were used (20 μM, 10 μM, 5 μM, 1 μM, 0.1 μM) so the concentration was chosen to minimize the amount of sensor required, but also to have a large enough signal to noise ratio (5 μM). The incubation time of the sensor (time in step 4) did not significantly alter the results, so 20 min was chosen (this incubation timeframe provided sufficient time to add the sensor and allow it to react with NO, but was not too long, so that the screening procedure became inefficient). A statistical Z-test was performed:

$$Z=1-3[(\sigma_+ + \sigma_-)/(\bar{x}_+ - \bar{x}_-)]$$

to determine if the signal observed for the positive results (+arabinose) was sufficiently greater than the signal observed for the negative results (−arabinose) to attempt a pilot screen. The standard for such a test is that if Z>0.5 the difference between the positive and negative results should be large enough to differentiate hits from non-hits. The protocol outlined above, under the optimized conditions, was used for the Z-test; this scored Z=0.52. A pilot screen was attempted using a sample of the small molecules available from the library at the Institute for Chemistry and Cell Biology (ICCB) at Harvard Medical School. The screen was performed in duplicate using a protocol similar to that of the Z-test. Briefly, after the cells were grown to $OD_{600}$~0.3-0.4, they were plated into 384-well plates. To the cells was added 100 nL of a small molecule using an Epson robot pin. The cells were then induced with arabinose and allowed to incubate overnight in a shaker. The rest of the protocol was followed as previously described. The duplicate screens matched each other, so the screen is consistent. However, a wide range of fluorescence signals was obtained, such that a hit was indistinguishable from a non-hit.

The screening conditions must be further optimized in order to increase the difference between a positive and negative signal to increase the Z value.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

We claim:

1. A method of determining if a small molecule is a bacterial nitric oxide synthase (bNOS) inhibitor, comprising the steps of:

a) preparing a first solution comprising bacteria taken up by macrophages, wherein said bacteria expresses bNOS;

b) adding to the first solution a transition metal-containing fluorescein-based sensor, thereby forming a first mixture;

c) incubating the first mixture for a first period of time, thereby forming a first sample;

d) measuring the fluorescence of the first sample;

e) preparing a second solution comprising the first solution and a small molecule;

f) adding to the second solution the transition metal-containing fluorescein-based sensor, thereby forming a second mixture;

g) incubating the second mixture for a second period of time, thereby forming a second sample;

h) measuring the fluorescence of the second sample;

i) comparing the fluorescence of the first sample with the fluorescence of the second sample; and k) identifying the small molecule as a bNOS inhibitor when the fluorescence of the second sample is reduced compared to the fluorescence of the first sample;

wherein steps (d) and (h) are both completed within less than about 8 hours after the bacteria are taken up by the macrophages.

2. The method of claim 1, wherein the bacteria is selected from the group consisting of Gram-positive bacteria that express native bNOS, Gram-positive bacteria that express non-native bNOS, Gram-negative bacteria that express native bNOS and Gram-negative bacteria that express non-native bNOS.

3. The method of claim 1, wherein the bacteria is *Bacillus* spp., *Bacillus subtilis, Bacillus anthracis, Bacillus anthracis* Sterne, *Staphylococcus* spp., *Staphylococcus aureus*, methicillin-resistant *Staphylococcus aureus* or *Norcardia* spp.

4. The method of claim 1, wherein the transition metal is Mn, Cu, Co, Fe, Ni, Zn, Ru, or Rh.

5. The method of claim 1, wherein the fluorescein-based sensor is selected from the group consisting of:

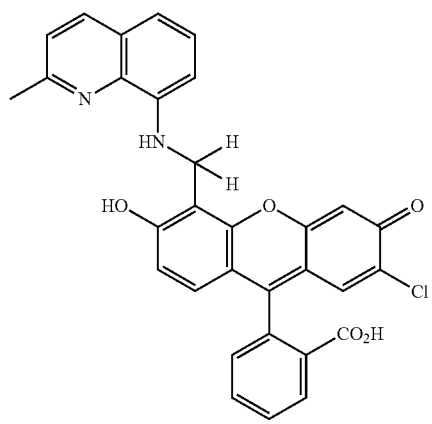

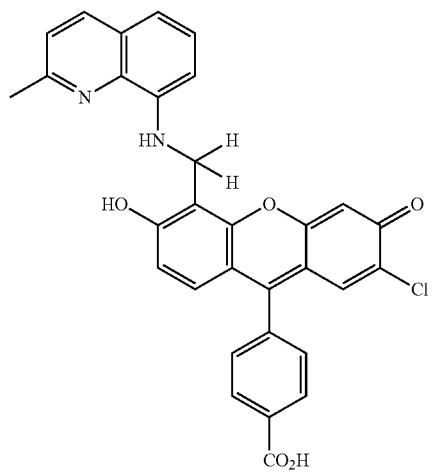

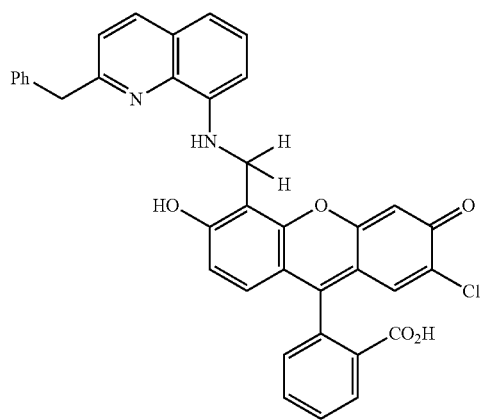

-continued

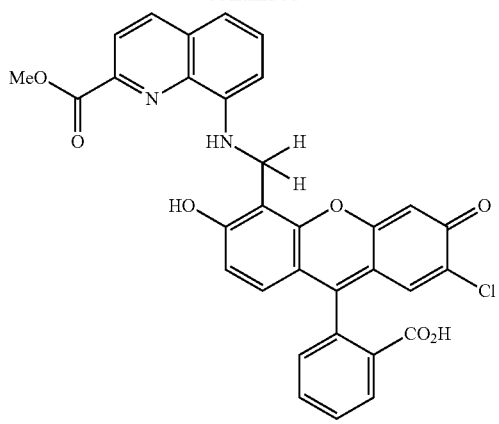

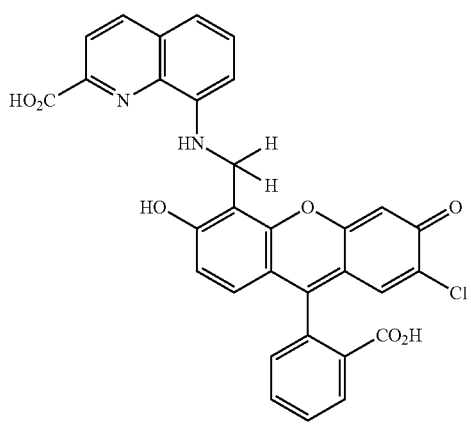

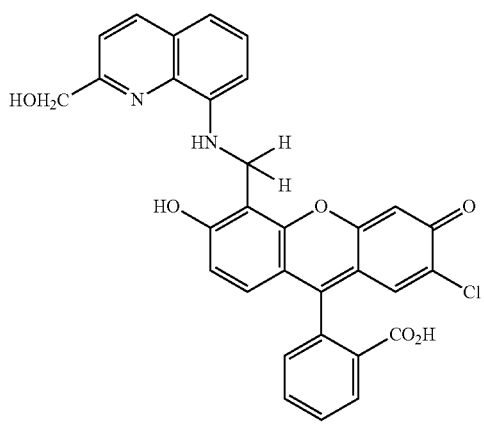

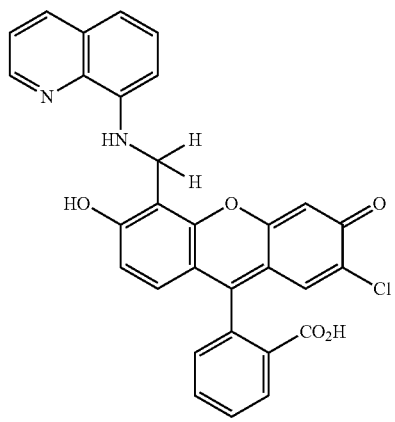

127
-continued
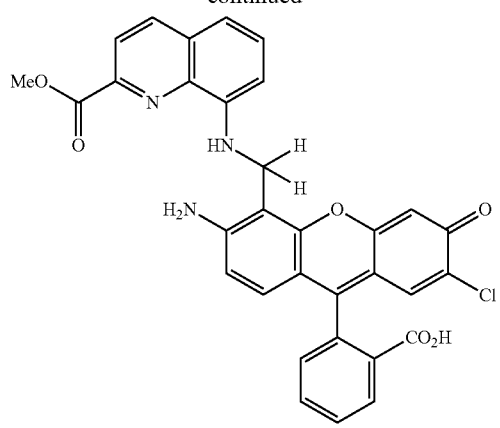
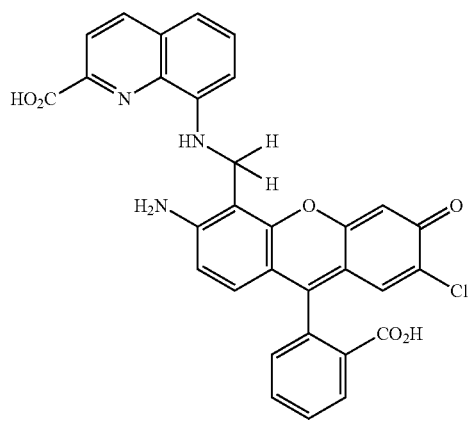
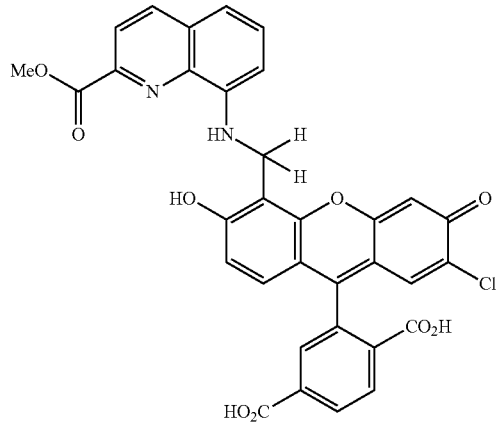
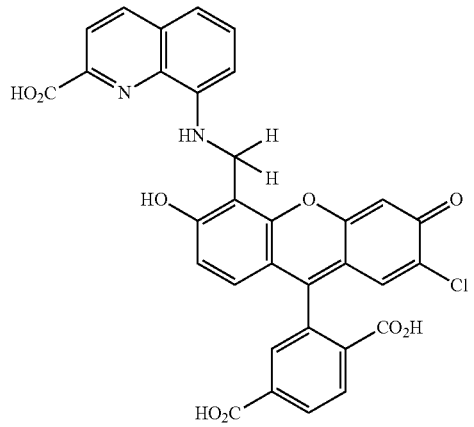
128
-continued
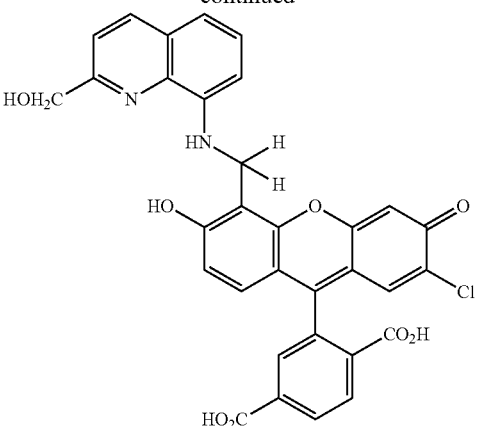
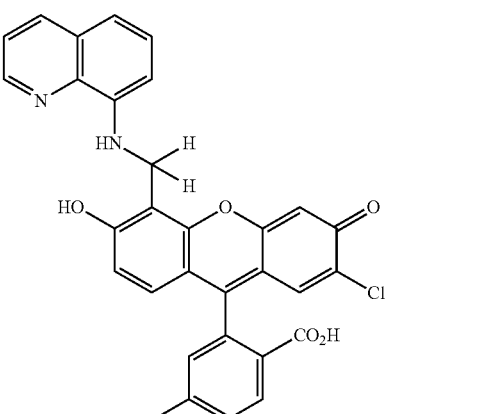
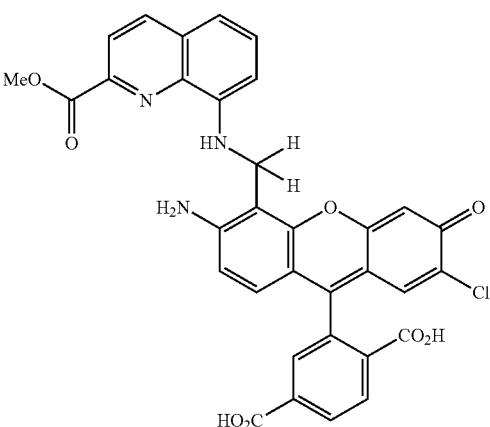
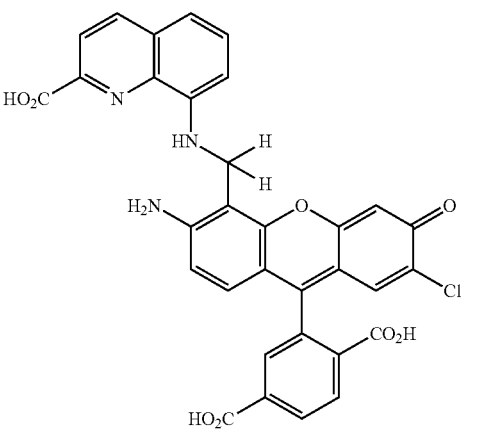

129
-continued
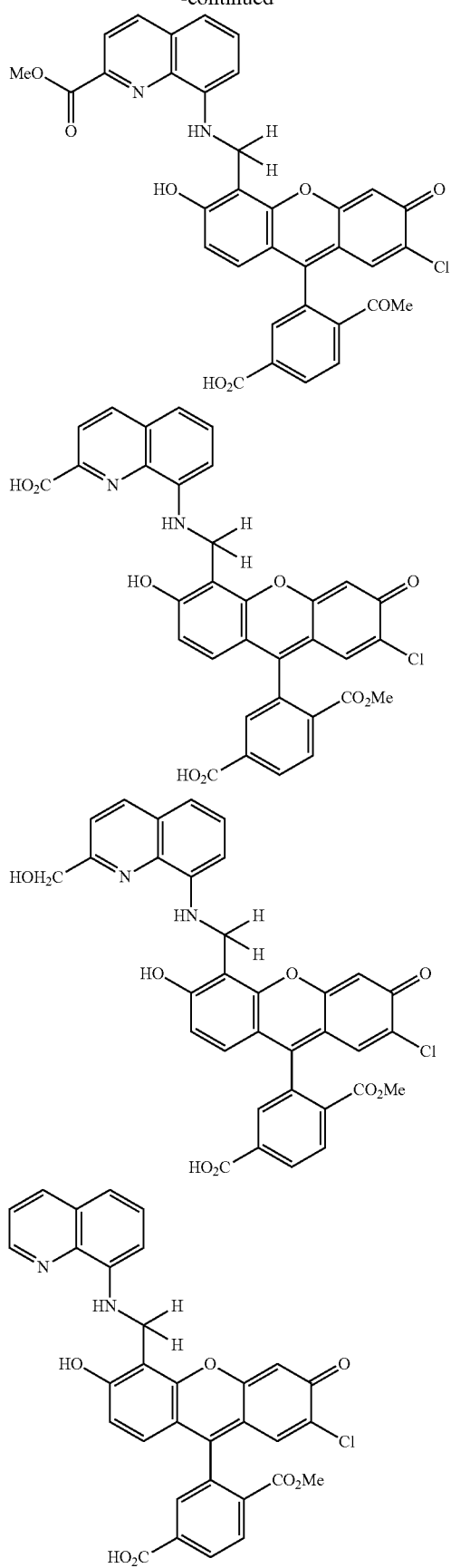
130
-continued
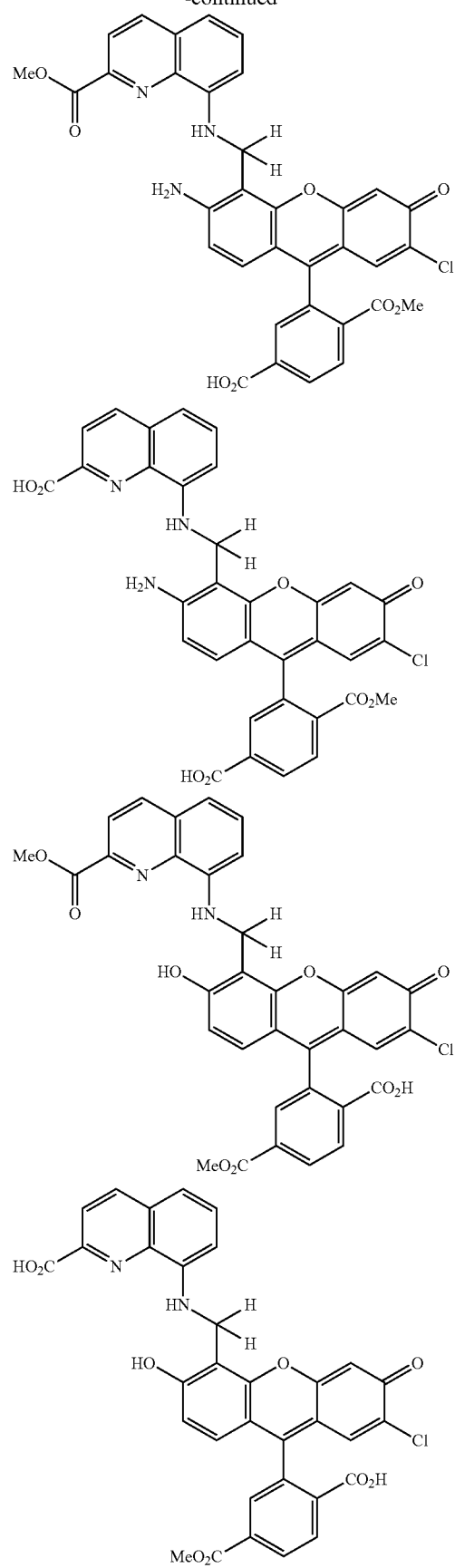

131
-continued
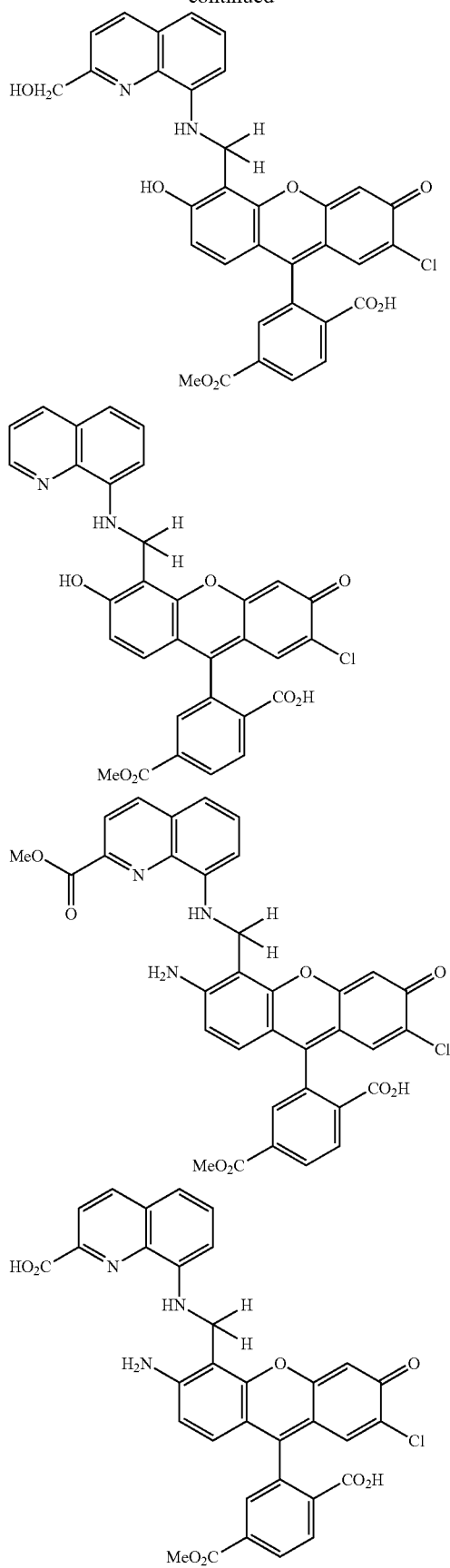
132
-continued
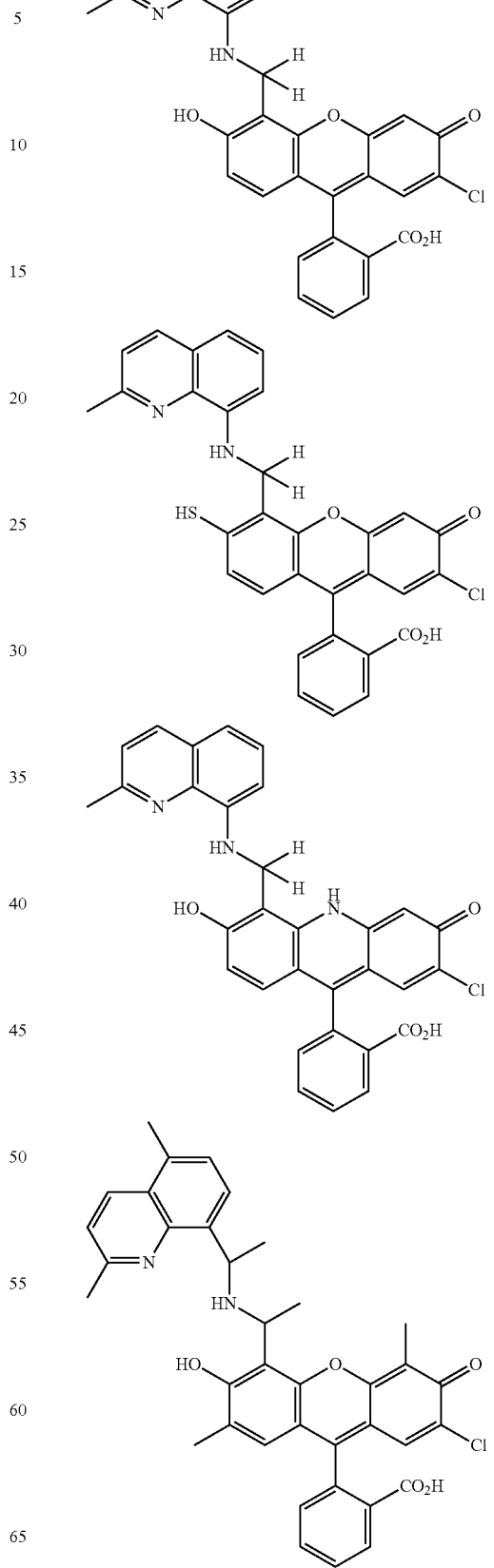

133
-continued
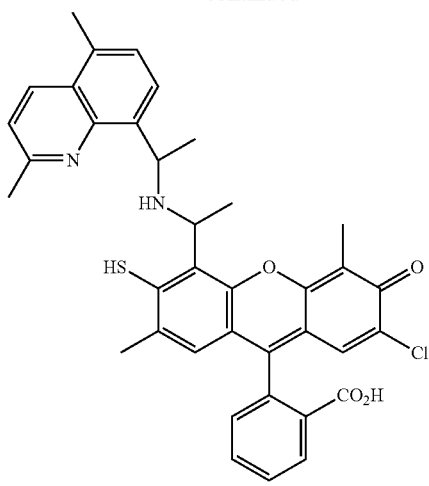
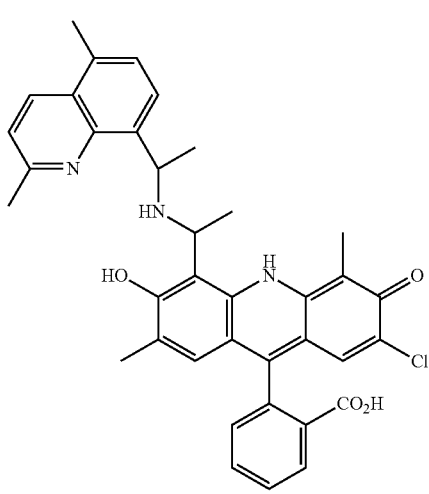
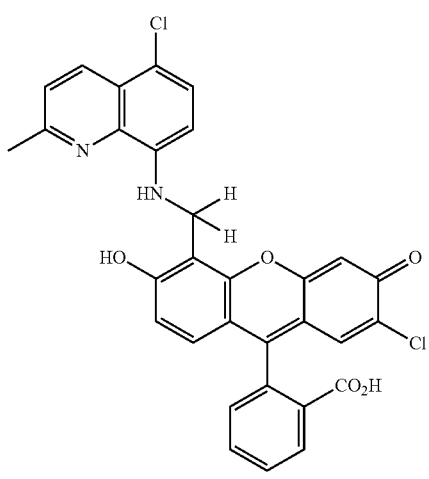
134
-continued
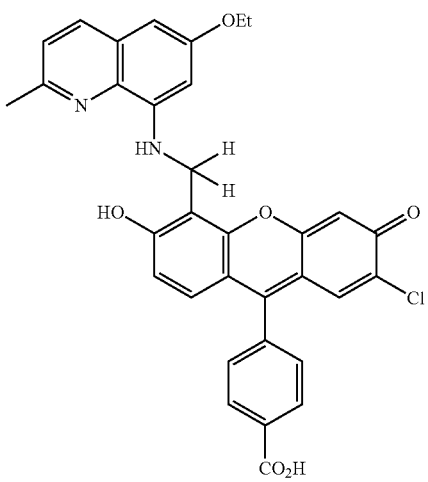
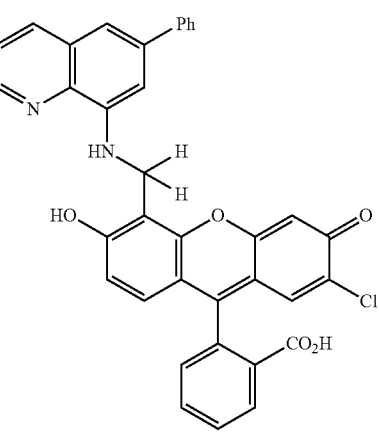
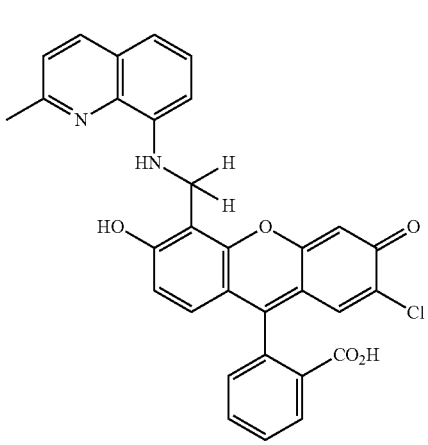

135
-continued
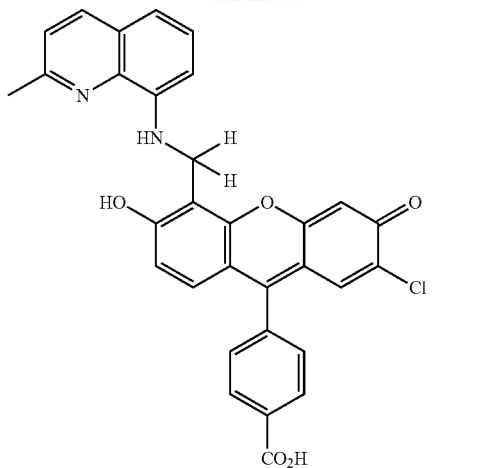
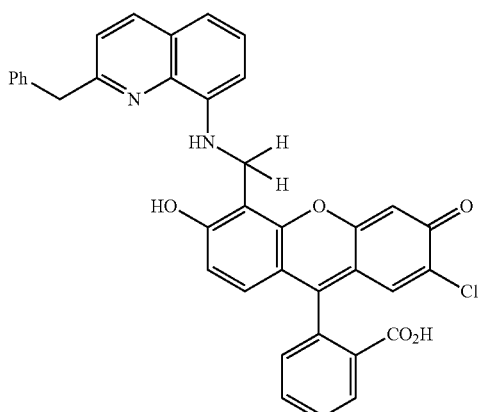
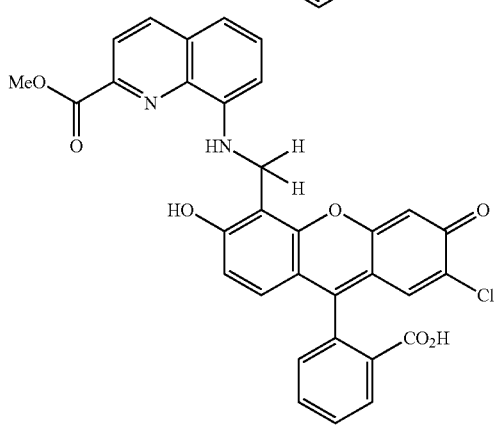
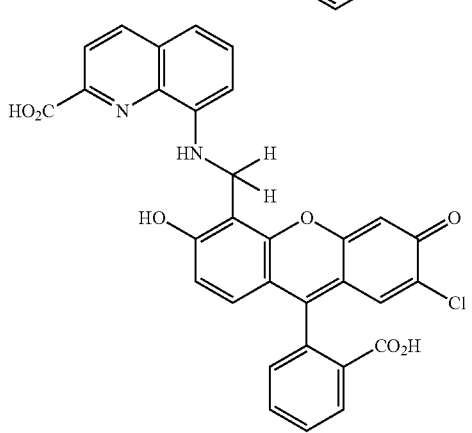
136
-continued
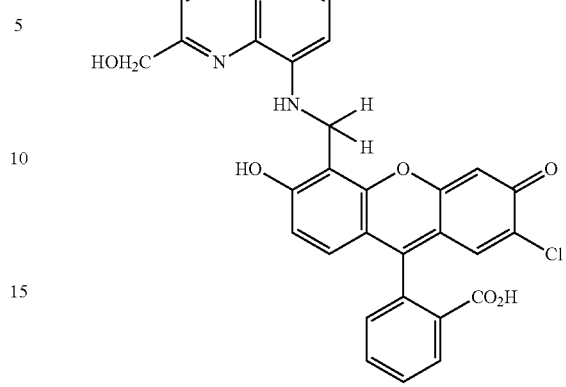
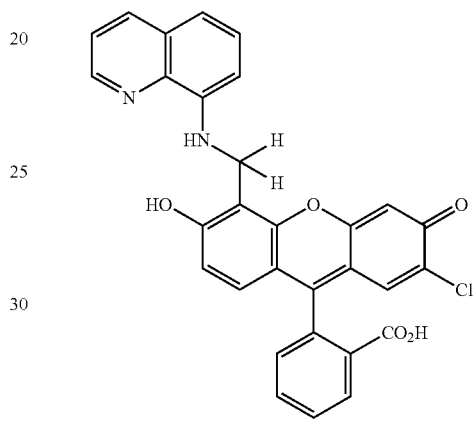
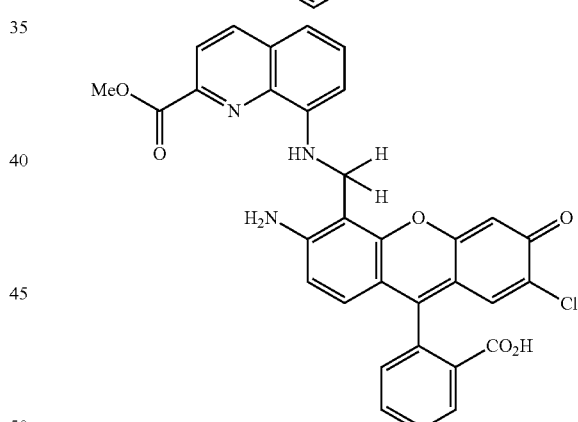
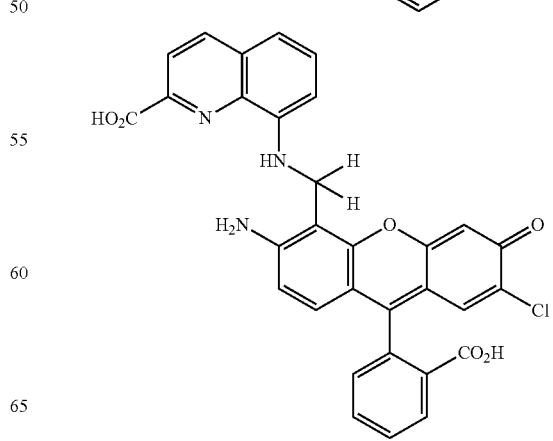

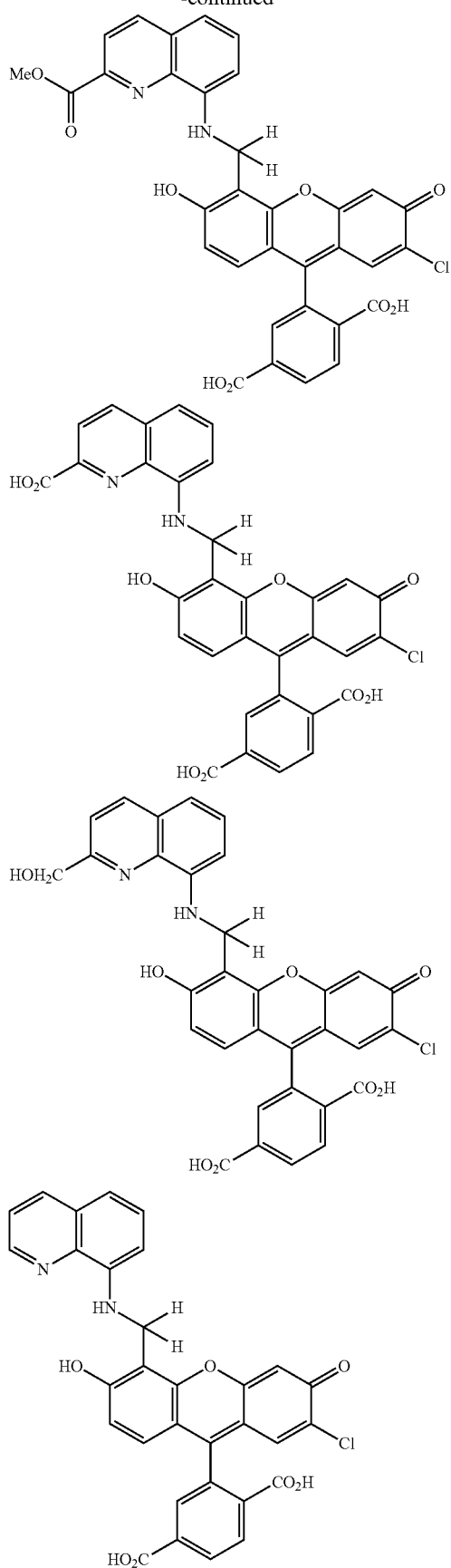
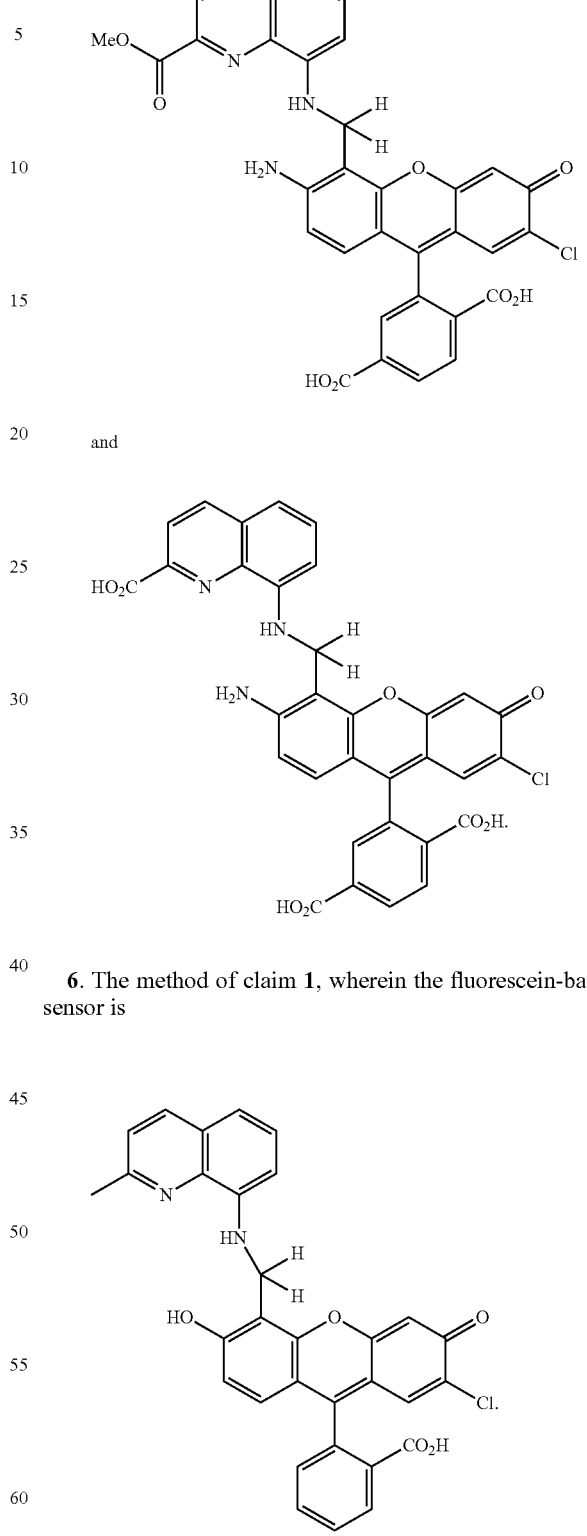
6. The method of claim 1, wherein the fluorescein-based sensor is
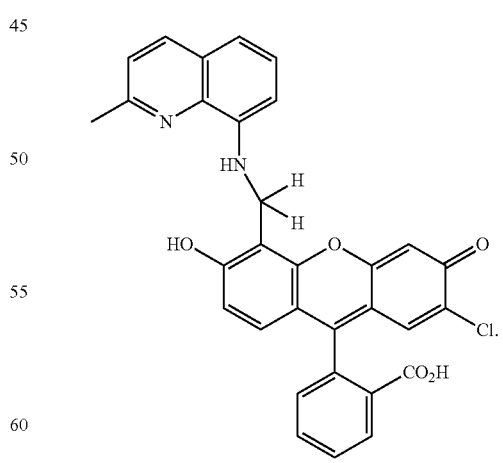
7. The method of claim 6, wherein the transition metal is Cu.
8. The method of claim 1, wherein the fluorescein-based sensor is selected from the group consisting of:

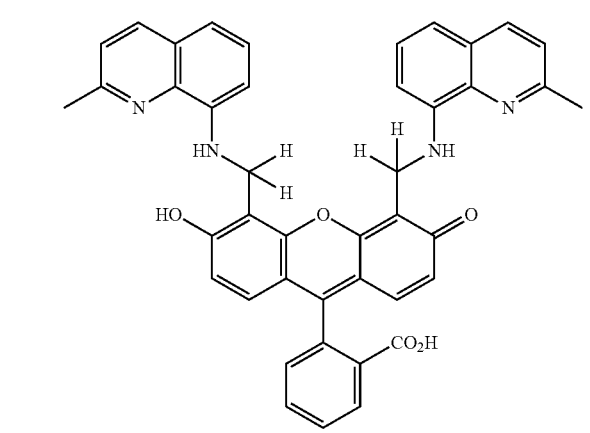
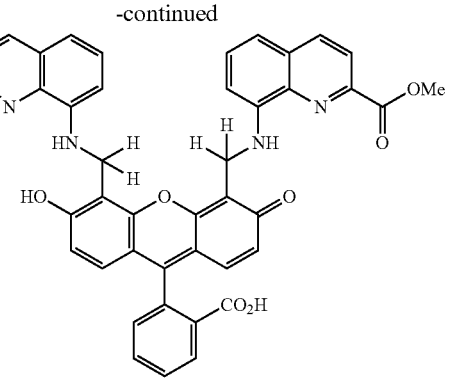
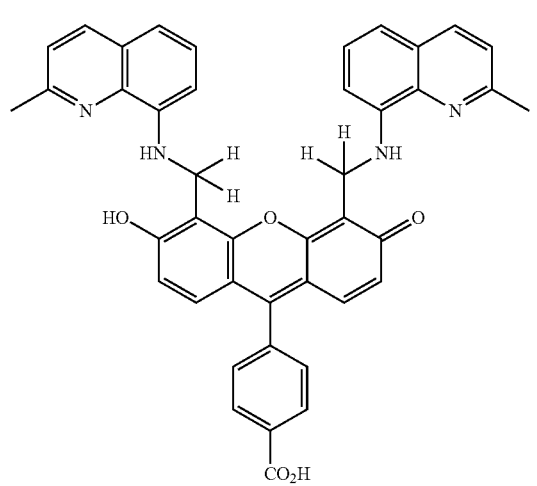
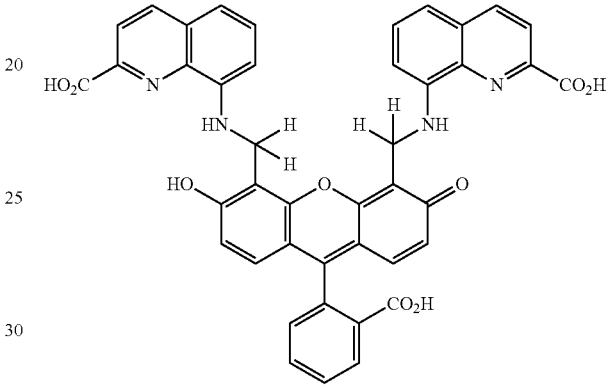
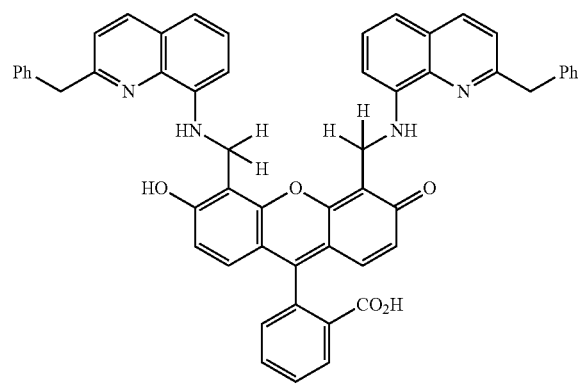
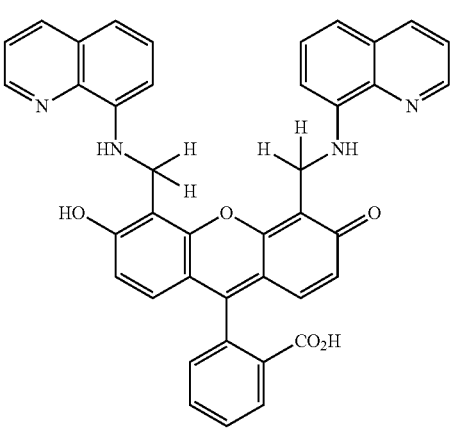
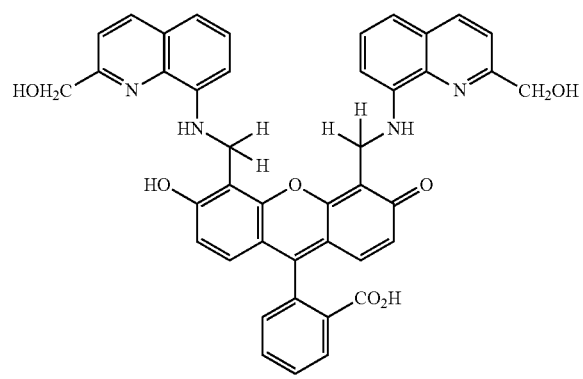
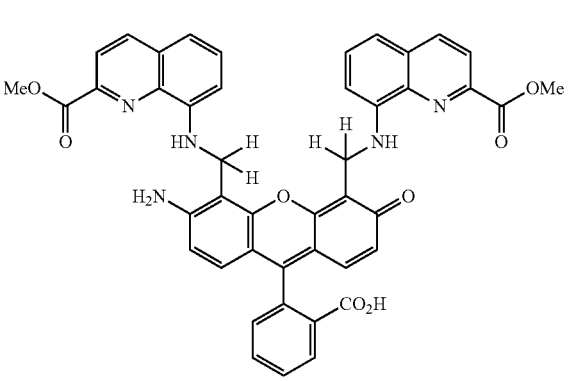

141
-continued
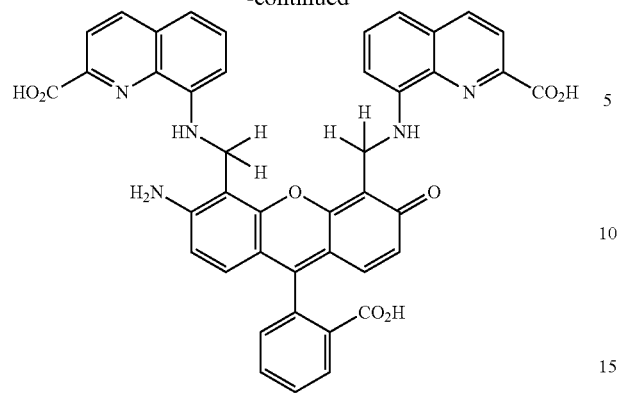
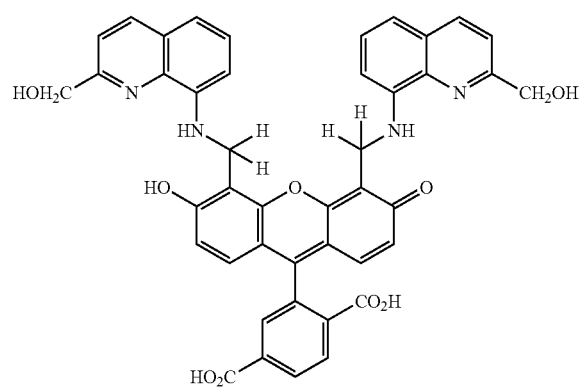
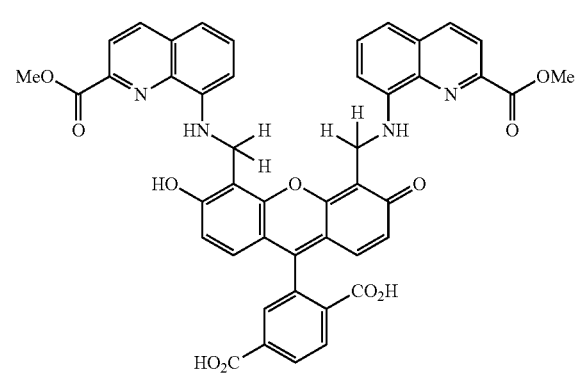
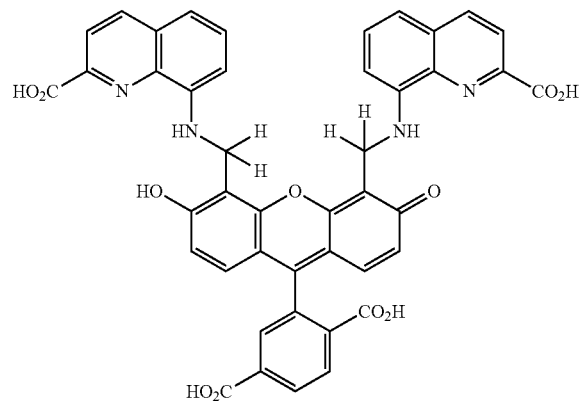
142
-continued
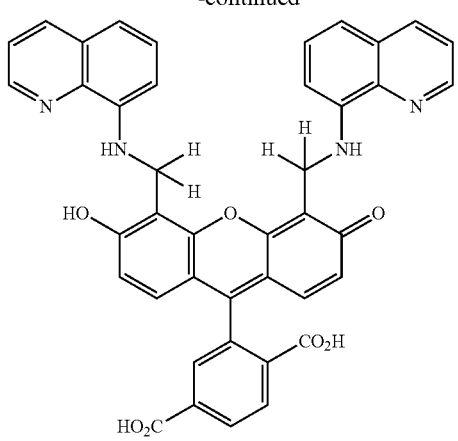
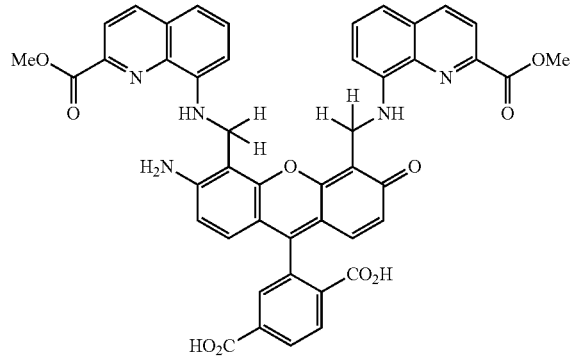
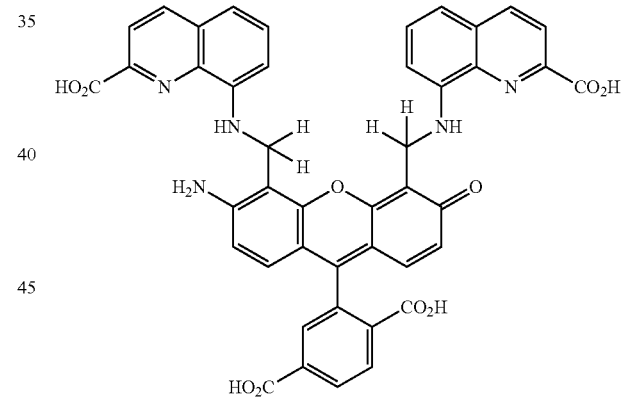
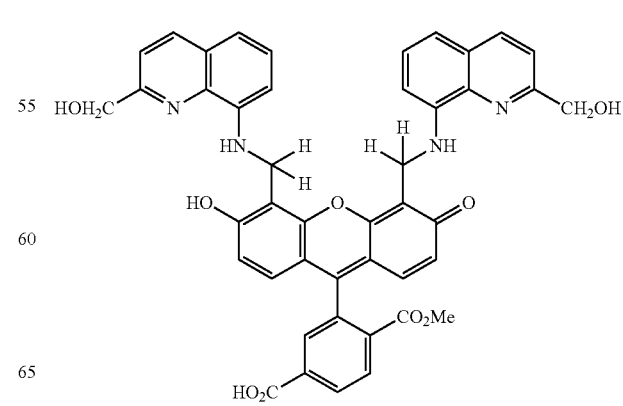

143
-continued
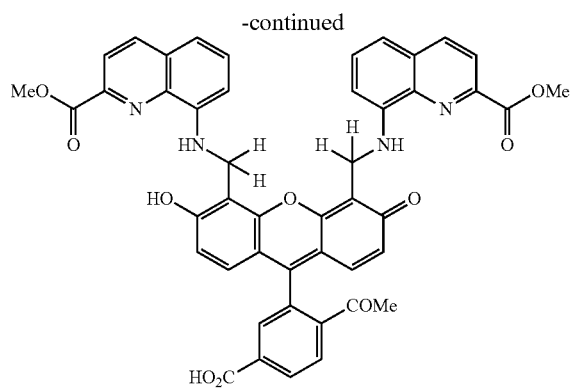
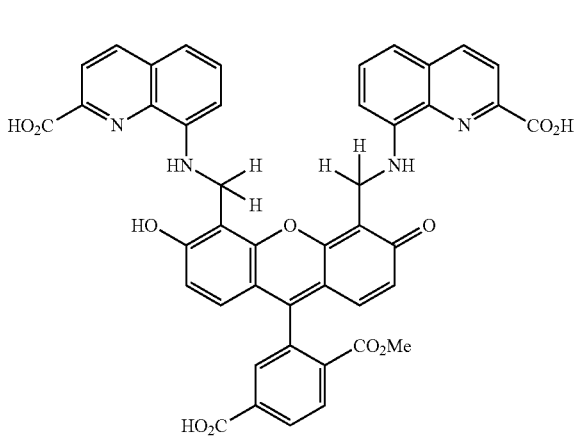
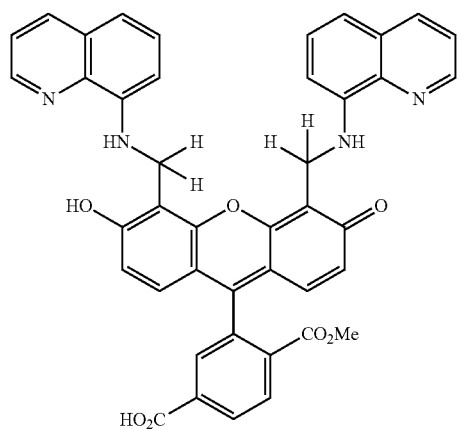
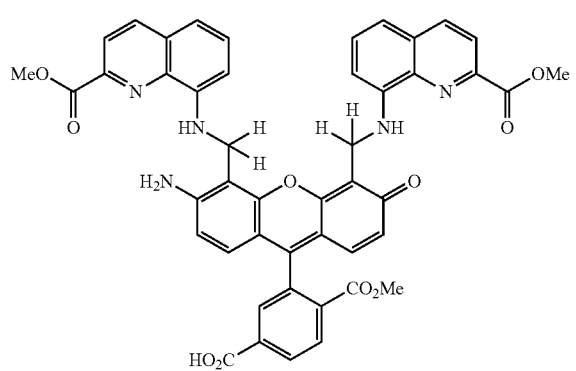
144
-continued
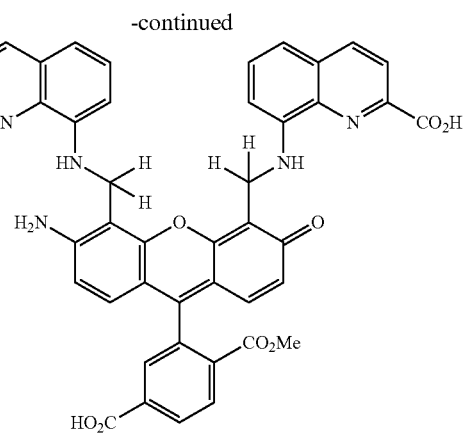
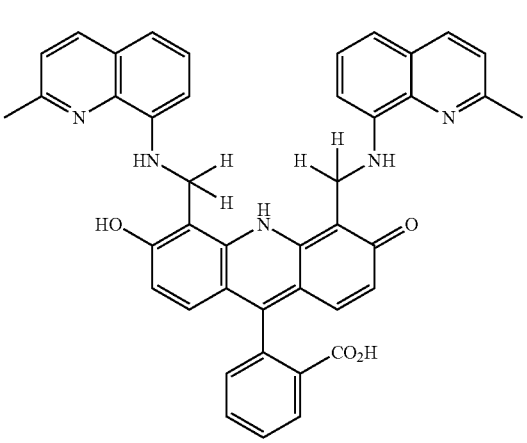
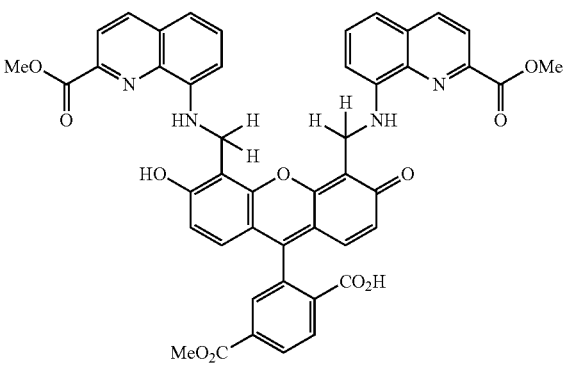
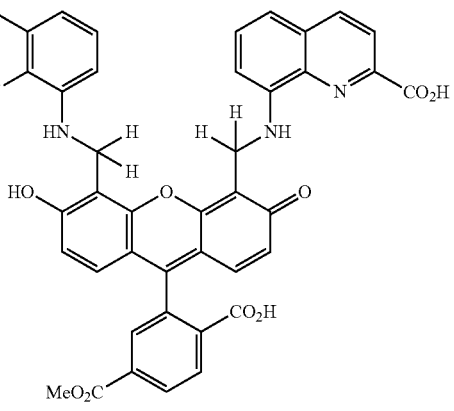

145
-continued
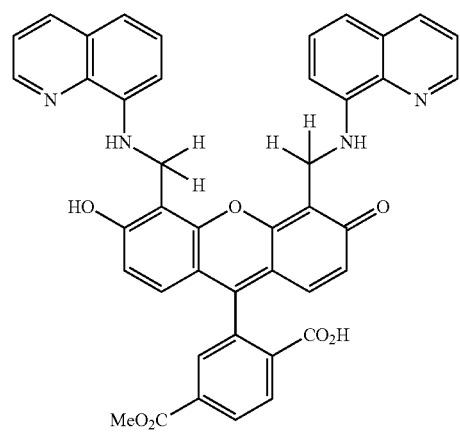
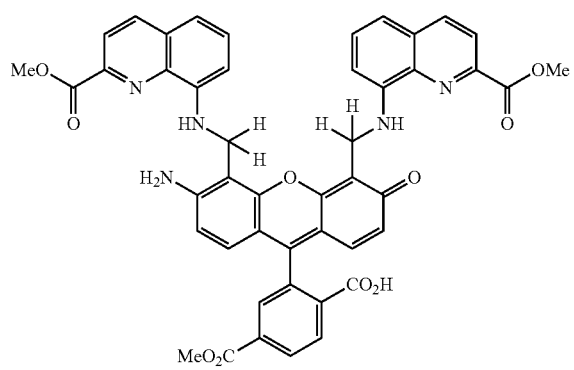
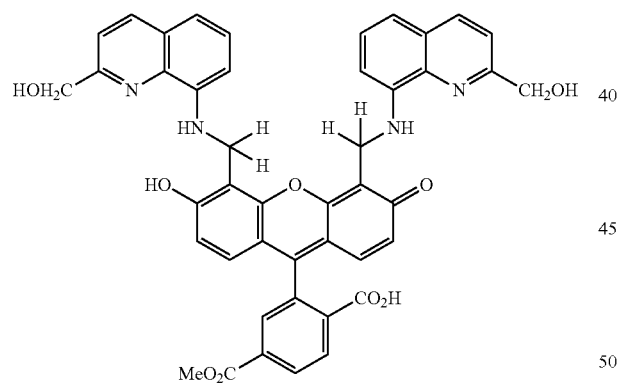
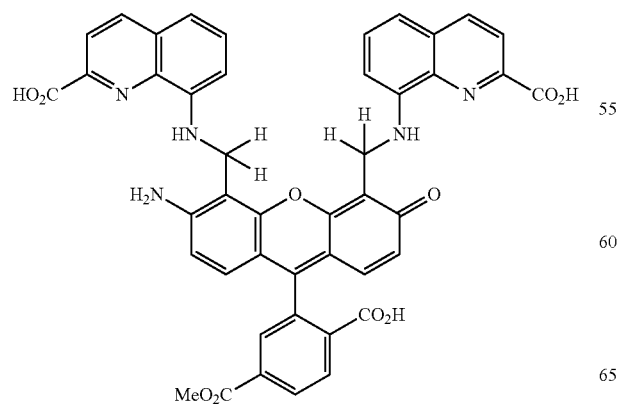
146
-continued
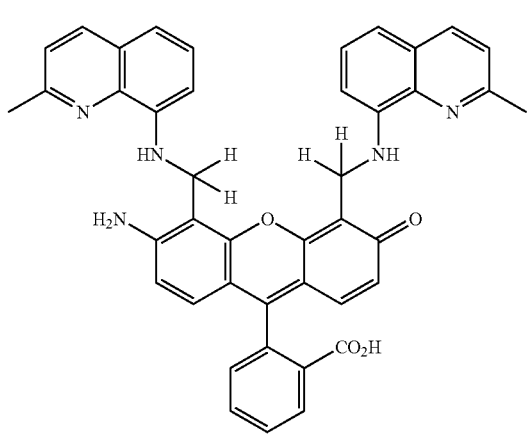
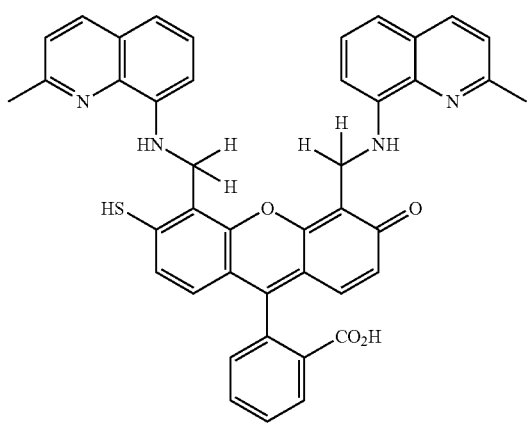
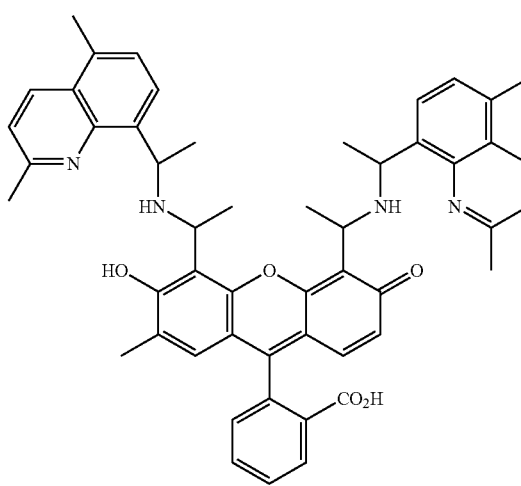

147
-continued
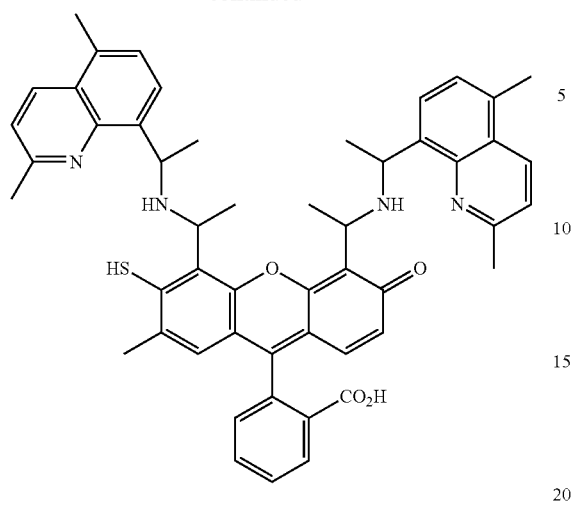
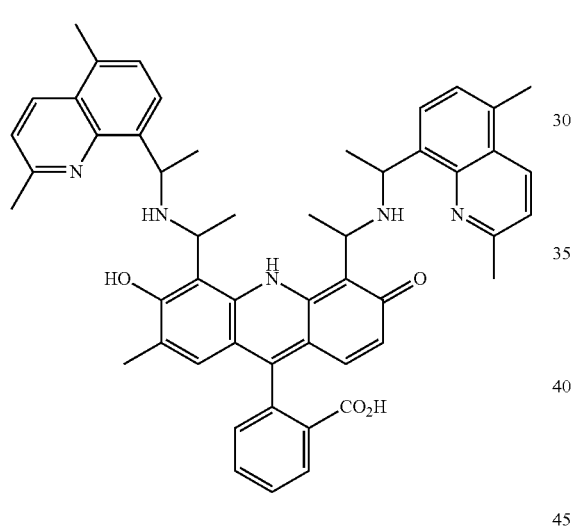
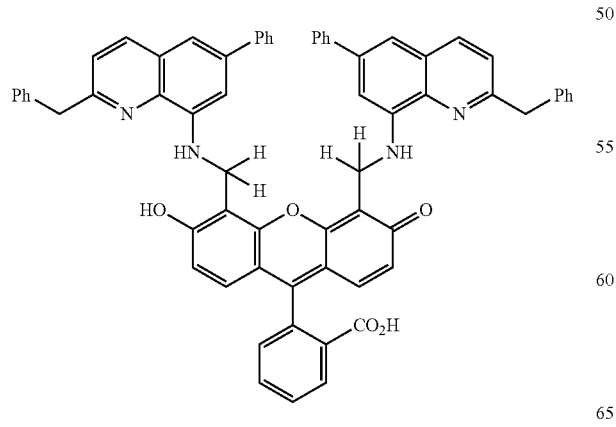
148
-continued
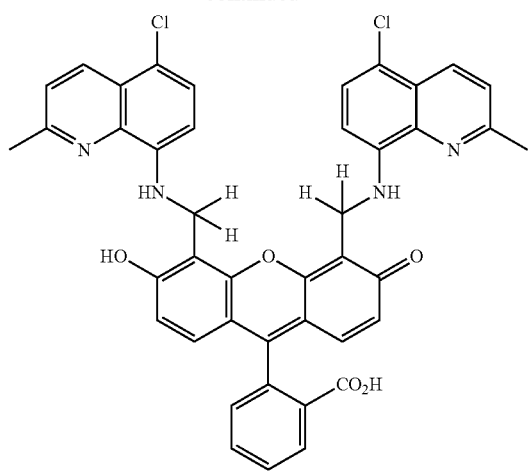
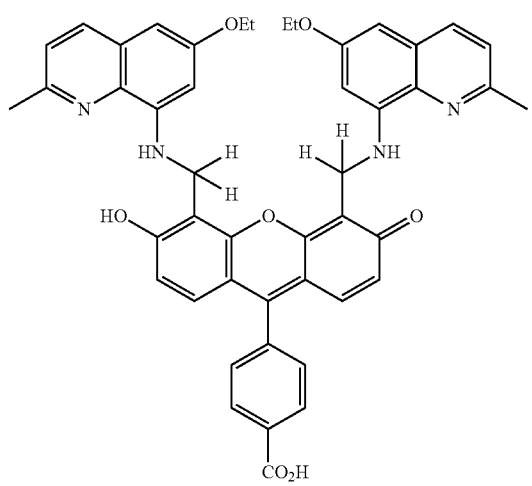
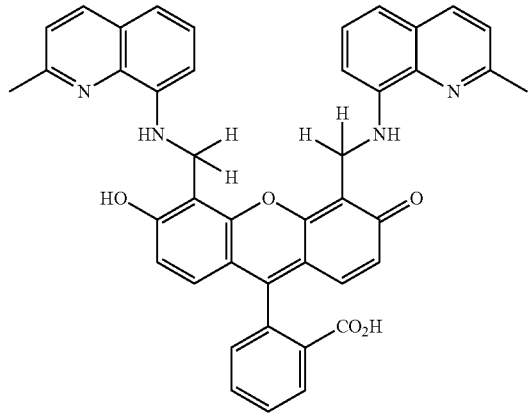

149
-continued
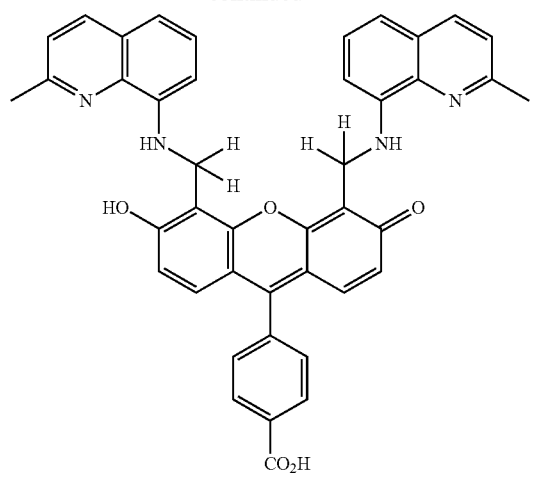
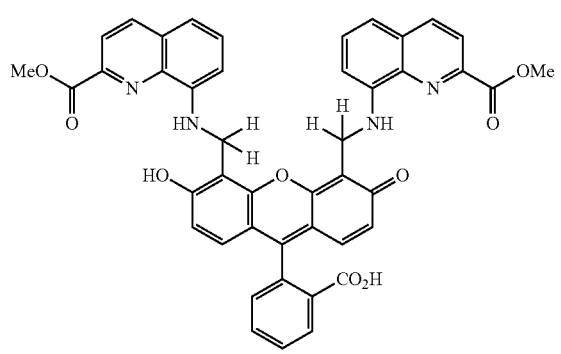
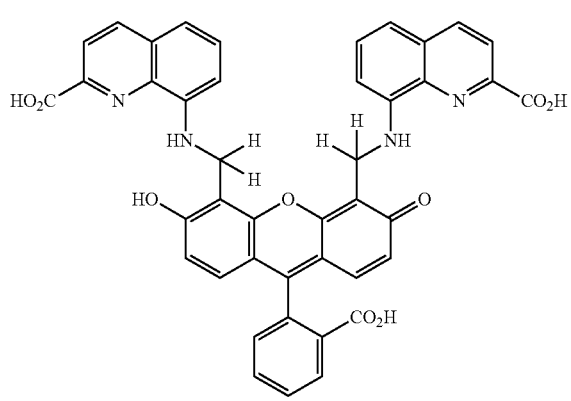
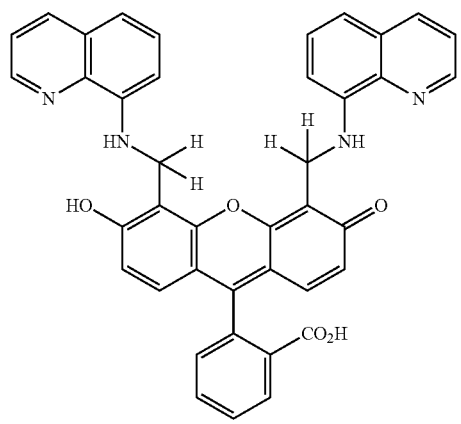
150
-continued
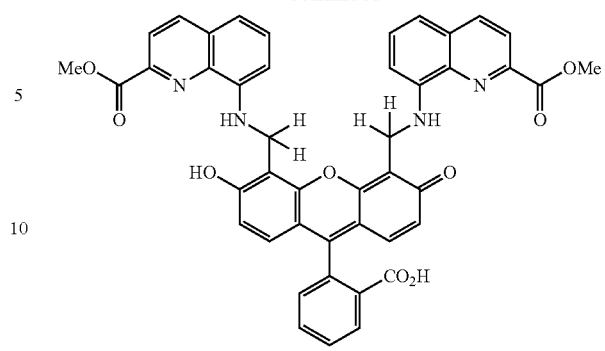
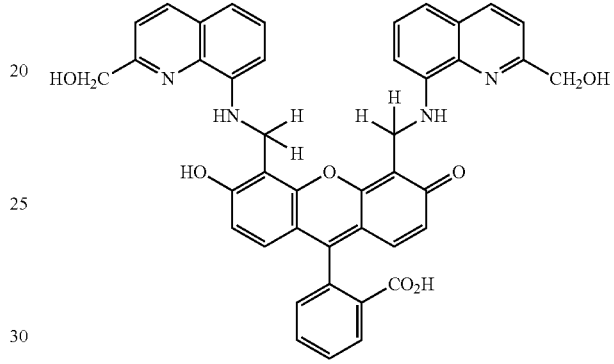
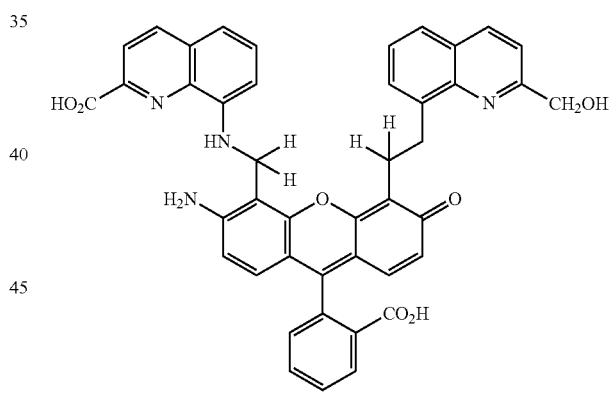
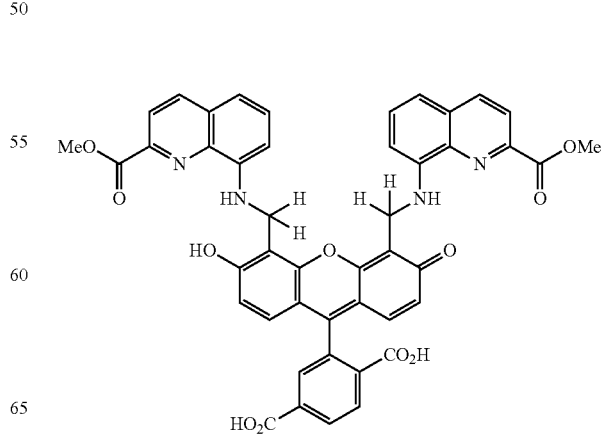

-continued

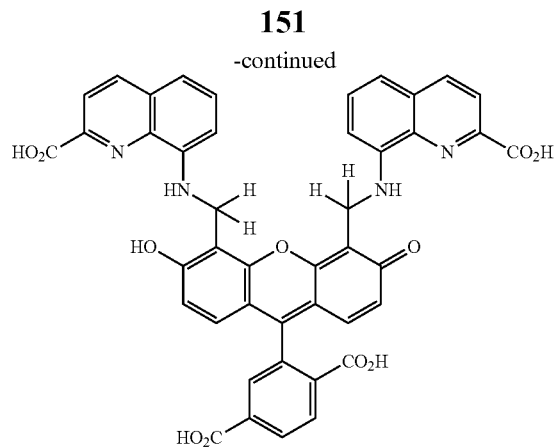

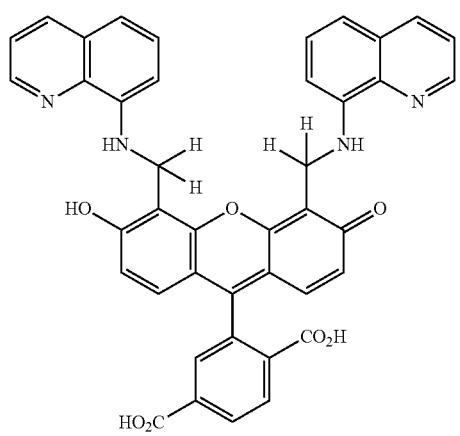

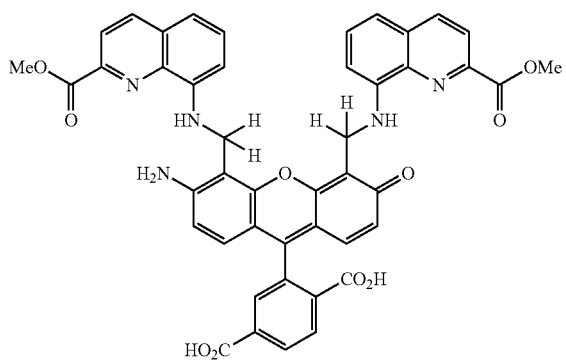

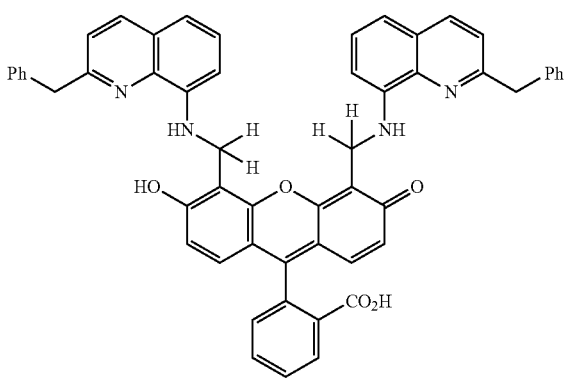

-continued

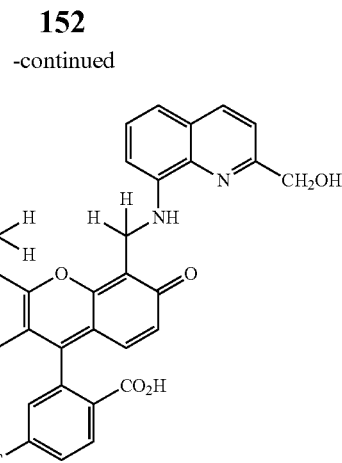

and

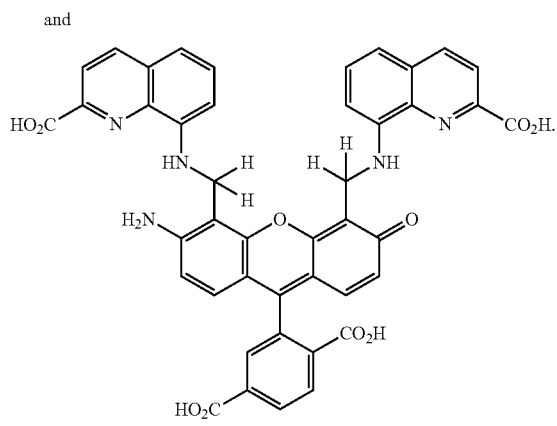

9. A method of determining if a small molecule is a selective bacterial nitric oxide synthase (bNOS) inhibitor, comprising the steps of:
 a) preparing a first solution comprising bacteria taken up by macrophages, wherein said bacteria expresses bNOS;
 b) adding to the first solution a transition metal-containing fluorescein-based sensor, thereby forming a first mixture;
 c) incubating the first mixture for a first period of time, thereby forming a first sample;
 d) measuring the fluorescence of the first sample;
 e) incubating the first sample for a second time, thereby forming a second sample;
 f) measuring the fluorescence of the second sample;
 g) preparing a second solution comprising the first solution and a small molecule;
 h) adding to the second solution the transition metal-containing fluorescein-based sensor, thereby forming a second mixture;
 i) incubating the second mixture for a third time, thereby forming a third sample;
 j) measuring the fluorescence of the third sample;
 k) incubating the third sample for a fourth time, thereby forming a fourth sample;
 l) measuring the fluorescence of the fourth sample;
 m) comparing the fluorescence of the first sample with the fluorescence of the third sample, and comparing the fluorescence of the second sample with the fluorescence of the fourth sample; and
 n) identifying the small molecule as a selective bNOS inhibitor when both (1) fluorescence of the third sample is reduced compared to the fluorescence of the first sample, and (2) fluorescence of the fourth sample is reduced compared to the fluorescence of the second sample;

wherein steps (d) and (j) are both completed within less than about 8 hours after the bacteria are taken up by the macrophages; and steps (f) and (l) are both completed greater than about 8 hours after the bacteria are taken up by the macrophages.

10. The method of claim 9, wherein the bacteria is selected from the group consisting of Gram-positive bacteria that express native bNOS, Gram-positive bacteria that express non-native bNOS, Gram-negative bacteria that express native bNOS, and Gram-negative bacteria that express non-native bNOS.

11. The method of claim 9, wherein the bacteria is *Bacillus* spp., *Bacillus subtilis, Bacillus anthracis, Bacillus anthracis* Sterne, *Staphylococcus* spp., *Staphylococcus aureus*, methicillin-resistant *Staphylococcus aureus* or *Norcardia* spp.

12. The method of claim 9, wherein the transition metal is Mn, Cu, Co, Fe, Ni, Zn, Ru, or Rh.

13. The method of claim 9, wherein the fluorescein-based sensor is selected from the group consisting of:

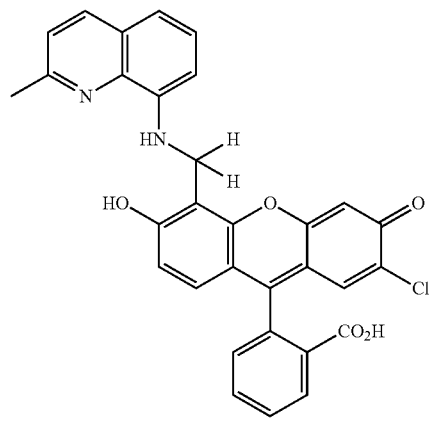

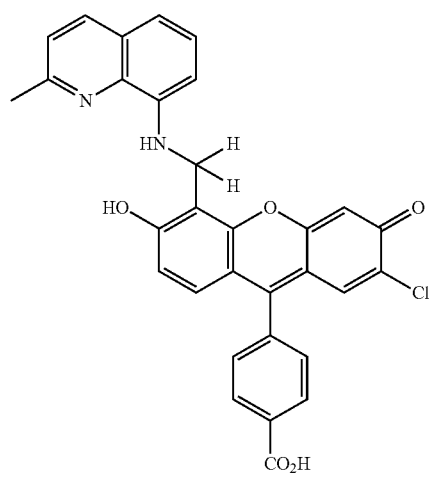

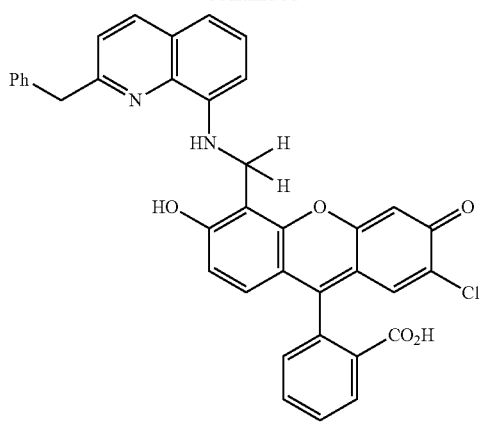

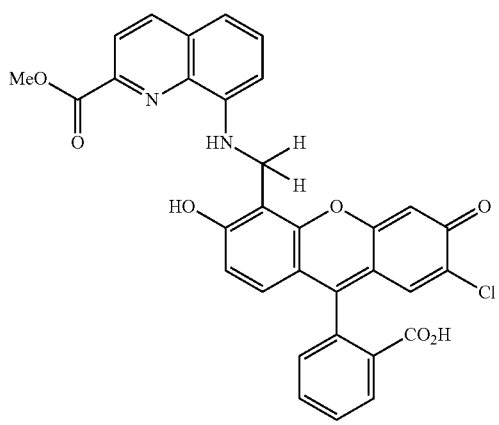

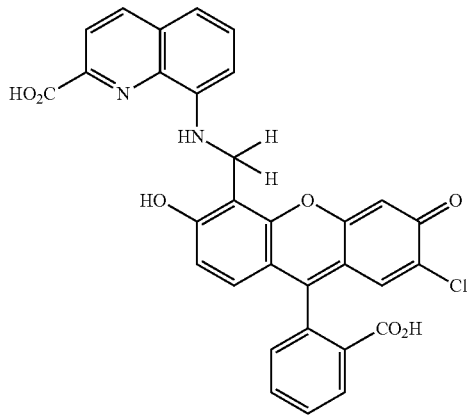

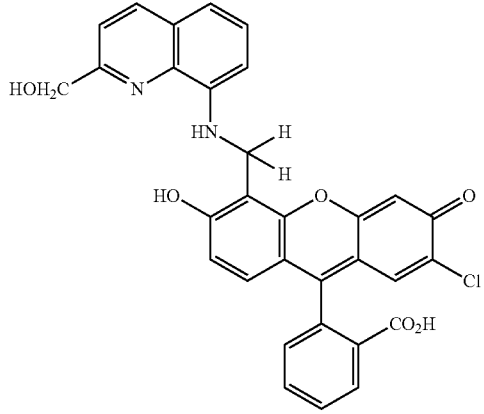

-continued
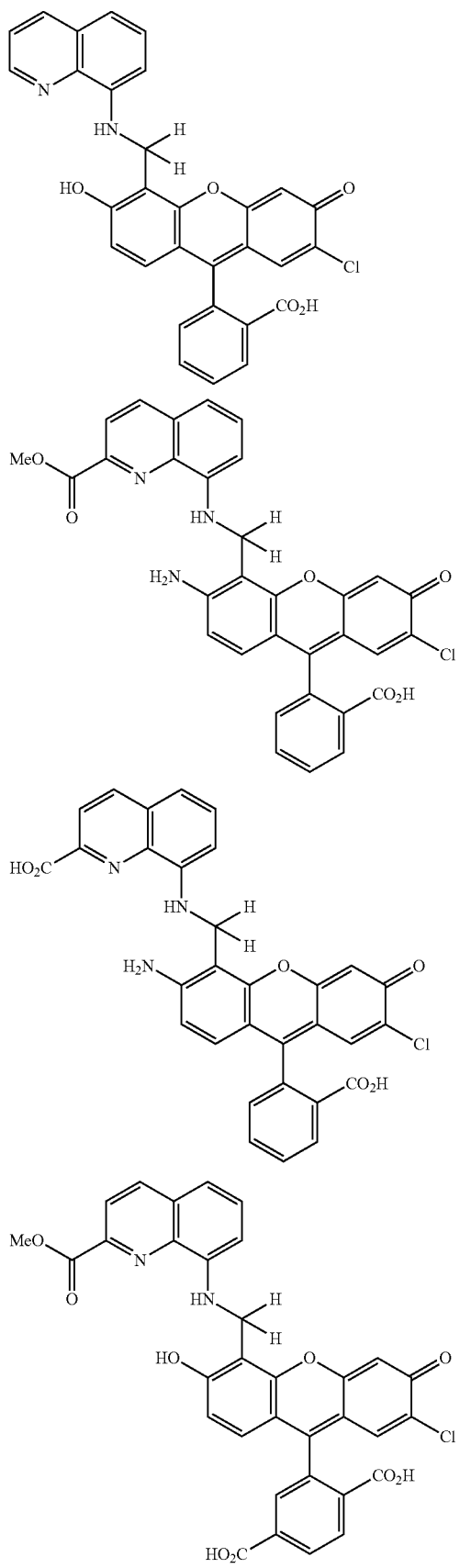
-continued
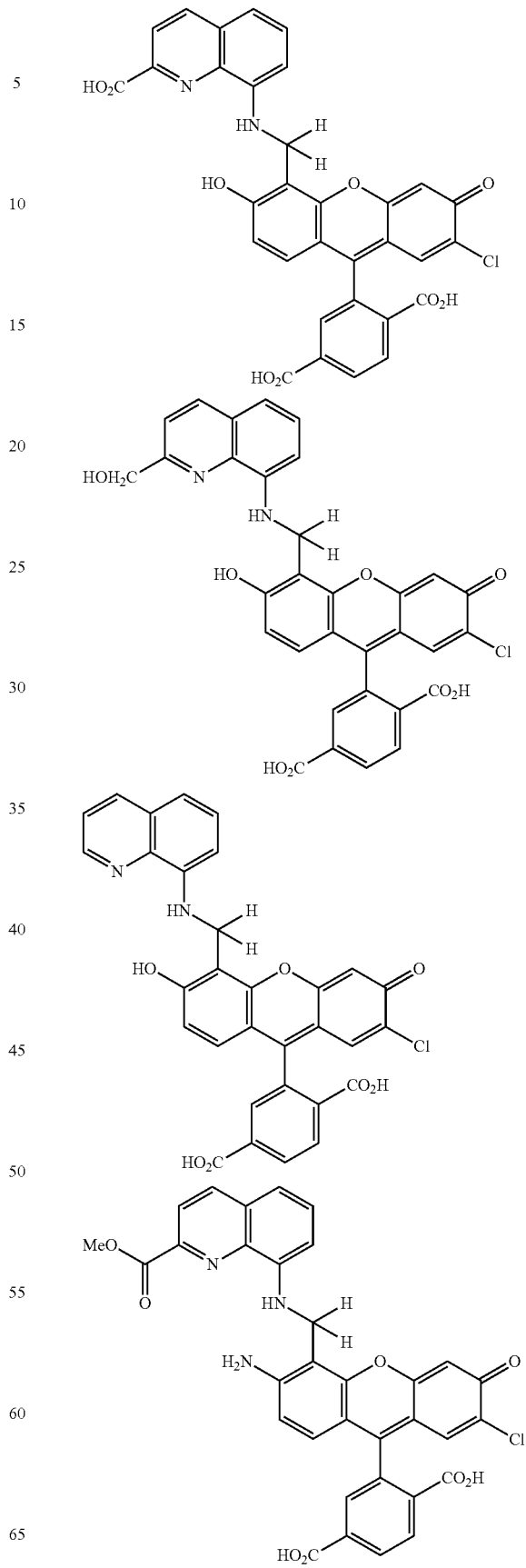

157
-continued
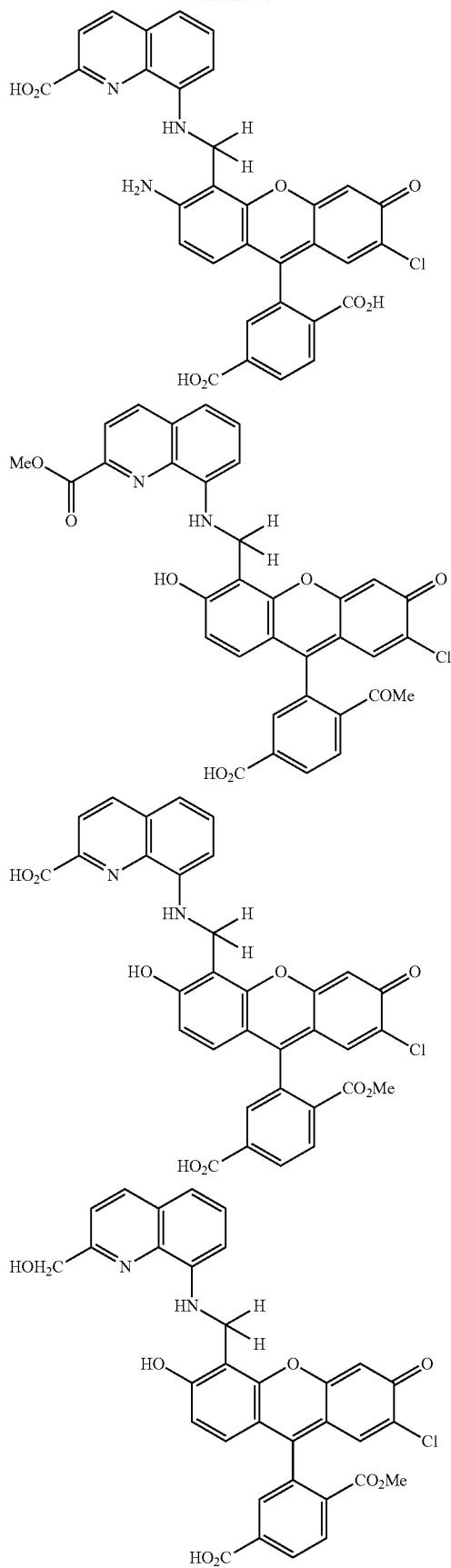
158
-continued
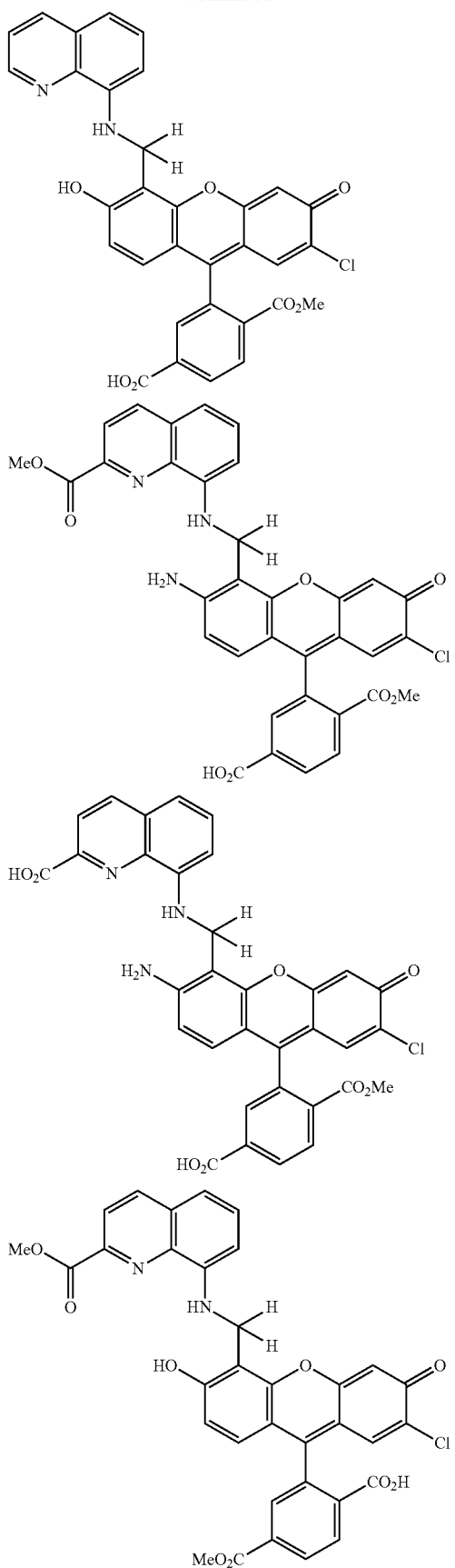

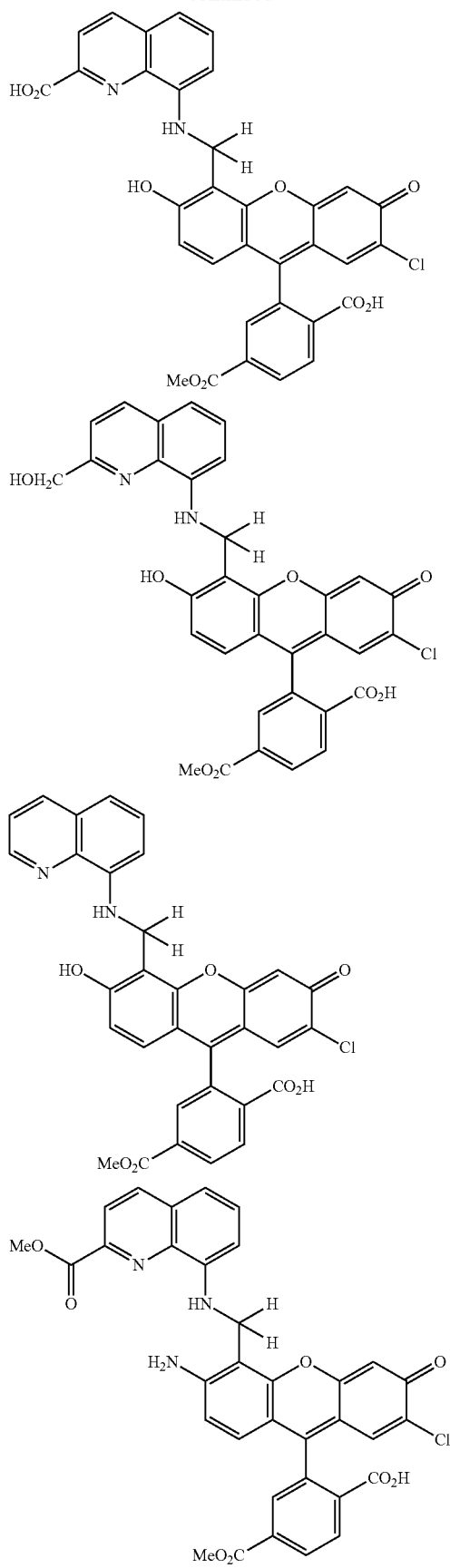

161
-continued
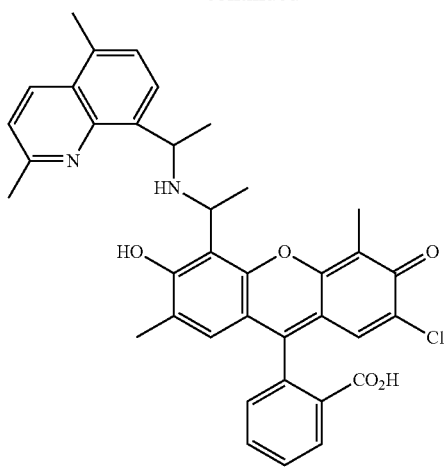
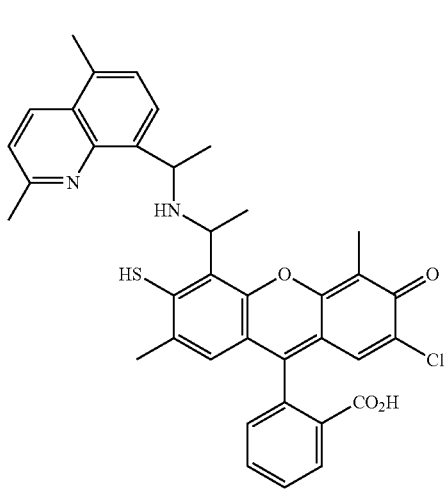
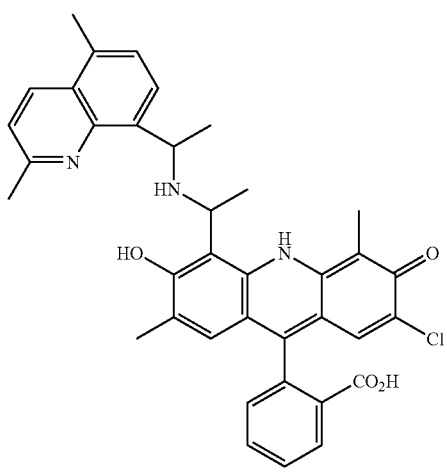
162
-continued
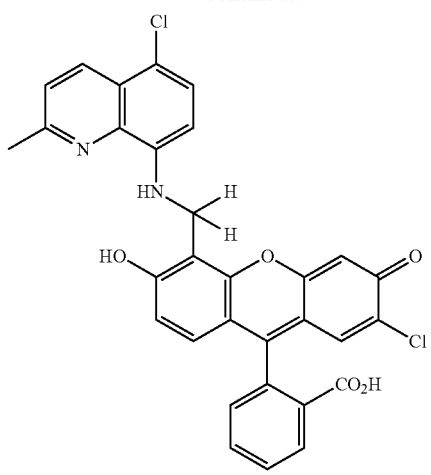
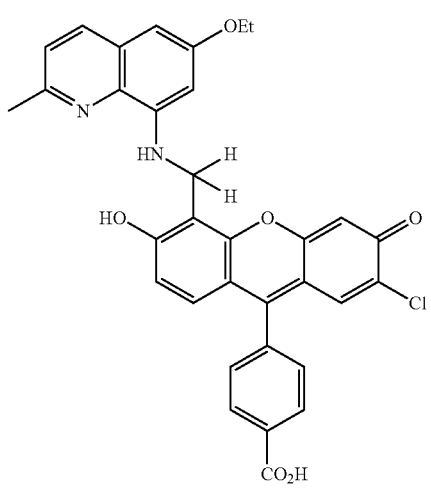
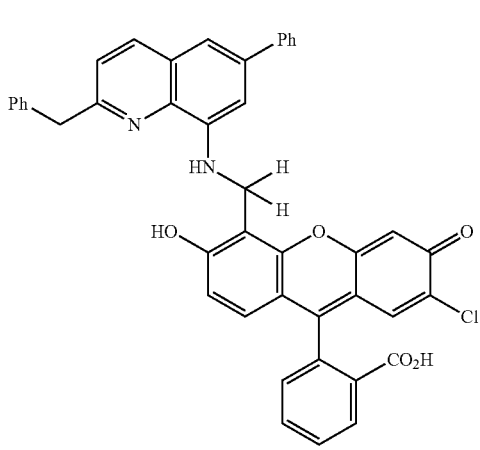

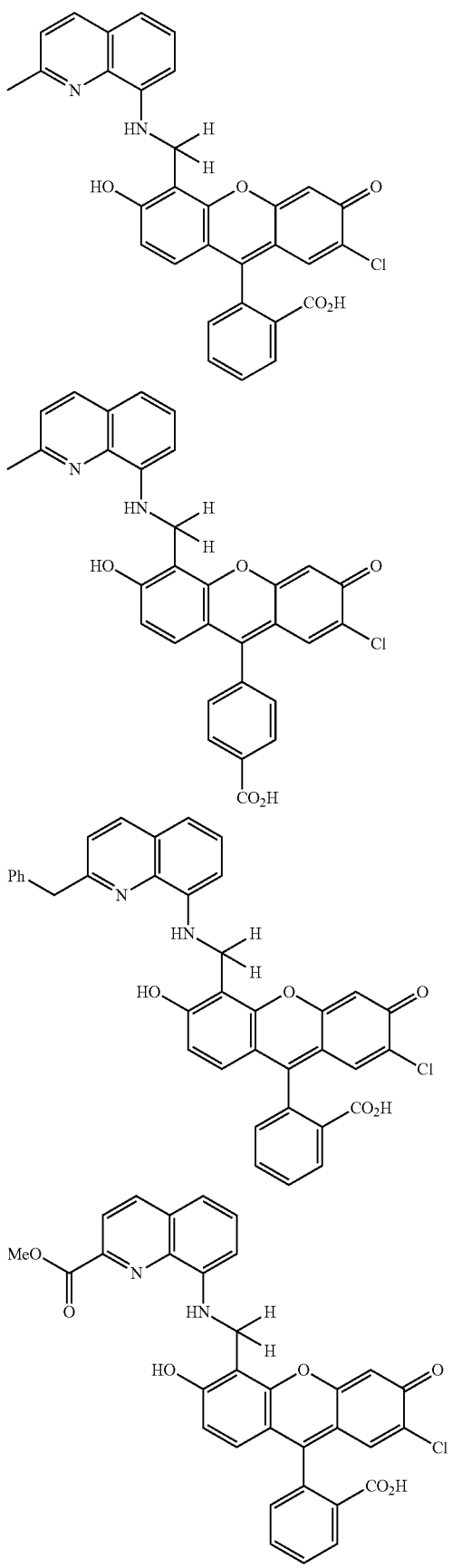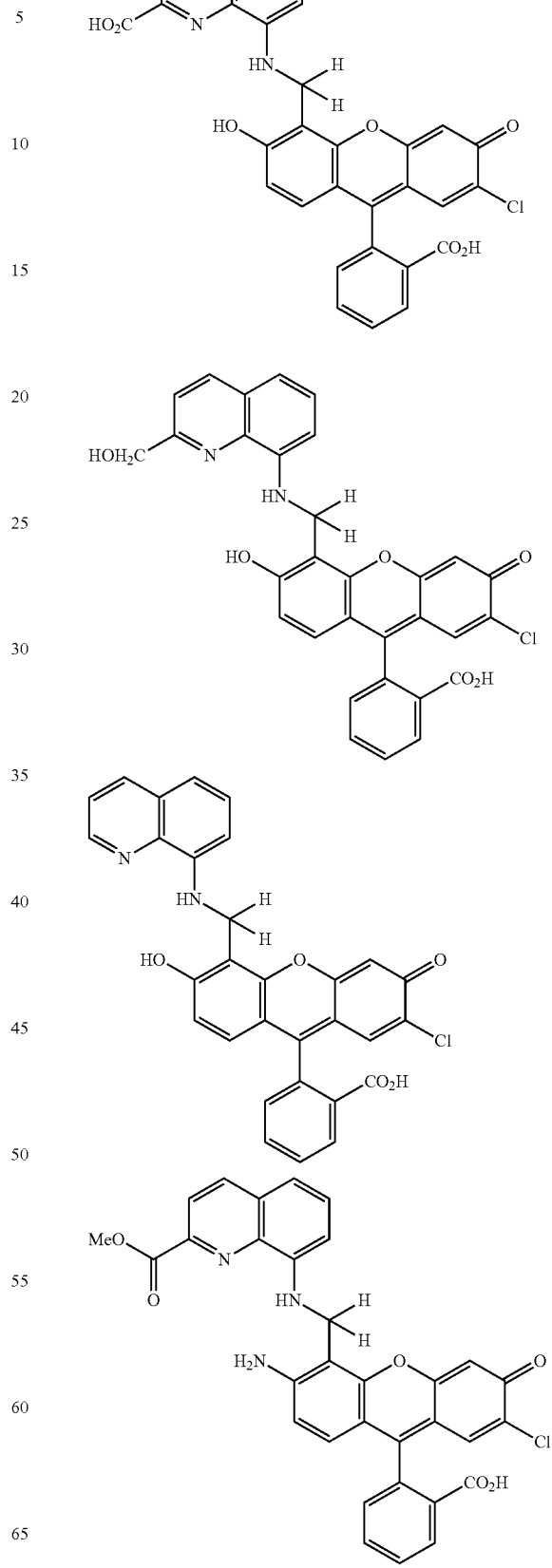

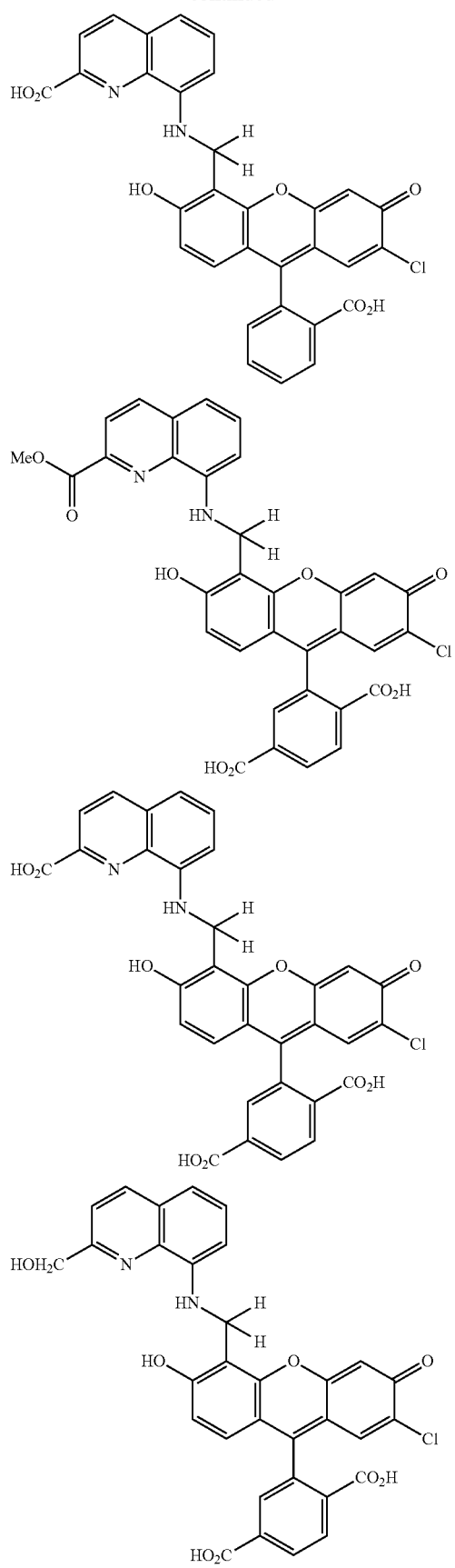
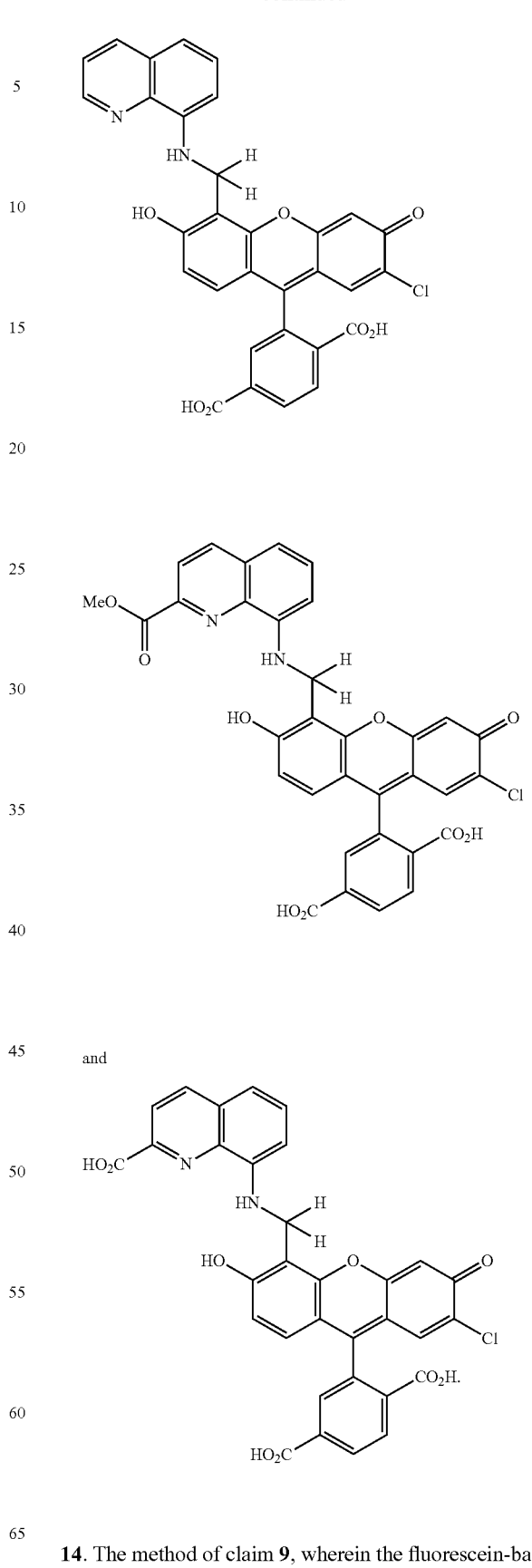
and
14. The method of claim 9, wherein the fluorescein-based sensor is

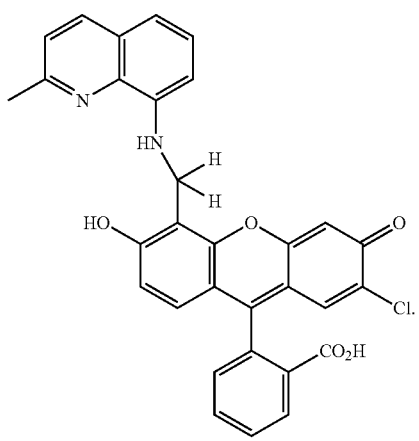 [SMILES: Cc1ccc2cccc(NCc3c(O)ccc4c(-c5ccccc5C(=O)O)c5cc(Cl)c(=O)cc-5oc34)c2n1]
15. The method of claim 14, wherein the transition metal is Cu.
16. The method of claim 9, wherein the fluorescein-based sensor is selected from the group consisting of:
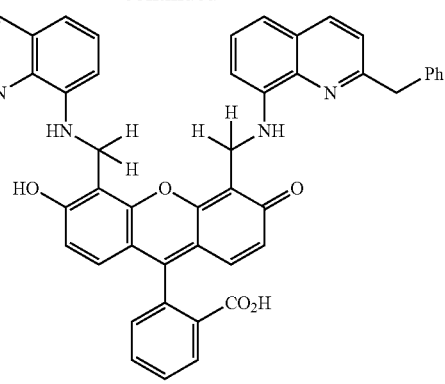
-continued
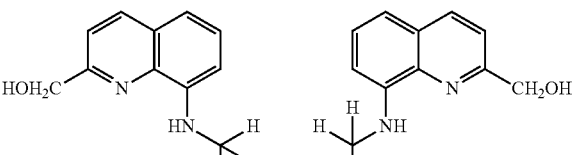
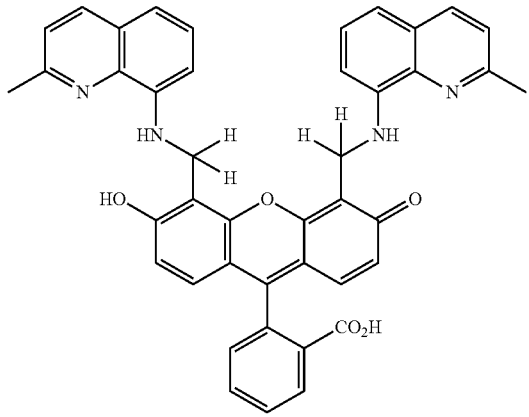
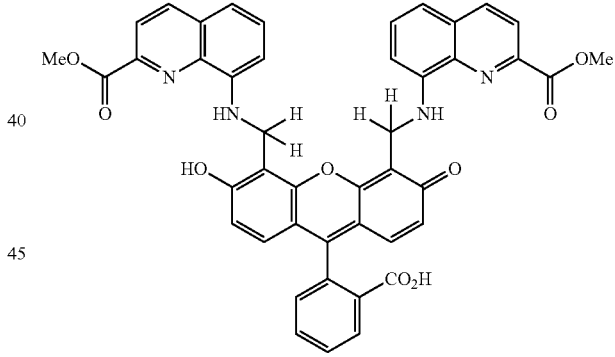
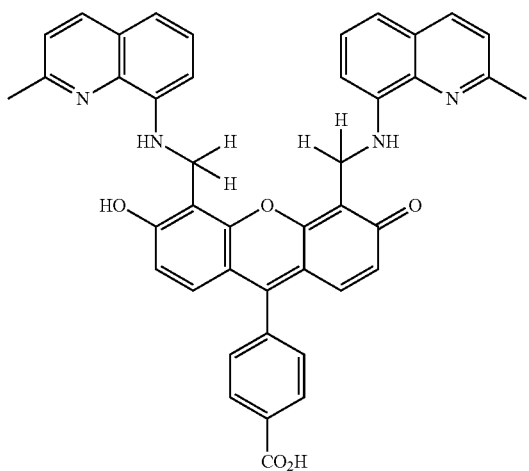
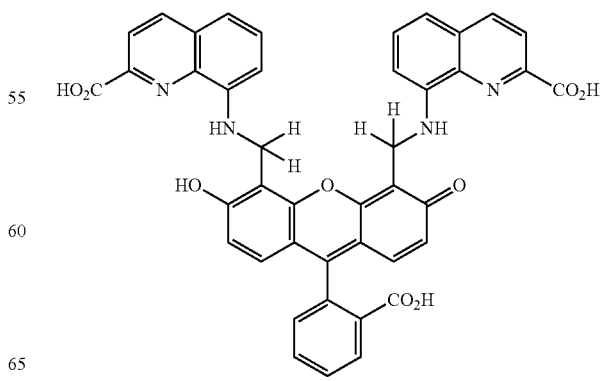

169
-continued
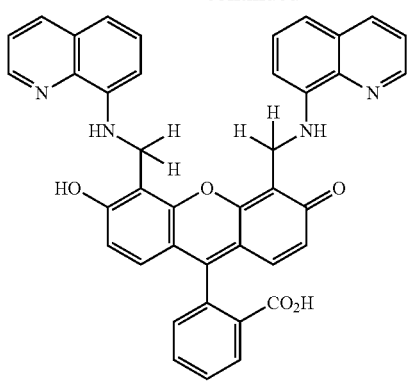
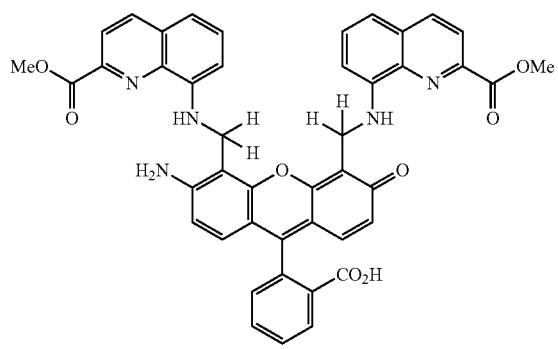
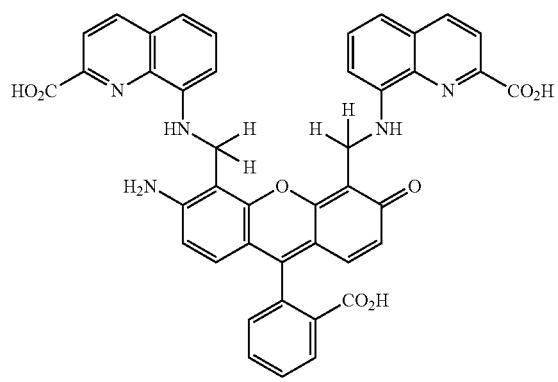
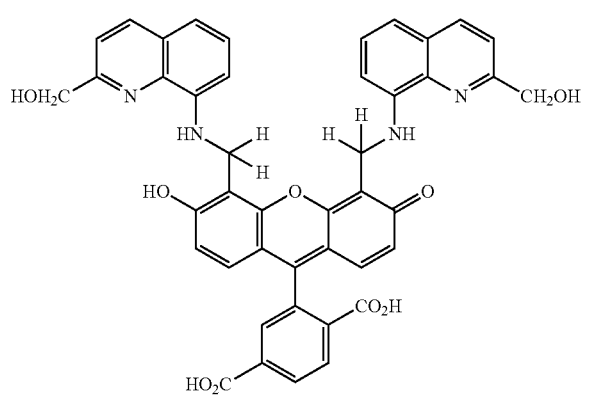
170
-continued
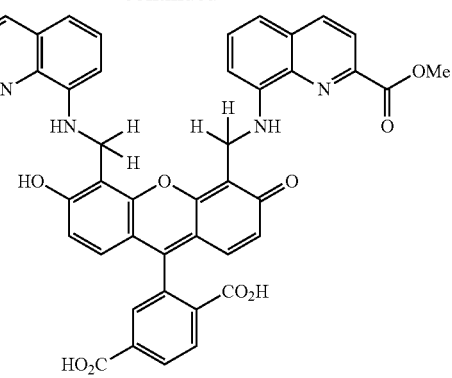
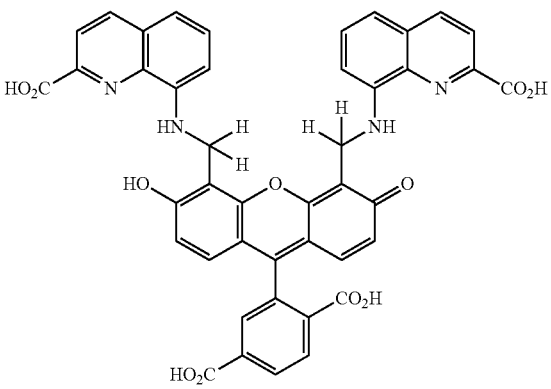
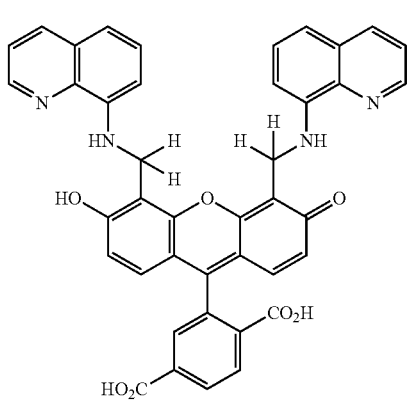
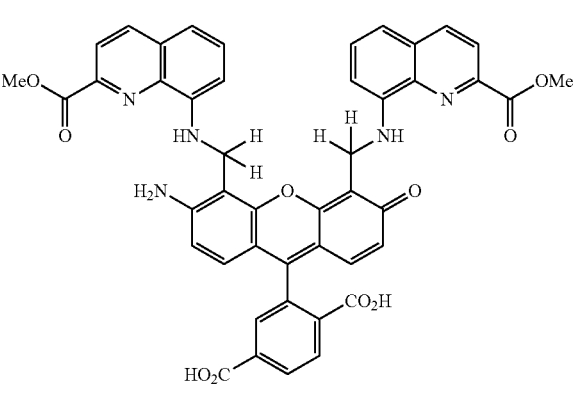

171
-continued
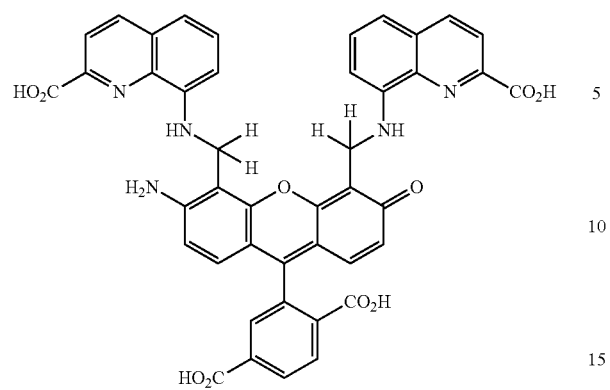
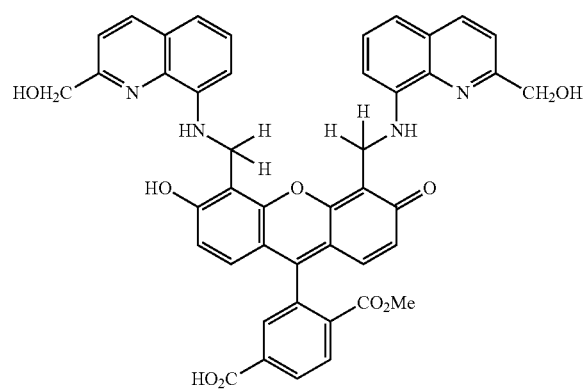
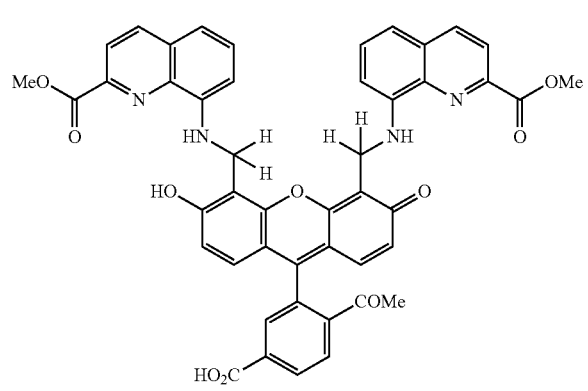
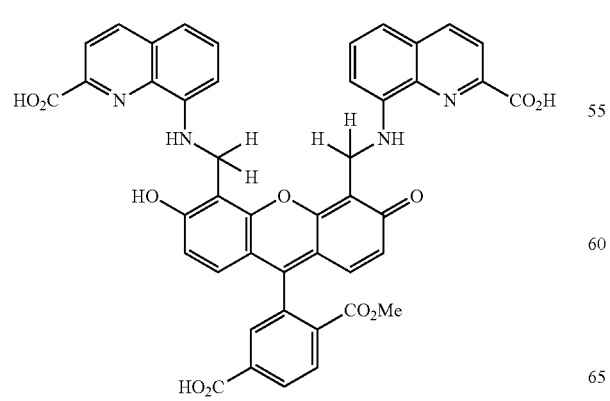
172
-continued
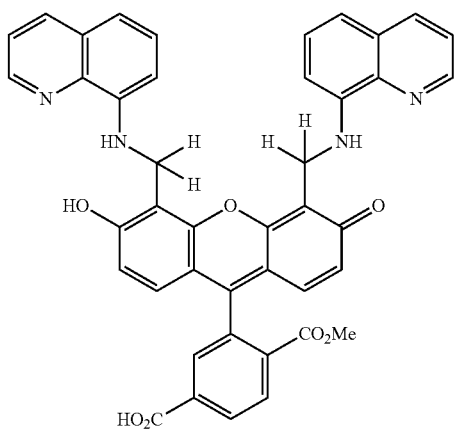
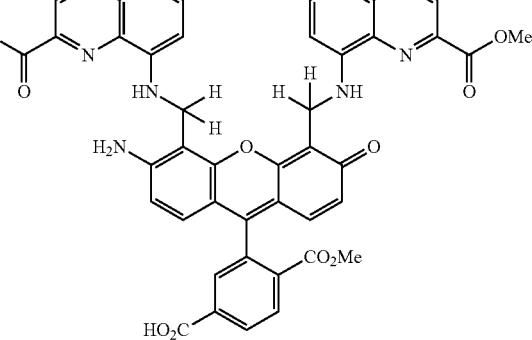
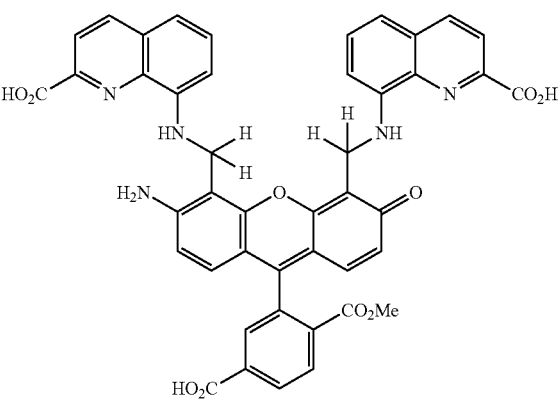
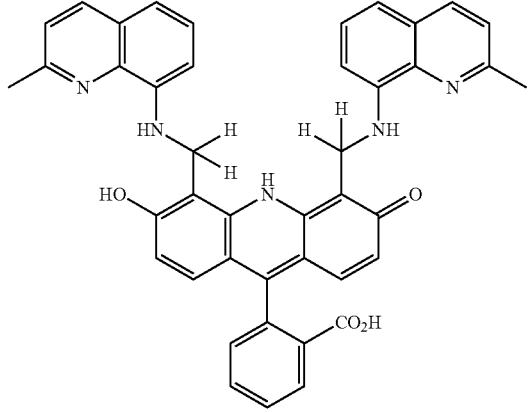

173
-continued
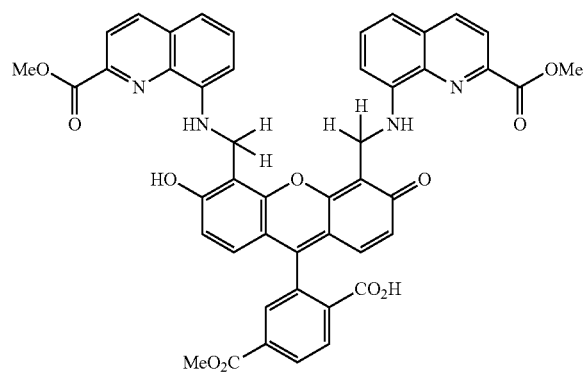
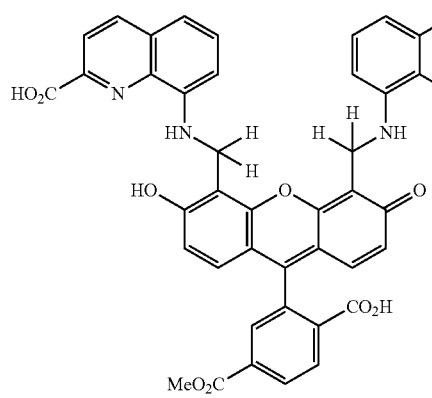
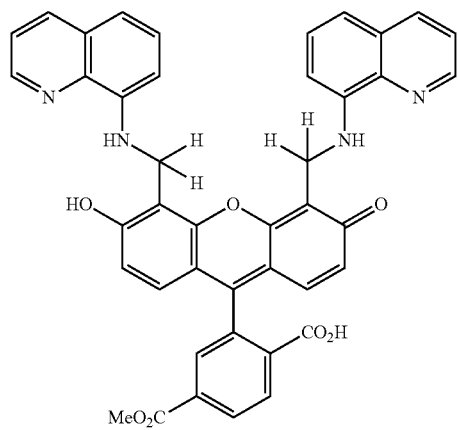
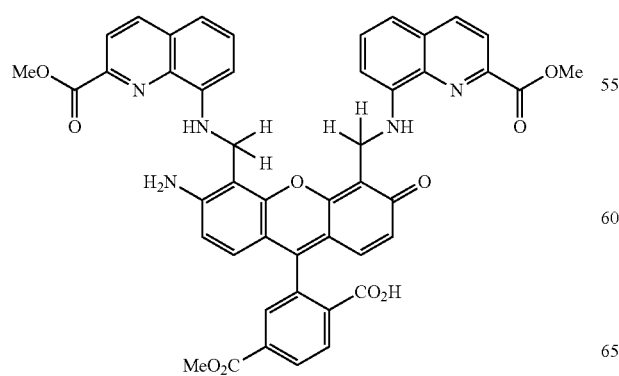
174
-continued
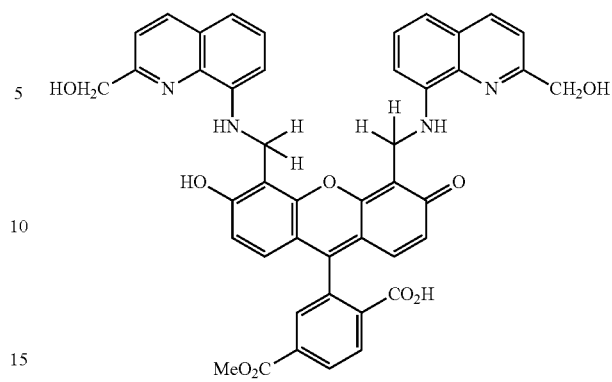
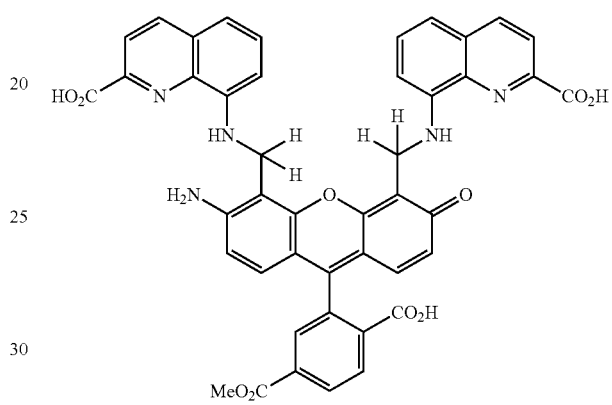
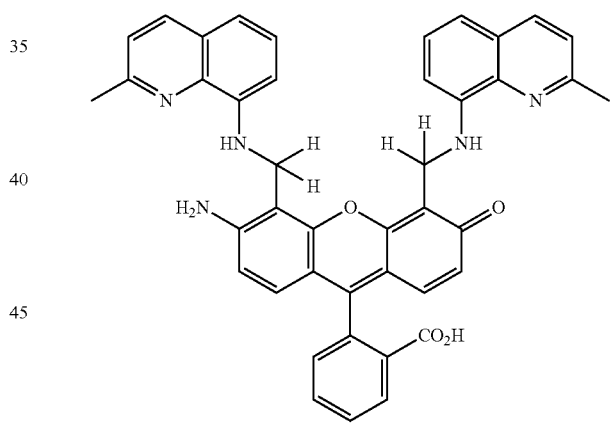
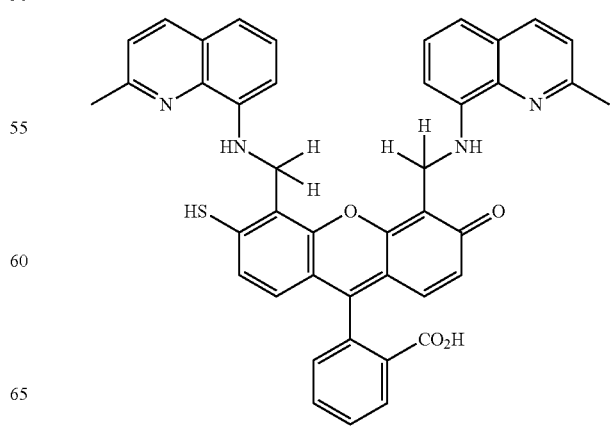

175
-continued
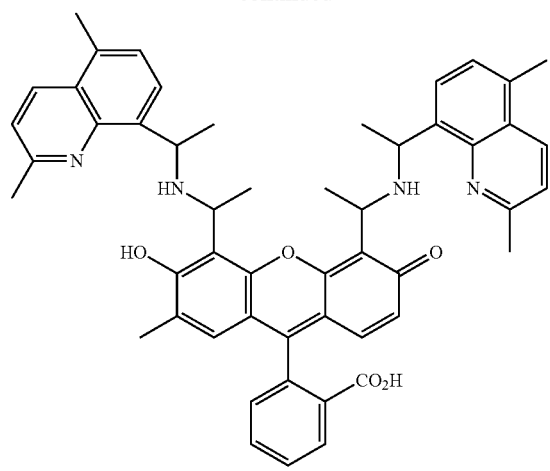
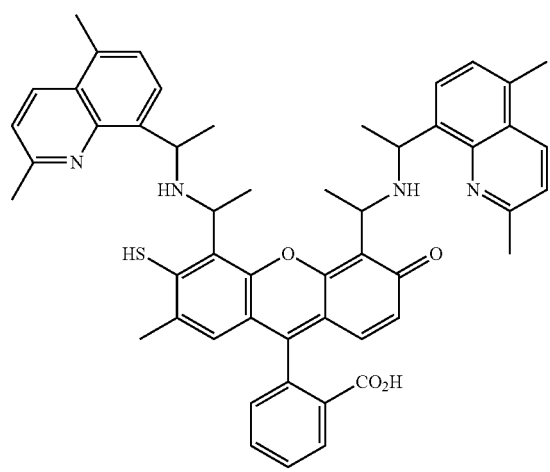
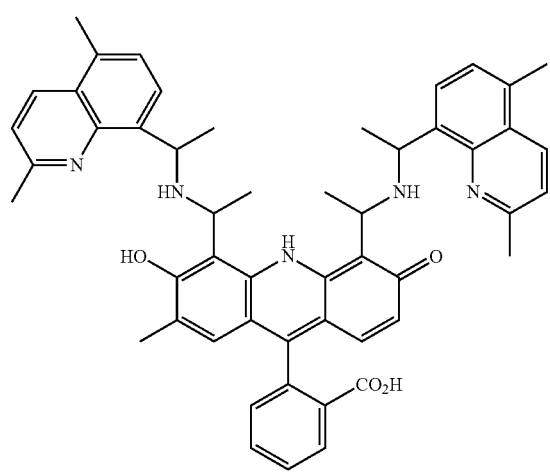
176
-continued
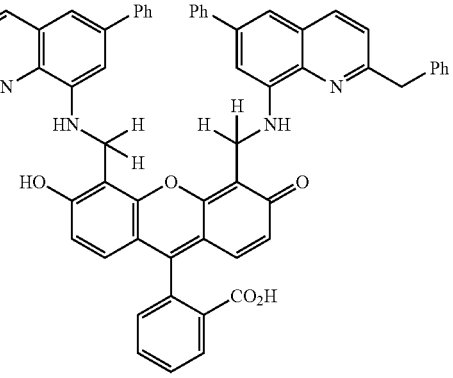
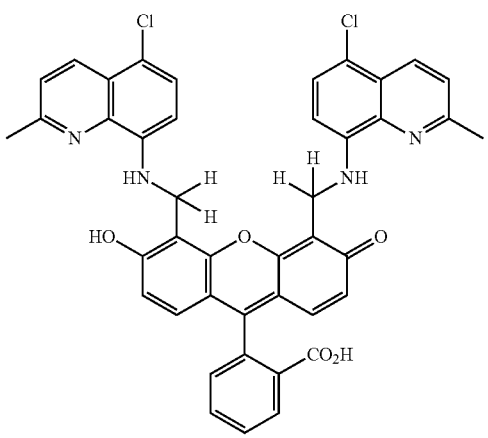
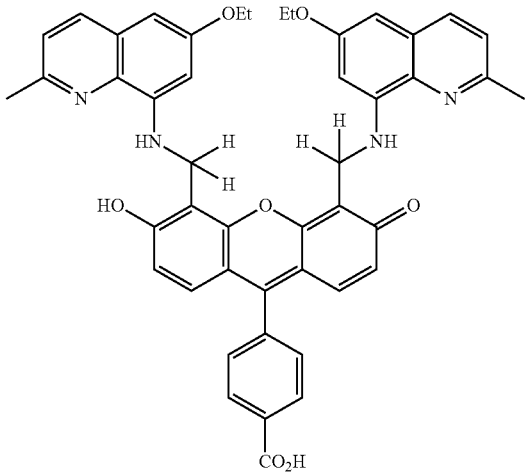

177
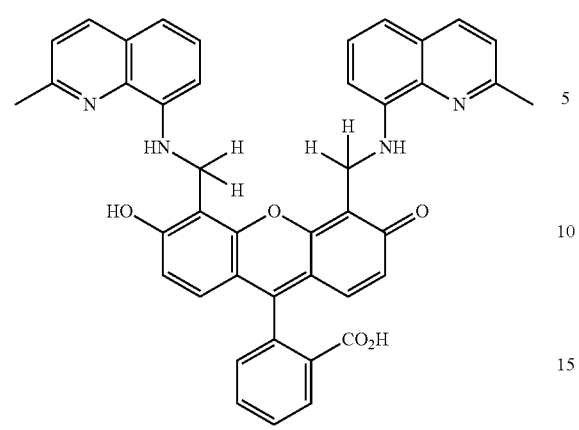
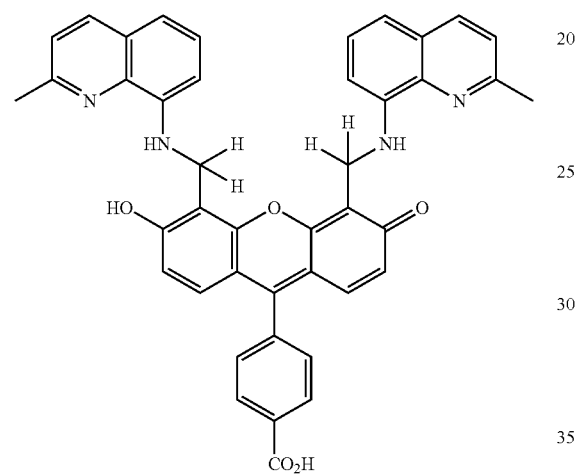
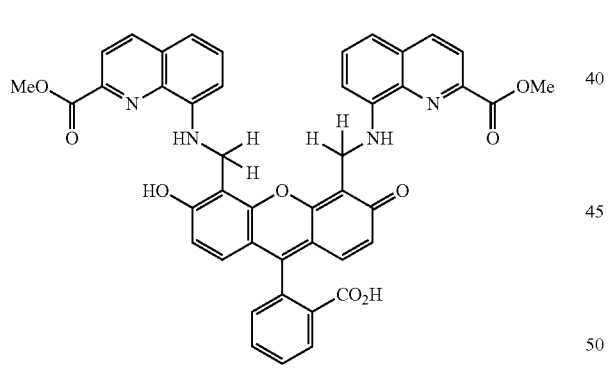
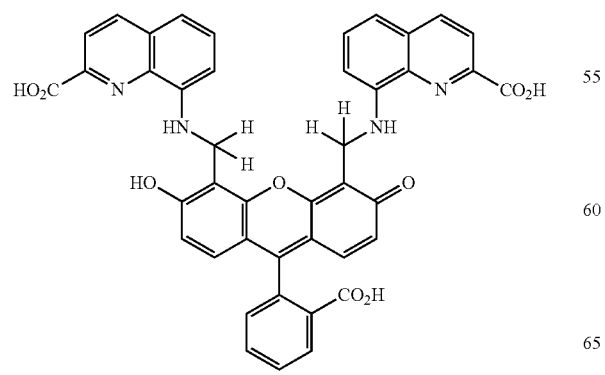
178
-continued
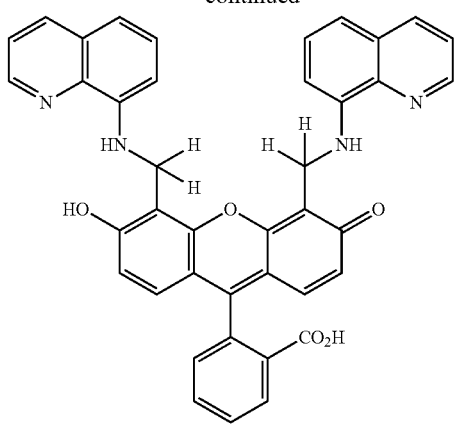
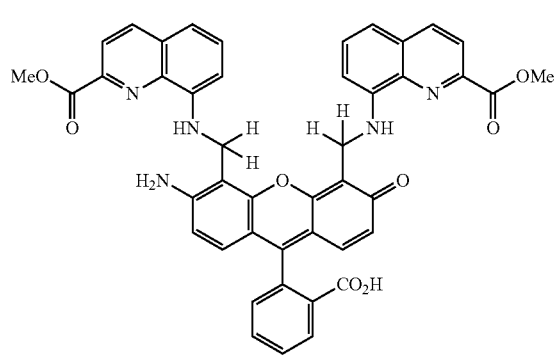
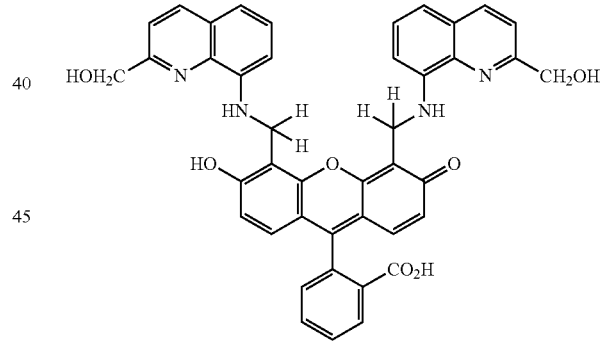
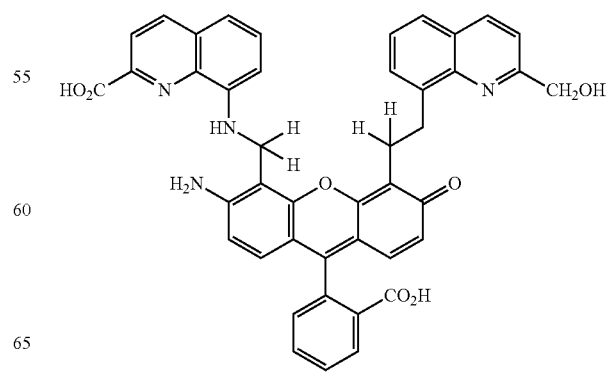

-continued

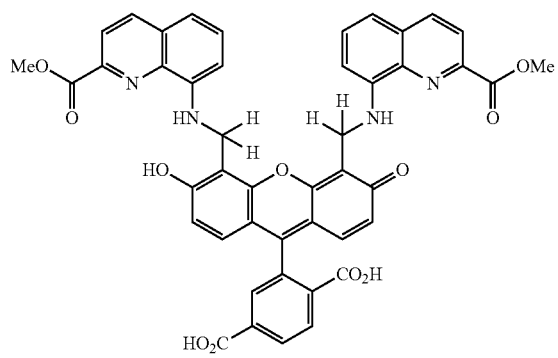 [SMILES: COC(=O)c1ccc2cccc(NCc3c4oc5c(CNc6cccc7ccc(C(=O)OC)nc67)c(O)ccc5c(-c5cc(C(=O)O)ccc5C(=O)O)c-4ccc3=O)c2n1]

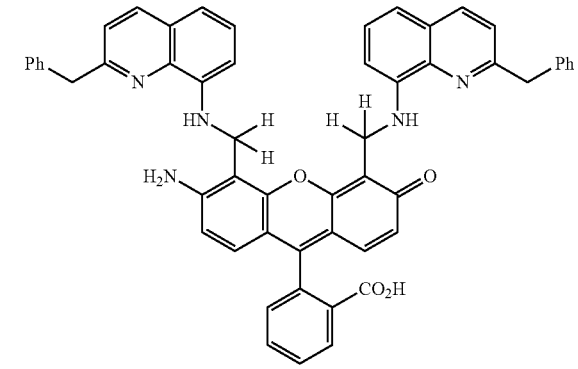

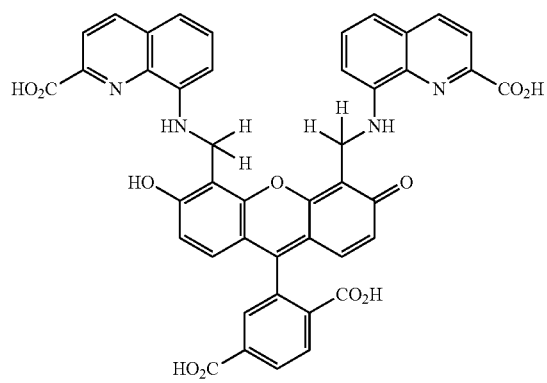 [SMILES: Nc1ccc2c(-c3cc(C(=O)O)ccc3C(=O)O)c3ccc(=O)c(CNc4cccc5ccc(C(=O)O)nc45)c-3oc2c1CNc1cccc2ccc(C(=O)O)nc12]

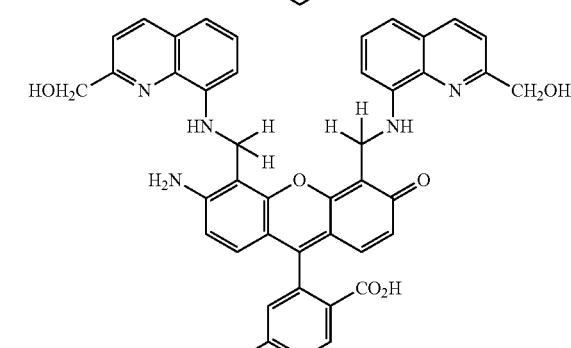

and

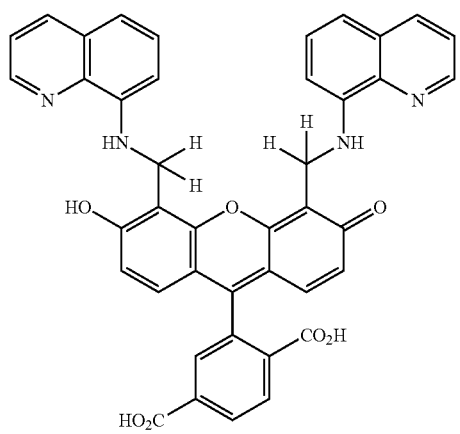

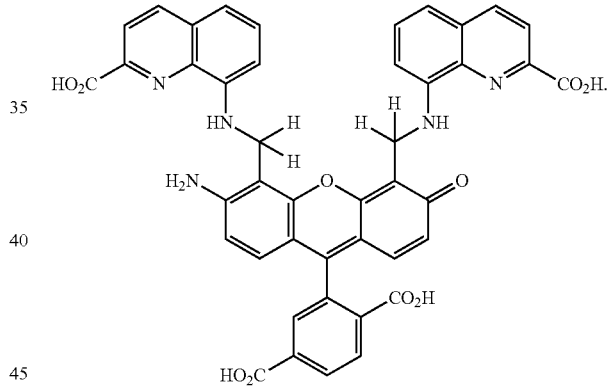

17. The method of claim 9, wherein steps (f) and (l) are both completed between about 8 hours and 12 hours after the bacteria are taken up by the macrophages.

18. The method of claim 17, wherein the bacteria is selected from the group consisting of Gram-positive bacteria that express native bNOS, Gram-positive bacteria that express non-native bNOS, Gram-negative bacteria that express native bNOS, and Gram-negative bacteria that express non-native bNOS.

19. The method of claim 17, wherein the bacteria is *Bacillus spp.*, *Bacillus subtilis*, *Bacillus anthracis*, *Bacillus anthracis* Sterne, *Staphylococcus spp.*, *Staphylococcus aureus*, methicillin-resistant *Staphylococcus aureus* or *Norcardia spp.*.

20. The method of claim 17, wherein the transition metal is Mn, Cu, Co, Fe, Ni, Zn, Ru, or Rh.

21. The method of claim 17, wherein the fluorescein-based sensor is selected from the group consisting of:

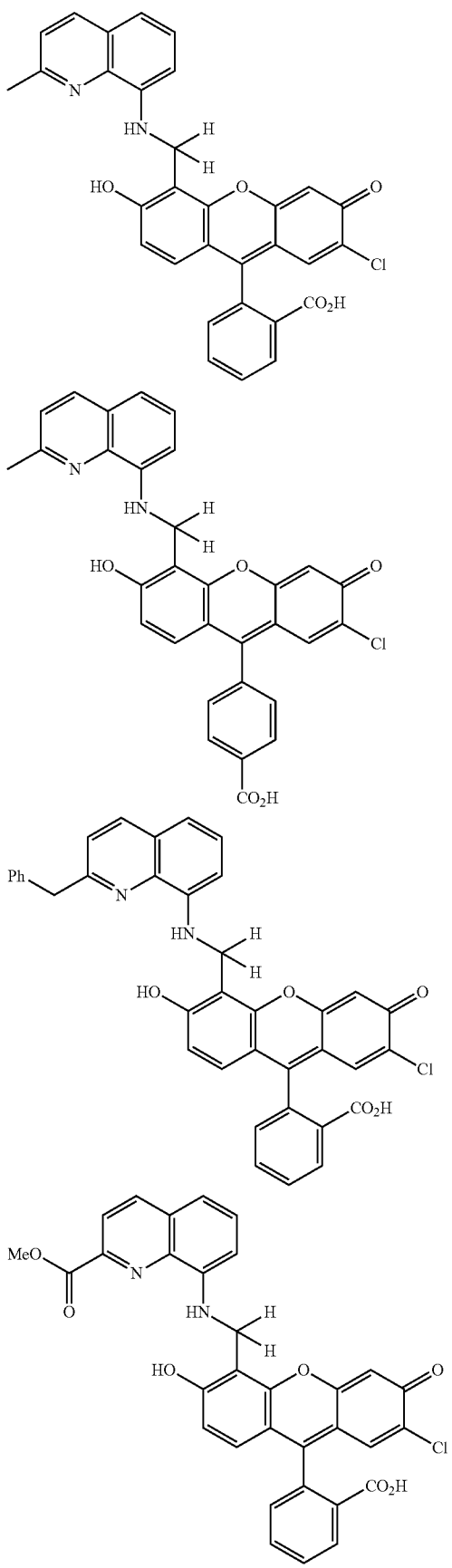
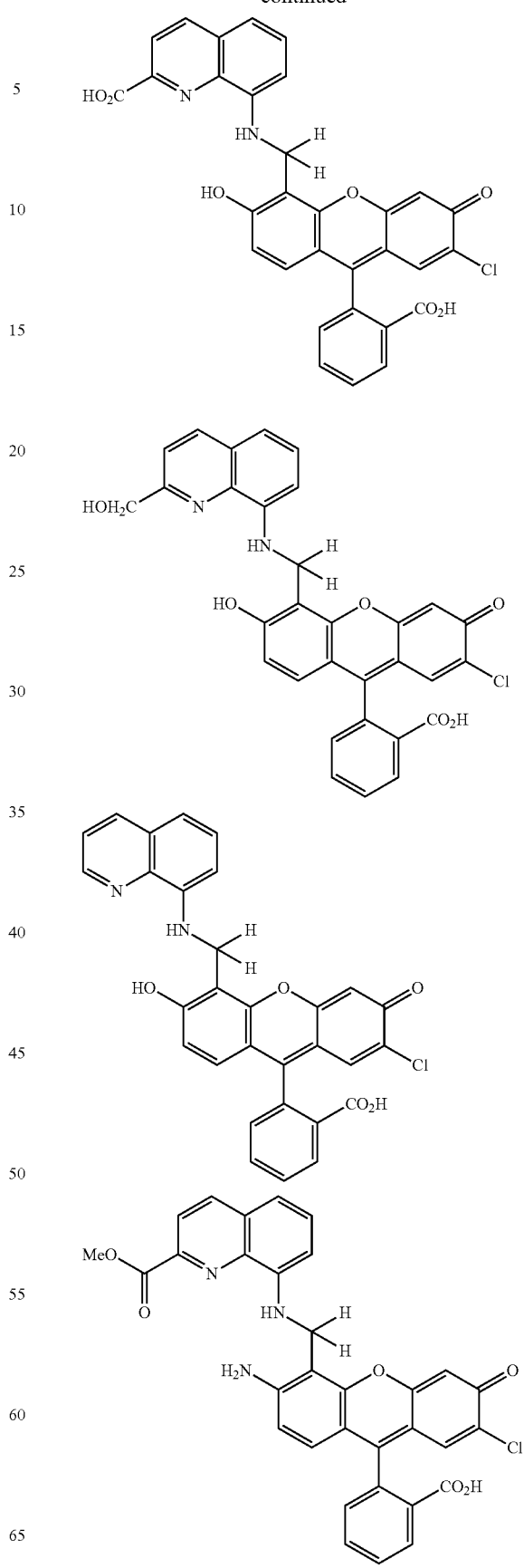

183
-continued
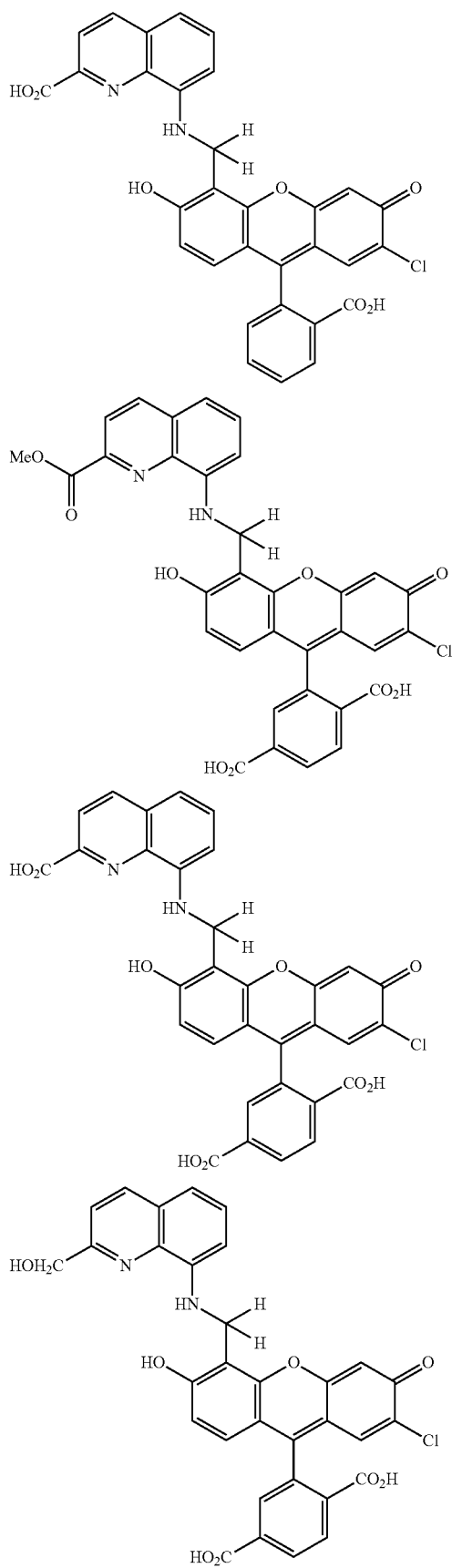
184
-continued
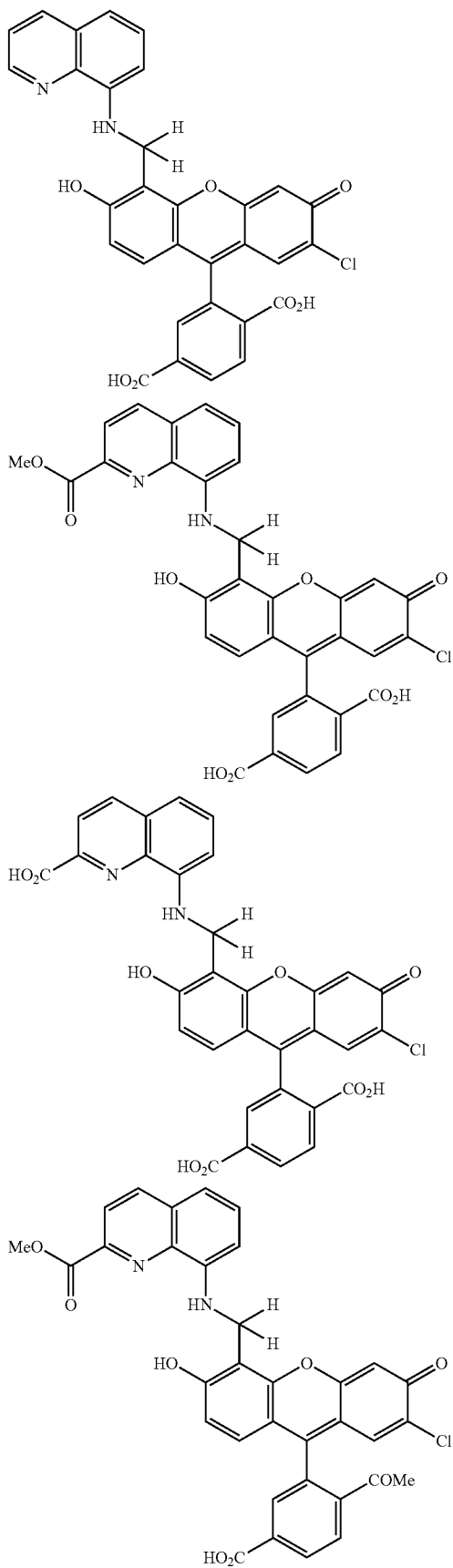

185
-continued
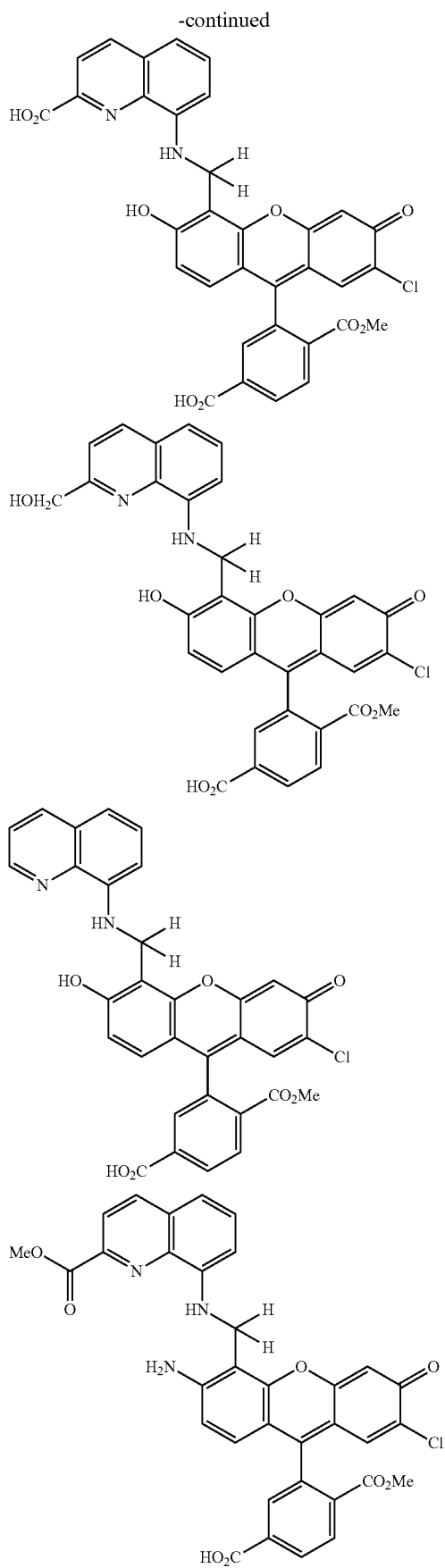
186
-continued
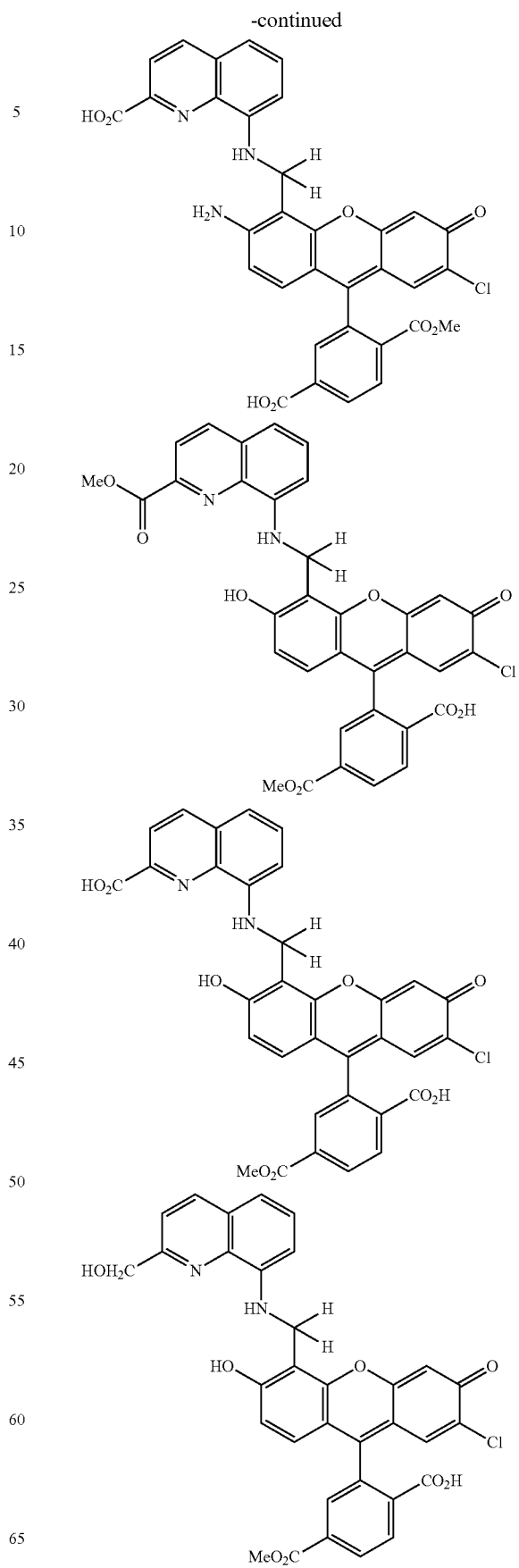

187
-continued
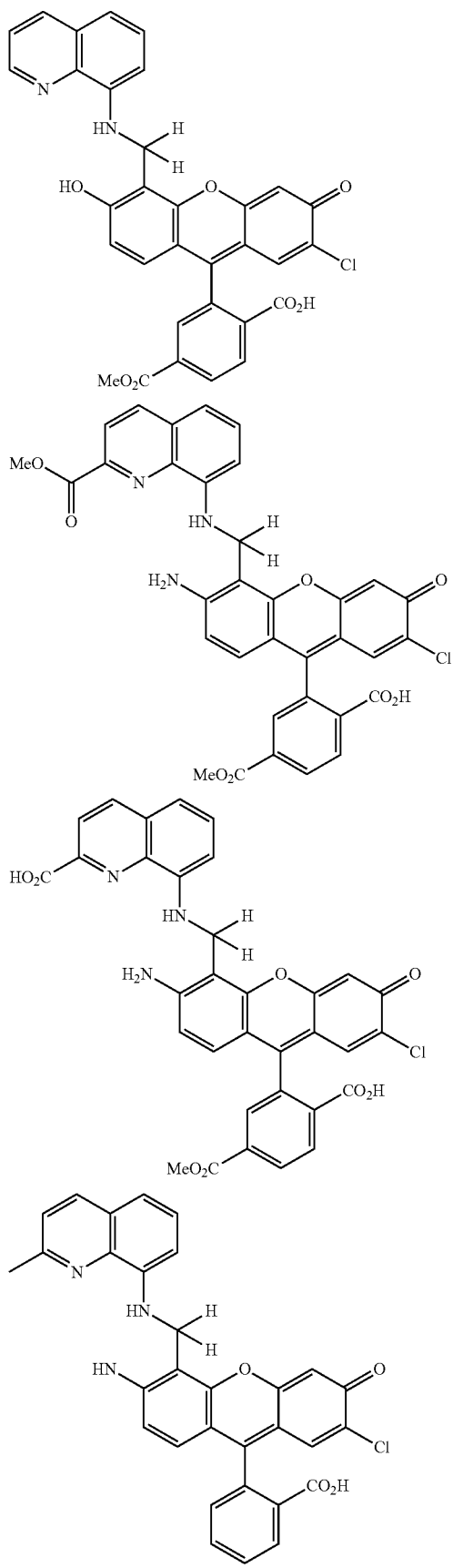
188
-continued
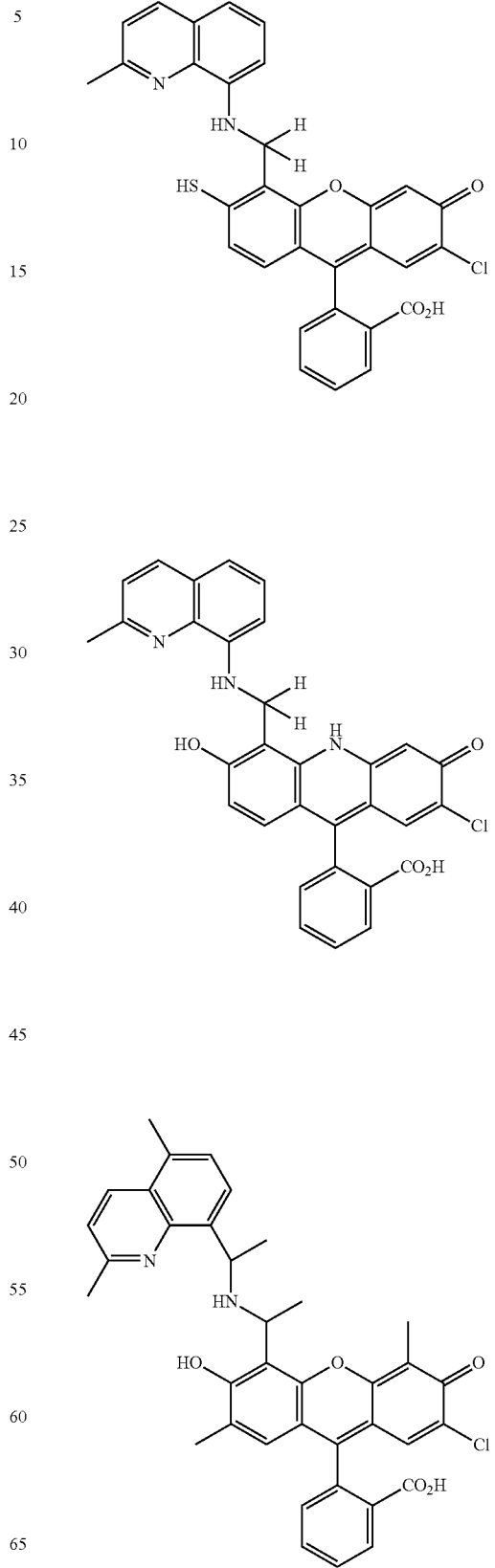

189
-continued
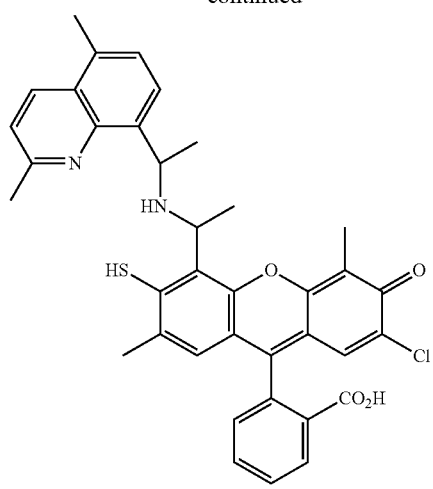
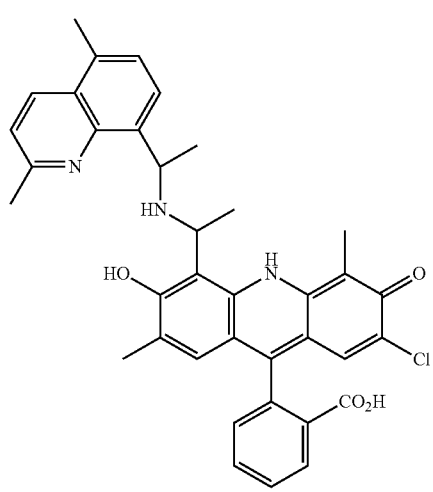
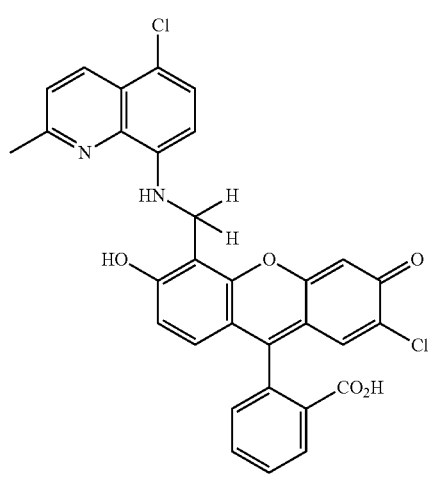
190
-continued
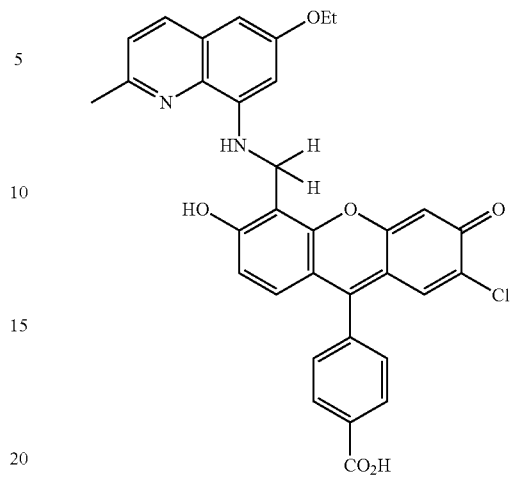
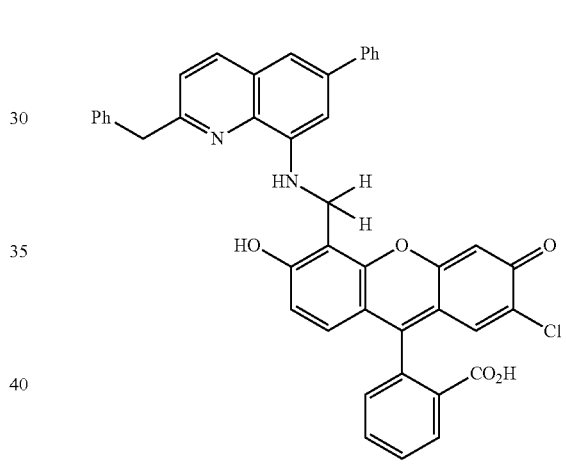
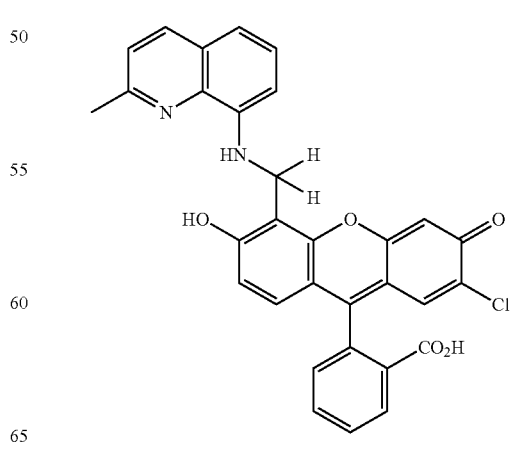

191
-continued
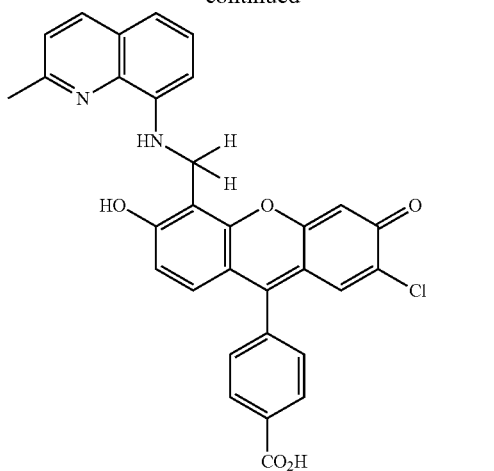
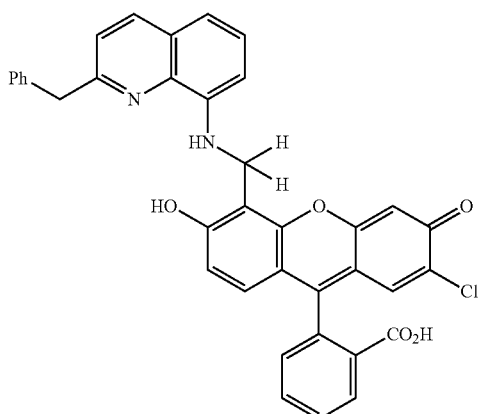
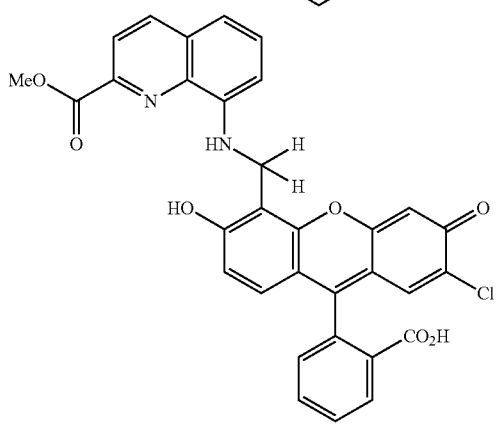
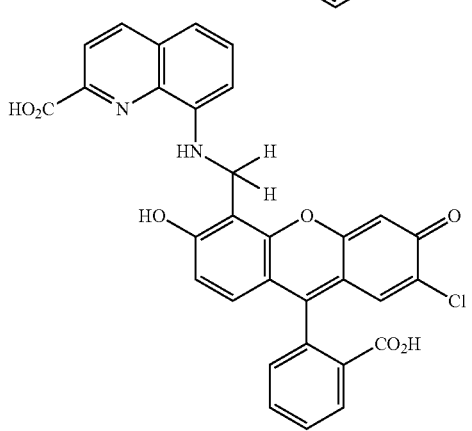
192
-continued
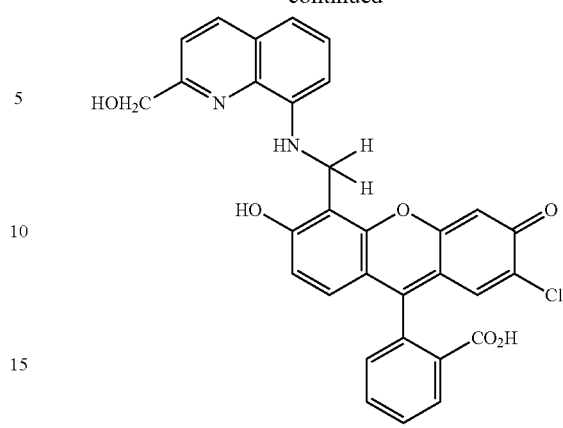
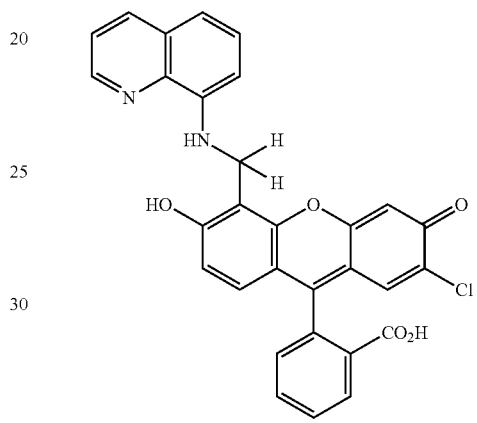
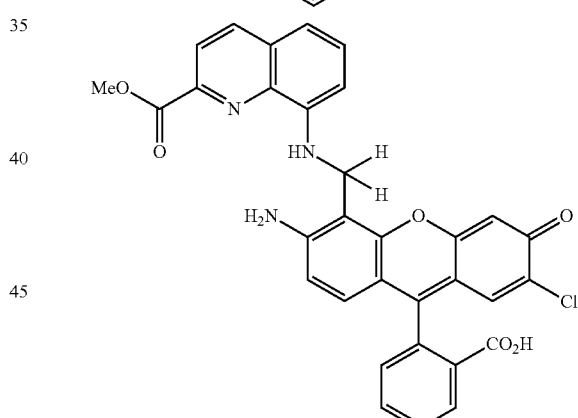
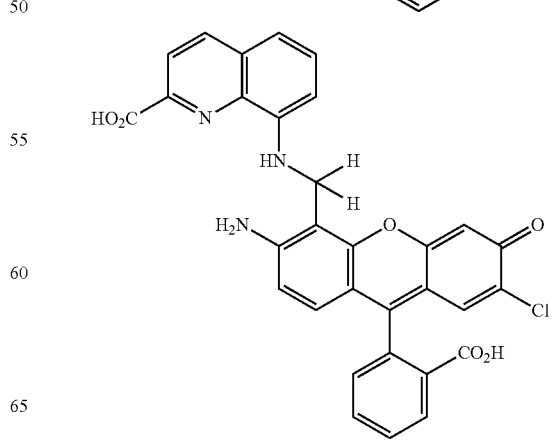

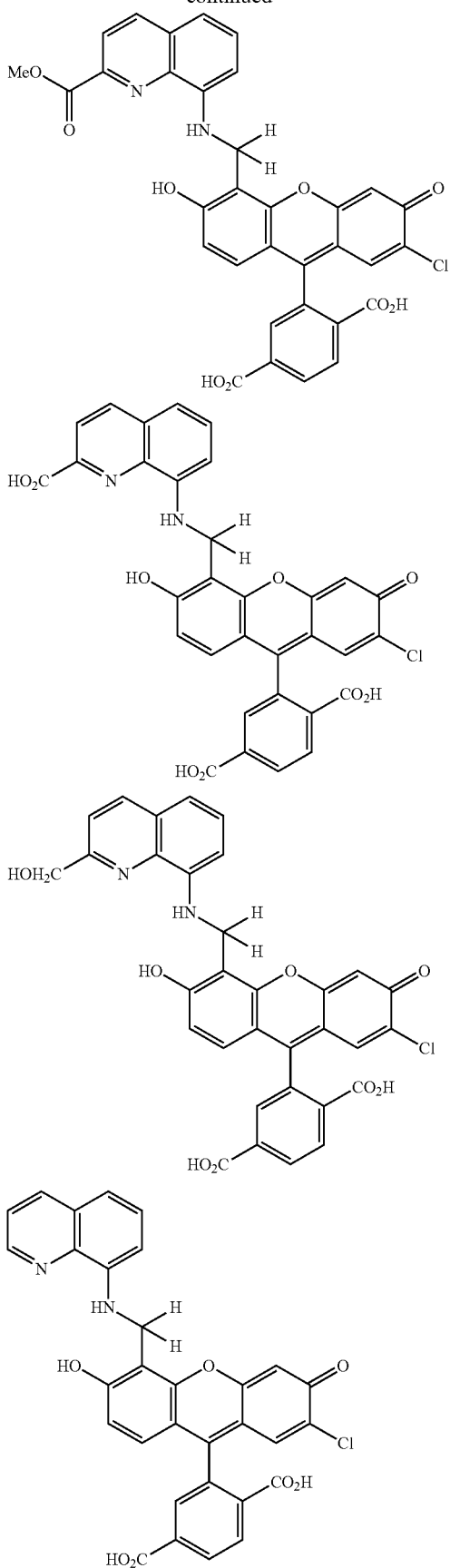
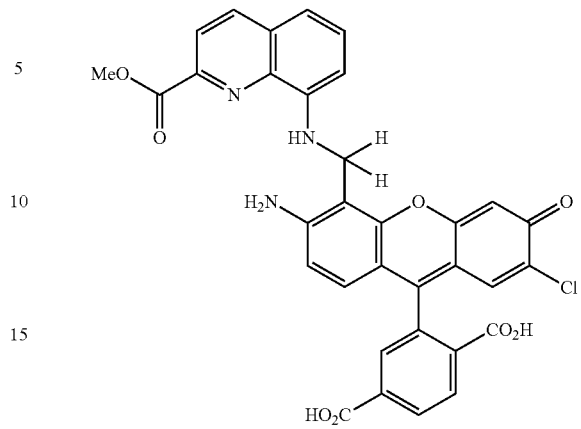
and
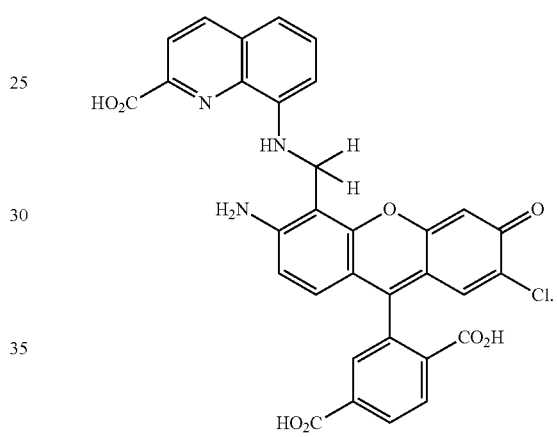
22. The method of claim 17, wherein the fluorescein-based sensor is
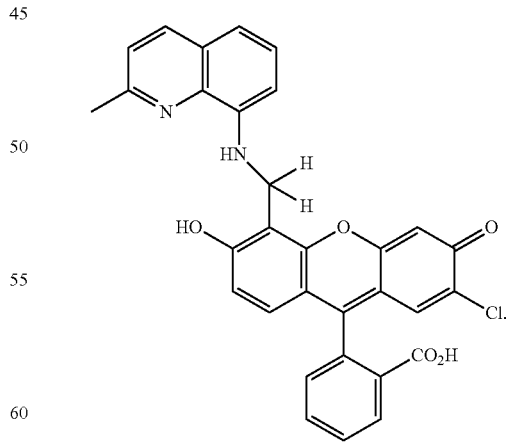
23. The method of claim 22, wherein the transition metal is Cu.
24. The method of claim 17, wherein the fluorescein-based sensor is selected from the group consisting of:

195
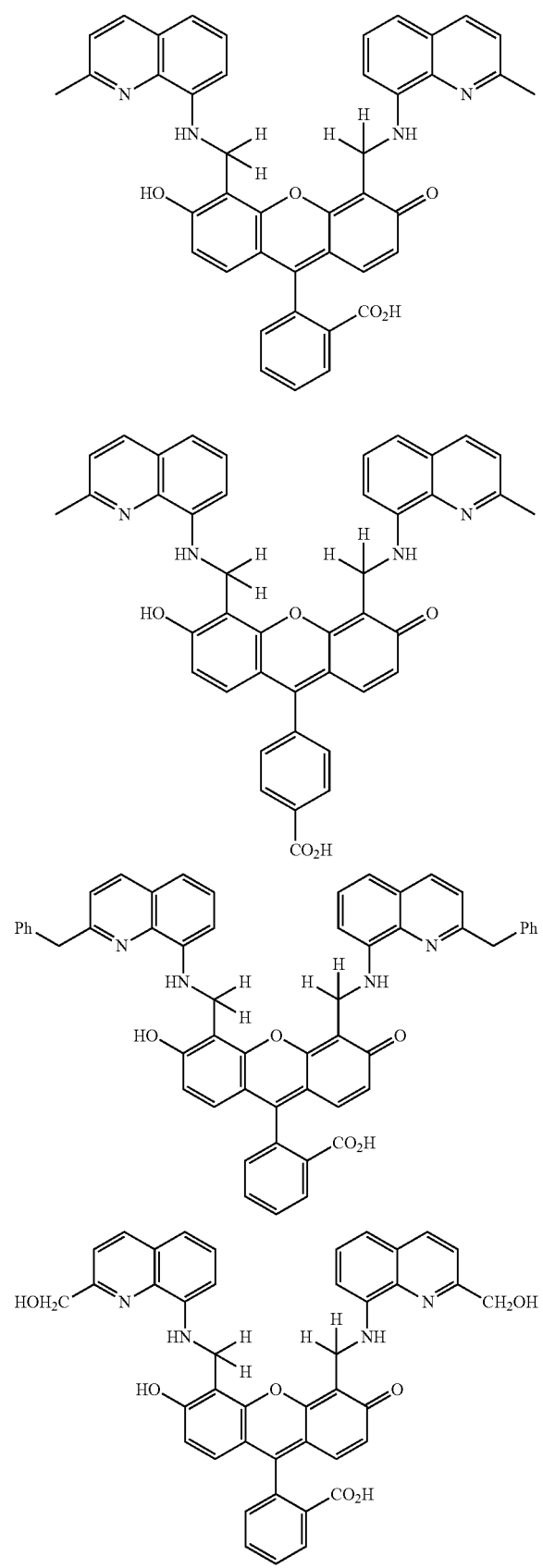
196
-continued
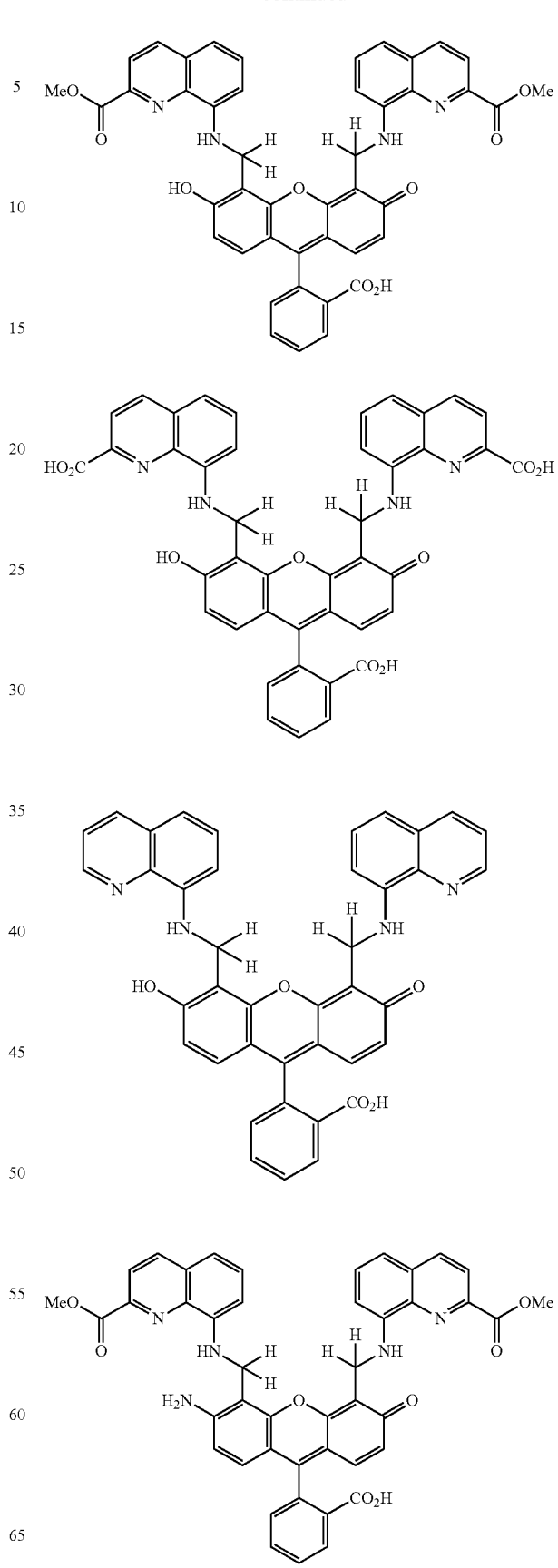

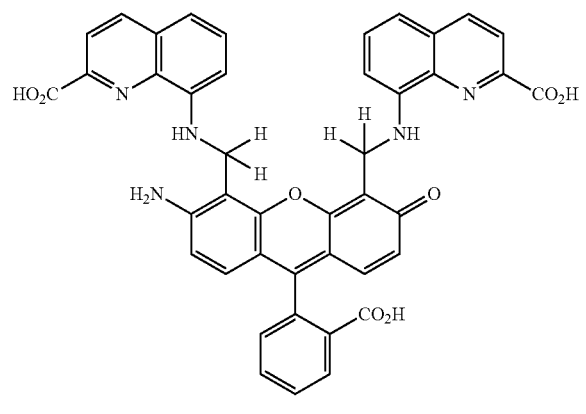
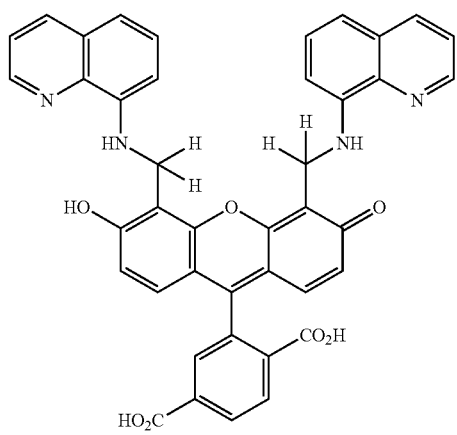
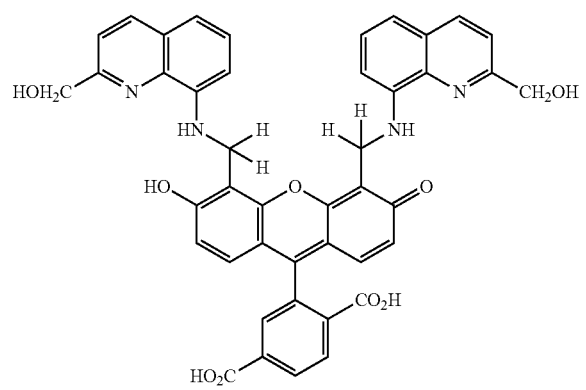
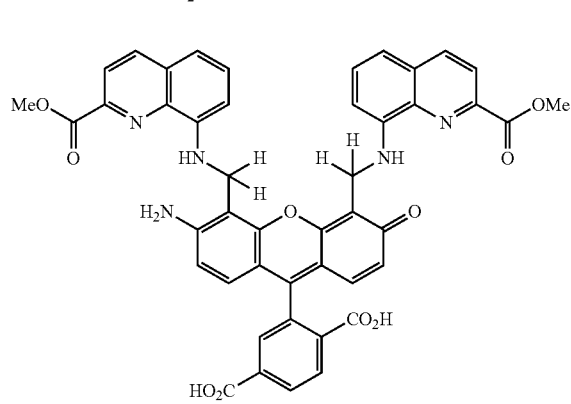
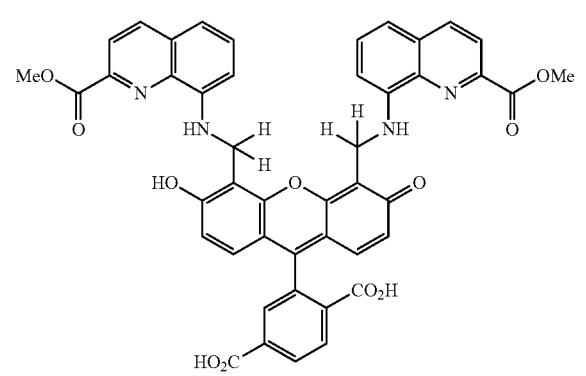
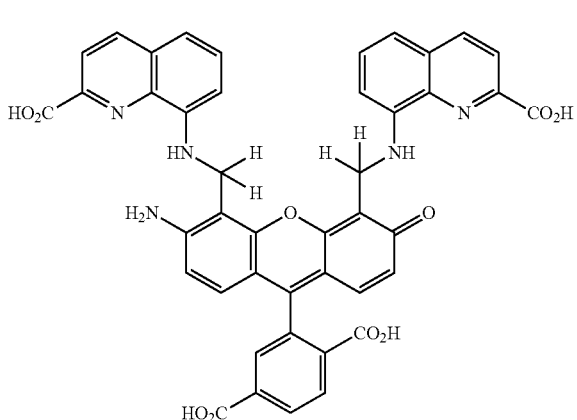
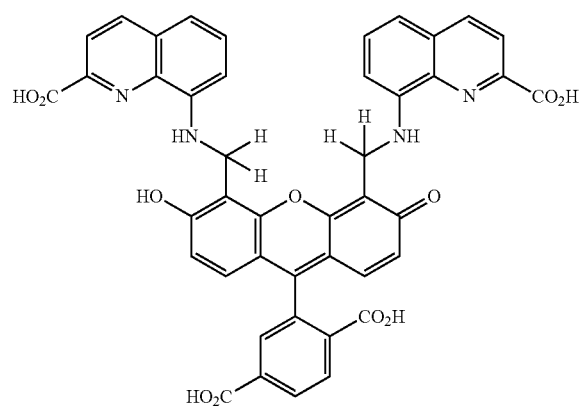
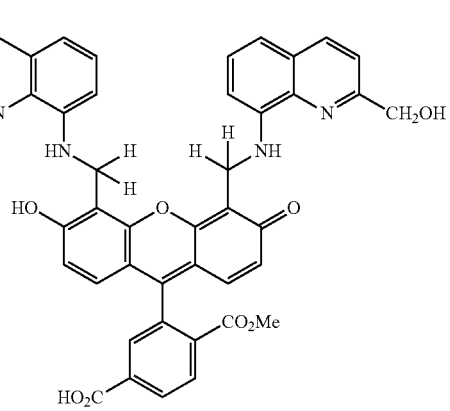

199
-continued
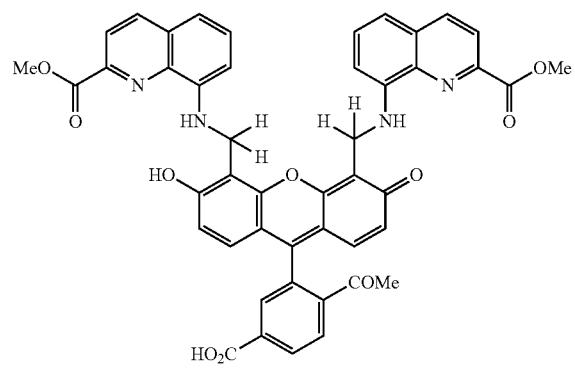
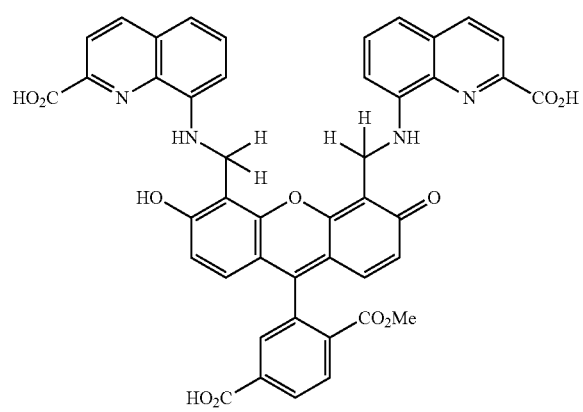
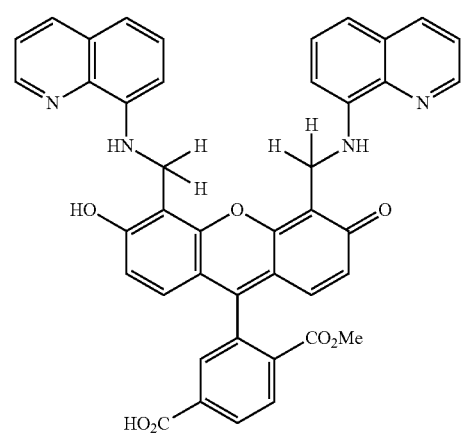
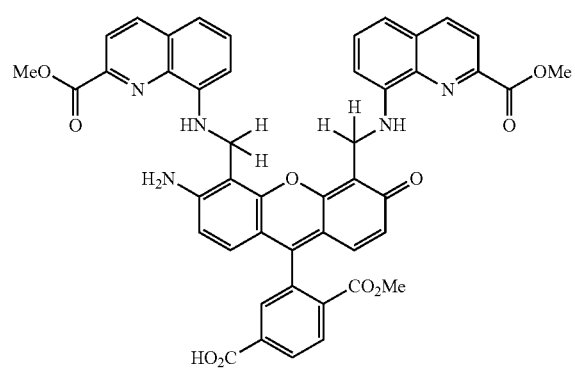
200
-continued
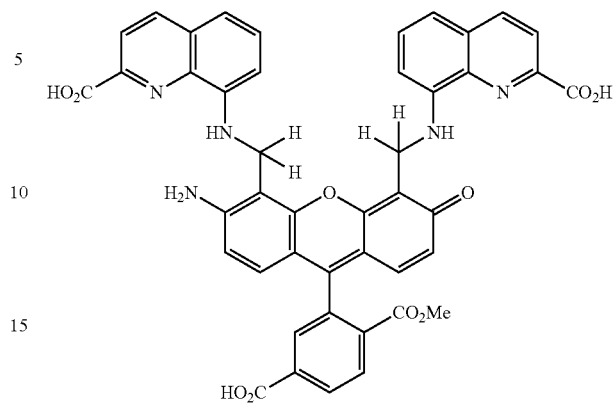
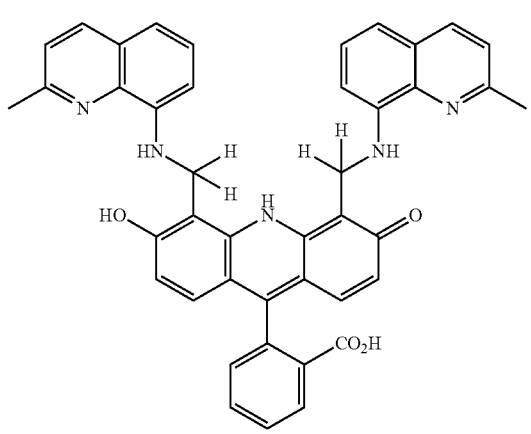
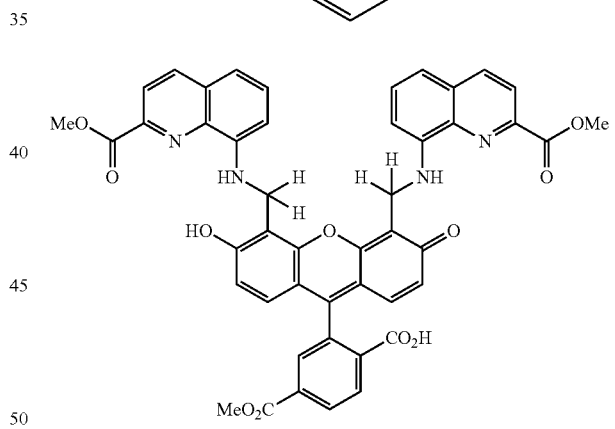
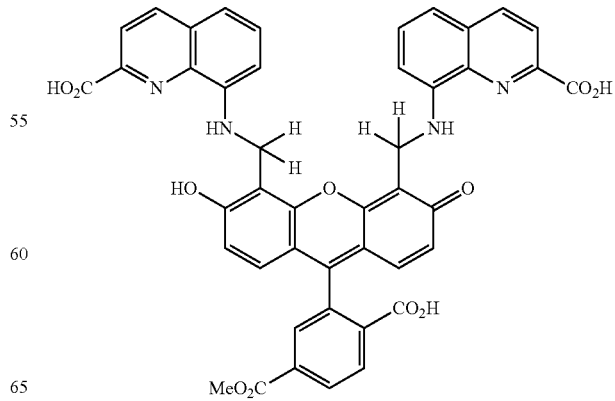

-continued
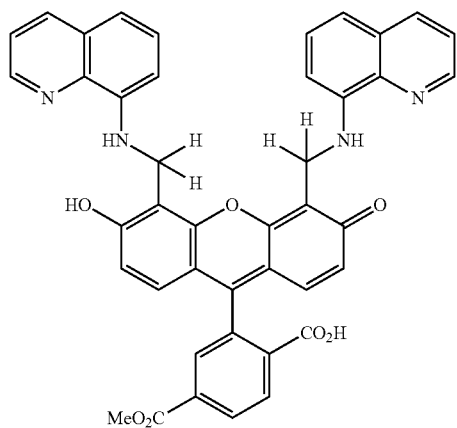
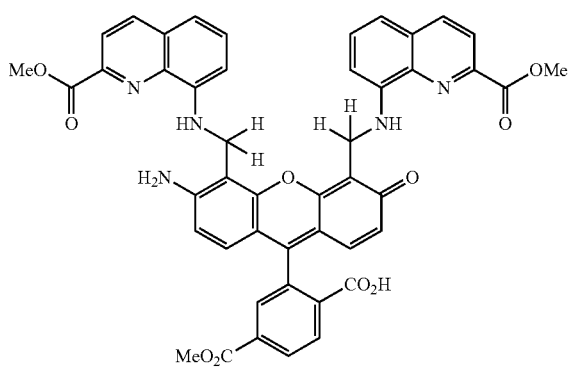
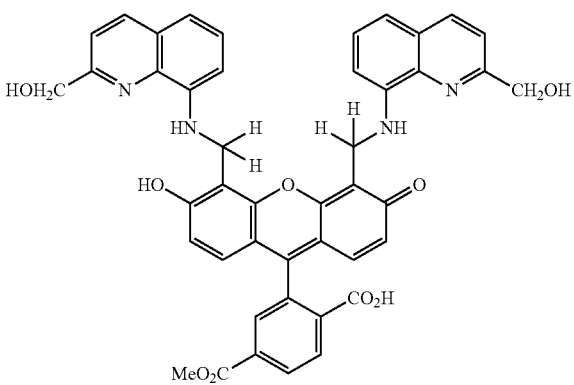
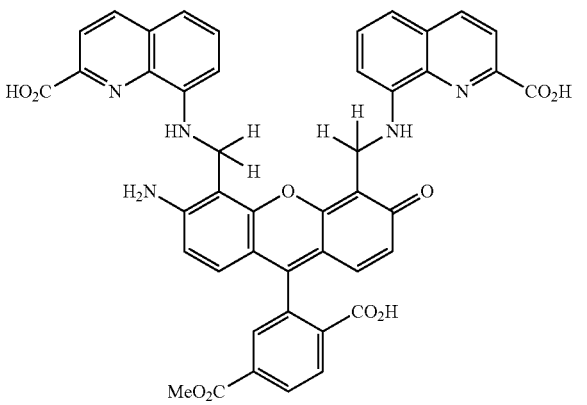
-continued
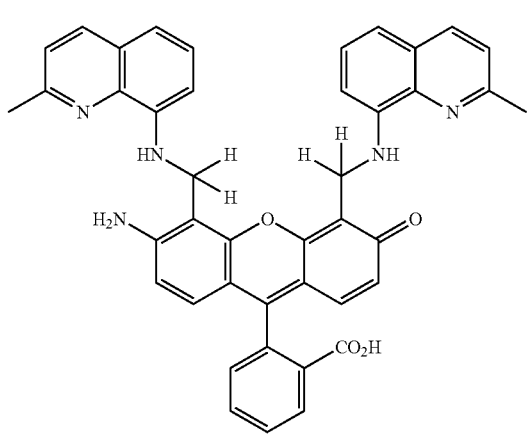
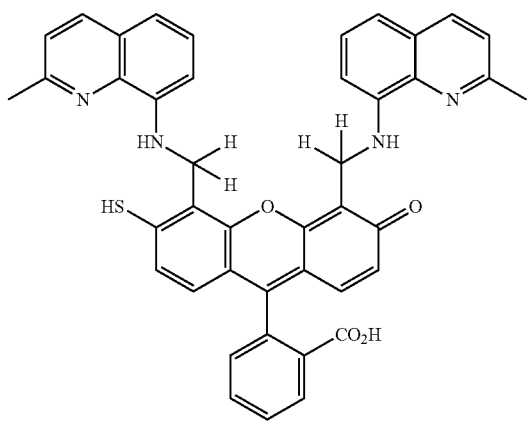
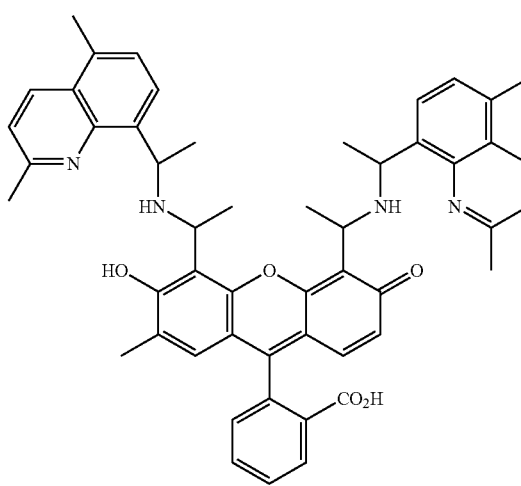

-continued
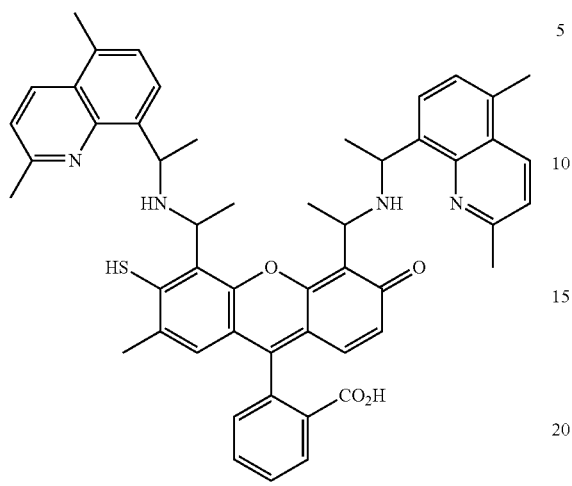
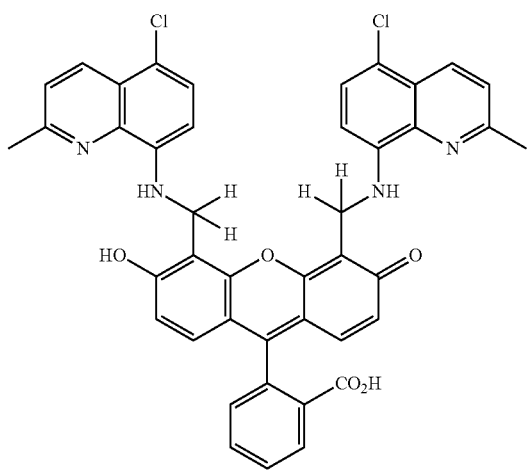
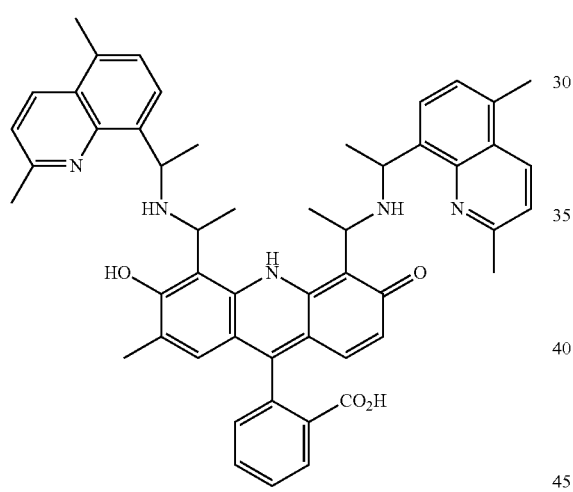
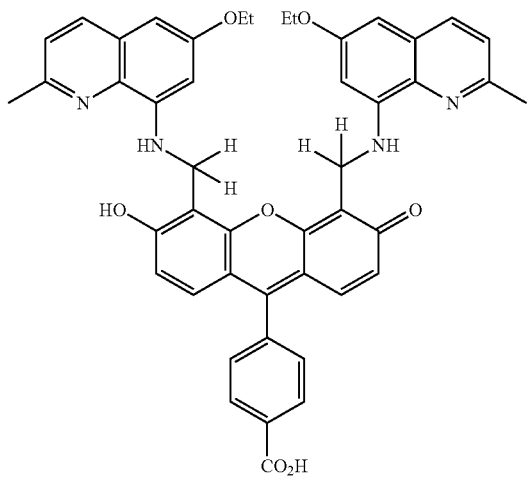
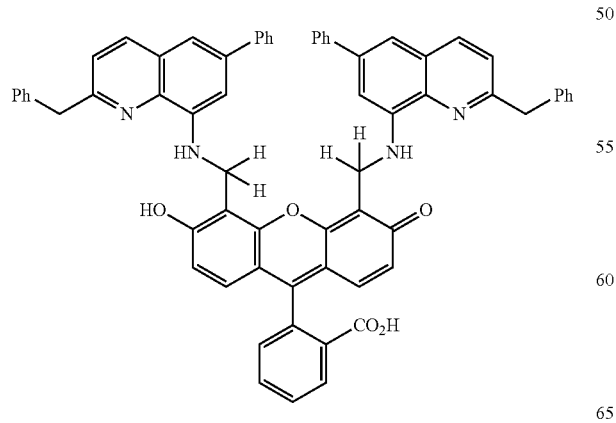
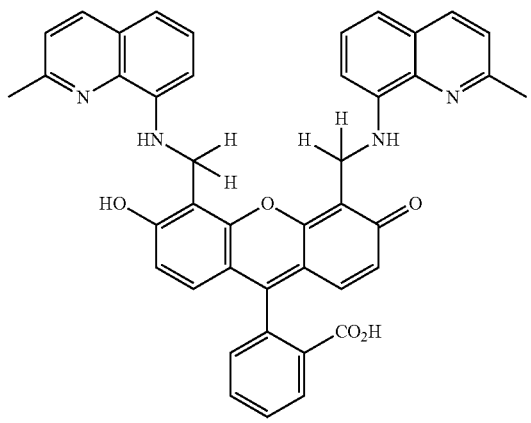

205
-continued
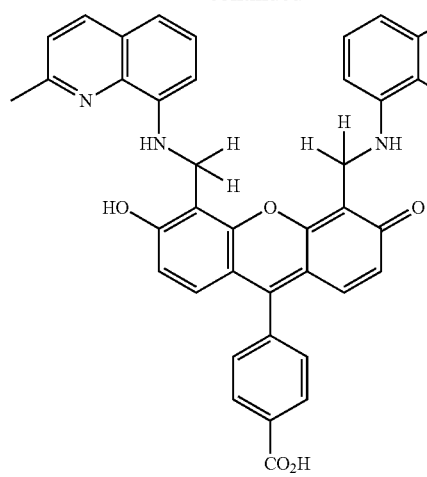
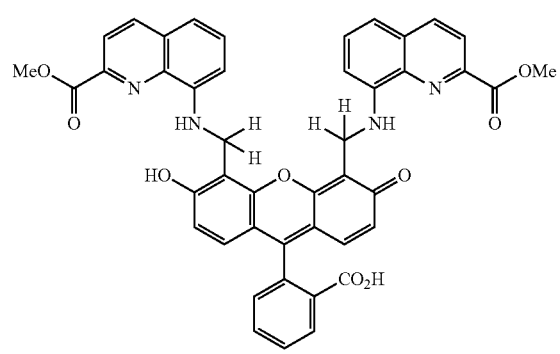
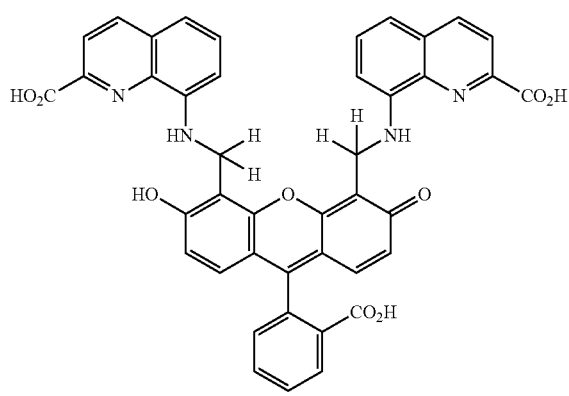
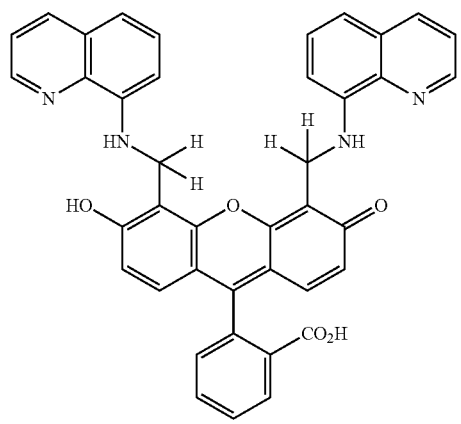
206
-continued
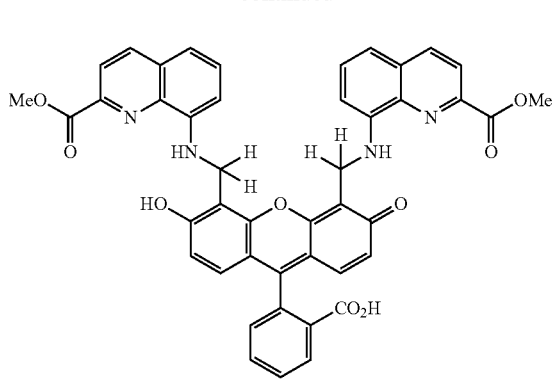
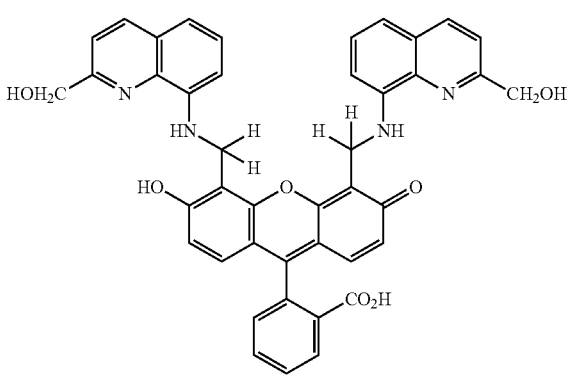
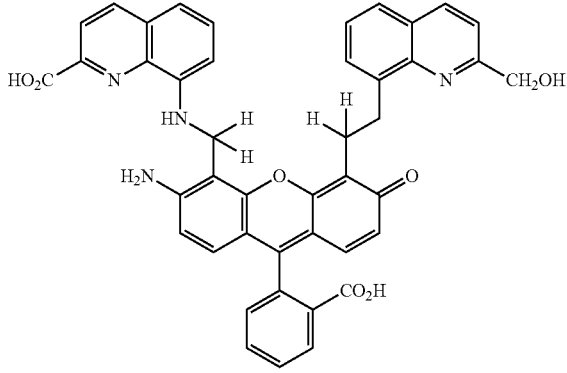
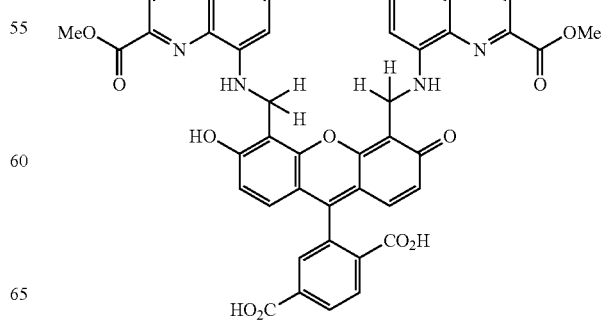

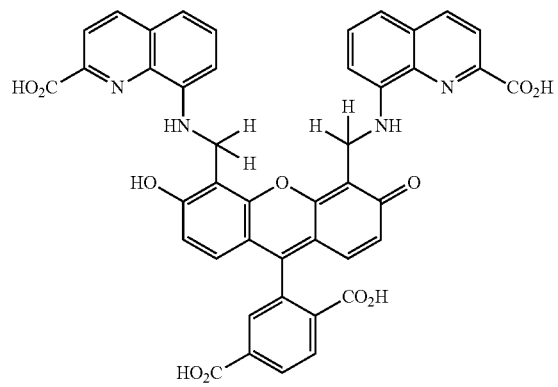
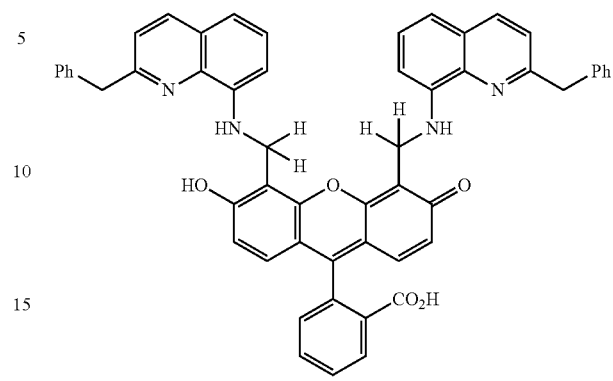
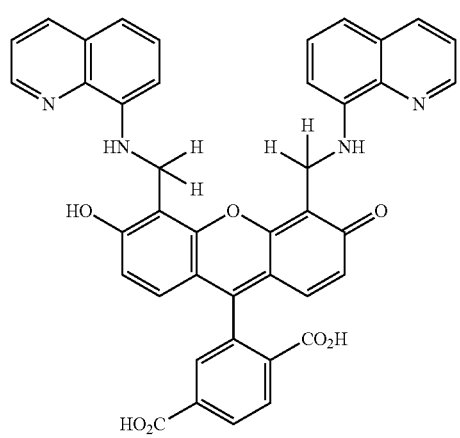
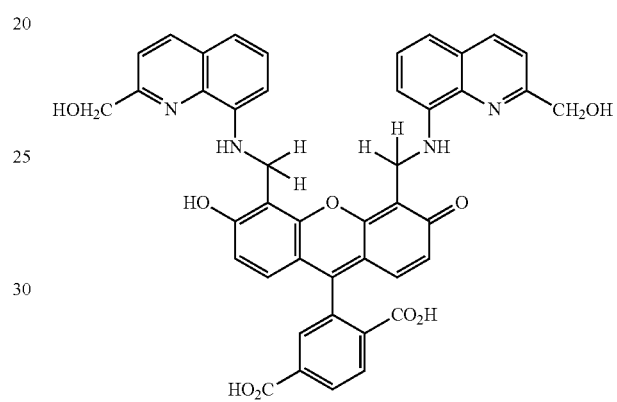
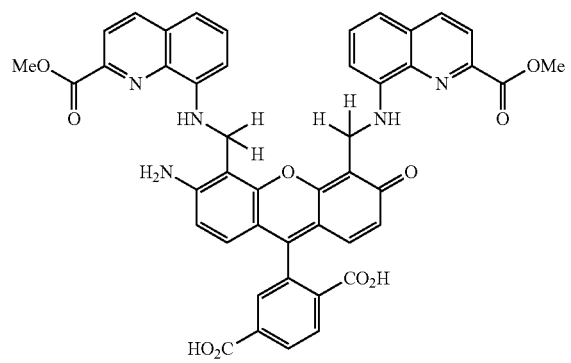
and
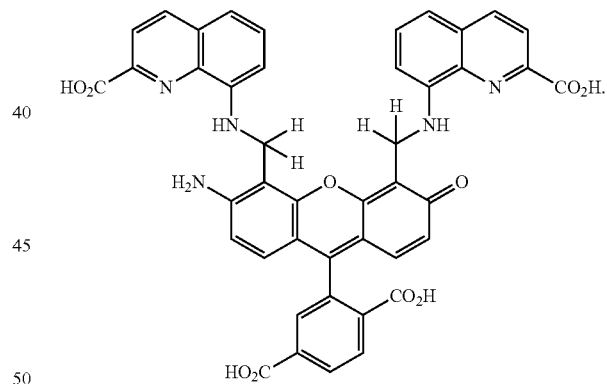
* * * * *